US008470593B2

(12) United States Patent
Saha

(10) Patent No.: US 8,470,593 B2
(45) Date of Patent: Jun. 25, 2013

(54) PLASMID SYSTEM FOR MULTIGENE EXPRESSION

(75) Inventor: Deba P. Saha, Nutley, NJ (US)

(73) Assignee: Merck Sharp Dohme & Corp., Rahway, NJ (US)

( * ) Notice: Subject to any disclaimer, the term of this patent is extended or adjusted under 35 U.S.C. 154(b) by 0 days.

(21) Appl. No.: 13/275,746

(22) Filed: Oct. 18, 2011

(65) Prior Publication Data

US 2012/0040402 A1 Feb. 16, 2012

Related U.S. Application Data

(60) Division of application No. 11/986,041, filed on Nov. 19, 2007, now Pat. No. 8,062,886, which is a continuation of application No. 10/986,498, filed on Nov. 10, 2004, now Pat. No. 7,326,567.

(60) Provisional application No. 60/519,230, filed on Nov. 12, 2003.

(51) Int. Cl.
*C12N 15/63* (2006.01)
*C12N 15/85* (2006.01)

(52) U.S. Cl.
USPC ........................................ 435/320.1; 435/325

(58) Field of Classification Search
None
See application file for complete search history.

(56) References Cited

U.S. PATENT DOCUMENTS

| | | | | |
|---|---|---|---|---|
| 6,511,967 | B1 * | 1/2003 | Weissleder et al. | 514/44 R |
| 2004/0152879 | A1 * | 8/2004 | Kimura et al. | 530/388.25 |

* cited by examiner

*Primary Examiner* — Michele K Joike

(57) ABSTRACT

The present invention provides a plasmid system which facilitates the construction of a single amplifiable plasmid that, having the potential to accommodate many independent expression cassettes, has the ability to express multi-subunit complex proteins such as antibodies and receptors.

2 Claims, 16 Drawing Sheets

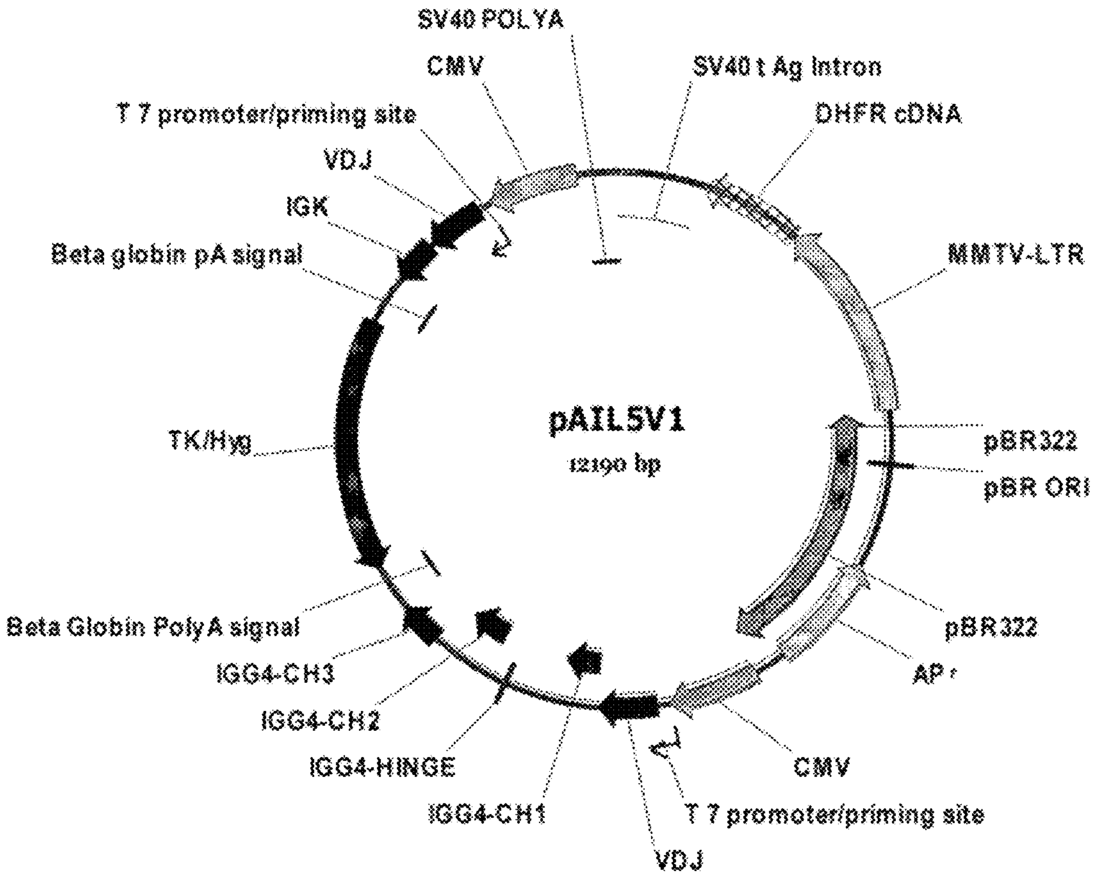
Figure 4: Plasmid map of pAIL5V1

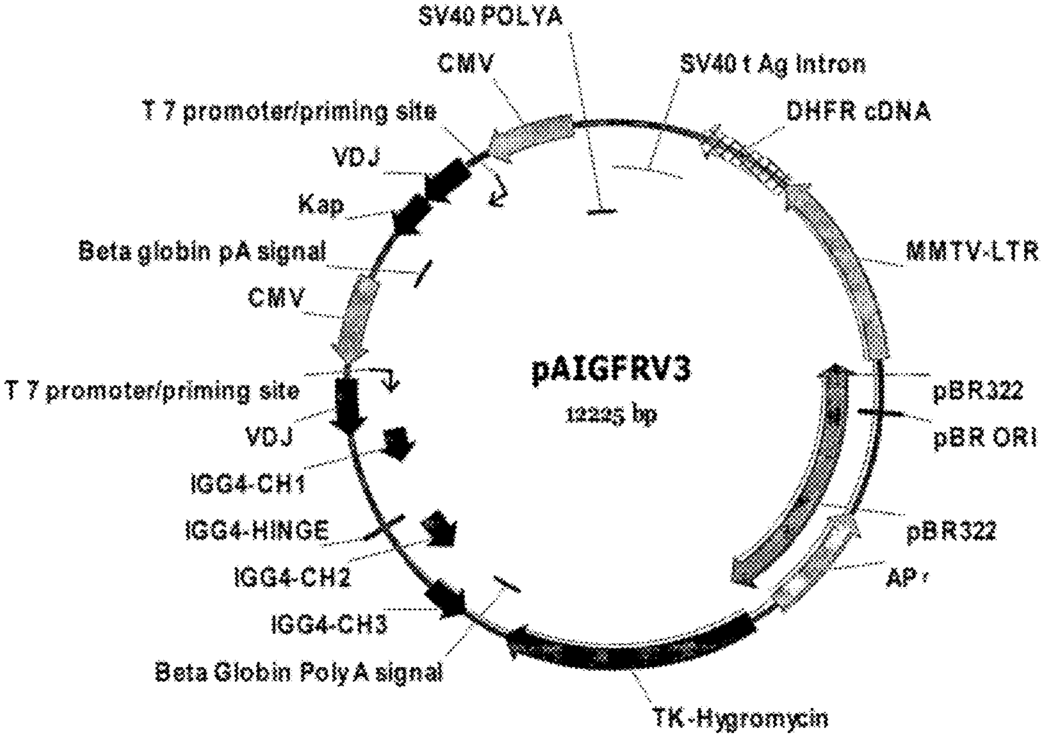
Figure 5: Plasmid map of pAIGFRV3

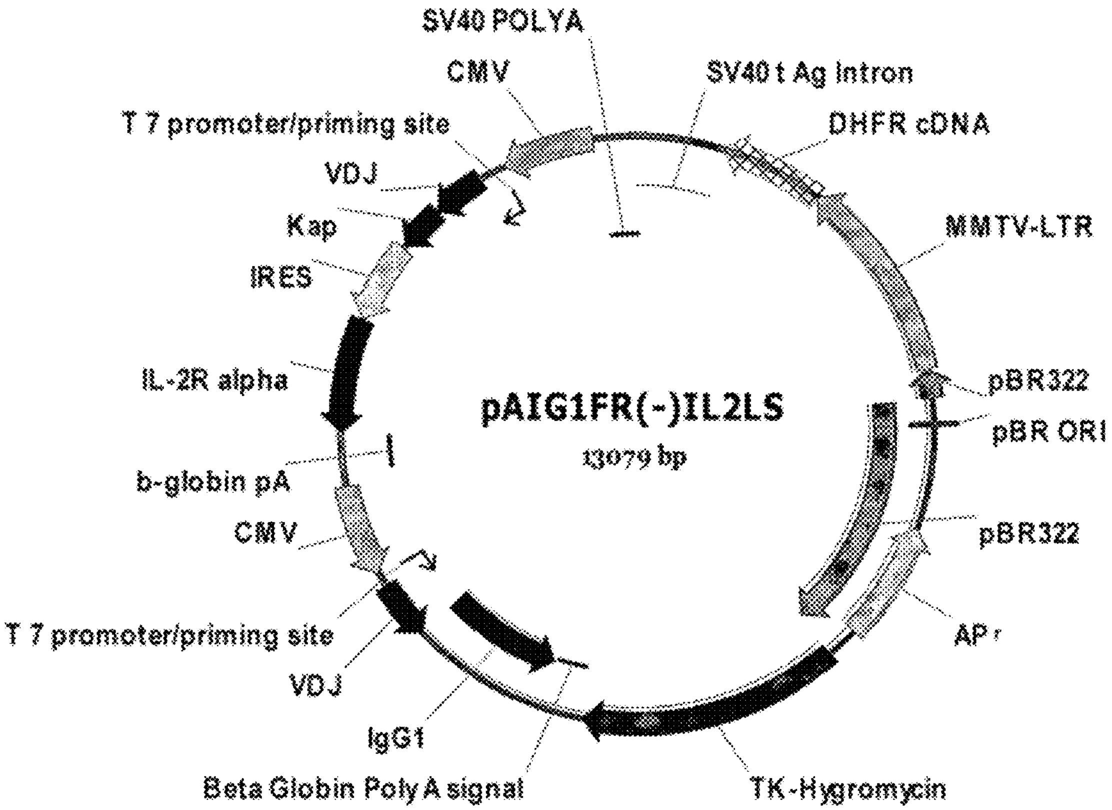
Figure 6: Plasmid map of pAIG1FR(-)IL2LS

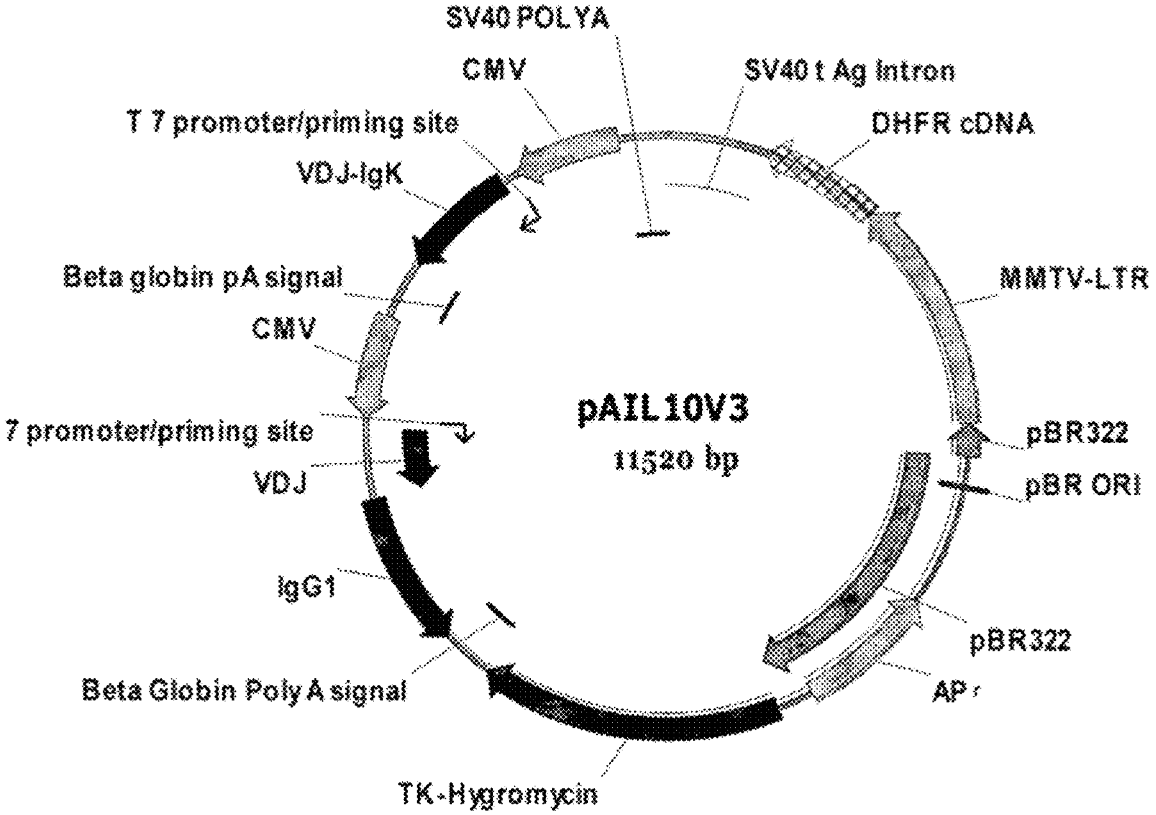
Figure 7: Plasmid map of pAIL10V3

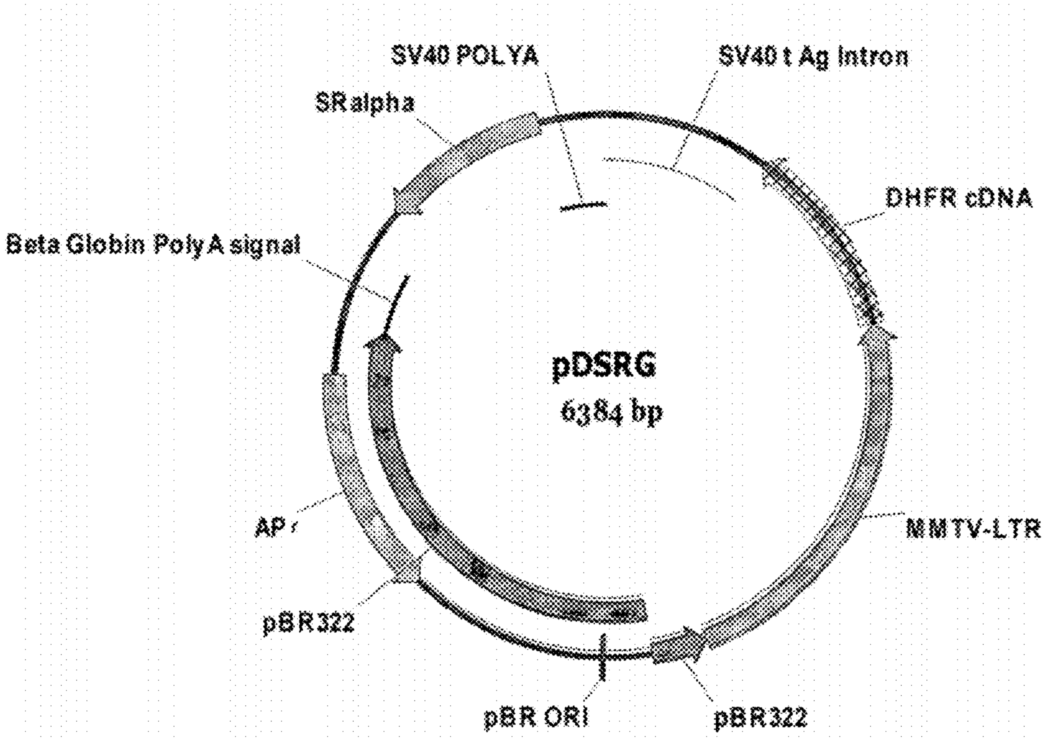
Figure 8: Plasmid map of pDSRG

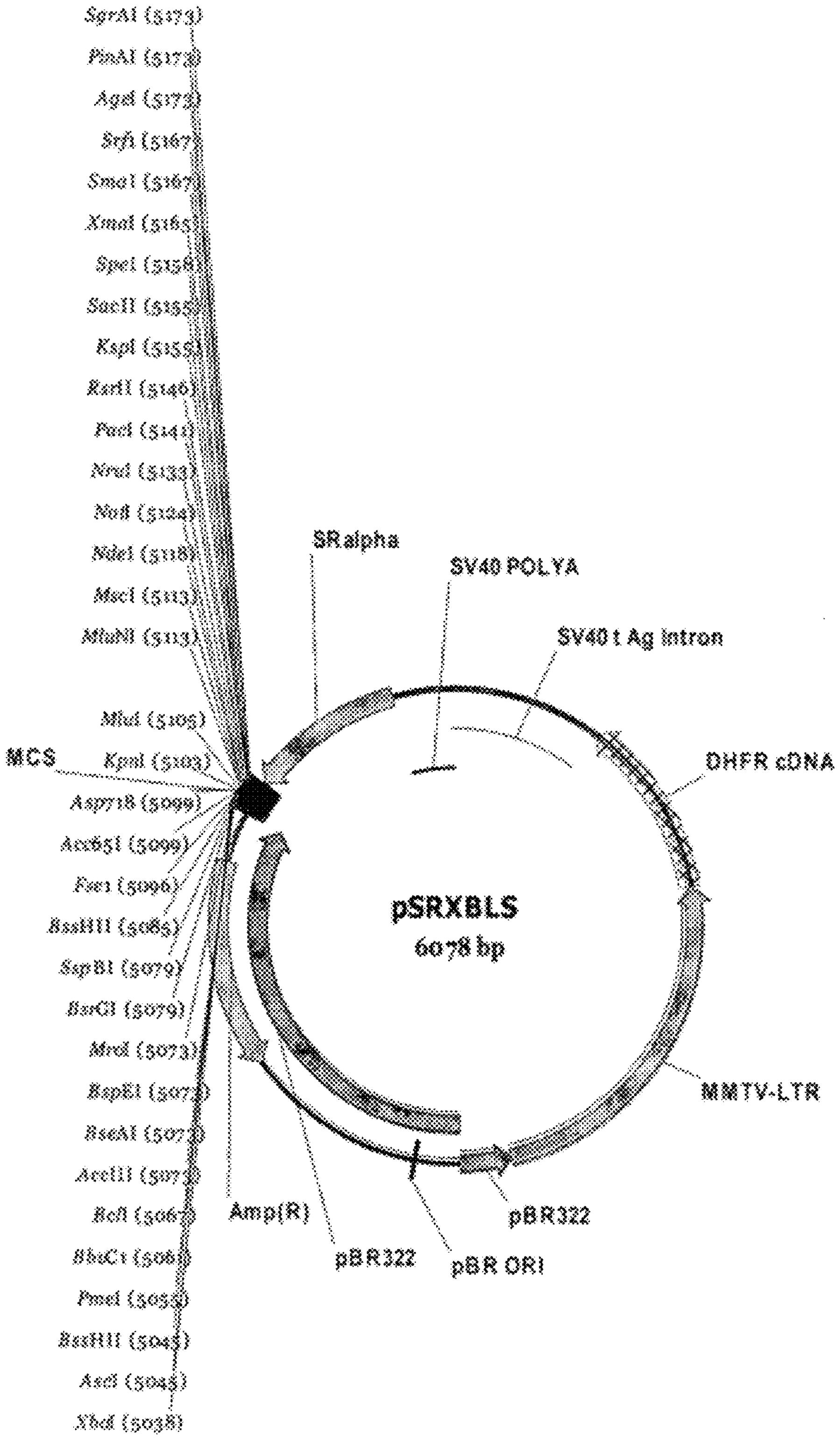
Figure 9: Plasmid map of pSRXBLS

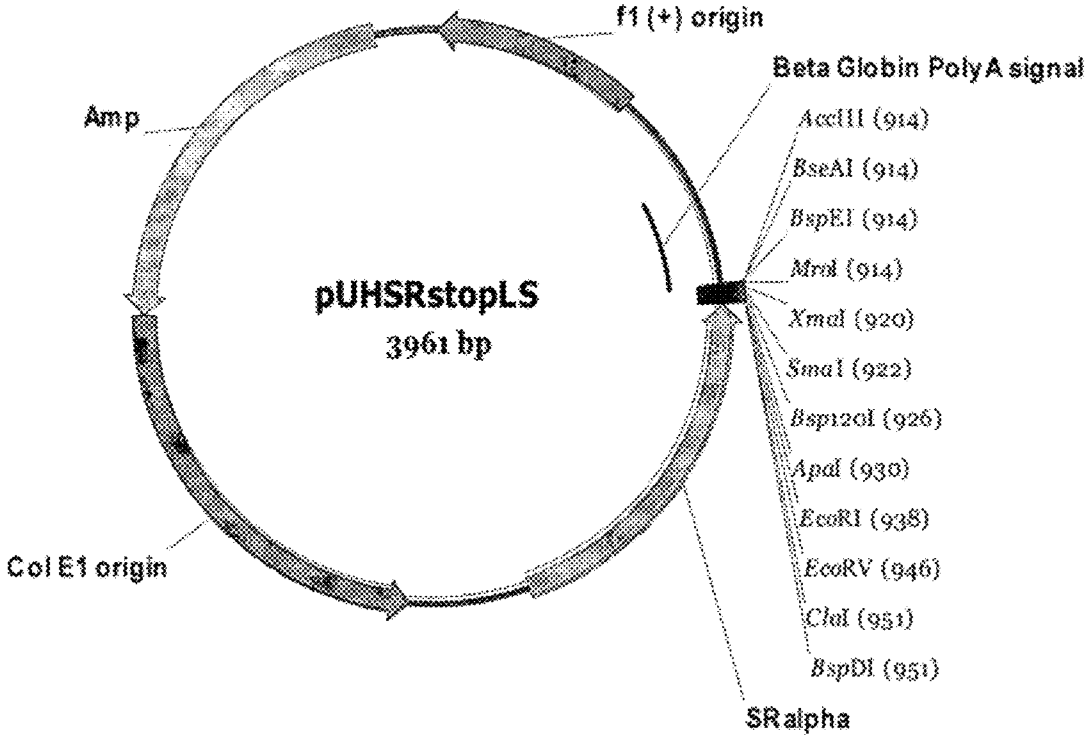
Figure 10: Plasmid map of pUHSRstopLS

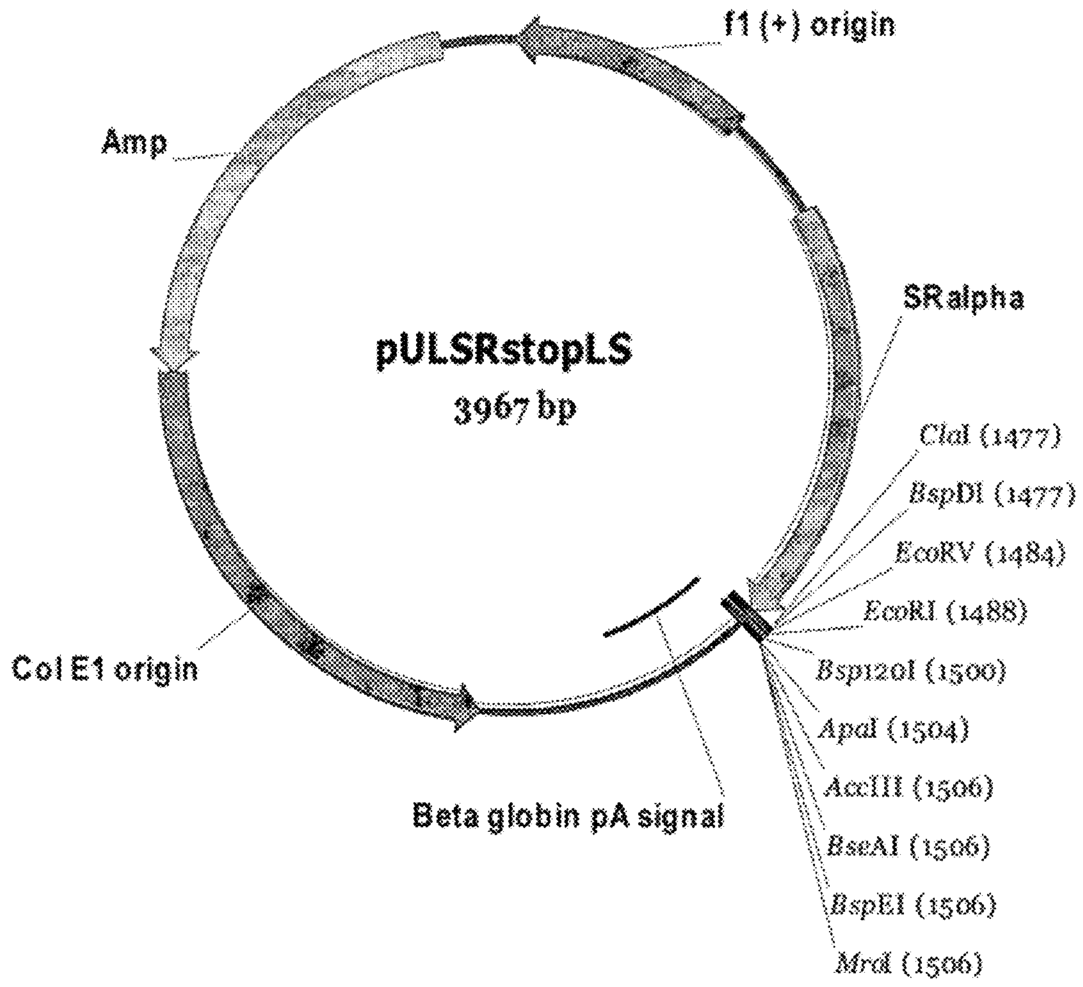
Figure 11: Plasmid map of pULSRstopLS

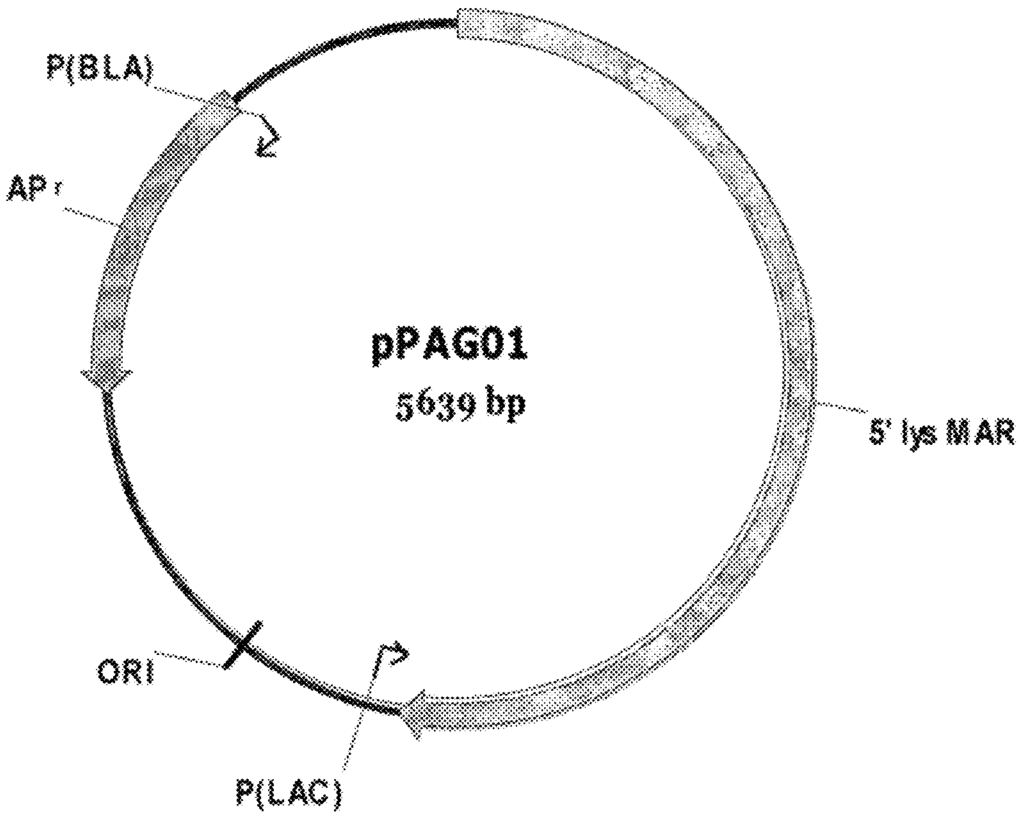
Figure 12: Plasmid map of pPAG01

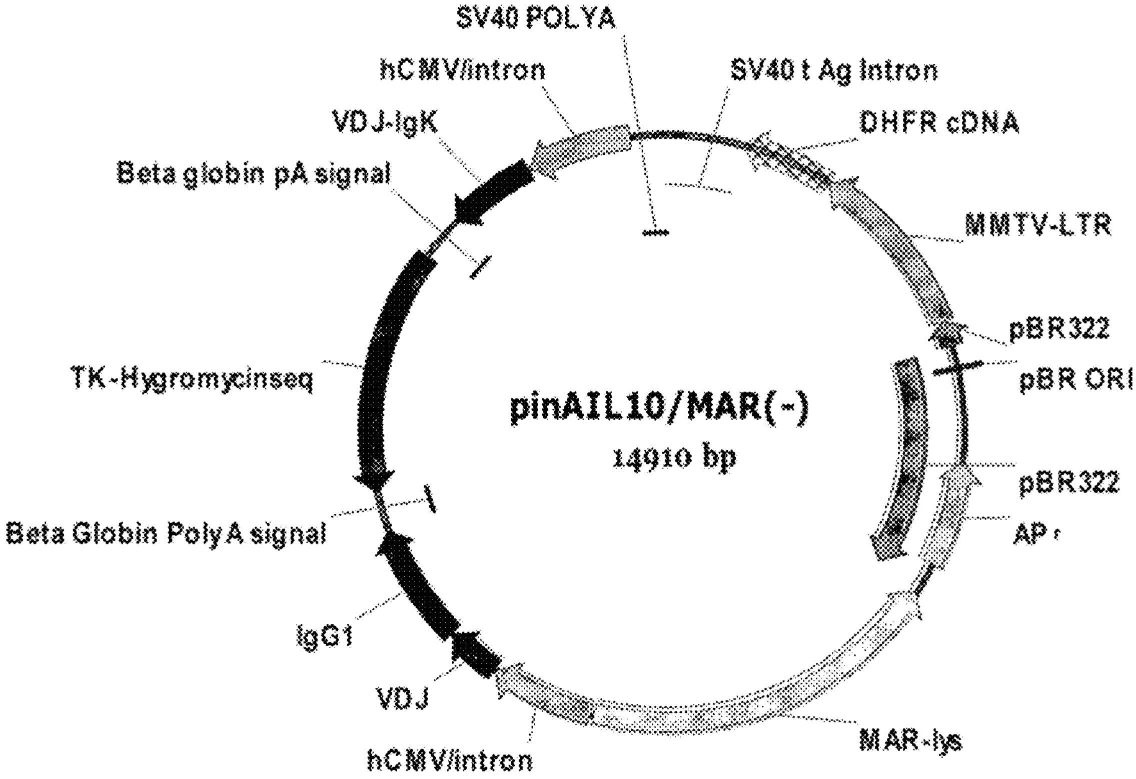
Figure 13: Plasmid map of pinAIL10/MAR(-)

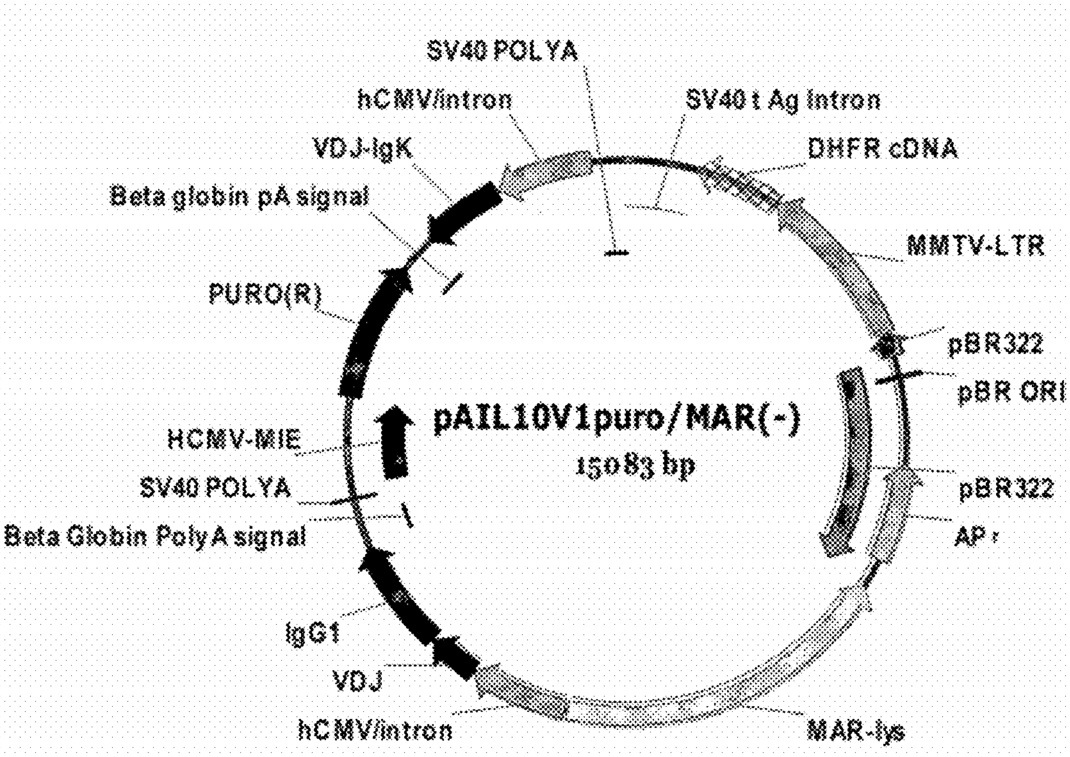
Figure 14: Plasmid map of pAIL10V1/puro/MAR(-)

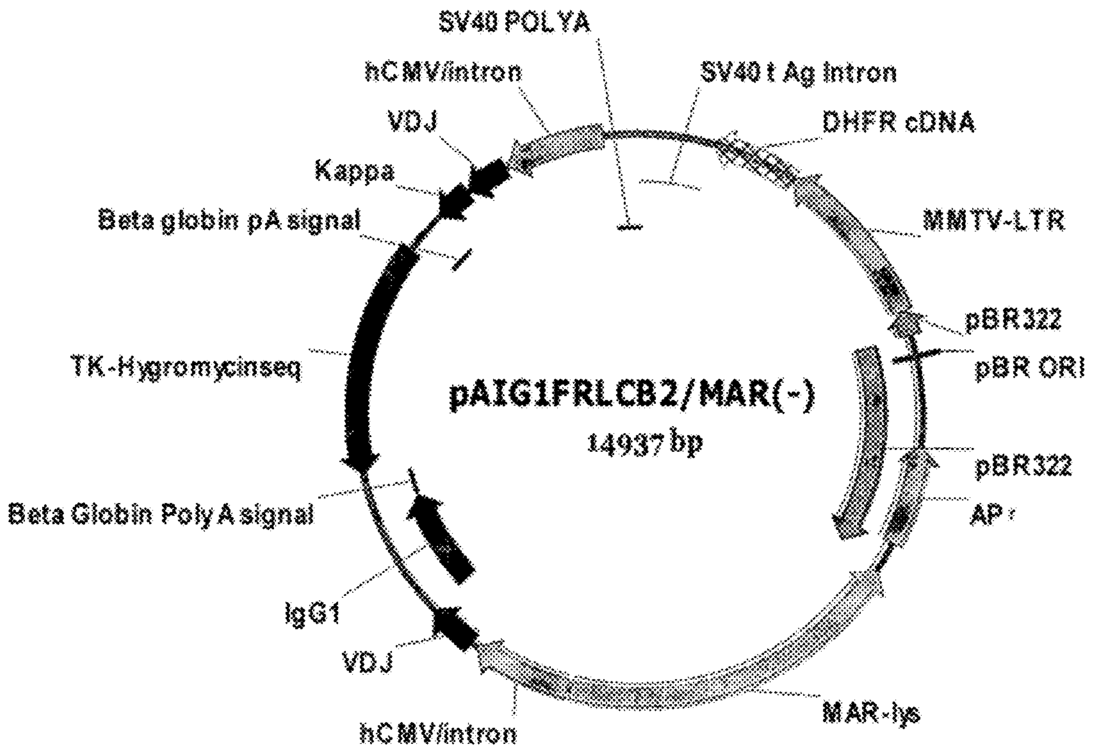
Figure 15: Plasmid map of pAIGFRLCb2/MAR(-)

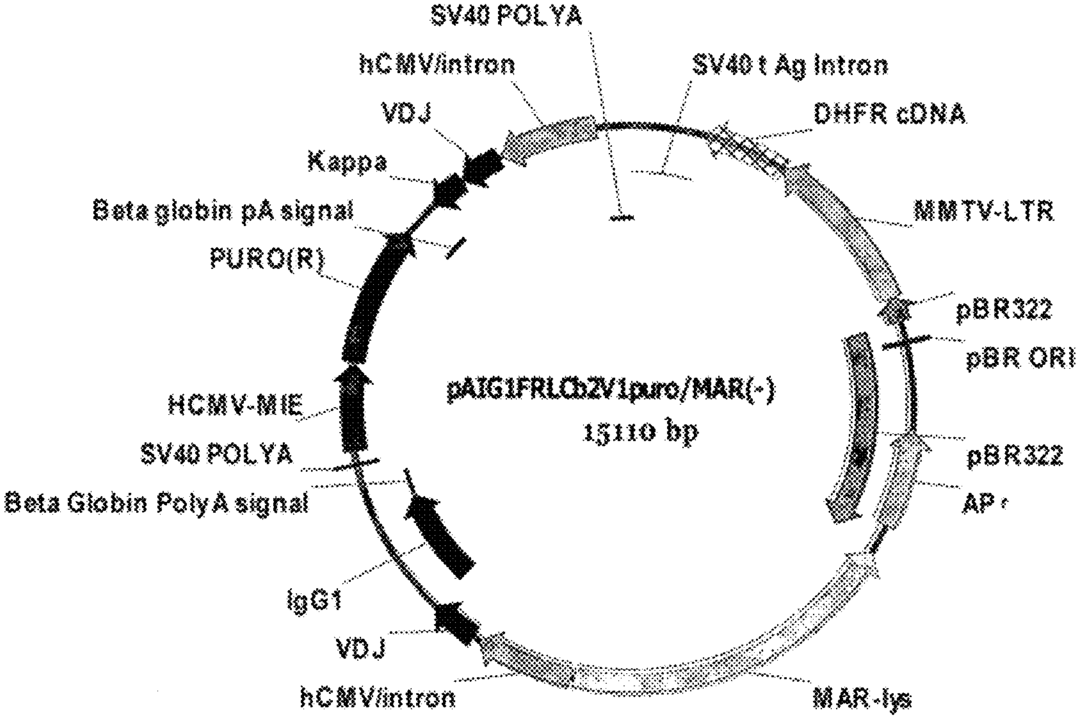
Figure 16: Plasmid map of pAIGFRLCb2V1/puro/MAR(-)

PLASMID SYSTEM FOR MULTIGENE EXPRESSION

This application is a divisional of U.S. patent application Ser. No. 11/986,041, filed Nov. 19, 2007, which is a continuation of U.S. patent application Ser. No. 10/986,498, filed Nov. 10, 2004; which claims the benefit of U.S. Provisional Patent Application No. 60/519,230, filed Nov. 12, 2003; each of which is herein incorporated by reference in its entirety.

FIELD OF THE INVENTION

A plasmid system which facilitates construction of a single amplifiable expression plasmid for multi-subunit proteins.

BACKGROUND OF THE INVENTION

Development of any mammalian cell based protein therapeutic requires an efficient expression system. Ideally, if a multi-subunit protein (e.g., an antibody) must be produced, each polypeptide should be expressed from a single plasmid. Construction of expression vectors containing multiple genes, using commercially available expression plasmids, is problematic. Typically, the multiple cloning sites (MCS), of currently available expression plasmids, are inadequate for insertion of multiple expression cassettes. The multiple cloning sites of currently available expression plasmids contain relatively few restriction sites. Ideally, an expression plasmid for expression of multiple polypeptides would contain a large multiple cloning site containing many common and rare restriction sites.

The present invention provides, inter alia, an ideal generic plasmid expression system which can help maintain uniformity in vector construction, decrease variability in downstream processing, facilitate running multiple protein therapeutic projects simultaneously, and reduce cycle time significantly. The present invention includes such a generic plasmid platform for mammalian expression and its use for the production of various polypeptides. The platform is flexible enough to be used for expression of simple proteins, such as interferon, as well as large, complex, multi-subunit proteins, such as antibodies.

SUMMARY OF THE INVENTION

The present invention provides a plasmid system comprising in separate containers:

(a) a first universal transfer vector comprising the following, first multiple cloning site: Bss HII, Pme I, Sna B1, Hin dIII, Asp 718, Kpn I, Pae R71, Xho I, Sal I, Acc I, Hinc II, Cla I, Eco RV, Eco RI, Pst I, Eco O109I, Eco O109I, Apa I, Xma I, Bsp EI, Barn H1, Dsa I, Eag I, Ecl XI, Not I, Sac II, Xma III, Xba I, Sac I, Mlu I, Bcl I, Bsr GI, Bss HII; (b) a second universal transfer vector comprising the following, second multiple cloning site: Bss HII, Sgr AI, Xma I, Rsr II, Spe I, Sna B1, Hin dIII, Asp 718, Kpn I, Pae R71, Xho I, Sal I, Acc I, Hinc II, Cla I, Eco RV, Eco RI, Pst I, Eco O109I, Eco O109I, Apa I, Bsp EI, Barn H1, Dsa I, Eag I, Ecl XI, Not I, Sac II, Xma III, Xba I, Sac I, Nde I, Msc I, Nru I, Pac I, Bss HII; and (c) an amplifiable vector comprising the following, third multiple cloning site:Sgr AI, Srf I, Xma I, Spe I, Sac II, Rsr II, Pac I, Nru I, Not I, Nde I, Msc I, Mlu I, Kpn I, Fse 1, Bss HII, Bsr GI, Bsp EI, Bcl I, Bbv C1, Pme I, Bss HII, Asc I, Xba I. In an embodiment of the invention, the plasmid system comprises: a first universal transfer vector comprising the plasmid map of FIG. 2, a second universal transfer vector comprising the plasmid map of FIG. 1 and an amplifiable vector comprising the plasmid map of FIG. 3. In another embodiment, the multiple cloning site of the first universal transfer vector comprises the nucleotide sequence set forth in SEQ ID NO: 11; the multiple cloning site of the second universal transfer vector comprises the nucleotide sequence set forth in SEQ ID NO: 12; and the multiple cloning site of the amplifiable vector comprises the nucleotide sequence set forth in SEQ ID NO: 10. In an embodiment of the invention, any of the universal transfer vectors or the amplifiable vector comprises a matrix attachment region (MAR; e.g., chicken lysozyme MAR).

In another embodiment of the invention, the plasmid system comprises only the first and second universal transfer vectors (supra).

In an embodiment of the invention, at least one of the plasmids comprises a promoter (e.g., SRα promoter, MMTV LTR, human cytomegalovirus (hCMV) immediate early promoter and murine cytomegalovirus (mCMV) immediate early promoter) located upstream of or within the multiple cloning site. Preferably, in this embodiment, the first universal transfer vector comprises the plasmid map of FIG. 10; the second universal transfer vector comprises the plasmid map of FIG. 11; and the amplifiable vector comprises the plasmid map of FIG. 9. In this embodiment, the first universal transfer vector can comprise the nucleotide sequence set forth in SEQ ID NO: 5; the second universal transfer vector comprise the nucleotide sequence set forth in SEQ ID NO: 4; and the amplifiable vector comprises the nucleotide sequence set forth in SEQ ID NO: 13.

Another embodiment of the present invention includes the plasmid system wherein at least one of the universal transfer vectors comprises a terminator/polyA addition site located in the multiple cloning site wherein the location of the terminator/polyA addition site is such that a gene located in the multiple cloning site would be operably linked to the terminator/polyA addition site.

The amplifiable vector in the plasmid system of the invention may comprise a selectable marker for amplification, such as the DHFR gene.

In an embodiment of the invention, the plasmid system of the present invention comprises in separate containers: (a) a first universal transfer vector comprising the nucleotide sequence set forth in SEQ ID NO: 2; (b) a second universal transfer vector comprising the nucleotide sequence set forth in SEQ ID NO: 1; and (c) an amplifiable vector comprising the nucleotide sequence set forth in SEQ ID NO: 3.

An embodiment of the invention includes a plasmid system wherein the first or second universal transfer vector comprises a first set of one or more expression cassettes, the other universal transfer vector comprise a second set of one or more expression cassettes and the amplifiable vector comprises said first set and second set of expression cassettes; wherein the expression cassettes encode an immunoglobulin heavy chain and an immunogloblin light chain (e.g., anti-IGFR1, anti-IL10 or anti-IL5 immunoglobulin chains); for example wherein (a) the first set of one or more expression cassettes comprises an anti-IL5 immunoglobulin heavy chain gene expression cassette and the second set of one or more expression cassettes comprises an anti-IL5 immunoglobulin light chain gene expression cassette; (b) the first set or one or more expression cassette comprises an anti-IGFR1 immunoglobulin heavy chain gene expression cassette and the second set of one or more expression cassette comprises an anti-IGFR1 immunoglobulin light chain gene expression cassette; (c) the first set of one or more expression cassettes comprises an expression cassette comprising a bicistronic gene expression cassette which bicistronic gene comprises an anti-IGFR1 immunoglobulin light chain gene and an IL2 receptor a gene wherein said genes are linked by an internal ribosome entry sequence (IRES) and the second set of one or more expression cassettes is an anti-IGFR1 immunoglobulin heavy chain gene expression cassette and a hygromycin resistance gene (Hyg-b) expression cassette; or (d) the first set of one or more expression cassettes comprises an anti-IL10 immunoglobulin heavy chain gene expression cassette and the second set of one or more expression cassettes comprises an anti-IL10 immunoglobulin light chain gene expression cassette and a hygromycin resistance gene expression cassette. In an embodiment of the invention, the amplifiable vector comprises a plasmid map as set forth in a figure selected from FIGS. 4-7. For example, the amplifiable vector can comprise a nucleotide sequence selected from SEQ ID NOs: 6-9.

In an embodiment of the present invention, the plasmid system includes the amplifiable vectors pinAIL10/MAR(−); pAIL10V1/puro/MAR(−); pAIGFRLCb2/MAR(−) or pAIGFRLCb2V1/puro/MAR(−). In an embodiment of the invention, the plasmids pinAIL10/MAR(−); pAIL10V1/puro/MAR(−); pAIGFRLCb2/MAR(−) and pAIGFRLCb2V1/puro/MAR(−) are characterized by FIGS. 13-16, respectively. In another embodiment of the invention, the plasmids pinAIL10/MAR(−); pAIL10V1/puro/MAR(−); pAIGFRLCb2/MAR(−) and pAIGFRLCb2V1/puro/MAR(−) comprise a nucleotide sequence selected from SEQ ID NOs: 24-27.

The present invention also provides a method for expressing a protein comprising two or more types of polypeptide comprising the steps of (a) introducing a set of one or more expression cassettes into a first universal transfer vector; (b) introducing one or more different expression cassettes into a second universal transfer vector; (c) moving the cassettes from the transfer vectors into an amplifiable vector; (d) causing expression of said cassettes; and (e) optionally, isolating/purifying the polypeptide; wherein said vectors are provided in a kit of the present invention. In one embodiment of the invention, the first universal transfer vector comprises the plasmid map of FIG. 2 or FIG. 10, or the nucleotide sequence set forth in SEQ ID NO: 2 or SEQ ID NO: 5. In another embodiment, the second universal transfer vector comprises the plasmid map of FIG. 1 or FIG. 11 or the nucleotide sequence set forth in SEQ ID NO: 1 or SEQ ID NO: 4. In another embodiment of the invention, the amplifiable vector comprises the plasmid map of FIG. 3 or FIG. 9 or the nucleotide sequence set forth in SEQ ID NO: 3 or SEQ ID NO: 13.

In an embodiment of the method, an anti-IGFR heavy chain or anti-IL10 heavy is expressed in an amplifiable vector, comprising a MAR and either the hygromycin resistance gene or the puromycin resistance gene, which selected from pinAIL10/MAR(−); pAIL10V1/puro/MAR(−); pAIGFRLCb2/MAR(−) and pAIGFRLCb2V1/puro/MAR(−). In an embodiment of the invention, the plasmids pinAIL10/MAR(−); pAIL10V1/puro/MAR(−); pAIGFRLCb2/MAR(−) and pAIGFRLCb2V1/puro/MAR(−) are characterized by FIGS. 13-16, respectively. In another embodiment of the invention, the plasmids pinAIL10/MAR(−); pAIL10V1/puro/MAR(−); pAIGFRLCb2/MAR(−) and pAIGFRLCb2V1/puro/MAR(−) comprise a nucleotide sequence selected from SEQ ID NOs: 24-27.

In an embodiment of the method for expressing a protein comprising two or more types of polypeptide, the expression cassettes encode an immunoglobulin heavy or light chain (e.g., anti-IGFR1, anti-IL5 or anti-IL10 immunoglobulin chain); for example: (i) one expression cassette encodes an anti-IL5 immunoglobulin heavy chain and the other expression cassette encodes an anti-IL5 immunoglobulin light chain; (ii) one expression cassette encodes an anti-IGFR1 immunoglobulin heavy chain (e.g., SEQ ID NO: 17 or 21 or any polynucleotide encoding a polypeptide comprising the amino acid sequence of SEQ ID NO: 18 or 22) and the other expression cassette encodes an anti-IGFR1 immunoglobulin light chain (e.g., SEQ ID NO: 15 or 19 or any polynucleotide encoding a polypeptide comprising the amino acid sequence of SEQ ID NO: 16 or 20); (iii) one expression cassette comprises a bicistronic gene encoding an anti-IGFR1 immunoglobulin light chain and an IL2 receptor α-subunit which are linked by an internal ribosome entry sequence (IRES) and the other expression cassette encodes an anti-IGFR1 immunoglobulin heavy chain and HYG-B; or (iv) one expression cassettes encodes an anti-IL10 immunoglobulin heavy chain and the other expression cassette encodes an anti-IL10 immunoglobulin light chain and HYG-B.

In an embodiment of the invention, the amplifiable vector comprises a plasmid map in a figure selected from FIGS. 4-7. The amplifiable vector may comprise a nucleotide sequence selected from SEQ ID NOs: 6-9.

The scope of the present invention also encompasses any product produced by any of the methods of the invention for producing a polypeptide (e.g., any immunoglobulin chain, such as that of an anti-IGFR1, anti-IL5 or anti-IL10 antibody).

In an embodiment of the method for expressing a protein comprising two or more types of polypeptide, expression is caused in a cell (e.g., a eukaryotic cell such as a CHO cell).

The present invention also comprises a method for producing an anti-IGFR1 antibody comprising the steps of (a) introducing an expression cassette comprising a polynucleotide encoding a polypeptide comprising an amino acid sequence selected from SEQ ID NOs: 18 and 22 or an expression cassette comprising a polynucleotide encoding a polypeptide comprising an amino acid sequence selected from SEQ ID NOs: 16 and 20 into a first universal transfer vector comprising the following, first multiple cloning site: Bss HII, Pme I, Sna B1, Hin dIII, Asp 718, Kpn I, Pae R71, Xho I, Sal I, Acc I, Hinc II, Cla I, Eco RV, Eco RI, Pst I, Eco O109I, Eco O109I, Apa I, Xma I, Bsp EI, Bam H1, Dsa I, Eag I, Ecl XI, Not I, Sac II, Xma III, Xba I, Sac I, Mlu I, BolI, Bsr GI, Bss HII (e.g., pUHLS or PUHSRstopLS); (b) introducing the other expression cassette, not introduced into said first vector, into a second universal transfer vector comprising the following, second multiple cloning site: Bss HII, Sgr AI, Xma I, Rsr II, Spe I, Sna B1, Hin dIII, Asp 718, Kpn I, Pae R71, Xho I, Sal I, Acc I, Hinc II, Cla I, Eco RV, Eco RI, Pst I, Eco O109I, Eco O109I, Apa I, Bsp EI, Bam H1, Dsa I, Eag I, Ecl XI, Not I, Sac II, Xma III, Xba I, Sac I, Nde I, Msc I, Nru I, Pac I, Bss HII (e.g., pULLS or PULSRstopLS); (c) optionally, moving the cassettes from the transfer vectors into an amplifiable vector comprising the following, third multiple cloning site: Sgr AI, Srf I, Xma I, Spe I, Sac II, Rsr II, Pac I, Nru I, Not I, Nde I, Msc I, Mlu I, Kpn I, Fse 1, Bss HII, Bsr GI, Bsp EI, Bcl I, Bbv C1, Pme I, Bss HII, Asc I, Xba I (e.g., pXBLS or pSRXBLS); (d) causing expression of said cassettes; and (e) optionally isolating/purifying the antibody. The polynucleotide encoding a polypeptide comprising an amino acid sequence selected from SEQ ID NOs: 18 and 22 can comprise a nucleotide sequence selected from SEQ ID NOs: 17 and 21. The polynucleotide encoding a polypeptide comprising an amino acid sequence selected from SEQ ID NOs: 16 and 20 can comprise a nucleotide sequence selected from SEQ ID NOs: 15 and 19. In one embodiment of the invention, the expression cassettes are operably linked to a human cytomegalovirus (hCMV) promoter. The scope of the present invention includes embodiments wherein the expression cassettes mentioned above are linked to an immunoglobulin constant region such as that of any one of κ or γ1 or γ2 or γ3 or γ4.

The present invention also provides a kit comprising the plasmid system of the invention and one or more components selected from: (i) sterile, distilled water; (ii) calcium phosphate transformation reagents $CaCl_2$ and 2×HEPES buffered saline; (iii) DEAE-dextran transformation reagents chloroquine in Phosphate buffered saline and phosphate buffered saline; (iv) DOTAP/cholesterol extruded liposomes; (v) transformation competent *E. coli*; (vi) Dulbecco/Vogt modified Eagle's minimal essential medium (DMEM); (vii) Fetal calf serum; (viii) luria broth media; and (ix) paper instructions for usage of the plasmid system.

One embodiment of the present invention includes a single stranded or double stranded polynucleotide (e.g., an oligonucleotide primer) comprising a nucleotide sequence of SEQ ID NO: 10, 11 or 12.

The present invention also includes a plasmid comprising a nucleotide sequence selected from the group consisting of SEQ ID NOs: 6-9.

BRIEF DESCRIPTION OF THE FIGURES

The scope of the present invention includes any plasmid or plasmid system containing a plasmid that comprises a plasmid map substantially identical to any of the following plasmid maps:

FIG. 4. Plasmid map of pAIL5V1.

Figure 1:
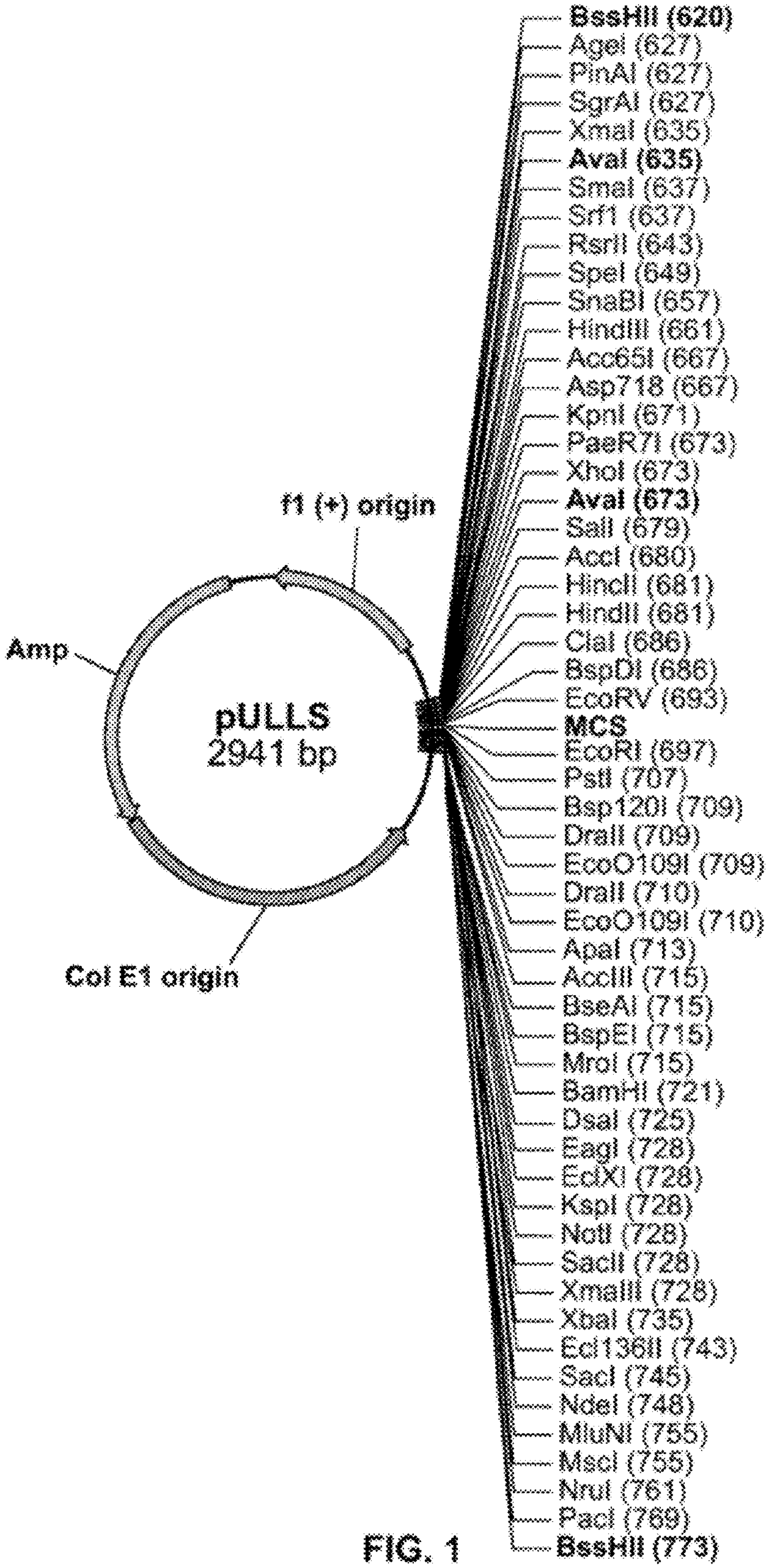
FIG. 1. Plasmid map of universal transfer vector pULLS.
Amp: Start: 1955 End: 2812
Col EI origin: Start: 1012 End: 1952
Multiple Cloning Site (MCS): Start: 620 End: 772
f1 (+) origin: Start: 3 End: 459

The anti-IL-5 antibody heavy (VDJ-IgG4) and light (VDJ-IgK) chain expression cassettes, driven by the CMV promoter, are inserted into the multiple cloning site of pXBLS along with the hygromycin B expression cassette driven by the TK promoter (TK/Hyg).

SV40 t Ag Intron: Start: 12177 End: 600
SV40 POLYA signal: Start: 11930 End: 12178
CMV Promoter: Start: 11238 End: 11892
T 7 promoter/priming site: Start: 11219 End: 11238
VDJ (Anti-IL-5 light chain): Start: 10718 End: 11148
IGκ (Anti-IL-5 light chain): Start: 10382 End: 10717
Beta Globin Poly A signal: Start: 10126 End: 10374
TK/Hyg: Start: 8161 End: 10033
Beta Globin Poly A signal: Start: 7877 End: 8115
IGG4-CH3 (Anti-IL-5 antibody heavy chain): Start: 7517 End: 7834
IGG4-CH2 (Anti-IL-5 antibody heavy chain): Start: 7087 End: 7419
IGG4-HINGE (Anti-IL-5 antibody heavy chain): Start: 6933 End: 6968
IGG4-CH1 (Anti-IL-5 antibody heavy chain): Start: 6247 End: 6540
VDJ (Anti-IL-5 antibody heavy chain): Start: 5813 End: 6247
T 7 promoter/priming site: Start: 5723 End: 5742
CMV Promoter: Start: 5069 End: 5723
$AP^r$ (Ampicillin resistance): Start: 3965 End: 4828
PBR ORI: Start: 3207 End: 3207
pBR322 sequences: Start: 3020 End: 5033
pBR322 sequences: Start: 2811 End: 3019
MMTV-LTR promoter: Start: 1348 End: 2810
DHFR cDNA: Start: 601 End: 1347

FIG. 5. Plasmid map of pAIGFRV3.

The anti-IGFR1 antibody heavy (VDJ-IgG4) and light (VDJ-IgK) chain expression cassettes, driven by the CMV promoter, are inserted into the multiple cloning site of pXBLS along with the hygromycin B expression cassette driven by the TK promoter (TK-Hygromycin). The DHFR cDNA, along with its promoter (MMTV-LTR) for plasmid amplification and the hygromycin B coding sequence, along with its TK promoter for selection in mammalian cells, are shown.

AP(R): Start: 3965 End: 4828
IgG1 non genomic region: Start: 7234 End: 8214
VDJ of IGFR1 of 11D8 hybridoma: Start: 8214 End: 8641
DHFR cDNA: Start: 601 End: 1347
SV40 t Ag Intron: Start: 11603 End: 600
Kappa chain of hu-antiIGFR gene: Start: 9761 End: 10096
VDJ Domain of hu-anti IGFR gene for light chain: Start: 10097 End: 10477
pBR322 sequence: Start: 2811 End: 3019
pBR322 sequence: Start: 3020 End: 5033
TK-Hygromycin: Start: 5053 End: 6925
Beta Globin Poly A signal: Start: 6971 End: 7209
Beta globin pA signal: Start: 9505 End: 9753
SV40 POLYA: Start: 11356 End: 11604
MMTV-LTR: Start: 1348 End: 2810
CMV promoter: Start: 10664 End: 11318
T 7 promoter/priming site: Start: 8723 End: 8742
CMV promoter: Start: 8742 End: 9396
T 7 promoter/priming site: Start: 10645 End: 10664
pBR ORI: Start: 3207 End: 3207

FIG. 6. Plasmid map of pAIG1 FR(−)IL2LS.

This plasmid drives expression of the anti-IGFR1 antibody and the membrane domain of the IL2 receptor. Three independent expression cassettes containing four genes including heavy and light chain anti-IGFR1, truncated IL2 receptor and hygromycin B are incorporated into the multiple cloning site of pXBLS.

SV40 t Ag Intron: Start: 13066 End: 600
SV40 POLYA: Start: 12819 End: 13067
CMV: Start: 12115 End: 12769
T7 promoter/priming site: Start: 12096 End: 12115
VDJ (Anti-IGFR1 light chain): Start: 11548 End: 11928
Kappa (Kap; Anti-IGFR1 light chain): Start: 11212 End: 11547
IRES: Start: 10621 End: 1119
IL-2R alpha: Start: 9787 End: 10615
Beta Globin Poly A signal (β-globin pA) Start: 9505 End: 9753
CMV: Start: 8742 End: 9396
T7 promoter/priming site: Start: 8723 End: 8742
VDJ (Anti-IGFR1 heavy chain of 11D8 hybridoma): Start: 8214 End: 8641
IgG1 (Anti-IGFR1 heavy chain of 11D8 hybridoma): Start: 7234 End: 8214

Beta Globin Poly A signal (b-globin pA): Start: 6971 End: 7209
TK-Hygromycin: Start: 5053 End: 6925
$AP^r$: Start: 3965 End: 4828
pBR ORI: Start: 3207 End: 3207
pBR322 sequences: Start: 3020 End: 5033
pBR322 sequences: Start: 2811 End: 3019
MMTV-LTR: Start: 1348 End: 2810
DHFR cDNA: Start: 601 End: 1347

FIG. 7. Plasmid map of pAIL10V3.

The plasmid drives expression of anti-IL10. The anti-IL10 antibody heavy (VDJ-IgG4) and light (VDJ-IgK) chain expression cassettes, driven by the CMV promoter, are inserted into the multiple cloning site of pXBLS along with the hygromycin B expression cassette driven by the TK promoter (TK-Hygromycin). The dhfr cDNA, along with its promoter (MMTV-LTR) for plasmid amplification and the hygromycin B coding sequence, along with its TK promoter for selection in mammalian cells, are shown.

SV40 t Ag Intron: Start: 11507 End: 600
SV40 POLYA signal: Start: 11260 End: 11508
CMV: Start: 10568 End: 11222
T7 promoter/priming site: Start: 10549 End: 10568
VDJ-IgK (anti-IL10 rat antibody 12G8 light chain): Start: 9739 End: 10468
Beta globin Poly A signal: Start: 9478 End: 9726
CMV promoter: Start: 8715 End: 9369
T7 promoter/priming site: Start: 8696 End: 8715
VDJ (anti-IL10 rat antibody 12G8 heavy chain): Start: 8214 End: 8644
IgG1 non genomic region (anti-IL10 rat antibody 12G8 heavy chain): Start: 7234 End: 8214
Beta Globin Poly A signal: Start: 6971 End: 7209
TK promoter driving Hygromycin gene (TK-Hygromycin): Start: 5053 End: 6925
$AP^r$: Start: 3965 End: 4828
pBR ORI: Start: 3207 End: 3207
pBR322 sequences: Start: 3020 End: 5033
pBR322 sequences: Start: 2811 End: 3019
MMTV-LTR promoter: Start: 1348 End: 2810
DHFR cDNA: Start: 601 End: 1347

FIG. 8. Plasmid map of pDSRG.

This plasmid is deposited at the American Type Culture Collection (10801 University Boulevard; Manassas, Va. 20110-2209), under catalogue number 68233. The plasmid includes the SRα promoter, a strong SV40-based promoter and the dihydrofolate reductase (DHFR) cDNA for plasmid amplification in the presence of methotrexate in dhfr(−) Chinese hamster ovary (CHO) cells.

SV40 t Ag Intron: Start: 6371 End: 600
SV40 POLYA signal: Start: 6124 End: 6372
SRα promoter: Start: 5486 End: 6123
Beta Globin Poly A signal: Start: 5038 End: 5298
$AP^r$: Start: 3965 End: 4828
pBR322 sequences: Start: 3020 End: 5033
pBR322 sequences: Start: 2811 End: 3019
MMTV-LTR promoter: Start: 1348 End: 2810
DHFR cDNA: Start: 601 End: 1347

FIG. 9. Plasmid map of pSRXBLS.

pSRXBLS is the direct descendent of pDSRG replacing its own multiple cloning site with a large multiple cloning site. pSRXBLS is the progenitor plasmid of pXBLS.

SV40 t Ag Intron: Start: 6065 End: 600
SV40 POLYA signal: Start: 5818 End: 6066
SRα promoter: Start: 5180 End: 5817
MCS: Start: 5038 End: 5179
Amp(R): Start: 3965 End: 4828
pBR ORI: Start: 3207 End: 3207
pBR322 sequences: Start: 3020 End: 5033
pBR322 sequences: Start: 2811 End: 3019
MMTV-LTR promoter: Start: 1348 End: 2810
DHFR cDNA: Start: 601 End: 1347.

FIG. 10. Plasmid map of pUHSRstopLS.

pUHSRstopLS is the descendent plasmid to pUHLS carrying the SRα promoter and 249 bp of chicken β-globin terminator. This plasmid alone can be used to express any gene of interest. Also, it can be used as a transfer vector to transfer a complete expression cassette of part of a complex protein to pXBLS where all the expression cassettes can be assembled on a single plasmid.

Amp: Start: 2975 End: 3832
Col E1 origin: Start: 2032 End: 2972
Srα promoter with Intron: Start: 955 End: 1764
Beta Globin Poly A signal: Start: 673 End: 911
f1 (+) origin: Start: 3 End: 459

FIG. 11. Plasmid map of pULSRstopLS.

pULSRstopLS is the descendent plasmid to pULLS carrying the SRα promoter and a 249 bp of chicken β-globin terminator. This plasmid alone can be used to express any gene of interest. Also, it can be used as a transfer vector to transfer a complete expression cassette of part of a complex protein to pXBLS where all the expression cassettes can be assembled on a single plasmid.

Amp: Start: 2981 End: 3838
Col E1 origin: Start: 2038 End: 2978
Beta globin poly A signal: Start: 1512 End: 1760
Srα promoter: Start: 665 End: 1474
f1 (+) origin: Start: 3 End: 459

FIG. 12. Plasmid map of pPAG01.

This plasmid contains Selexis's (Geneva, Switzerland) ~3 kb chicken lysozyme MAR, flanked by Xba1 and BamH1 site.

AP(R) (bla gene-Ap(r) determinant): Start: 4165 End: 5022
Selexis Inc. 5' lys MAR: Start: 1 End: 2960
P(LAC): Start: 3043 End: 3043
P(BLA) (bla gene promoter): Start: 5057 End: 5057
Replication Origin ORI (RNaseH cleavage point): Start: 3403 End: 3403

FIG. 13. Plasmid map of pinAIL10/MAR(−).

The figure describes the map of plasmid, pinAIL10/MAR (−), that has the chicken lysozyme MAR element juxtaposed to the heavy chain expression cassette of the anti-IL10 gene containing the hygromycin resistance marker.

AP(R): Start: 3965 End: 4828
MAR-lys (MAR-lys is Matrix Attachment Region): Start: 5087 End: 8045
VDJ (VDJ region of anti-IL10 (12G8)): Start: 8928 End: 9369
IgG1 (IgG1 non genomic region): Start: 9374 End: 10354
DHFR cDNA: Start: 601 End: 1347
SV40 t Ag Intron: Start: 14897 End: 600
VDJ-IgK (VDJ-IgK for 12G8 light chain (anti-IL10)): Start: 13026 End: 13755
pBR322: Start: 2811 End: 3019
pBR322: Start: 3020 End: 5033
TK-Hygromycin: Start: 10663 End: 12672
Beta Globin Poly A signal: Start: 10379 End: 10617
Beta globin pA signal: Start: 12765 End: 13013
SV40 POLYA: Start: 14650 End: 14898
MMTV-LTR: Start: 1348 End: 2810
hCMV/intron (Human CMV promoter with hybrid intron): Start: 8077 End: 8918 hCMV/intron (Human CMV promoter and hybrid intron): Start: 13771 End: 14612 pBR ORI: Start: 3207 End: 3207

FIG. 14. Plasmid map of pAIL10V1/puro/MAR(−).

The figure describes the map of plasmid, pAIL10/puro/MAR(−), that has chicken lysozyme MAR element juxtaposed to the heavy chain expression cassette of the anti-IL10 gene containing the puromycin instead of the hygromycin resistance marker.

AP: Start: 3965 End: 4828

MAR-lys (MAR-lys is Matrix Attachment Region): Start: 5087 End: 8045

VDJ: Start (VDJ region of anti-IL10 (12G8)): 8928 End: 9369

IgG1 (IgG1 non genomic region): Start: 9374 End: 10354

PURO: Start: 11674 End: 12905

DHFR cDNA: Start: 601 End: 1347

SV40 t Ag Intron: Start: 15070 End: 600

VDJ-IgK (VDJ-IgK for 12G8 light chain (anti-IL10)): Start: 13199 End: 13928 (Complementary)

pBR322: Start: 2811 End: 3019 pBR322: Start: 3020 End: 5033

Beta Globin Poly A signal: Start: 10379 End: 10617

SV40 POLYA: Start: 10784 End: 10789

Beta globin pA signal: Start: 12938 End: 13186

SV40 POLYA: Start: 14823 End: 15071

MMTV-LTR: Start: 1348 End: 2810 hCMV/intron (Human CMV promoter with hybrid intron): Start: 8077 End: 8918

HCMV-MIE: Start: 10902 End: 11660 hCMV/intron (Human CMV promoter and hybrid intron): Start: 13944 End: 14785 (Complementary)

pBR ORI: Start: 3207 End: 3207

FIG. 15. Plasmid map of pAIGFRLCb2/MAR(−).

The figure describes the map of plasmid, that has chicken lysozyme MAR element juxtaposed to the heavy chain expression cassette of the anti-IGFR1 gene containing the hygromycin resistance marker.

AP(R): Start: 3965 End: 4828

MAR-Iys (MAR-Iys is Matrix Attachment Region): Start: 5087 End: 8045

VDJ (VDJ of IGFR1 of 11D8 hybridoma): Start: 8974 End: 9401

IgG1 (IgG1 non genomic region): Start: 9401 End: 10381

DHFR cDNA: Start: 601 End: 1347

SV40 t Ag Intron: Start: 14924 End: 600

Kappa (Kappa Chain): Start: 13063 End: 13386

VDJ (VDJ of IGFR1 (LCb, human germline sequence)): Start: 13387 End: 13764 pBR322: Start: 2811 End: 3019 pBR322: Start: 3020 End: 5033

TK-Hygromycin: Start: 10690 End: 12699

Beta Globin Poly A signal: Start: 10406 End: 10644

Beta globin pA signal: Start: 12792 End: 13040

SV40 POLYA: Start: 14677 End: 14925

MMTV-LTR: Start: 1348 End: 2810 hCMV/intron (Human CMV promoter with hybrid intron): Start: 8077 End: 8918 hCMV/intron (Human CMV promoter and hybrid intron): Start: 13786 End: 14627 pBR ORI: Start: 3207 End: 3207

FIG. 16. Plasmid map of pAIGFRLCb2V1/puro/MAR(−).

The figure describes the map of plasmid, that has chicken lysozyme MAR element juxtaposed to the heavy chain expression cassette of the anti-IGFR1 gene containing the puromycin instead of the hygromycin resistance marker.

AP(R): Start: 3965 End: 4828

MAR-Iys (MAR-Iys is Matrix Attachment Region): Start: 5087 End: 8045

VDJ (VDJ of IGFR1 of 11D8 hybridoma): Start: 8974 End: 9401

IgG1 (IgG1 non genomic region): Start: 9401 End: 10381

PURO(R): Start: 11701 End: 12932

DHFR cDNA: Start: 601 End: 1347

SV40 t Ag Intron: Start: 15097 End: 600

Kappa (Kappa Chain): Start: 13236 End: 13559

VDJ (VDJ of IGFR1 (LCb, human germline sequence)): Start: 13560 End: 13937 pBR322: Start: 2811 End: 3019 pBR322: Start: 3020 End: 5033

Beta Globin Poly A signal: Start: 10406 End: 10644

SV40 POLYA: Start: 10811 End: 10816

Beta globin pA signal: Start: 12965 End: 13213

SV40 POLYA: Start: 14850 End: 15098

MMTV-LTR: Start: 1348 End: 2810 hCMV/intron (Human CMV promoter with hybrid intron): Start: 8077 End: 8918

HCMV-MIE: Start: 10929 End: 11687 hCMV/intron (Human CMV promoter and hybrid intron): Start: 13959 End: 14800 pBR ORI: Start: 3207 End: 3207

DETAILED DESCRIPTION

The present invention provides a plasmid system useful for recombinant protein expression in any cell, for example in a mammalian cell, a bacterial cell, a yeast cell or an insect cell. The plasmid system is amenable to any cell based expression of a broad range of recombinant proteins, ranging from simple proteins, such as interferon, to complex proteins, such as antibodies. The system offers many common and rare restriction sites to accommodate a variety of expression cassettes. It also provides flexibility in the choice of various elements of an expression cassette, such as a promoter, enhancer, and terminator, as well as an antibiotic resistance marker. The plasmids can also be used as simple transfer vectors. The system offers potential for both transient as well as stable expression. The pXBLS vector carries the dihydrofolate reductase (DHFR) coding region for selection and amplification of the plasmid in DHFR deficient mammalian cells, e.g. CHO DXB-11 and CHO DG44. Thus, the system can be used for isolating stable clones, harnessing gene amplification and selection. The plasmid system includes two universal transfer plasmids, pUHLS and pULLS, which are useful for carrying out expression of the parts of a complex protein such as an antibody. Thus, the system offers options of co-transfection with universal vectors and single transfection with pXBLS. The ability of the plasmid system to cause such segregated expression of various parts is advantageous since it is sometimes necessary to take a deeper insight into the expression of individual units of a multi-subunit protein in order to analyze the overall expression of the complex protein. The system can also be used to address the effect of directional variability, resulting from the orientation of the multiple genes in the plasmid for the expression of multi-subunit proteins. Thus, a strategy in placing multiple expression cassettes can be arrived at for optimal expression of a complex protein.

The plasmid system of the invention has been demonstrated to direct high levels of expression of multiple polypeptides including anti-IL5 antibody, anti-IGFR1 antibody, 12 receptor membrane domain, and anti-IL10 antibody. Other proteins may also be expressed in the plasmid system of the invention including interferon, fibrinogen, ion channels, bacterial porins (e.g., ompF), and the nicotinic acetylcholine receptor (nAChR).

In one embodiment of the invention, the plasmid system comprises the light and heavy chain of the fully human, monoclonal anti-IGFR1 antibody 15H12/19D12 which may also be referred to as 15H12 or as 19D12.

The parts to the plasmid system can be provided separately or, conveniently, together as part of a kit.

The present invention includes any of the polynucleotide comprising or consisting of a nucleotide sequence set forth, below, in Table 1, individually or as part of a plasmid system or kit. Polynucleotides of the invention can be in any form, including circular, linear, double-stranded or single-stranded.

TABLE 1

Polynucleotides of the invention.

| Polynucleotide | Sequence Identifier |
|---|---|
| pULLS | SEQ ID NO: 1 |
| pUHLS | SEQ ID NO: 2 |
| pXBLS | SEQ ID NO: 3 |
| pULSRstopLS | SEQ ID NO: 4 |
| pUHSRstopLS | SEQ ID NO: 5 |
| pAIL5V1 | SEQ ID NO: 6 |
| pAIGFRV3 | SEQ ID NO: 7 |
| pAIG1FR(-)IL2LS | SEQ ID NO: 8 |
| pAIL10V3 | SEQ ID NO: 9 |
| pXBLS multiple cloning site | SEQ ID NO: 10 |
| pUHLS multiple cloning site | SEQ ID NO: 11 |
| pULLS multiple cloning site | SEQ ID NO: 12 |
| pSRXBLS | SEQ ID NO: 13 |
| pDSRG | SEQ ID NO: 14 |
| Nucleotide sequence encoding the 15H12 and 19D12 light chain variable region-including signal peptide (15H12/19D12 LC) | SEQ ID NO: 15 |
| Amino acid sequence of the 15H12 and 19D12 light chain variable region-including signal peptide | SEQ ID NO: 16 |
| Nucleotide sequence encoding the 15H12 and 19D12 heavy chain variable region including signal peptide (15H12/19D12 HC) | SEQ ID NO: 17 |
| Amino acid sequence of the 15H12 and 19D12 heavy chain variable region including signal peptide | SEQ ID NO: 18 |
| Nucleotide sequence encoding the 15H12/19D12 light chain F (LCF) | SEQ ID NO: 19 |
| Amino acid sequence of the 15H12/19D12 light chain F | SEQ ID NO: 20 |
| Nucleotide sequence encoding the 15H12/19D12 heavy chain A (HCA) | SEQ ID NO: 21 |
| Amino acid sequence of the 15H12/19D12 heavy chain A | SEQ ID NO: 22 |
| Nucleotide sequence of the chicken lysozyme MAR element | SEQ ID NO: 23 |
| pinAIL10/MAR(−) | SEQ ID NO: 24 |
| pAIL10V1/puro/MAR(−) | SEQ ID NO: 25 |
| pAIGFRLCb2/MAR(−) | SEQ ID NO: 26 |
| PAIGFRLCb2/puro/MAR(−) | SEQ ID NO: 27 |

Molecular Biology

In accordance with the present invention there may be employed conventional molecular biology, microbiology, and recombinant DNA techniques within the skill of the art. Such techniques are explained in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook, et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* (B. D. Hames & S. J. Higgins eds. (1985)); *Transcription And Translation* (B. D. Hames & S. J. Higgins, eds. (1984)); *Animal Cell Culture* (R. I. Freshney, ed. (1986)); *Immobilized Cells And Enzymes* (IRL Press, (1986)); B. Perbal, *A Practical Guide To Molecular Cloning* (1984); F. M. Ausubel, et al. (eds.), *Current Protocols in Molecular Biology*, John Wiley & Sons, Inc. (1994).

A "polynucleotide", "nucleic acid" or "nucleic acid molecule" includes the polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in single stranded form, double-stranded form or otherwise.

A "polynucleotide sequence", "nucleic acid sequence" or "nucleotide sequence" is a series of nucleotide bases (also called "nucleotides") in a nucleic acid, such as DNA or RNA, and means any chain of two or more nucleotides.

A "coding sequence" or a sequence "encoding" an expression product, such as a RNA or peptide, is a nucleotide sequence that, when expressed, results in production of the product.

The term "gene" means a DNA sequence that codes for or corresponds to a particular sequence of ribonucleotides or amino acids which comprise all or part of one or more RNA molecules, proteins or enzymes, and may or may not include regulatory DNA sequences, such as promoter sequences, which determine, for example, the conditions under which the gene is expressed. Genes may be transcribed from DNA to RNA which may or may not be translated into an amino acid sequence.

As used herein, the term "oligonucleotide" refers to a nucleic acid, generally of no more than about 300 nucleotides (e.g., 30, 40, 50, 60, 70, 80, 90, 150, 175, 200, 250, 300), that may be hybridizable to a genomic DNA molecule, a cDNA molecule, or an mRNA molecule encoding a gene, mRNA, cDNA, or other nucleic acid of interest. Oligonucleotides are usually single-stranded, but may be double-stranded. Oligonucleotides can be labeled, e.g., by incorporation of $^{32}$P-nucleotides, $^{3}$H-nucleotides, $^{14}$C-nucleotides, $^{35}$S-nucleotides or nucleotides to which a label, such as biotin, has been covalently conjugated. In one embodiment, a labeled oligonucleotide can be used as a probe to detect the presence of a nucleic acid. In another embodiment, oligonucleotides (one or both of which may be labeled) can be used as PCR primers, either for cloning full length or a fragment of the gene, or to detect the presence of nucleic acids. Generally, oligonucleotides are prepared synthetically, preferably on a nucleic acid synthesizer.

A "protein sequence", "peptide sequence" or "polypeptide sequence" or "amino acid sequence" refers to a series of two or more amino acids in a protein, peptide or polypeptide.

"Protein", "peptide" or "polypeptide" includes a contiguous string of two or more amino acids.

The term "isolated polynucleotide" or "isolated polypeptide" includes a polynucleotide (e.g., RNA or DNA molecule, or a mixed polymer) or a polypeptide, respectively, which is partially or fully separated from other components that are normally found in cells or in recombinant DNA expression systems or any other contaminant. These components include, but are not limited to, cell membranes, cell walls, ribosomes, polymerases, serum components and extraneous genomic sequences.

An isolated polynucleotide or polypeptide will, preferably, be an essentially homogeneous composition of molecules but may contain some heterogeneity.

"PCR amplification" of DNA as used herein includes the use of polymerase chain reaction (PCR) to increase the concentration of a particular DNA sequence within a mixture of DNA sequences. For a description of PCR see Saiki, et al., Science (1988) 239:487. Genes can be amplified, for example, in a plasmid in a cell. Cells harboring a plasmid containing an amplifiable, selectable marker, but lacking an endogenous marker gene, such as DHFR, can be selected with increasing amounts of a selecting agent, such as methotrexate (e.g., if the DHFR gene is on the plasmid). Typically, this procedure will cause the copy number of the plasmid containing the amplifiable, selectable marker in the cell to increase.

The term "host cell" includes any cell of any organism that is selected, modified, transfected, transformed, grown, or used or manipulated in any way, for the production of a substance by the cell, for example the expression or replication, by the cell, of a gene, a DNA or RNA or a protein. For example, a host cell may be a bacteria such as *E. coli* or an eukaryotic cell such as a CHO cell.

A "cassette" or an "expression cassette" refers to a DNA coding sequence or segment of DNA that codes for an expression product (e.g., peptide or RNA) that can be inserted into a vector at defined restriction sites. The DNA coding sequence can be operably linked to a promoter and/or to a terminator and/or polyA signal.

The sequence of a nucleic acid may be determined by any method known in the art (e.g., chemical sequencing or enzymatic sequencing). "Chemical sequencing" of DNA includes methods such as that of Maxam and Gilbert (Proc. Natl. Acad. Sci. USA (1977) 74:560), in which DNA is randomly cleaved using individual base-specific reactions. "Enzymatic sequencing" of DNA includes methods such as that of Sanger (Sanger, et al., Proc. Natl. Acad. Sci. USA (1977) 74:5463).

The present invention includes nucleic acids of the invention flanked by natural regulatory (expression control) sequences, which may be associated with heterologous sequences, including promoters, internal ribosome entry sites (IRES) and other ribosome binding site sequences, enhancers, response elements, suppressors, signal sequences, polyadenylation sequences, introns, 5'- and 3'-non-coding regions, and the like.

"Internal ribosome entry sites" "IRES" are commonly known in the art. Internal ribosome entry sites have been identified in a several genes including eIF4G (Johannes et al., RNA 4: 1500-1513 (1998)), DAPS (Henis-Korenblit et al., Molecular and Cellular Biology 20: 496-506 (2000)), c-Myc (Stoneley et al., Molecular and Cellular Biology 20: 1162-1169 (2000)), NF-κ-b repressing factor (Oumard et al., Molecular and Cellular Biology 20: 2755-2759 (2000)), VEGF (Huez et al., Molecular and Cellular Biology 18: 6178-6190 (1998)), FGF-2 (Creancier et al., Journal of Cell Biology 150: 275-281 (2000)), PDGF-B (Bernstein et al., Journal of Biological Chemistry 272: 9356-9362 (1997)), X-linked inhibitor of apoptosis (XIAP) (Holcik et al., Oncogene 19: 4174-4177 (2000)), Apaf-1 (Coldwell et al., Oncogene 19: 899-905 (2000)) and BiP (Macejak et al., Nature 353: 90-94 (1991)).

In general, a "promoter" or "promoter sequence" is a DNA regulatory region capable of binding an RNA polymerase in a cell (e.g., directly or through other promoter-bound proteins or substances) and initiating transcription of a coding sequence. A promoter sequence is, in general, bounded at its 3' terminus by the transcription initiation site and extends upstream (5' direction) to include the minimum number of bases or elements necessary to initiate transcription at any level. Within the promoter sequence may be found a transcription initiation site (conveniently defined, for example, by mapping with nuclease S1), as well as protein binding domains (consensus sequences) responsible for the binding of RNA polymerase. The promoter may be operably associated with other expression control sequences, including enhancer and repressor sequences or with a nucleic acid of the invention.

A coding sequence is "under the control of", "functionally associated with", "operably linked to" or "operably associated with" transcriptional and translational control sequences in a cell when the sequences direct or regulate expression of the sequence. For example, a promoter operably linked to a gene will direct RNA polymerase mediated transcription of the coding sequence into RNA, preferably mRNA, which then may be RNA spliced (if it contains introns) and, optionally, translated into a protein encoded by the coding sequence. A terminator/polyA signal operably linked to a gene terminates transcription of the gene into RNA and directs addition of a poly A signal onto the RNA.

The terms "express" and "expression" mean allowing or causing the information in a gene, RNA or DNA sequence to become manifest; for example, producing a protein by activating the cellular functions involved in transcription and translation of a corresponding gene. "Express" and "expression" include transcription of DNA to RNA and RNA to protein. A DNA sequence is expressed in or by a cell to form an "expression product" such as an RNA (e.g., mRNA) or a protein. The expression product itself may also be said to be "expressed" by the cell.

The term "transformation" means the introduction of a nucleic acid into a cell. The introduced gene or sequence may be called a "clone". A host cell that receives the introduced DNA or RNA has been "transformed" and is a "transformant" or a "clone." The DNA or RNA introduced to a host cell can come from any source, including cells of the same genus or species as the host cell, or from cells of a different genus or species. Examples of transformation methods which are very well known in the art include liposome delivery, electroporation, $CaPO_4$ transformation, DEAE-Dextran transformation, microinjection and viral infection.

The present invention includes vectors which comprise polynucleotides of the invention. The term "vector" may refer to a vehicle (e.g., a plasmid) by which a DNA or RNA sequence can be introduced into a host cell, so as to transform the host and, optionally, promote expression and/or replication of the introduced sequence.

The polynucleotides of the invention may be expressed in an expression system. The term "expression system" means a host cell and compatible vector which, under suitable conditions, can express a protein or nucleic acid which is carried by the vector and introduced to the host cell. Common expression systems include *E. coli* host cells and plasmid vectors, insect host cells and baculovirus vectors, and mammalian host cells and vectors such as plasmids, cosmids, BACs, YACs and viruses such as adenovirus and adenovirus associated virus (AAV).

Plasmids

In one embodiment, the present invention comprises a kit comprising a first universal transfer vector comprising a multiple cloning site, a replication origin, and a selectable marker; a second universal transfer vector comprising a multiple cloning site, a replication origin, and a selectable marker and an amplifiable vector comprising a multiple cloning site, a promoter, a replication origin or a chromosomal integration site, a poly-adenylation site and an amplifiable selectable marker. Generally, the multiple cloning sites comprise about 20, 25 or 30 restriction sites.

Plasmids of the present invention may include any of several amplifiable markers known in the art. Use of amplifiable markers is discussed in Maniatis, *Molecular Biology: A Laboratory Manual*, Cold Spring Harbor Laboratory, NY (1989)). Useful selectable markers for gene amplification in drug-resistant mammalian cells include DHFR (MTX (methotrexate) resistance) (Alt et al., J. Biol. Chem. 253:1357 (1978); Wigler et al., Proc. Natl. Acad. Sci. USA 77:3567 (1980)); metallothionein (cadmium resistance) (Beach et al., Proc Natl. Acad. Sci. USA 78:210 (1981)); CAD (N-(phosphonoacetyl)-I-aspartate (PALA) resistance) (Wahl et al., J. Biol. Chem. 254: 8679 (1979)); adenylate deaminase (coformycin resistance) (Debatisse et al., Mol. Cell. Biol. 6:1776 (1986)); IMP 5'-dehydrogenase (mycophenolic acid resistance) (Huberman et al., Proc. Natl. Acad. Sci. USA 78:3151 (1981)) and other markers known in the art (as reviewed, for example, in Kaufman et al., Meth. Enzymology 185:537-566 (1988)).

In one embodiment, the metallothionein II A gene under the control of a metallothionein promoter is an amplifiable marker in cell lines such as CHO-K1. Amplification can be induced by addition of $Cd^{2+}$ or $Zn^{2+}$ to the cell culture.

Plasmids of the invention may include other eukaryotic, non-amplifiable selectable markers known in the art. In an embodiment of the invention, the drug-resistance marker is the hygromycin B gene which confers resistance to hygromycin. Other markers include the G418 resistance gene. The plasmids of the invention may also include a prokaryotic antibiotic resistance marker such as the ampicillin resistance gene or the kanamycin resistance gene.

Plasmids of the invention may also include a matrix attachment region (MAR). Generally, MARs are DNA sequences capable of specific binding to nuclear proteins that are part of a fibrillar nuclear matrix analogous to the cytoskeleton. In one embodiment, the MAR is the chicken lysozyme MAR.

Promoters which may be used to control gene expression include, but are not limited to, SRα promoter (Takebe et al., Molec. and Cell. Bio. 8:466-472 (1988)), the human CMV immediate early promoter (Boshart et al., Cell 41:521-530 (1985); Foecking et al., Gene 45:101-105 (1986)), the mouse CMV immediate early promoter, the SV40 early promoter region (Benoist, et al., Nature 290:304-310 (1981)), the Orgyia pseudotsugata immediate early promoter, the herpes thymidine kinase promoter (Wagner, et al., Proc. Natl. Acad. Sci. USA 78:1441-1445 (1981)), the regulatory sequences of the metallothionein gene (Brinster, et al., Nature 296:39-42 (1982)); prokaryotic expression vectors such as the β-lactamase promoter (Villa-Komaroff, et al., Proc. Natl. Acad. Sci. USA 75:3727-3731 (1978)), or the tac promoter (DeBoer, et al., Proc. Natl. Acad. Sci. USA 80:21-25 (1983)); and promoter elements from yeast or other fungi such as the GAL1, GAL4 or GAL10 promoter, the ADH (alcohol dehydrogenase) promoter, PGK (phosphoglycerol kinase) promoter or the alkaline phosphatase promoter.

Viral long terminal repeat promoters such as the mouse mammary tumor virus long terminal repeat (MMTV-LTR) (Fasel et al., EMBO J. 1 (1):3-7 (1982)), the moloney murine sarcoma virus long terminal repeat (Reddy et al., Proc. Natl. Acad. Sci. USA 77(9): 5234-5238 (1980)), the moloney murine leukemia virus long terminal repeat (Van Beveren et al., Proc. Natl. Acad. Sci. USA 77(6): 3307-3311 (1980)), the HIV LTR (Genbank Accession No. AB100245), the bovine foamy virus LTR (Genbank Accession No. NC_001831), RSV 5'-LTR (Genbank Accession No. K00087), the HIV-2 LTR (Genbank Accession No. NC_001722), an avian retroviral LTR (Ju et al., Cell 22: 379-386 (1980)) and the human herpesvirus LTR (Genbank Accession No. NC_001806) may be included in the plasmids of the present invention.

Other acceptable promoters include the human CMV promoter, the human CMV5 promoter, the murine CMV promoter, the EF1α promoter, the SV40 promoter, a hybrid CMV promoter for liver specific expression (e.g., made by conjugating CMV immediate early promoter with the transcriptional promoter elements of either human al-antitrypsin (HAT) or albumin (HAL) promoter), or promoters for hepatoma specific expression (e.g., wherein the transcriptional promoter elements of either human albumin (HAL; about 1000 bp) or human α1-antitrypsin (HAT, about 2000 bp) are combined with a 145 bp long enhancer element of human α1-microglobulin and bikunin precursor gene (AMBP); HAL-AMBP and HAT-AMBP).

In addition, bacterial promoters, such as the T7 RNA Polymerase promoter or the tac promoter, may be used to control expression.

A promoter (e.g., SRα promoter) may be linked to the cassette and then moved into a transfer vector (e.g., pULLS or pUHLS). In another embodiment, the transfer vector can contain a promoter upstream of the multiple cloning site (e.g., pULSRstopLS or pUHSRstopLS). When a gene, not linked to a promoter, is inserted into the multiple cloning site, it will be operably linked to the upstream promoter.

In yet another embodiment of the invention, a gene in a transfer vector, not linked to a promoter, can be moved into the amplifiable vector comprising a promoter (e.g., SRα promoter) upstream of the multiple cloning site (e.g., pSRXBLS). When the unlinked gene is placed in the multiple cloning site, it will become operably linked to the promoter.

Plasmids of the invention may also include a polyadenylation signal/terminator for termination of the transcription of a gene in the plasmid and for the addition of a polyA tail to the transcript. For example, the chicken β-globin terminator/polyA signal may be included in a plasmid of the invention. Other acceptable poly A signals include the SV40 Poly A signal and the bovine growth hormone poly A signal.

In one embodiment of the invention, the amplifiable vector comprises a multiple cloning site including the following restriction sites: Sgr AI, Srf I, Xma I, Spe I, Sac II, Rsr II, Pac I, Nru I, Not I, Nde I, Msc I, Mlu I, Kpn I, Fse 1, Bss HII, Bsr GI, Bsp EI, Bcl I, Bbv C1, Pme I, Bss HII, Asc I, Xba I; for example, wherein the amplifiable vector multiple cloning site is that of pXBLS:

```
                                              (SEQ ID NO: 10)
  AscI                              BclI        BsrGI
~~~~~~~~~                          ~~~~~~      ~~~~~~
                   PmeI
                 ~~~~~~~~~
  XbaI   BssHII           BbvC1           BspEI
 ~~~~~~  ~~~~~~          ~~~~~~~~        ~~~~~~~
```

```
                                             Fsel             MluI            NdeI            NruI
                                          ~~~~~~~~~         ~~~~~~          ~~~~~~          ~~~~
          BssHII            KpnI            MscI                NotI
          ~~~~~~          ~~~~~~~         ~~~~~~~           ~~~~~~~~~
   51 GCGCGCGGCC GGCCGGTACC ACGCGTTGGC CACATATGGC GGCCGCTCGC
      CGCGCGCCGG CCGGCCATGG TGCGCAACCG GTGTATACCG CCGGCGAGCG

          PacI              SacII           Srf1             XhoI
          ~~~~~~~~~        ~~~~~~~        ~~~~~~~~~        ~~~~~
          NruI      RsrII         SpeI       XmaI    SgrAI
          ~~       ~~~~~~~       ~~~~~~    ~~~~~~  ~~~~~~~~~
  101 GATTAATTAA CGGACCGCCG CGGACTAGTG CCCGGGCCAC CGGTGCTCGA
      CTAATTAATT GCCTGGCGGC GCCTGATCAC GGGCCCGGTG GCCACGAGCT

          XhoI
          ~
  151 GAAAA
      CTTTT.
```

In an embodiment of the invention, a universal transfer vector comprises a multiple cloning site including the following restriction sites: Bss HII, Pme I, Sna B1, Hin dIII, Asp 718, Kpn I, Pae R71, Xho I, Sal I, Acc I, Hinc II, Cla I, Eco RV, Eco RI, Pst I, Eco O109I, Eco O109I, Apa I, Xma I, Bsp EI, Bam H1, Dsa I, Eag I, Ecl XI, Not I, Sac II, Xma III, Xba I, Sac I, Mlu I, Bcl I, Bsr GI, Bss HII; for example, wherein the transfer vector multiple cloning site is that of pUHLS:

```
                                                           (SEQ ID NO: 11)
                     AscI                           HindIII         PaeR7I
                 ~~~~~~~~~                          ~~~~~~          ~~~~~~
                             PmeI         SnaBI            KpnI
                           ~~~~~~~~      ~~~~~~          ~~~~~~~
         XmaI                                                      XhoI
         ~~~                                                      ~~~~~
              BssHII           BbvCl              Asp718
              ~~~~~~          ~~~~~~~~           ~~~~~~~
     1 GGGGGCGCGC CGTTTAAACC CTCAGCTACG TAAAGCTTGG TACCCTCGAG
       CCCCCGCGCG GCAAATTTGG GAGTCGATGC ATTTCGAACC ATGGGAGCTC

                                 ClaI                              BspEI
                                ~~~~~~                            ~~~~~~
             HincII    EcoRV       PstI
             ~~~~~~   ~~~~~~     ~~~~~~~
             SalI                             XmaI
            ~~~~~~                           ~~~~~~~
             AccI         EcoRI       ApaI             BamHI
            ~~~~~~      ~~~~~~~     ~~~~~~             ~~
    51 GTCGACATCG ATGATATCGA ATTCCTGCAG GGGCCCCCCG GGTCCGGAGG
       CAGCTGTAGC TACTATAGCT TAAGGACGTC CCCGGGGGGC CCAGGCCTCC

                    NotI               MluI          BsrGI
                ~~~~~~~~~             ~~~~~~        ~~~~~~
                              SacI
                             ~~~~~~
         BamHI        XbaI               BclI           FseI
         ~~~~        ~~~~~~            ~~~~~~         ~~~~~~~~
   101 ATCCGCGGCC GCTCTAGAGA GCTCACGCGT TGATCATGTA CAGGCCGGCC
       TAGGCGCCGG CGAGATCTCT CGAGTGCGCA ACTAGTACAT GTCCGGCCGG

                                XmaI
                                ~~~
                             BssHII
                             ~~~~~~
   151 AGCGCGCCCC
       TCGCGCGGGG.
```

A universal transfer vector may comprise a multiple cloning site including the following restriction sites: Bss HII, Sgr AI, Xma I, Rsr II, Spe I, Sna B1, Hin dIII, Asp 718, Kpn I, Pae R71, Xho I, Sal I, Acc I, Hinc II, Cla I, Eco RV, Eco RI, Pst I, Eco O109I, Eco O109I, Apa I, Bsp EI, Barn H1, Dsa I, Eag I, Ecl XI, Not I, Sac II, Xma III, Xba I, Sac I, Nde I, Msc I, Nru I, Pac I, Bss HII; for example, wherein the transfer vector multiple cloning site is that of pULLS:

```
                                                       (SEQ ID NO: 12)
                SgrAI                               SnaBI
               ~~~~~~~~                             ~~~~~~~
      XmaI                 Srf1             SpeI
      ~~~                ~~~~~~~~~         ~~~~~~
         BssHII            XmaI    RsrII                HindIII
         ~~~~~~~         ~~~~~~~ ~~~~~~~~               ~~~~~
    1 GGGGGCGCGC CACCGGTGGC CCGGGCCGGT CCGACTAGTT ACGTAAAGCT
      CCCCCGCGCG GTGGCCACCG GGCCCGGCCA GGCTGATCAA TGCATTTCGA

            PaeR7I         ClaI                            BspEI
            ~~~~~~~      ~~~~~~~                           ~
       KpnI         HincII       EcoRV         PstI
      ~~~~~~        ~~~~~~      ~~~~~~~      ~~~~~~~
                     SalI
                    ~~~~~~
             XhoI
            ~~~~~~~
      HindIII        AccI               EcoRI        ApaI
      ~             ~~~~~~             ~~~~~~      ~~~~~~
   51 TGGTACCCTC GAGGTCGACA TCGATGATAT CGAATTCCTG CAGGGGCCCT
      ACCATGGGAG CTCCAGCTGT AGCTACTATA GCTTAAGGAC GTCCCCGGGA

      BspEI         NotI                NdeI         NruI
      ~~~~~       ~~~~~~~~             ~~~~~~       ~~~~~~
                                 SacI
                                ~~~~~~~
          BamHI            XbaI                MscI          PacI
          ~~~~~~~        ~~~~~~~             ~~~~~~~         ~
  101 CCGGAGGATC CGCGGCCGCT CTAGAGAGCT CCATATGTGG CCATCGCGAT
      GGCCTCCTAG GCGCCGGCGA GATCTCTCGA GGTATACACC GGTAGCGCTA

       PacI          XmaI
      ~~~~~~~        ~~~
            BssHII
            ~~~~~~~
  151 TAATTAAGCG CGCCCC
      ATTAATTCGC GCGGGG.
```

The present invention contemplates amplifiable vectors or universal transfer vectors comprising the above-referenced multiple cloning sites in the orientation shown or in the opposite orientation.

The plasmids of the present invention can be introduced into any cell line for expression of the target polypeptides. In one embodiment of the invention, the plasmids are introduced into a mammalian cell line, preferably a Chinese hamster ovary (CHO) cell line. A commonly used cell line is DHFR-CHO cell line which can be transformed to the DHFR$^+$ phenotype using DHFR cDNA as an amplifiable dominant marker. One such known DHFR-CHO cell line is DX-B11 or DG-44. In another embodiment, the plasmids of the invention can be introduced into a lower eukaryotic cell line, such as from *S. cerevisiae, K. lactis, P. pastoris, C. albicans* or *A. fumigatus*. Further, the plasmids of the invention may also be introduced into higher eukaryotic non-mammalian cell lines such as from insect cells (e.g., *Drosophila melanogaster*, sf9 cells, sf21 cells), amphibian cells (e.g., *X. laevis*), plant cells (e.g., *A. thaliana*) and avian cells.

Plasmids of the invention can also be introduced into a bacterial cell. In one embodiment, competent *E. coli* are transformed. Examples of suitable *E. coli* include DH1, DH5, DH5α, XL1-Blue, SURE, SCS110, OneShot Top 10, and HB101.

Plasmids may be introduced into a cell by any of the many methods which are commonly known in the art. For example, a plasmid of the invention can be used to transform a cell by the calcium phosphate method, electroporation, the DEAE-dextran method or the liposome method.

The plasmids of the invention can include any gene or combination of genes. In an embodiment of the invention the plasmids include heavy and light chain immunoglobulin genes. The immunoglobulin chains may be part of antibodies which specifically recognize any antigen such as IL-5, IGFR1 or IL-10. Receptors or receptor subunits may also be expressed. For example, a gene encoding the IL-2 receptor or a portion thereof (e.g., membrane domain) can be included in a plasmid of the invention.

U.S. patent application Ser. No. 10/443,466; filed May 22, 2003, which is herein incorporated by reference in its entirety, sets forth the nucleotide and amino acid sequences of immunoglobulin light chain and heavy chain variable regions of anti-IGFR1 antibodies. Any of the light and heavy chain variable regions disclosed therein can be incorporated into the plasmid system of the invention and expressed. In one embodiment, the anti-IGFR1 antibody light chain variable region is encoded by the nucleotide sequence set forth in SEQ ID NO: 15 or 19 or is any polynucleotide encoding a polypeptide comprising the amino acid sequence of SEQ ID NO: 16 or 20 and/or the anti-IGFR1 antibody heavy chain variable region is encoded by the nucleotide sequence set forth in SEQ ID NO: 17 or 21 or is any polynucleotide encoding a polypeptide comprising the amino acid sequence of SEQ ID NO: 18 or 22.

Expression cassettes encoding the immunoglobulin heavy and light chain of the anti-IGFR1 antibody can each be introduced into the multiple cloning site of either pULLS or pUHLS. Preferably, the immunoglobulin heavy and light chains, in the expression cassettes, are linked to an immunoglobulin constant region such as γ1, γ4 or κ. Preferably, the expression cassettes are then inserted into the amplifiable vector pXBLS which is then introduced into a cell suitable for causing the expression of the light and heavy chains. For example, the plasmid, pAIGFRV3, which contains the immunoglobulin heavy and light chains of an anti-IGFR1 antibody, can be introduced into a $dhfr^-$ mammalian cell line (e.g., CHO-DXB11) wherein the chains are expressed.

Kits

The plasmid system of the invention may be provided in a kit. The kits of the invention may include, in addition to the plasmid system, any reagent which may be employed in the use of the plasmid system. In one embodiment, the kit includes reagents necessary for transformation of the plasmids into mammalian cells. For example, the kit may include reagents for a calcium phosphate transformation procedure: calcium chloride, buffer (e.g., 2×HEPES buffered saline), and sterile, distilled water. In another embodiment, the kit includes reagents for a DEAE-Dextran transformation: Chloroquine in PBS, DEAE-dextran in PBS and Phosphate buffered saline. In yet another embodiment, reagents for a liposome transformation are included in the kit: Liposomes extruded from DOTAP/cholesterol extruded liposomes. For example, the kit may include the cationic lipid-based transfection reagent Lipofectamine™ (Invitrogen Life Technologies; Carlsbad, Calif.).

The kit may include reagents required for bacterial transformation of the plasmids of the invention. For example, the kit may include transformation competent bacteria (e.g., DH1, DH5, DH5α, XL1-Blue, SURE, SCS110, OneShot Top 10, or HB101).

The kit may include growth media or reagents required for making growth media. For example, in one embodiment, the kit can include fetal calf serum or DMEM (Dulbecco/Vogt modified Eagle's (Harry Eagle) minimal essential medium) for growth of mammalian cells. In another embodiment, the kit can contain powdered luria broth media or luria broth plates containing an appropriate antibiotic (e.g., ampicillin or kanamycin) for growing bacteria.

Components supplied in the kit may be provided in appropriate vials or containers (e.g., plastic or glass vials). The kit can include appropriate label directions for storage, and appropriate instructions for usage.

Protein Expression and Purification

Polypeptides produced in the plasmid system of the invention can be purified by standard methods, including, but not limited to, salt or alcohol precipitation, affinity chromatography (e.g., used in conjunction with a purification tag), preparative disc-gel electrophoresis, isoelectric focusing, high pressure liquid chromatography (HPLC), reversed-phase HPLC, gel filtration, cation and anion exchange and partition chromatography, and countercurrent distribution. Such purification methods are well known in the art and are disclosed, e.g., in *"Guide to Protein Purification", Methods in Enzymology*, Vol. 182, M. Deutscher, Ed., 1990, Academic Press, New York, N.Y.

Particularly where a polypeptide is being isolated from a cellular or tissue source, it is preferable to include one or more inhibitors of proteolytic enzymes in the assay system, such as phenylmethanesulfonyl fluoride (PMSF), Pefabloc SC, pepstatin, leupeptin, chymostatin and EDTA.

Polypeptides of the invention may be fused with a second polypeptide or polynucleotide moiety, which may be referred to as a "tag". A tag may be used, for example, to facilitate purification or detection of the polypeptide after expression. A fused polypeptide may be constructed, for example, by in-frame insertion of a polynucleotide encoding the tag on the 5' or 3' end of the polynucleotide encoding the polypeptide to be expressed. The fused polynucleotide may then be expressed in the plasmid system of the invention. Such tags include glutathione-S-transferase (GST), hexahistidine (His6) tags, maltose binding protein (MBP) tags, haemagglutinin (HA) tags, cellulose binding protein (CBP) tags and myc tags. Detectable tags such as $^{32}P$, $^{35}S$, $^{3}H$, $^{99m}Tc$, $^{123}I$, $^{111}In$, $^{68}Ga$, $^{18}F$, $^{125}I$, $^{131}I$, $^{113m}In$, $^{76}Br$, $^{67}Ga$, $^{99m}Tc$, $^{123}I$, $^{111}In$ and $^{68}Ga$ may also be used to label the polypeptides and polynucleotides of the invention. Methods for constructing and using such fusions are very conventional and well known in the art.

EXAMPLES

The following examples are provided to further describe the present invention and should not be construed as a limitation thereof. The scope of the present invention includes any and all plasmids set forth, below, in the following examples either individually or as part of a kit. Also included within the scope of the invention are any and all of the methods which are set forth below in the following examples.

Example 1

Construction of Amplifiable Cloning Vectors, pSRXBLS and pXBLS

This example describes the construction of the mammalian expression vectors, pSRXBLS and pXBLS. A large multicloning site was inserted in the plasmid pDSRG downstream of the SRα promoter, to generate pSRXBLS. pXBLS, a derivative of pSRXBLS, is devoid of any promoter. Both of the plasmids can serve as amplifiable vectors into which more than one expression cassette, e.g., for the heavy and light chain cDNAs of an antibody gene, can be easily inserted.

A multiple cloning site of 155 bp, pDSRG-xba-xho, was designed, synthesized by PCR and cloned initially in the TA Cloning Vector (Invitrogen; Carlsbad, Calif.). It was later cloned at the XhoI and XbaI sites of pDSRG, resulting in pSRXBLS. The SRα promoter was retained in the pSRXBLS vector.

pSRXBLS was further digested with XhoI and HindIII to remove the SRα promoter. The ends were then filled in by Klenow and religated, regenerating the HindIII site, to construct pXBLS.

Example 2

Construction of Universal Transfer Vectors pUHLS, pULLS and their Descendents This example describes the construction of universal transfer vectors, each having a large multiple cloning site, and their descendents, each carrying a promoter and a terminator/poly A addition site. pUHLS and pULLS are the universal transfer vectors, and pUHSRstopLS and pULSRstopLS are their corresponding descendents that carry the SRα promoter and the chicken β-globin terminator. The plasmid system is so constructed that different subunits of a large, complex protein can be expressed in these vectors separately. Later, the expression cassettes for each subunit can be transferred to a single vector, such as pXBLS or pSRXBLS, to facilitate transfection, integration and equimolar production of a multi-subunit protein.

Two multiple cloning sites, Universal Plasmid Primer 1 of 160 bp and Universal Plasmid Primer 2 of 166 bp, were designed to construct pUHLS and pULLS. Both of the cloning sites were synthesized by PCR, cloned in the TA Cloning Vector (Invitrogen) and later cloned at the BssHII sites of the pCRScript vector (Stratagene). Thus, the original multiple cloning site of pCRScript was replaced with newly synthesized multiple cloning sites. The new vectors, pUHLS and pULLS, were derived from the Universal Plasmid Primer 1 and Universal Plasmid Primer 2, respectively.

A 249 bp region of the chicken β-globin terminator, derived from pDSRG by digestion with BamHI and XbaI, was inserted in both pUHLS and pULLS at the BamHI and XbaI sites to generate pUHstopLS and pULstopLS, respectively. The SRα promoter and its accompanying intron, derived from pDSRG by digestion with HindIII and SalI, was inserted in pUHstopLS and pULstopLS at the HindIII and XhoI sites to generate pUHSRstopLS and pULSRstopLS, respectively.

Example 3

Construction of pAIL5V1

The construction of pAIL5V1 for the expression of heavy and light antibody chains in a single vector is described here. Aside from variations in their orientations, two types of plasmids have been constructed. The first carries only the dhfr marker for selection with amplification. The second type of expression plasmid carries the dhfr marker, along with the gene for hygromycin resistance (Hyg). This adds versatility, allowing selection with or without amplification.

The heavy chain gene of the anti-huIL5 human monoclonal antibody, (MAb) was isolated and inserted in the pUHSRstopLS vector (supra) at the EcoRI and XmaI sites to generate pUSRHLS. The light chain gene of the anti-huIL5 MAb was isolated and inserted in pULSRstopLS at the EcoRI and ApaI sites to generate pUSRLLS.

The hCMV minimal promoter, derived from pcDNA3.1 (Invitrogen; Carlsbad, Calif.) by digestion with NruI and EcoRI, replaced the SRα promoter, which was removed by digestion with SnaBI and EcoRI, in pUSRHLS and pUSRLLS to generate pUhCMVHLS and pUhCMVLLS. The TK-hygromycin gene (TK/Hyg) was inserted in pUhCMVHLS at the FseI sites to construct pUHhyg(+)hCMVLS and pUHhyg(−)hCMVLS. The light chain antibody cassette was transferred from pUhCMVLLS, by digestion with PacI and SrfI, to pXBLS at the PacI and SrfI sites to construct pAIL5L(−)hCMVLS and pAIL5L(+)hCMVLS. The heavy chain antibody cassette was transferred from pUHhyg(−)hCMVLS to pAIL5L(−)hCMVLS at the BssHII sites to generate pAIL5V1.

Example 4

Construction of pAIGFRV3 cDNAs encoding the variable regions from a hybridoma expressing an anti-IGFR1 monoclonal antibody 19D12/15H12 were isolated and cloned in TA cloning vectors (Invitrogen; Carlsbad, Calif.). The light and heavy chain amino acid and nucleotide sequences of antibody 19D12/15H12 are set forth in U.S. patent application Ser. No. 10/443,466; filed May 22, 2003 which is herein incorporated by reference in its entirety. The heavy chain was transferred from the EcoRI and ApaI sites of the TA vector containing cDNA for heavy chain of variable region of anti-IGFR1 to the same sites of pUhCMVHLS (supra) to construct pUhCMVIGFRHLS containing cDNA for light chain of anti-IGFR1. For selection, a TK-hygromycin resistance cassette was inserted at the FseI site of pUhCMVIGFRHLS to construct pUhCMVHyg(−)IGFRHLS. The light chain was transferred from the EcoRI and BbsI sites of the TA plasmid to the same sites of pUhCMVLLS (supra) to construct pUhCMVIGFRLLS. The entire light chain expression cassette was then transferred from pUhCMVIGFRLLS to pXBLS at the PacI and SrfI sites to construct pAIGFRLLS. The heavy chain expression cassette, along with the hygromycin expression cassette, was transferred to pAIGFRLLS at the BssHII sites to construct pAIGFRV1 and pAIGFRV3 (pIAGFRVI is essentially identical to pAIGFRV3 except that the orientation of the heavy chain and the TK-Hyg genes are opposite).

Example 5

Construction of pAIL10V3 cDNAs encoding the variable regions of 12G8, a rat antibody which recognizes IL-10 were isolated. The heavy chain variable region of 12G8 was transferred to KpnI and ApaI site of pUhyg(−)IG1 FRhuH plasmid to construct pUILL10H. The pUhyg(−)IG1FrhuH plasmid carries the modified cDNA for variable region of IGFR1 along with IgG1 cDNA and TK-Hygromycin cassette. The light chain variable region of 12G8 was transferred to the EcoRI and ApaI sites of pAIL5(−)hCMVLS to construct pAIL10(−)L. The heavy chain expression cassette from the pUIL10H was transferred to pAIL10(−)L at BssHll restriction sites to construct pAIL10V3.

Example 6

Construction of pAIG1FR(−)IL2LS pAIG1 FR(−)IL2LS was constructed in a three step process. The construction process started with transfer of an IRES-IL2Rα element to pULstopLS. The plasmid containing the IRES-IL2Rα, pme18IRES, was digested with SpeI and NotI restriction enzymes and the NotI site was completely filled in using Klenow enzyme to derive the IRES-IL2Rα element. Simultaneously, pULstopLS was digested with EcoRV and SpeI enzymes and the SpeI site was filled in, using the Klenow enzyme, and ligated with the IRES-IL2Rα element to construct pULstopIRESIL2R. pULstopIRESIL2R was further digested with SpeI and XbaI enzyme and SpeI site was completely filled in with Klenow enzyme. Also pUhCMVIGFRLLS was digested with XbaI and BspEI enzymes and the BspEI site was completely filled in using Klenow enzyme and ligated with the XbaI-SpeI fragment that was generated from pULstopIRESIL2R to construct pUIGFRLIRESIL2R. The heavy chain expression cassette of IGFR1 was transferred from pUhyg(−)IG1FRhuH to pUIGFRLIRESIL2R at BssHII restriction sites to construct pAIG1FR(−)IL2LS.

Example 7

Development of Cell Lines for Expressing Anti-IGFR1 Monoclonal Antibody 19D12

In this example, the development and growth of cell lines for expressing the 19D12 antibody (LCF/HCA) are presented.

DXB11 Cell Culture. Cells were grown in MEM Alpha Medium with ribonucleosides and deoxyribonucleosides (GIBCO Cat. #12571-063; Gibco-Invitrogen Corp; Carlsbad, Calif.) plus 10% FBS (HyClone Cat. # SH30071.03; Hyclone; Logan, Utah).

Hygromycin selection media. Cells were split at 48 hours post-transfection. Cells were grown in MEM Alpha Medium without ribonucleosides and deoxyribonucleosides (GIBCO Cat. #12561-056) plus 10% Dialyzed FBS (HyClone Cat. # SH30079.03) plus Hygromycin B (CLONTECH Cat. #8057-1; BD Biosciences-Clontech; Palo Alto, Calif.) at 300 μg/mL.

Subcloning media. Subcloning was performed in MEM Alpha Medium without ribonucleosides and deoxyribonucleosides (GIBCO Cat. #12561-056) plus 10% Dialyzed FBS (HyClone Cat. # SH30079.03).

Methotrexate (MTX) amplification media. Methotrexate amplification was carried out in MEM Alpha Medium without ribonucleosides and deoxyribonucleosides (GIBCO Cat. #12561-056) plus 10% Dialyzed FBS (HyClone Cat. # SH30079.03) plus MTX (Sigma Cat. # M8407; Sigma-Aldrich Corp; St. Louis, Mo.) at 20, 80 and 320 nM, respectively.

Media for adaptation to serum free suspension. Adaptation to serum free suspension was performed in CHO Protein-Free Medium (Sigma Cat. # C5467) supplemented with 20 ml/L L-Glutamine-200 mM (GIBCO Cat. #25030-081) and 10 ml/L Lipids (Cholesterol rich) (Sigma Cat. # L4646).

Feed medium for 3 L production batch. L-Glutamine-200 mM (GIBCO Cat. #25030-081) and Glucose Solution (Sigma Cat. # G8769) were served as the feed during production runs.

Transfection and Subcloning method. DXB11 cells were trypsinized, counted and plated @$2\times10^6$ cells/T25 flask on the day before transfection, so that they became 50-90% confluent on the day of transfection. Transfections were performed using 2.5 μg DNA (pAIGFRV3)/T25 flask and LipofectAMINE PLUS™ reagent (GIBCO, cat. #10964-013). As per the vendor's instructions, the DNA was first complexed with PLUS reagent, the DNA-PLUS complex was mixed with LipofectAMINE reagent and the DNA-PLUS-LipofectAMINE complex was then used to transfect the cells. The cells were incubated at 37° C. at 5% $CO_2$ for 3 hours. Following incubation, DXB11 cell culture medium was added to the desired volume, the cells and medium were transferred to a T75 flask, and the cells were grown for 2 days. The medium was exchanged with hygromycin selection medium, and the cells were grown for 10 days to 2 weeks. Some cells were banked at this stage, and the remaining cells were subcloned in 96 well plates.

Subcloning was initiated in 96 well plates with subcloning media. Single clones were successively grown in 24 well plates, 6 well plates, T-25 flasks and T-75 flasks, following detection of satisfactory expression by ELISA at each stage. Methotrexate media was added on 20-30% confluent cultures for amplification. Amplification was carried out at 20, 40, 80, and 320 nM methotrexate for 10 days to 2 weeks. Following amplification, the media was exchanged with the subcloning media and the cells were allowed to grow to ~10% confluence. The cells were subjected to another round of subcloning at this stage. Following the second round of subcloning, the cells were subjected to adaptation to serum free suspension culture with the designated media at the T-25 flask stage. Serum was sequentially eliminated from the media by dilution with serum free adaptation medium, and the cells were finally transferred to shake flasks with 2.5% serum. The remaining serum was eliminated by subsequent dilution (splitting) of the cultures. The serum free culture was scaled to 3 liters.

Example 8

Propagation of Cells Expressing Anti-IL5 Antibody

Cells carrying pAIL5V1 from a frozen vial are thawed and propagated in suspension using Sigma CHO protein-free medium (C-5467 supplemented with 0.57 g/L L-glutamine). All cultures are maintained in a 37° C., 7.5% $CO_2$ incubator or on a rocker bag platform set at 37° C. and supplying 7.5% $CO_2$. The inoculum train begins in a shake flask and is continuously passaged and scaled-up until there is enough culture to start a 20-Liter bag with a 2-liter working volume. When the bag reaches the predetermined split criteria, it is scaled up to a 10-liter working volume. When the bag reaches the predetermined split criteria, it is split and the remaining culture will be used to start another 20-liter rocker bag (10-liter working volume) in parallel. When the two rocker bags reach the appropriate split density, they are used to seed the production bioreactor. Shake flasks and rocker bags are typically split at 1:4 dilutions when the viable cell density reaches $1\text{-}1.5\times10^6$ viable cells/mL. The inoculum pool is diluted 1:4 going into the bioreactor.

Flow diagram illustrating the propagation process:

Vial then

Thaw

SF-250V (C-5467 CHO media supplemented with L-glutamine)

then 20 ml, then to 60 ml (2 passages)

SF-1000V (C-5467 CHO media supplemented with L-glutamine) 250 ml (1 passage), then create another SF-1000V with a 250 ml working volume.

then 20-liter rocker bag (C-5467 CHO media supplemented with L-glutamine)

2 L (1 passage), then to 10 L (1 passage), then create another 20-liter bag with 10 L working volume.

then

Production Bioreactor at quarter volume (C-5467 CHO media supplemented with 20 L-glutamine)

60 L (1 passage), then to full volume (200 L)

Example 9

Process for Purifying Anti-IL10 Antibody

This example describes the process for purifying the anti-IL10 antibody encoded by pAIL10V3 from a 200 liter CHO cell fermentation. The steps include:

- Harvesting of cell culture supernatant by filtration with a positively charged CUNO filter in series with a 0.2 μm filter.
- Affinity chromatography on Amersham rProtein-A Sepharose™ Fast Flow (4 L) eluted by a pH 3.0 step.
- Viral Inactivation by incubation at pH 3.5 for 1 hour at 20-22° C., followed by pH adjustment to 5.5.
- Cation exchange chromatography on EMD Fractogel® SE HiCap (4 L) at pH 5.5 eluted with a 20 BV gradient to 250 mM NaCl.
- Concentration (2×)/Diafiltration (10×) into 20 mM Tris, pH 8.0.
- Anion exchange chromatography on Amersham Q Sepharose™ Fast Flow (4 L) in flow-through mode. The unretained peak is pooled and adjusted to pH 5.5.
- Viral Filtration with Planova filters: one 0.1 $m^2$ Planova 35 in series with 2-4 0.1 $m^2$ Planova 20 filters.

Final concentration (6-10×) and diafiltration (10×) into 20 mM sodium acetate followed by filtration (0.2 μm).

This process yields material that is >99% pure by RP-HPLC. Overall yield is 70%.

Example 10

Expression of Anti-IGFR1 and Anti-IL-10 Antibody

In this example, expression plasmids including the anti-IGFR and anti-IL-10 antibody chains were constructed wherein the antibody chain genes were situated, in the plasmids, adjacent to a MAR element (Selexis; Geneva, Switzerland; Kim et al., J. Biotechnol. 107(2): 95-105 (2004); Stief at al., Nature 341: 343-345 (1989); Phi-Van et al., Mol. Cell. Biol. 10: 2302-2307 (1990); Kalos et al., Mol. Cell. Biol. 15: 198-207 (1995)). The MAR element is a ~3 kb DNA element that aids the expression of a recombinant gene which is stably integrated in the host chromosome following incorporation into the cell.

The MAR element was inserted into the mammalian expression plasmids, pAIL10Vi, having anti-IL10 along with hygromycin expression cassette, pAIL10V1/puro, having anti-IL10 along with puromycin instead of hygromycin expression cassette, pAIGFRLCb2V1, having anti-IGFR1 along with hygromycin expression cassette, and pAIGFRLCb2V1/puro, having anti-IGFR1 along with puromycin instead of hygromycin expression cassette. Each plasmid already contained four independent mammalian expression cassettes.

The vector, pPAG01 contained the ~3 kb chicken lysozyme matrix attachment region (MAR) DNA element. One of the universal vectors, pULLS was digested by restriction enzymes, Age1 and BamH1 and was religated, following end filling by Klenow enzyme, to construct vector pULLSmod. The pPAG01 plasmid was digested by BamH1 and Xba1 to transfer the MAR element over to pULLSmod at the same sites to construct the plasmid pULMAR. The MAR element was finally transferred to the plasmids expressing anti-IL10 and anti-IGFR1. pULMAR was digested with BssHll and the fragment containing MAR element was transferred to the Asc1 sites of the plasmids pAIL10Vi, pAIL10V1/puro, pAIGFRLCb2V1 and pAIGFRLCb2V1/puro to construct pinAIL10/MAR(−), pAIL10V1/puro/MAR(−), pAIGFRLCb2/MAR(−) and pAIGFRLCb2/puro/MAR(−), respectively.

The MAR containing plasmids were introduced into the CHO cell line, DXB11 cells and the antibody chains were expressed. Expression of the antibody chains were confirmed by ELISA as well as HPLC analysis. In the HPLC analysis, the proteins isolated from the CHO cells was fractionated using a reverse-phase column or a protein-A column. Eluted protein was detected spectrophotometrically at $A_{280nm}$.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

Patents, patent applications, publications, product descriptions, and protocols are cited throughout this application, the disclosures of which are incorporated herein by reference in their entireties for all purposes.

SEQUENCE LISTING

<160> NUMBER OF SEQ ID NOS: 27

<210> SEQ ID NO 1
<211> LENGTH: 2941
<212> TYPE: DNA
<213> ORGANISM: Artificial sequence
<220> FEATURE:
<223> OTHER INFORMATION: pULLs plasmid

<400> SEQUENCE: 1

```
ctaaattgta agcgttaata ttttgttaaa attcgcgtta aatttttgtt aaatcagctc     60

atttttaac caataggccg aaatcggcaa aatcccttat aaatcaaaag aatagaccga     120

gatagggttg agtgttgttc cagtttggaa caagagtcca ctattaaaga acgtggactc    180

caacgtcaaa gggcgaaaaa ccgtctatca gggcgatggc ccactacgtg aaccatcacc    240

ctaatcaagt tttttggggt cgaggtgccg taaagcacta aatcggaacc ctaaagggag    300

cccccgattt agagcttgac ggggaaagcc ggcgaacgtg gcgagaaagg aagggaagaa    360

agcgaaagga gcgggcgcta gggcgctggc aagtgtagcg gtcacgctgc gcgtaaccac    420

cacacccgcc gcgcttaatg cgccgctaca gggcgcgtcc cattcgccat tcaggctgcg    480

caactgttgg gaagggcgat cggtgcgggc ctcttcgcta ttacgccagc tggcgaaagg    540

gggatgtgct gcaaggcgat taagttgggt aacgccaggg ttttcccagt cacgacgttg    600

taaaacgacg gccagtgagc gcgccaccgg tggcccgggc cggtccgact agttacgtaa    660

agcttggtac cctcgaggtc gacatcgatg atatcgaatt cctgcagggg ccctccggag    720

gatccgcggc cgctctagag agctccatat gtggccatcg cgattaatta agcgcgcttg    780
```

```
gcgtaatcat ggtcatagct gtttcctgtg tgaaattgtt atccgctcac aattccacac    840
aacatacgag ccggaagcat aaagtgtaaa gcctggggtg cctaatgagt gagctaactc    900
acattaattg cgttgcgctc actgcccgct ttccagtcgg gaaacctgtc gtgccagctg    960
cattaatgaa tcggccaacg cgcggggaga ggcggtttgc gtattgggcg ctcttccgct   1020
tcctcgctca ctgactcgct gcgctcggtc gttcggctgc ggcgagcggt atcagctcac   1080
tcaaaggcgg taatacggtt atccacagaa tcaggggata acgcaggaaa gaacatgtga   1140
gcaaaaggcc agcaaaaggc caggaaccgt aaaaaggccg cgttgctggc gtttttccat   1200
aggctccgcc cccctgacga gcatcacaaa aatcgacgct caagtcagag gtggcgaaac   1260
ccgacaggac tataaagata ccaggcgttt ccccctggaa gctccctcgt gcgctctcct   1320
gttccgaccc tgccgcttac cggatacctg tccgcctttc tcccttcggg aagcgtggcg   1380
ctttctcata gctcacgctg taggtatctc agttcggtgt aggtcgttcg ctccaagctg   1440
ggctgtgtgc acgaaccccc cgttcagccc gaccgctgcg ccttatccgg taactatcgt   1500
cttgagtcca acccggtaag acacgactta tcgccactgg cagcagccac tggtaacagg   1560
attagcagag cgaggtatgt aggcggtgct acagagttct tgaagtggtg gcctaactac   1620
ggctacacta gaaggacagt atttggtatc tgcgctctgc tgaagccagt taccttcgga   1680
aaaagagttg gtagctcttg atccggcaaa caaaccaccg ctggtagcgg tggttttttt   1740
gtttgcaagc agcagattac gcgcagaaaa aaaggatctc aagaagatcc tttgatcttt   1800
tctacggggt ctgacgctca gtggaacgaa aactcacgtt aagggatttt ggtcatgaga   1860
ttatcaaaaa ggatcttcac ctagatcctt ttaaattaaa aatgaagttt taaatcaatc   1920
taaagtatat atgagtaaac ttggtctgac agttaccaat gcttaatcag tgaggcacct   1980
atctcagcga tctgtctatt tcgttcatcc atagttgcct gactccccgt cgtgtagata   2040
actacgatac gggagggctt accatctggc cccagtgctg caatgatacc gcgagaccca   2100
cgctcaccgg ctccagattt atcagcaata aaccagccag ccggaagggc cgagcgcaga   2160
agtggtcctg caactttatc cgcctccatc cagtctatta attgttgccg ggaagctaga   2220
gtaagtagtt cgccagttaa tagtttgcgc aacgttgttg ccattgctac aggcatcgtg   2280
gtgtcacgct cgtcgtttgg tatggcttca ttcagctccg gttcccaacg atcaaggcga   2340
gttacatgat cccccatgtt gtgcaaaaaa gcggttagct ccttcggtcc tccgatcgtt   2400
gtcagaagta agttggccgc agtgttatca ctcatggtta tggcagcact gcataattct   2460
cttactgtca tgccatccgt aagatgcttt tctgtgactg gtgagtactc aaccaagtca   2520
ttctgagaat agtgtatgcg gcgaccgagt tgctcttgcc cggcgtcaat acgggataat   2580
accgcgccac atagcagaac tttaaaagtg ctcatcattg gaaaacgttc ttcggggcga   2640
aaactctcaa ggatcttacc gctgttgaga tccagttcga tgtaacccac tcgtgcaccc   2700
aactgatctt cagcatcttt tactttcacc agcgtttctg ggtgagcaaa aacaggaagg   2760
caaaatgccg caaaaaaggg aataagggcg acacggaaat gttgaatact catactcttc   2820
ctttttcaat attattgaag catttatcag ggttattgtc tcatgagcgg atacatattt   2880
gaatgtattt agaaaaataa acaaataggg gttccgcgca catttccccg aaaagtgcca   2940
c                                                                   2941
```

<210> SEQ ID NO 2
<211> LENGTH: 2935
<212> TYPE: DNA
<213> ORGANISM: Artificial sequence
<220> FEATURE:
<223> OTHER INFORMATION: pUHLS plasmid

<400> SEQUENCE: 2
ctaaattgta agcgttaata ttttgttaaa attcgcgtta aatttttgtt aaatcagctc 60
atttttaac caataggccg aaatcggcaa aatcccttat aaatcaaaag aatagaccga 120
gatagggttg agtgttgttc cagtttggaa caagagtcca ctattaaaga acgtggactc 180
caacgtcaaa gggcgaaaaa ccgtctatca gggcgatggc ccactacgtg aaccatcacc 240
ctaatcaagt tttttggggt cgaggtgccg taaagcacta aatcggaacc ctaaagggag 300
cccccgattt agagcttgac ggggaaagcc ggcgaacgtg gcgagaaagg aagggaagaa 360
agcgaaagga gcgggcgcta gggcgctggc aagtgtagcg gtcacgctgc gcgtaaccac 420
cacacccgcc gcgcttaatg cgccgctaca gggcgcgtcc cattcgccat tcaggctgcg 480
caactgttgg gaagggcgat cggtgcgggc ctcttcgcta ttacgccagc tggcgaaagg 540
gggatgtgct gcaaggcgat taagttgggt aacgccaggg ttttcccagt cacgacgttg 600
taaaacgacg gccagtgagc gcgccgttta aaccctcagc tacgtaaagc ttggtaccct 660
cgaggtcgac atcgatgata tcgaattcct gcaggggccc cccgggtccg gaggatccgc 720
ggccgctcta gagagctcac gcgttgatca tgtacaggcc ggccagcgcg cttggcgtaa 780
tcatggtcat agctgtttcc tgtgtgaaat tgttatccgc tcacaattcc acacaacata 840
cgagccggaa gcataaagtg taaagcctgg ggtgcctaat gagtgagcta actcacatta 900
attgcgttgc gctcactgcc cgctttccag tcgggaaacc tgtcgtgcca gctgcattaa 960
tgaatcggcc aacgcgcggg gagaggcggt ttgcgtattg ggcgctcttc cgcttcctcg 1020
ctcactgact cgctgcgctc ggtcgttcgg ctgcggcgag cggtatcagc tcactcaaag 1080
gcggtaatac ggttatccac agaatcaggg gataacgcag gaaagaacat gtgagcaaaa 1140
ggccagcaaa aggccaggaa ccgtaaaaag gccgcgttgc tggcgttttt ccataggctc 1200
cgcccccctg acgagcatca caaaaatcga cgctcaagtc agaggtggcg aaacccgaca 1260
ggactataaa gataccaggc gtttccccct ggaagctccc tcgtgcgctc tcctgttccg 1320
accctgccgc ttaccggata cctgtccgcc tttctccctt cgggaagcgt ggcgctttct 1380
catagctcac gctgtaggta tctcagttcg gtgtaggtcg ttcgctccaa gctgggctgt 1440
gtgcacgaac cccccgttca gcccgaccgc tgcgccttat ccggtaacta tcgtcttgag 1500
tccaacccgg taagacacga cttatcgcca ctggcagcag ccactggtaa caggattagc 1560
agagcgaggt atgtaggcgg tgctacagag ttcttgaagt ggtggcctaa ctacggctac 1620
actagaagga cagtatttgg tatctgcgct ctgctgaagc cagttacctt cggaaaaaga 1680
gttggtagct cttgatccgg caaacaaacc accgctggta gcggtggttt ttttgtttgc 1740
aagcagcaga ttacgcgcag aaaaaaagga tctcaagaag atcctttgat cttttctacg 1800
gggtctgacg ctcagtggaa cgaaaactca cgttaaggga ttttggtcat gagattatca 1860
aaaaggatct tcacctagat ccttttaaat taaaaatgaa gttttaaatc aatctaaagt 1920
atatatgagt aaacttggtc tgacagttac caatgcttaa tcagtgaggc acctatctca 1980
gcgatctgtc tatttcgttc atccatagtt gcctgactcc ccgtcgtgta gataactacg 2040
atacgggagg gcttaccatc tggccccagt gctgcaatga taccgcgaga cccacgctca 2100
ccggctccag atttatcagc aataaaccag ccagccggaa gggccgagcg cagaagtggt 2160
cctgcaactt tatccgcctc catccagtct attaattgtt gccgggaagc tagagtaagt 2220
agttcgccag ttaatagttt gcgcaacgtt gttgccattg ctacaggcat cgtggtgtca 2280

```
cgctcgtcgt ttggtatggc ttcattcagc tccggttccc aacgatcaag gcgagttaca   2340

tgatccccca tgttgtgcaa aaaagcggtt agctccttcg gtcctccgat cgttgtcaga   2400

agtaagttgg ccgcagtgtt atcactcatg gttatggcag cactgcataa ttctcttact   2460

gtcatgccat ccgtaagatg cttttctgtg actggtgagt actcaaccaa gtcattctga   2520

gaatagtgta tgcggcgacc gagttgctct tgcccggcgt caatacggga taataccgcg   2580

ccacatagca gaactttaaa agtgctcatc attggaaaac gttcttcggg gcgaaaactc   2640

tcaaggatct taccgctgtt gagatccagt tcgatgtaac ccactcgtgc acccaactga   2700

tcttcagcat cttttacttt caccagcgtt tctgggtgag caaaaacagg aaggcaaaat   2760

gccgcaaaaa agggaataag ggcgacacgg aaatgttgaa tactcatact cttccttttt   2820

caatattatt gaagcattta tcagggttat tgtctcatga gcggatacat atttgaatgt   2880

atttagaaaa ataaacaaat aggggttccg cgcacatttc cccgaaaagt gccac        2935


<210> SEQ ID NO 3
<211> LENGTH: 5444
<212> TYPE: DNA
<213> ORGANISM: Artificial sequence
<220> FEATURE:
<223> OTHER INFORMATION: pXBLS plasmid

<400> SEQUENCE: 3

gcactataca tcaaatattc cttattaacc cctttacaaa ttaaaaagct aaaggtacac     60

aatttttgag catagttatt aatagcagac actctatgcc tgtgtggagt aagaaaaaac    120

agtatgttat gattataact gttatgccta cttataaagg ttacagaata tttttccata    180

attttcttgt atagcagtgc agctttttcc tttgtggtgt aaatagcaaa gcaagcaaga    240

gttctattac taaacacagc atgactcaaa aaacttagca attctgaagg aaagtccttg    300

gggtcttcta cctttctctt ctttttgga ggagtagaat gttgagagtc agcagtagcc    360

tcatcatcac tagatggcat ttcttctgag caaaacaggt tttcctcatt aaaggcattc    420

caccactgct cccattcatc agttccatag gttggaatct aaaatacaca aacaattaga    480

atcagtagtt taacacatta tacacttaaa aattttatat ttaccttaga gctttaaatc    540

tctgtaggta gtttgtccaa ttatgtcaca ccacagaagt aaggttcctt cacaaagatc    600

gatctaaagc cagcaaaagt cccatggtct tataaaaatg catagcttta ggaggggagc    660

agagaacttg aaagcatctt cctgttagtc tttcttctcg tagacttcaa acttatactt    720

gatgcctttt tcctcctgga cctcagagag gacgcctggg tattctggga gaagtttata    780

tttccccaaa tcaatttctg ggaaaaacgt gtcactttca aattcctgca tgatccttgt    840

cacaaagagt ctgaggtggc ctggttgatt catggcttcc tggtaaacag aactgcctcc    900

gactatccaa accatgtcta ctttacttgc caattccggt tgttcaataa gtcttaaggc    960

atcatccaaa cttttggcaa gaaaatgagc tcctcgtggt ggttctttga gttctctact   1020

gagaactata ttaattctgt cctttaaagg tcgattcttc tcaggaatgg agaaccaggt   1080

tttcctaccc ataatcacca gattctgttt accttccact gaagaggttg tggtcattct   1140

ttggaagtac ttgaactcgt tcctgagcgg aggccagggt aggtctccgt tcttgccaat   1200

ccccatattt tgggacacgg cgacgatgca gttcaatggt cgaaccatga tggcagcggg   1260

gataaaatcc taccagcctt cacgctagga ttgccgtcaa gtttggcgcg aaatcgcagc   1320

cctgagctgt cccccccccc aagctcagat ctgagcttgg tccctatggt gagtccgttc   1380

cgctcttgtg atgatagcca gacaagaaag agacaataca agacaaacac caaatagtag   1440
```

-continued

```
aaatagagac aagggtcact tatccgaggg tccctgttcg ggcgccagct gccgcagtcg   1500
gccgacctga gggtcgccgg ggtctgcggg gggaccctct ggaaagtgaa ggataagtga   1560
cgagcggaga cgggatggcg aacagacaca aacacacaag aggtgaatgt taggactgtt   1620
gcaagtttac tcaaaaaatc agcactcttt tatatcttgg tttacataag catttacata   1680
agatttggat aaattccaaa agaacatagg aaaatagaac actcagagct cagatcagaa   1740
cctttgatac caaaccaagt caggaaacca cttgtctcac atcctcgttt taagaacagt   1800
ttgtaaccaa aaacttactt aagccctggg aaccgcaagg ttgggccaat aaaggctatt   1860
cataataact catgccatga gtttttgcag aataatgttc tattagtcca gccactgtcc   1920
cctccttggt atggaaaatc tttccccaaa agtgcattcc tgttcctaga taaatataat   1980
catgtacctg ttgtttcatg tcgtcttttt cttcttgaga caacatacac caaggaggtc   2040
tagctctggc gagtctttca cgaaaaggga gggatctata taacacttta tagccattga   2100
ctgtaaccca cctatcccaa tttaagtcat atcttcctgt atatggtaag gggcatctg   2160
ttggtctgta gatgtaaggt cccctataag tccctggttg ccaccacctg tctcctattt   2220
tgacaaaaac actctttttt ccctttttta cttctaggcc tgtggtcaat agtccttgca   2280
cctgttcttc aattgaggtt gagcgtctct ttctattttc tattcccatt tctaacttct   2340
gaatttgagt aaaaatagta ctaaaagata atgattcatt tcttaacata gtaactaata   2400
atctacctat tggattggtc ttattggtaa aaatataatt tttagcaagc attcttattt   2460
ctatttctga aggacaaaat cgatgcggct tgtaagagga agttggctgt ggtccttgcc   2520
tcaggaggaa ggtcgagttc tccgaattgt ttagattgta atcttgcaca gaagagctat   2580
taaaagagtc aagggtgaga gccctgcgag cacgaaccgc aacttccccc aatagcccca   2640
ggcaaagcag agctatgcca agtttgcagc agagaatgaa tatgtctttg tctgatgggc   2700
tcatccgttt gtgcgcagac gggtcgtcct tggtgggaaa caaccccttg gctgcttctc   2760
ccctaggtgt aggacactct cgggagttca accatttctg cccaagctca gatctgagct   2820
ttaatgcggt agtttatcac agttaaattg ctaacgcagt caggcaccgt gtatgaaatc   2880
taacaatgcg ctcatcgtca tcctcggcac cgtcaccctg gatgctgtag gcataggctt   2940
ggttatgccg gtactgccgg gcctcttgcg ggatatcgtc cattccgaca gcatcgccag   3000
tcactatggc gtgctgctag cgctcttccg cttcctcgct cactgactcg ctgcgctcgg   3060
tcgttcggct gcggcgagcg gtatcagctc actcaaaggc ggtaatacgg ttatccacag   3120
aatcagggga taacgcagga aagaacatgt gagcaaaagg ccagcaaaag gccaggaacc   3180
gtaaaaaggc cgcgttgctg gcgtttttcc ataggctccg cccccctgac gagcatcaca   3240
aaaatcgacg ctcaagtcag aggtggcgaa acccgacagg actataaaga taccaggcgt   3300
ttccccctgg aagctccctc gtgcgctctc ctgttccgac cctgccgctt accggatacc   3360
tgtccgcctt tctcccttcg ggaagcgtgg cgctttctca tagctcacgc tgtaggtatc   3420
tcagttcggt gtaggtcgtt cgctccaagc tgggctgtgt gcacgaaccc cccgttcagc   3480
ccgaccgctg cgccttatcc ggtaactatc gtcttgagtc caacccggta agacacgact   3540
tatcgccact ggcagcagcc actggtaaca ggattagcag agcgaggtat gtaggcggtg   3600
ctacagagtt cttgaagtgg tggcctaact acggctacac tagaaggaca gtatttggta   3660
tctgcgctct gctgaagcca gttaccttcg gaaaaagagt tggtagctct tgatccggca   3720
aacaaaccac cgctggtagc ggtggttttt ttgtttgcaa gcagcagatt acgcgcagaa   3780
aaaaaggatc tcaagaagat cctttgatct tttctacggg gtctgacgct cagtggaacg   3840
```

aaaactcacg ttaagggatt ttggtcatga gattatcaaa aaggatcttc acctagatcc 3900
ttttaaatta aaaatgaagt tttaaatcaa tctaaagtat atatgagtaa acttggtctg 3960
acagttacca atgcttaatc agtgaggcac ctatctcagc gatctgtcta tttcgttcat 4020
ccatagttgc ctgactcccc gtcgtgtaga taactacgat acgggagggc ttaccatctg 4080
gccccagtgc tgcaatgata ccgcgagacc cacgctcacc ggctccagat ttatcagcaa 4140
taaaccagcc agccggaagg gccgagcgca gaagtggtcc tgcaacttta tccgcctcca 4200
tccagtctat taattgttgc cgggaagcta gagtaagtag ttcgccagtt aatagtttgc 4260
gcaacgttgt tgccattgct acaggcatcg tggtgtcacg ctcgtcgttt ggtatggctt 4320
cattcagctc cggttcccaa cgatcaaggc gagttacatg atcccccatg ttgtgcaaaa 4380
aagcggttag ctccttcggt cctccgatcg ttgtcagaag taagttggcc gcagtgttat 4440
cactcatggt tatggcagca ctgcataatt ctcttactgt catgccatcc gtaagatgct 4500
tttctgtgac tggtgagtac tcaaccaagt cattctgaga atagtgtatg cggcgaccga 4560
gttgctcttg cccggcgtca acacgggata ataccgcgcc acatagcaga actttaaaag 4620
tgctcatcat tggaaaacgt tcttcggggc gaaaactctc aaggatctta ccgctgttga 4680
gatccagttc gatgtaaccc actcgtgcac ccaactgatc ttcagcatct tttactttca 4740
ccagcgtttc tgggtgagca aaaacaggaa ggcaaaatgc cgcaaaaaag ggaataaggg 4800
cgacacggaa atgttgaata ctcatactct tcctttttca atattattga agcatttatc 4860
agggttattg tctcatgagc ggatacatat ttgaatgtat ttagaaaaat aaacaaatag 4920
gggttccgcg cacatttccc cgaaaagtgc cacctgacgt ctaagagacc attattatca 4980
tgacattaac ctataaaaat aggcgtatca cgaggccctt tcgtcttcaa gaattgtcta 5040
gaggcgcgcc gtttaaaccc tcagctgatc atccggatgt acagcgcgcg gccggccggt 5100
accacgcgtt ggccacatat ggcggccgct cgcgattaat taacggaccg ccgcggacta 5160
gtgcccgggc caccggtgct cgaagcttgg atcgatccag acatgataag atacattgat 5220
gagtttggac aaaccacaac tagaatgcag tgaaaaaaat gctttatttg tgaaatttgt 5280
gatgctattg ctttatttgt aaccattata agctgcaata aacaagttaa caacaacaat 5340
tgcattcatt ttatgtttca ggttcagggg gaggtgtggg aggtttttta aagcaagtaa 5400
aacctctaca aatgtggtat ggctgattat gatctctagt caag 5444

<210> SEQ ID NO 4
<211> LENGTH: 3176
<212> TYPE: DNA
<213> ORGANISM: Artificial sequence
<220> FEATURE:
<223> OTHER INFORMATION: pULstopLs plasmid

<400> SEQUENCE: 4
ctaaattgta agcgttaata ttttgttaaa attcgcgtta aatttttgtt aaatcagctc 60 atttttaac caataggccg aaatcggcaa aatcccttat aaatcaaaag aatagaccga 120
gatagggttg agtgttgttc cagtttggaa caagagtcca ctattaaaga acgtggactc 180
caacgtcaaa gggcgaaaaa ccgtctatca gggcgatggc ccactacgtg aaccatcacc 240
ctaatcaagt tttttggggt cgaggtgccg taaagcacta aatcggaacc ctaaagggag 300
cccccgattt agagcttgac ggggaaagcc ggcgaacgtg gcgagaaagg aagggaagaa 360
agcgaaagga gcgggcgcta gggcgctggc aagtgtagcg gtcacgctgc gcgtaaccac 420
cacacccgcc gcgcttaatg cgccgctaca gggcgcgtcc cattcgccat tcaggctgcg 480

-continued

```
caactgttgg gaagggcgat cggtgcgggc ctcttcgcta ttacgccagc tggcgaaagg    540
gggatgtgct gcaaggcgat taagttgggt aacgccaggg ttttcccagt cacgacgttg    600
taaaacgacg gccagtgagc gcgccaccgg tggcccgggc cggtccgact agttacgtaa    660
agcttggtac cctcgaggtc gacatcgatg atatcgaatt cctgcagggg ccctccggag    720
gatccagatc cccctcgctt tcttgctgtc caatttctat taaaggttcc tttgttccct    780
aagtccaact actaaactgg gggatattat gaagggcctt gagcatctgg attctgccta    840
ataaaaaaca tttattttca ttgcaatgat gtatttaaat tatttctgaa tattttacta    900
aaaagggaat gtgggaggtc agtgcattta aaacataaag aaatgaagag gggatctgt     960
cgacaagctc tagagagctc catatgtggc catcgcgatt aattaagcgc gcttggcgta   1020
atcatggtca tagctgtttc ctgtgtgaaa ttgttatccg ctcacaattc cacacaacat   1080
acgagccgga agcataaagt gtaaagcctg gggtgcctaa tgagtgagct aactcacatt   1140
aattgcgttg cgctcactgc ccgctttcca gtcgggaaac ctgtcgtgcc agctgcatta   1200
atgaatcggc caacgcgcgg ggagaggcgg tttgcgtatt gggcgctctt ccgcttcctc   1260
gctcactgac tcgctgcgct cggtcgttcg gctgcggcga gcggtatcag ctcactcaaa   1320
ggcggtaata cggttatcca cagaatcagg ggataacgca ggaaagaaca tgtgagcaaa   1380
aggccagcaa aaggccagga accgtaaaaa ggccgcgttg ctggcgtttt tccataggct   1440
ccgcccccct gacgagcatc acaaaaatcg acgctcaagt cagaggtggc gaaacccgac   1500
aggactataa agataccagg cgtttccccc tggaagctcc ctcgtgcgct ctcctgttcc   1560
gaccctgccg cttaccggat acctgtccgc ctttctccct tcgggaagcg tggcgctttc   1620
tcatagctca cgctgtaggt atctcagttc ggtgtaggtc gttcgctcca agctgggctg   1680
tgtgcacgaa ccccccgttc agcccgaccg ctgcgcctta tccggtaact atcgtcttga   1740
gtccaacccg gtaagacacg acttatcgcc actggcagca gccactggta acaggattag   1800
cagagcgagg tatgtaggcg gtgctacaga gttcttgaag tggtggccta actacggcta   1860
cactagaagg acagtatttg gtatctgcgc tctgctgaag ccagttacct tcggaaaaag   1920
agttggtagc tcttgatccg gcaaacaaac caccgctggt agcggtggtt tttttgtttg   1980
caagcagcag attacgcgca gaaaaaaagg atctcaagaa gatcctttga tcttttctac   2040
ggggtctgac gctcagtgga acgaaaactc acgttaaggg attttggtca tgagattatc   2100
aaaaaggatc ttcacctaga tccttttaaa ttaaaaatga agttttaaat caatctaaag   2160
tatatatgag taaacttggt ctgacagtta ccaatgctta atcagtgagg cacctatctc   2220
agcgatctgt ctatttcgtt catccatagt tgcctgactc cccgtcgtgt agataactac   2280
gatacgggag ggcttaccat ctggccccag tgctgcaatg ataccgcgag acccacgctc   2340
accggctcca gatttatcag caataaacca gccagccgga agggccgagc gcagaagtgg   2400
tcctgcaact ttatccgcct ccatccagtc tattaattgt tgccgggaag ctagagtaag   2460
tagttcgcca gttaatagtt tgcgcaacgt tgttgccatt gctacaggca tcgtggtgtc   2520
acgctcgtcg tttggtatgg cttcattcag ctccggttcc caacgatcaa ggcgagttac   2580
atgatccccc atgttgtgca aaaaagcggt tagctccttc ggtcctccga tcgttgtcag   2640
aagtaagttg gccgcagtgt tatcactcat ggttatggca gcactgcata attctcttac   2700
tgtcatgcca tccgtaagat gcttttctgt gactggtgag tactcaacca agtcattctg   2760
agaatagtgt atgcggcgac cgagttgctc ttgcccggcg tcaatacggg ataataccgc   2820
gccacatagc agaactttaa aagtgctcat cattggaaaa cgttcttcgg ggcgaaaact   2880
```

ctcaaggatc ttaccgctgt tgagatccag ttcgatgtaa cccactcgtg cacccaactg 2940
atcttcagca tcttttactt tcaccagcgt ttctgggtga gcaaaaacag gaaggcaaaa 3000
tgccgcaaaa aagggaataa gggcgacacg gaaatgttga atactcatac tcttcctttt 3060
tcaatattat tgaagcattt atcagggtta ttgtctcatg agcggataca tatttgaatg 3120
tatttagaaa aataaacaaa taggggttcc gcgcacattt ccccgaaaag tgccac 3176

<210> SEQ ID NO 5
<211> LENGTH: 3170
<212> TYPE: DNA
<213> ORGANISM: Artificial sequence
<220> FEATURE:
<223> OTHER INFORMATION: pUHstopLS plasmid

<400> SEQUENCE: 5
ctaaattgta agcgttaata ttttgttaaa attcgcgtta aatttttgtt aaatcagctc 60 atttttaac caataggccg aaatcggcaa aatcccttat aaatcaaaag aatagaccga 120
gatagggttg agtgttgttc cagtttggaa caagagtcca ctattaaaga acgtggactc 180
caacgtcaaa gggcgaaaaa ccgtctatca gggcgatggc ccactacgtg aaccatcacc 240
ctaatcaagt tttttggggt cgaggtgccg taaagcacta aatcggaacc ctaaagggag 300
cccccgattt agagcttgac ggggaaagcc ggcgaacgtg gcgagaaagg aagggaagaa 360
agcgaaagga gcgggcgcta gggcgctggc aagtgtagcg gtcacgctgc gcgtaaccac 420
cacacccgcc gcgcttaatg cgccgctaca gggcgcgtcc cattcgccat tcaggctgcg 480
caactgttgg gaagggcgat cggtgcgggc ctcttcgcta ttacgccagc tggcgaaagg 540
gggatgtgct gcaaggcgat taagttgggt aacgccaggg ttttcccagt cacgacgttg 600
taaaacgacg gccagtgagc gcgccgttta aaccctcagc tacgtaaagc ttggtaccct 660
cgaggtcgac atcgatgata tcgaattcct gcaggggccc cccgggtccg gaggatccag 720
atccccctcg ctttcttgct gtccaatttc tattaaaggt tcctttgttc cctaagtcca 780
actactaaac tgggggatat tatgaagggc cttgagcatc tggattctgc ctaataaaaa 840
acatttattt tcattgcaat gatgtattta aattatttct gaatatttta ctaaaaaggg 900
aatgtgggag gtcagtgcat ttaaaacata aagaaatgaa gagggggatc tgtcgacaag 960
ctctagagag ctcacgcgtt gatcatgtac aggccggcca gcgcgcttgg cgtaatcatg 1020
gtcatagctg tttcctgtgt gaaattgtta tccgctcaca attccacaca acatacgagc 1080
cggaagcata aagtgtaaag cctggggtgc ctaatgagtg agctaactca cattaattgc 1140
gttgcgctca ctgcccgctt tccagtcggg aaacctgtcg tgccagctgc attaatgaat 1200
cggccaacgc gcggggagag gcggtttgcg tattgggcgc tcttccgctt cctcgctcac 1260
tgactcgctg cgctcggtcg ttcggctgcg gcgagcggta tcagctcact caaaggcggt 1320
aatacggtta tccacagaat caggggataa cgcaggaaag aacatgtgag caaaaggcca 1380
gcaaaaggcc aggaaccgta aaaaggccgc gttgctggcg tttttccata ggctccgccc 1440
ccctgacgag catcacaaaa atcgacgctc aagtcagagg tggcgaaacc cgacaggact 1500
ataaagatac caggcgtttc cccctggaag ctccctcgtg cgctctcctg ttccgaccct 1560
gccgcttacc ggatacctgt ccgcctttct cccttcggga agcgtggcgc tttctcatag 1620
ctcacgctgt aggtatctca gttcggtgta ggtcgttcgc tccaagctgg gctgtgtgca 1680
cgaacccccc gttcagcccg accgctgcgc cttatccggt aactatcgtc ttgagtccaa 1740
cccggtaaga cacgacttat cgccactggc agcagccact ggtaacagga ttagcagagc 1800
gaggtatgta ggcggtgcta cagagttctt gaagtggtgg cctaactacg gctacactag 1860
aaggacagta tttggtatct gcgctctgct gaagccagtt accttcggaa aaagagttgg 1920
tagctcttga tccggcaaac aaaccaccgc tggtagcggt ggtttttttg tttgcaagca 1980
gcagattacg cgcagaaaaa aaggatctca agaagatcct ttgatctttt ctacggggtc 2040
tgacgctcag tggaacgaaa actcacgtta agggattttg gtcatgagat tatcaaaaag 2100
gatcttcacc tagatccttt taaattaaaa atgaagtttt aaatcaatct aaagtatata 2160
tgagtaaact tggtctgaca gttaccaatg cttaatcagt gaggcaccta tctcagcgat 2220
ctgtctattt cgttcatcca tagttgcctg actccccgtc gtgtagataa ctacgatacg 2280
ggagggctta ccatctggcc ccagtgctgc aatgataccg cgagacccac gctcaccggc 2340
tccagattta tcagcaataa accagccagc cggaagggcc gagcgcagaa gtggtcctgc 2400
aactttatcc gcctccatcc agtctattaa ttgttgccgg gaagctagag taagtagttc 2460
gccagttaat agtttgcgca acgttgttgc cattgctaca ggcatcgtgg tgtcacgctc 2520
gtcgtttggt atggcttcat tcagctccgg ttcccaacga tcaaggcgag ttacatgatc 2580
ccccatgttg tgcaaaaaag cggttagctc cttcggtcct ccgatcgttg tcagaagtaa 2640
gttggccgca gtgttatcac tcatggttat ggcagcactg cataattctc ttactgtcat 2700
gccatccgta agatgctttt ctgtgactgg tgagtactca accaagtcat tctgagaata 2760
gtgtatgcgg cgaccgagtt gctcttgccc ggcgtcaata cgggataata ccgcgccaca 2820
tagcagaact ttaaaagtgc tcatcattgg aaaacgttct tcggggcgaa aactctcaag 2880
gatcttaccg ctgttgagat ccagttcgat gtaacccact cgtgcaccca actgatcttc 2940
agcatctttt actttcacca gcgtttctgg gtgagcaaaa acaggaaggc aaaatgccgc 3000
aaaaaaggga ataagggcga cacggaaatg ttgaatactc atactcttcc tttttcaata 3060
ttattgaagc atttatcagg gttattgtct catgagcgga tacatatttg aatgtattta 3120
gaaaaataaa caaatagggg ttccgcgcac atttccccga aaagtgccac 3170

<210> SEQ ID NO 6
<211> LENGTH: 12190
<212> TYPE: DNA
<213> ORGANISM: Artificial sequence
<220> FEATURE:
<223> OTHER INFORMATION: pAIL5V1 plasmid

<400> SEQUENCE: 6
gcactataca tcaaatattc cttattaacc cctttacaaa ttaaaaagct aaaggtacac 60
aatttttgag catagttatt aatagcagac actctatgcc tgtgtggagt aagaaaaaac 120
agtatgttat gattataact gttatgccta cttataaagg ttacagaata tttttccata 180 atttcttgt atagcagtgc agctttttcc tttgtggtgt aaatagcaaa gcaagcaaga 240
gttctattac taaacacagc atgactcaaa aaacttagca attctgaagg aaagtccttg 300
gggtcttcta cctttctctt ctttttgga ggagtagaat gttgagagtc agcagtagcc 360
tcatcatcac tagatggcat ttcttctgag caaaacaggt tttcctcatt aaaggcattc 420
caccactgct cccattcatc agttccatag gttggaatct aaaatacaca aacaattaga 480
atcagtagtt taacacatta tacacttaaa aattttatat ttaccttaga gctttaaatc 540
tctgtaggta gtttgtccaa ttatgtcaca ccacagaagt aaggttcctt cacaaagatc 600
gatctaaagc cagcaaaagt cccatggtct tataaaaatg catagcttta ggaggggagc 660
agagaacttg aaagcatctt cctgttagtc tttcttctcg tagacttcaa acttatactt 720

-continued

```
gatgcctttt tcctcctgga cctcagagag gacgcctggg tattctggga gaagtttata    780
tttccccaaa tcaatttctg ggaaaaacgt gtcactttca aattcctgca tgatccttgt    840
cacaaagagt ctgaggtggc ctggttgatt catggcttcc tggtaaacag aactgcctcc    900
gactatccaa accatgtcta ctttacttgc caattccggt tgttcaataa gtcttaaggc    960
atcatccaaa cttttggcaa gaaaatgagc tcctcgtggt ggttctttga gttctctact   1020
gagaactata ttaattctgt cctttaaagg tcgattcttc tcaggaatgg agaaccaggt   1080
tttcctaccc ataatcacca gattctgttt accttccact gaagaggttg tggtcattct   1140
ttggaagtac ttgaactcgt tcctgagcgg aggccagggt aggtctccgt tcttgccaat   1200
ccccatattt tgggacacgg cgacgatgca gttcaatggt cgaaccatga tggcagcggg   1260
gataaaatcc taccagcctt cacgctagga ttgccgtcaa gtttggcgcg aaatcgcagc   1320
cctgagctgt cccccccccc aagctcagat ctgagcttgg tccctatggt gagtccgttc   1380
cgctcttgtg atgatagcca gacaagaaag agacaataca agacaaacac caaatagtag   1440
aaatagagac aagggtcact tatccgaggg tccctgttcg ggcgccagct gccgcagtcg   1500
gccgacctga gggtcgccgg ggtctgcggg gggaccctct ggaaagtgaa ggataagtga   1560
cgagcggaga cgggatggcg aacagacaca aacacacaag aggtgaatgt taggactgtt   1620
gcaagtttac tcaaaaaatc agcactcttt tatatcttgg tttacataag catttacata   1680
agatttggat aaattccaaa agaacatagg aaaatagaac actcagagct cagatcagaa   1740
cctttgatac caaaccaagt caggaaacca cttgtctcac atcctcgttt taagaacagt   1800
ttgtaaccaa aaacttactt aagccctggg aaccgcaagg ttgggccaat aaaggctatt   1860
cataataact catgccatga gtttttgcag aataatgttc tattagtcca gccactgtcc   1920
cctccttggt atggaaaatc tttccccaaa agtgcattcc tgttcctaga taaatataat   1980
catgtacctg ttgtttcatg tcgtcttttt cttcttgaga caacatacac caaggaggtc   2040
tagctctggc gagtctttca cgaaaaggga gggatctata taacacttta tagccattga   2100
ctgtaaccca cctatcccaa tttaagtcat atcttcctgt atatggtaag gggcatctg   2160
ttggtctgta gatgtaaggt cccctataag tccctggttg ccaccacctg tctcctattt   2220
tgacaaaaac actctttttt ccctttttta cttctaggcc tgtggtcaat agtccttgca   2280
cctgttcttc aattgaggtt gagcgtctct ttctattttc tattcccatt tctaacttct   2340
gaatttgagt aaaaatagta ctaaaagata atgattcatt tcttaacata gtaactaata   2400
atctacctat tggattggtc ttattggtaa aaatataatt tttagcaagc attcttattt   2460
ctatttctga aggacaaaat cgatgcggct tgtaagagga agttggctgt ggtccttgcc   2520
tcaggaggaa ggtcgagttc tccgaattgt ttagattgta atcttgcaca gaagagctat   2580
taaaagagtc aagggtgaga gccctgcgag cacgaaccgc aacttccccc aatagcccca   2640
ggcaaagcag agctatgcca agtttgcagc agagaatgaa tatgtctttg tctgatgggc   2700
tcatccgttt gtgcgcagac gggtcgtcct tggtgggaaa caaccccttg gctgcttctc   2760
ccctaggtgt aggacactct cgggagttca accatttctg cccaagctca gatctgagct   2820
ttaatgcggt agtttatcac agttaaattg ctaacgcagt caggcaccgt gtatgaaatc   2880
taacaatgcg ctcatcgtca tcctcggcac cgtcaccctg gatgctgtag gcataggctt   2940
ggttatgccg gtactgccgg gcctcttgcg ggatatcgtc cattccgaca gcatcgccag   3000
tcactatggc gtgctgctag cgctcttccg cttcctcgct cactgactcg ctgcgctcgg   3060
tcgttcggct gcggcgagcg gtatcagctc actcaaaggc ggtaatacgg ttatccacag   3120
```

-continued

```
aatcagggga taacgcagga aagaacatgt gagcaaaagg ccagcaaaag gccaggaacc   3180
gtaaaaaggc cgcgttgctg gcgtttttcc ataggctccg cccccctgac gagcatcaca   3240
aaaatcgacg ctcaagtcag aggtggcgaa acccgacagg actataaaga taccaggcgt   3300
ttccccctgg aagctccctc gtgcgctctc ctgttccgac cctgccgctt accggatacc   3360
tgtccgcctt tctcccttcg ggaagcgtgg cgctttctca tagctcacgc tgtaggtatc   3420
tcagttcggt gtaggtcgtt cgctccaagc tgggctgtgt gcacgaaccc cccgttcagc   3480
ccgaccgctg cgccttatcc ggtaactatc gtcttgagtc caacccggta agacacgact   3540
tatcgccact ggcagcagcc actggtaaca ggattagcag agcgaggtat gtaggcggtg   3600
ctacagagtt cttgaagtgg tggcctaact acggctacac tagaaggaca gtatttggta   3660
tctgcgctct gctgaagcca gttaccttcg gaaaaagagt tggtagctct tgatccggca   3720
aacaaaccac cgctggtagc ggtggttttt ttgtttgcaa gcagcagatt acgcgcagaa   3780
aaaaaggatc tcaagaagat cctttgatct tttctacggg gtctgacgct cagtggaacg   3840
aaaactcacg ttaagggatt ttggtcatga gattatcaaa aaggatcttc acctagatcc   3900
ttttaaatta aaaatgaagt tttaaatcaa tctaaagtat atatgagtaa acttggtctg   3960
acagttacca atgcttaatc agtgaggcac ctatctcagc gatctgtcta tttcgttcat   4020
ccatagttgc ctgactcccc gtcgtgtaga taactacgat acgggagggc ttaccatctg   4080
gccccagtgc tgcaatgata ccgcgagacc cacgctcacc ggctccagat ttatcagcaa   4140
taaaccagcc agccggaagg gccgagcgca gaagtggtcc tgcaacttta tccgcctcca   4200
tccagtctat taattgttgc cgggaagcta gagtaagtag ttcgccagtt aatagtttgc   4260
gcaacgttgt tgccattgct acaggcatcg tggtgtcacg ctcgtcgttt ggtatggctt   4320
cattcagctc cggttcccaa cgatcaaggc gagttacatg atcccccatg ttgtgcaaaa   4380
aagcggttag ctccttcggt cctccgatcg ttgtcagaag taagttggcc gcagtgttat   4440
cactcatggt tatggcagca ctgcataatt ctcttactgt catgccatcc gtaagatgct   4500
tttctgtgac tggtgagtac tcaaccaagt cattctgaga atagtgtatg cggcgaccga   4560
gttgctcttg cccggcgtca acacgggata ataccgcgcc acatagcaga actttaaaag   4620
tgctcatcat tggaaaacgt tcttcggggc gaaaactctc aaggatctta ccgctgttga   4680
gatccagttc gatgtaaccc actcgtgcac ccaactgatc ttcagcatct tttactttca   4740
ccagcgtttc tgggtgagca aaaacaggaa ggcaaaatgc cgcaaaaaag ggaataaggg   4800
cgacacggaa atgttgaata ctcatactct tcctttttca atattattga agcatttatc   4860
agggttattg tctcatgagc ggatacatat ttgaatgtat ttagaaaaat aaacaaatag   4920
gggttccgcg cacatttccc cgaaaagtgc cacctgacgt ctaagagacc attattatca   4980
tgacattaac ctataaaaat aggcgtatca cgaggccctt tcgtcttcaa gaattgtcta   5040
gaggcgcgcc gtttaaaccc tcagctaccg atgtacgggc cagatatacg cgttgacatt   5100
gattattgac tagttattaa tagtaatcaa ttacggggtc attagttcat agcccatata   5160
tggagttccg cgttacataa cttacggtaa atggcccgcc tggctgaccg cccaacgacc   5220
cccgcccatt gacgtcaata atgacgtatg ttcccatagt aacgccaata gggactttcc   5280
attgacgtca atgggtggac tatttacggt aaactgccca cttggcagta catcaagtgt   5340
atcatatgcc aagtacgccc cctattgacg tcaatgacgg taaatggccc gcctggcatt   5400
atgcccagta catgacctta tgggactttc ctacttggca gtacatctac gtattagtca   5460
tcgctattac catggtgatg cggttttggc agtacatcaa tgggcgtgga tagcggtttg   5520
```

```
actcacgggg atttccaagt ctccacccca ttgacgtcaa tgggagtttg ttttggcacc   5580
aaaatcaacg ggactttcca aaatgtcgta acaactccgc cccattgacg caaatgggcg   5640
gtaggcgtgt acggtgggag gtctatataa gcagagctct ctggctaact agagaaccca   5700
ctgcttactg gcttatcgaa attaatacga ctcactatag ggagacccaa gctggctagc   5760
gtttaaactt aagcttggta ccgagctcgg atccactagt ccagtgtggt ggaattccag   5820
agagaactca ccatggagtt tgggctgagc tggctttttc ttgtggctat tttaaaaggt   5880
gtccagtgtg aggtgcagct gttggagtct gggggaggct tggtacagcc tggggggtcc   5940
ctgagactct cctgtgcagc ctctggattc acctttagca gctatgccat gagctgggtc   6000
cgccaggctc cagggaaggg gctggagtgg gtctcaacta ttagtggtag tggtggtagc   6060
acatactacg cagactccgt gaagggccgg ttcaccatct ccagagacaa ttccaagaac   6120
acgctgtatc tgcaaatgaa cagcctgaga gccgaggaca cggccgtata ttactgtgcg   6180
aaagagaggt ataactggaa ctacctacac tactggggcc agggaaccct ggtcaccgtc   6240
tcctcagcta gcaccaaggg cccatccgtc ttccccctgg cgccctgctc caggagcacc   6300
tccgagagca cagccgccct gggctgcctg gtcaaggact acttccccga accggtgacg   6360
gtgtcgtgga actcaggcgc cctgaccagc ggcgtgcaca ccttcccggc tgtcctacag   6420
tcctcaggac tctactccct cagcagcgtg gtgaccgtgc cctccagcag cttgggcacg   6480
aagacctaca cctgcaacgt agatcacaag cccagcaaca ccaaggtgga caagagagtt   6540
ggtgagaggc cagcacaggg agggagggtg tctgctggaa gccaggctca gccctcctgc   6600
ctggacgcac cccggctgtg cagccccagc ccagggcagc aaggcatgcc ccatctgtct   6660
cctcacccgg aggcctctga ccaccccact catgctcagg gagagggtct tctggatttt   6720
tccaccaggc tccgggcagc cacaggctgg atgcccctac cccaggccct gcgcatacag   6780
gggcaggtgc tgcgctcaga cctgccaaga gccatatccg ggaggaccct gcccctgacc   6840
taagcccacc ccaaaggcca aactctccac tccctcagct cagacacctt ctctcctccc   6900
agatctgagt aactcccaat cttctctctg cagagtccaa atatggtccc ccatgcccat   6960
catgcccagg taagccaacc caggcctcgc cctccagctc aaggcgggac aggtgcccta   7020
gagtagcctg catccaggga caggccccag ccgggtgctg acgcatccac ctccatctct   7080
tcctcagcac ctgagttcct ggggggacca tcagtcttcc tgttcccccc aaaacccaag   7140
gacactctca tgatctcccg gacccctgag gtcacgtgcg tggtggtgga cgtgagccag   7200
gaagaccccg aggtccagtt caactggtac gtggatggcg tggaggtgca taatgccaag   7260
acaaagccgc gggaggagca gttcaacagc acgtaccgtg tggtcagcgt cctcaccgtc   7320
ctgcaccagg actggctgaa cggcaaggag tacaagtgca aggtctccaa caaaggcctc   7380
ccgtcctcca tcgagaaaac catctccaaa gccaaaggtg ggacccacgg ggtgcgaggg   7440
ccacatggac agaggtcagc tcggcccacc ctctgccctg ggagtgaccg ctgtgccaac   7500
ctctgtccct acagggcagc cccgagagcc acaggtgtac accctgcccc catcccagga   7560
ggagatgacc aagaaccagg tcagcctgac ctgcctggtc aaaggcttct accccagcga   7620
catcgccgtg gagtgggaga gcaatgggca gccggagaac aactacaaga ccacgcctcc   7680
cgtgctggac tccgacggct ccttcttcct ctacagcagg ctaaccgtgg acaagagcag   7740
gtggcaggag gggaatgtct tctcatgctc cgtgatgcat gaggctctgc acaaccacta   7800
cacacagaag agcctctccc tgtctctggg taaatgagtg ccagggccgg caagcccccg   7860
ctccccgggt ccggaggatc cagatccccc tcgctttctt gctgtccaat ttctattaaa   7920
```

-continued

```
ggttcctttg ttccctaagt ccaactacta aactggggga tattatgaag ggccttgagc   7980
atctggattc tgcctaataa aaaacattta ttttcattgc aatgatgtat ttaaattatt   8040
tctgaatatt ttactaaaaa gggaatgtgg gaggtcagtg catttaaaac ataaagaaat   8100
gaagaggggg atctgtcgac aagctctaga gagctcacgc gttgatcatg tacaggccgg   8160
cctgtgccac tgggcgccag aaatccgcgc ggtggttttt gggggtcggg ggtgtttggc   8220
agccacagac gcccggtgtt cgtgtcgcgc cagtacatgc ggtccatgcc caggccatcc   8280
aaaaaccatg ggtctgtctg ctcagtccag tcgtggacca gaccccacgc aacgcccaaa   8340
ataataaccc ccacgaacca taaaccattc cccatggggg accccgtccc taacccacgg   8400
ggccagtggc tatggcaggg cctgccgccc cgacgttggc tgcgagccct gggccttcac   8460
ccgaacttgg ggggtggggt ggggaaaagg aagaaacgcg ggcgtattgg ccccaatggg   8520
gtctcggtgg ggtatcgaca gagtgccagc cctgggaccg aaccccgcgt ttatgaacaa   8580
acgacccaac acccgtgcgt tttattctgt ctttttattg ccgtcatagc gcgggttcct   8640
tccggtattg tctccttccg tgtttcagtt agcctccccc atctccccta ttcctttgcc   8700
ctcggacgag tgctggggcg tcggtttcca ctatcggcga gtacttctac acagccatcg   8760
gtccagacgg ccgcgcttct gcgggcgatt tgtgtacgcc cgacagtccc ggctccggat   8820
cggacgattg cgtcgcatcg accctgcgcc caagctgcat catcgaaatt gccgtcaacc   8880
aagctctgat agagttggtc aagaccaatg cggagcatat acgcccggag ccgcggcgat   8940
cctgcaagct ccggatgcct ccgctcgaag tagcgcgtct gctgctccat acaagccaac   9000
cacggcctcc agaagaagat gttggcgacc tcgtattggg aatccccgaa catcgcctcg   9060
ctccagtcaa tgaccgctgt tatgcggcca ttgtccgtca ggacattgtt ggagccgaaa   9120
tccgcgtgca cgaggtgccg gacttcgggg cagtcctcgg cccaaagcat cagctcatcg   9180
agagcctgcg cgacggacgc actgacggtg tcgtccatca cagtttgcca gtgatacaca   9240
tggggatcag caatcgcgca tatgaaatca cgccatgtag tgtattgacc gattccttgc   9300
ggtccgaatg ggccgaaccc gctcgtctgg ctaagatcgg ccgcagcgat cgcatccatg   9360
gcctccgcga ccggctgcag aacagcgggc agttcggttt caggcaggtc ttgcaacgtg   9420
acaccctgtg cacggcggga gatgcaatag gtcaggctct cgctgaattc cccaatgtca   9480
agcacttccg gaatcgggag cgcggccgat gcaaagtgcc gataaacata acgatctttg   9540
tagaaaccat cggcgcagct atttacccgc aggacatatc cacgccctcc tacatcgaag   9600
ctgaaagcac gagattcttc gccctccgag agctgcatca ggtcggagac gctgtcgaac   9660
ttttcgatca gaaacttctc gacagacgtc gcggtgagtt caggcttttt catatctcat   9720
tgcccgggat ctgcggcacg ctgttgacgc tgttaagcgg gtcgctgcag ggtcgctcgg   9780
tgttcgaggc cacacgcgtc accttaatat gcgaagtgga cctgggaccg cgccgccccg   9840
actgcatctg cgtgttcgaa ttcgccaatg acaagacgct gggcggggtt tgtgtcatca   9900
tagaactaaa gacatgcaaa tatatttctt ccggggacac cgccagcaaa cgcgagcaac   9960
gggccacggg gatgaagcag ggcatggcgg ccgacgcgct gggctacgtc ttgctggcgt  10020
tcgcacaggc cggccagcgc gcggccggcc ggtaccacgc gttggccaca tatggcggcc  10080
gctcgcgatt aattaatcgc gatggccaca tatggagctc tctagagctt gtcgacagat  10140
ccccctcttc atttctttat gttttaaatg cactgacctc ccacattccc tttttagtaa  10200
aatattcaga aataatttaa atacatcatt gcaatgaaaa taaatgtttt ttattaggca  10260
gaatccagat gctcaaggcc cttcataata tcccccagtt tagtagttgg acttagggaa  10320
```

```
caaaggaacc tttaatagaa attggacagc aagaaagcga gggggatctg gatcctccgg  10380
agggcccctt ctccctctaa cactctcccc tgttgaagct ctttgtgacg ggcgagctca  10440
ggccctgatg ggtgacttcg caggcgtaga ctttgtgttt ctcgtagtct gctttgctca  10500
gcgtcagggt gctgctgagg ctgtaggtgc tgtccttgct gtcctgctct gtgacactct  10560
cctgggagtt acccgattgg agggcgttat ccaccttcca ctgtactttg gcctctctgg  10620
gatagaagtt attcagcagg cacacaacag aggcagttcc agatttcaac tgctcatcag  10680
atggcgggaa gatgaagaca gatggtgcag ccacagttcg tctgatctcc accttggtcc  10740
ctccgccgaa agtgagcggg tgattatcat actgttgaca ataatatgtt gcaatatctt  10800
caggctgcag gctgctgatg gtgaaagtaa aatctgtccc agaaccactt ccactgaacc  10860
ttgatgggac tcttgtttcc aaattggaag cactgtagat caggagttta ggggctttcc  10920
ctggtttctg ctgataccaa tttaaatagt tgataatgtc ctgactcgcc tggcaagtga  10980
tggtgactct gtctcccaca gatgcagaca gggaggatgg agactgggtc atctggatgt  11040
cacatctggc acctgagagc cagagcagca ggagccccag gagctgagca gggaccctca  11100
tgtccatgct gtgtcccggt tggactgac tcctgcacag ggtgaattcc accacactgg  11160
actagtggat ccgagctcgg taccaagctt aagtttaaac gctagccagc ttgggtctcc  11220
ctatagtgag tcgtattaat ttcgataagc cagtaagcag tgggttctct agttagccag  11280
agagctctgc ttatatagac ctcccaccgt acacgcctac cgcccatttg cgtcaatggg  11340
gcggagttgt tacgacattt tggaaagtcc cgttgatttt ggtgccaaaa caaactccca  11400
ttgacgtcaa tggggtggag acttggaaat ccccgtgagt caaaccgcta tccacgccca  11460
ttgatgtact gccaaaaccg catcaccatg gtaatagcga tgactaatac gtagatgtac  11520
tgccaagtag gaaagtccca taaggtcatg tactgggcat aatgccaggc gggccattta  11580
ccgtcattga cgtcaatagg gggcgtactt ggcatatgat acacttgatg tactgccaag  11640
tgggcagttt accgtaaata gtccacccat tgacgtcaat ggaaagtccc tattggcgtt  11700
actatgggaa catacgtcat tattgacgtc aatgggcggg ggtcgttggg cggtcagcca  11760
ggcgggccat ttaccgtaag ttatgtaacg cggaactcca tatatgggct atgaactaat  11820
gaccccgtaa ttgattacta ttaataacta gtcaataatc aatgtcaacg cgtatatctg  11880
gcccgtacat cggtaactag tcggaccggc ccgggccacc ggtgctcgaa gcttggatcg  11940
atccagacat gataagatac attgatgagt ttggacaaac cacaactaga atgcagtgaa  12000
aaaaatgctt tatttgtgaa atttgtgatg ctattgcttt atttgtaacc attataagct  12060
gcaataaaca agttaacaac aacaattgca ttcattttat gtttcaggtt cagggggagg  12120
tgtgggaggt tttttaaagc aagtaaaacc tctacaaatg tggtatggct gattatgatc  12180
tctagtcaag                                                         12190
```

```
<210> SEQ ID NO 7
<211> LENGTH: 12225
<212> TYPE: DNA
<213> ORGANISM: Artificial sequence
<220> FEATURE:
<223> OTHER INFORMATION: pAIGFRV3 plasmid

<400> SEQUENCE: 7

gcactataca tcaaatattc cttattaacc cctttacaaa ttaaaaagct aaaggtacac     60
aatttttgag catagttatt aatagcagac actctatgcc tgtgtggagt aagaaaaaac    120
agtatgttat gattataact gttatgccta cttataaagg ttacagaata tttttccata    180
```

```
attttcttgt atagcagtgc agctttttcc tttgtggtgt aaatagcaaa gcaagcaaga    240
gttctattac taaacacagc atgactcaaa aaacttagca attctgaagg aaagtccttg    300
gggtcttcta cctttctctt ctttttgga ggagtagaat gttgagagtc agcagtagcc    360
tcatcatcac tagatggcat ttcttctgag caaaacaggt tttcctcatt aaaggcattc    420
caccactgct cccattcatc agttccatag gttggaatct aaaatacaca aacaattaga    480
atcagtagtt taacacatta tacacttaaa aattttatat ttaccttaga gctttaaatc    540
tctgtaggta gtttgtccaa ttatgtcaca ccacagaagt aaggttcctt cacaaagatc    600
gatctaaagc cagcaaaagt cccatggtct tataaaaatg catagcttta ggaggggagc    660
agagaacttg aaagcatctt cctgttagtc tttcttctcg tagacttcaa acttatactt    720
gatgcctttt tcctcctgga cctcagagag gacgcctggg tattctggga gaagtttata    780
tttccccaaa tcaatttctg ggaaaaacgt gtcactttca aattcctgca tgatccttgt    840
cacaaagagt ctgaggtggc ctggttgatt catggcttcc tggtaaacag aactgcctcc    900
gactatccaa accatgtcta ctttacttgc caattccggt tgttcaataa gtcttaaggc    960
atcatccaaa cttttggcaa gaaaatgagc tcctcgtggt ggttctttga gttctctact   1020
gagaactata ttaattctgt cctttaaagg tcgattcttc tcaggaatgg agaaccaggt   1080
tttcctaccc ataatcacca gattctgttt accttccact gaagaggttg tggtcattct   1140
ttggaagtac ttgaactcgt tcctgagcgg aggccagggt aggtctccgt tcttgccaat   1200
ccccatattt tgggacacgg cgacgatgca gttcaatggt cgaaccatga tggcagcggg   1260
gataaaatcc taccagcctt cacgctagga ttgccgtcaa gtttggcgcg aaatcgcagc   1320
cctgagctgt cccccccccc aagctcagat ctgagcttgg tccctatggt gagtccgttc   1380
cgctcttgtg atgatagcca gacaagaaag agacaataca agacaaacac caaatagtag   1440
aaatagagac aagggtcact tatccgaggg tccctgttcg ggcgccagct gccgcagtcg   1500
gccgacctga gggtcgccgg ggtctgcggg gggaccctct ggaaagtgaa ggataagtga   1560
cgagcggaga cgggatggcg aacagacaca aacacacaag aggtgaatgt taggactgtt   1620
gcaagtttac tcaaaaaatc agcactcttt tatatcttgg tttacataag catttacata   1680
agatttggat aaattccaaa agaacatagg aaaatagaac actcagagct cagatcagaa   1740
cctttgatac caaaccaagt caggaaacca cttgtctcac atcctcgttt taagaacagt   1800
ttgtaaccaa aaacttactt aagccctggg aaccgcaagg ttgggccaat aaaggctatt   1860
cataataact catgccatga gtttttgcag aataatgttc tattagtcca gccactgtcc   1920
cctccttggt atggaaaatc tttccccaaa agtgcattcc tgttcctaga taaatataat   1980
catgtacctg ttgtttcatg tcgtcttttt cttcttgaga caacatacac caaggaggtc   2040
tagctctggc gagtctttca cgaaaaggga gggatctata taacacttta tagccattga   2100
ctgtaaccca cctatcccaa tttaagtcat atcttcctgt atatggtaag ggggcatctg   2160
ttggtctgta gatgtaaggt cccctataag tccctggttg ccaccacctg tctcctattt   2220
tgacaaaaac actctttttt ccctttttta cttctaggcc tgtggtcaat agtccttgca   2280
cctgttcttc aattgaggtt gagcgtctct ttctattttc tattcccatt tctaacttct   2340
gaatttgagt aaaaatagta ctaaaagata atgattcatt tcttaacata gtaactaata   2400
atctacctat tggattggtc ttattggtaa aaatataatt tttagcaagc attcttattt   2460
ctatttctga aggacaaaat cgatgcggct tgtaagagga agttggctgt ggtccttgcc   2520
tcaggaggaa ggtcgagttc tccgaattgt ttagattgta atcttgcaca gaagagctat   2580
```

-continued

```
taaaagagtc aagggtgaga gccctgcgag cacgaaccgc aacttccccc aatagcccca   2640
ggcaaagcag agctatgcca agtttgcagc agagaatgaa tatgtctttg tctgatgggc   2700
tcatccgttt gtgcgcagac gggtcgtcct tggtgggaaa caaccccttg gctgcttctc   2760
ccctaggtgt aggacactct cgggagttca accatttctg cccaagctca gatctgagct   2820
ttaatgcggt agtttatcac agttaaattg ctaacgcagt caggcaccgt gtatgaaatc   2880
taacaatgcg ctcatcgtca tcctcggcac cgtcaccctg gatgctgtag gcataggctt   2940
ggttatgccg gtactgccgg gcctcttgcg ggatatcgtc cattccgaca gcatcgccag   3000
tcactatggc gtgctgctag cgctcttccg cttcctcgct cactgactcg ctgcgctcgg   3060
tcgttcggct gcggcgagcg gtatcagctc actcaaaggc ggtaatacgg ttatccacag   3120
aatcagggga taacgcagga aagaacatgt gagcaaaagg ccagcaaaag gccaggaacc   3180
gtaaaaaggc cgcgttgctg gcgtttttcc ataggctccg cccccctgac gagcatcaca   3240
aaaatcgacg ctcaagtcag aggtggcgaa acccgacagg actataaaga taccaggcgt   3300
ttccccctgg aagctccctc gtgcgctctc ctgttccgac cctgccgctt accggatacc   3360
tgtccgcctt tctcccttcg ggaagcgtgg cgctttctca tagctcacgc tgtaggtatc   3420
tcagttcggt gtaggtcgtt cgctccaagc tgggctgtgt gcacgaaccc cccgttcagc   3480
ccgaccgctg cgccttatcc ggtaactatc gtcttgagtc caacccggta agacacgact   3540
tatcgccact ggcagcagcc actggtaaca ggattagcag agcgaggtat gtaggcggtg   3600
ctacagagtt cttgaagtgg tggcctaact acggctacac tagaaggaca gtatttggta   3660
tctgcgctct gctgaagcca gttaccttcg gaaaaagagt tggtagctct tgatccggca   3720
aacaaaccac cgctggtagc ggtggttttt ttgtttgcaa gcagcagatt acgcgcagaa   3780
aaaaaggatc tcaagaagat cctttgatct tttctacggg gtctgacgct cagtggaacg   3840
aaaactcacg ttaagggatt ttggtcatga gattatcaaa aaggatcttc acctagatcc   3900
ttttaaatta aaaatgaagt tttaaatcaa tctaaagtat atatgagtaa acttggtctg   3960
acagttacca atgcttaatc agtgaggcac ctatctcagc gatctgtcta tttcgttcat   4020
ccatagttgc ctgactcccc gtcgtgtaga taactacgat acgggagggc ttaccatctg   4080
gccccagtgc tgcaatgata ccgcgagacc cacgctcacc ggctccagat ttatcagcaa   4140
taaaccagcc agccggaagg gccgagcgca gaagtggtcc tgcaacttta tccgcctcca   4200
tccagtctat taattgttgc cgggaagcta gagtaagtag ttcgccagtt aatagtttgc   4260
gcaacgttgt tgccattgct acaggcatcg tggtgtcacg ctcgtcgttt ggtatggctt   4320
cattcagctc cggttcccaa cgatcaaggc gagttacatg atcccccatg ttgtgcaaaa   4380
aagcggttag ctccttcggt cctccgatcg ttgtcagaag taagttggcc gcagtgttat   4440
cactcatggt tatggcagca ctgcataatt ctcttactgt catgccatcc gtaagatgct   4500
tttctgtgac tggtgagtac tcaaccaagt cattctgaga atagtgtatg cggcgaccga   4560
gttgctcttg cccggcgtca acacgggata ataccgcgcc acatagcaga actttaaaag   4620
tgctcatcat tggaaaacgt tcttcggggc gaaaactctc aaggatctta ccgctgttga   4680
gatccagttc gatgtaaccc actcgtgcac ccaactgatc ttcagcatct tttactttca   4740
ccagcgtttc tgggtgagca aaaacaggaa ggcaaaatgc cgcaaaaaag ggaataaggg   4800
cgacacggaa atgttgaata ctcatactct tcctttttca atattattga agcatttatc   4860
agggttattg tctcatgagc ggatacatat ttgaatgtat ttagaaaaat aaacaaatag   4920
gggttccgcg cacatttccc cgaaaagtgc cacctgacgt ctaagagacc attattatca   4980
```

tgacattaac ctataaaaat aggcgtatca cgaggccctt tcgtcttcaa gaattgtcta 5040
gaggcgcgct ggccggcctg tgcgaacgcc agcaagacgt agcccagcgc gtcggccgcc 5100
atgccctgct tcatccccgt ggcccgttgc tcgcgtttgc tggcggtgtc cccggaagaa 5160
atatatttgc atgtctttag ttctatgatg acacaaaccc cgcccagcgt cttgtcattg 5220
gcgaattcga acacgcagat gcagtcgggg cggcgcggtc ccaggtccac ttcgcatatt 5280
aaggtgacgc gtgtggcctc gaacaccgag cgaccctgca gcgacccgct taacagcgtc 5340
aacagcgtgc cgcagatccc gggcaatgag atatgaaaaa gcctgaactc accgcgacgt 5400
ctgtcgagaa gtttctgatc gaaaagttcg acagcgtctc cgacctgatg cagctctcgg 5460
agggcgaaga atctcgtgct ttcagcttcg atgtaggagg gcgtggatat gtcctgcggg 5520
taaatagctg cgccgatggt ttctacaaag atcgttatgt ttatcggcac tttgcatcgg 5580
ccgcgctccc gattccggaa gtgcttgaca ttggggaatt cagcgagagc ctgacctatt 5640
gcatctcccg ccgtgcacag ggtgtcacgt tgcaagacct gcctgaaacc gaactgcccg 5700
ctgttctgca gccggtcgcg gaggccatgg atgcgatcgc tgcggccgat cttagccaga 5760
cgagcgggtt cggcccattc ggaccgcaag gaatcggtca atacactaca tggcgtgatt 5820
tcatatgcgc gattgctgat ccccatgtgt atcactggca aactgtgatg gacgacaccg 5880
tcagtgcgtc cgtcgcgcag gctctcgatg agctgatgct ttgggccgag gactgccccg 5940
aagtccggca cctcgtgcac gcggatttcg gctccaacaa tgtcctgacg gacaatggcc 6000
gcataacagc ggtcattgac tggagcgagg cgatgttcgg ggattcccaa tacgaggtcg 6060
ccaacatctt cttctggagg ccgtggttgg cttgtatgga gcagcagacg cgctacttcg 6120
agcggaggca tccggagctt gcaggatcgc cgcggctccg ggcgtatatg ctccgcattg 6180
gtcttgacca actctatcag agcttggttg acggcaattt cgatgatgca gcttgggcgc 6240
agggtcgatg cgacgcaatc gtccgatccg gagccgggac tgtcgggcgt acacaaatcg 6300
cccgcagaag cgcggccgtc tggaccgatg gctgtgtaga agtactcgcc gatagtggaa 6360
accgacgccc cagcactcgt ccgagggcaa aggaataggg gagatggggg aggctaactg 6420
aaacacggaa ggagacaata ccggaaggaa cccgcgctat gacggcaata aaaagacaga 6480
ataaaacgca cgggtgttgg gtcgtttgtt cataaacgcg gggttcggtc ccagggctgg 6540
cactctgtcg ataccccacc gagaccccat tggggccaat acgcccgcgt ttcttccttt 6600
tccccacccc acccccaag ttcgggtgaa ggcccagggc tcgcagccaa cgtcggggcg 6660
gcaggccctg ccatagccac tggccccgtg ggttagggac ggggtccccc atggggaatg 6720
gtttatggtt cgtgggggtt attattttgg gcgttgcgtg gggtctggtc cacgactgga 6780
ctgagcagac agacccatgg tttttggatg gcctgggcat ggaccgcatg tactggcgcg 6840
acacgaacac cgggcgtctg tggctgccaa acacccccga cccccaaaaa ccaccgcgcg 6900
gatttctggc gcccagtggc acaggccggc ctgtacatga tcaacgcgtg agctctctag 6960
agcttgtcga cagatccccc tcttcatttc tttatgtttt aaatgcactg acctcccaca 7020
ttcccttttt agtaaaatat tcagaaataa tttaaataca tcattgcaat gaaaataaat 7080
gtttttattt aggcagaatc cagatgctca aggcccttca taatatcccc cagtttagta 7140
gttggactta gggaacaaag gaacctttaa tagaaattgg acagcaagaa agcgaggggg 7200
atctggatcc tccggacccg gggagcgggg gcttgccggc cctggcactc atttacccag 7260
agacagggag aggctcttct gtgtgtagtg gttgtgcaga gcctcatgca tcacggagca 7320
tgagaagaca ttcccctcct gccacctgct cttgtccacg gttagcctgc tgtagaggaa 7380

```
gaaggagccg tcggagtcca gcacgggagg cgtggtcttg tagttgttct ccggctgccc   7440
attgctctcc cactccacgg cgatgtcgct ggggtagaag cctttgacca ggcaggtcag   7500
gctgacctgg ttcttggtca tctcctcctg ggatgggggc agggtgtaca cctgtggctc   7560
tcggggctgc cctgtaggga cagaggttgg cacagcggtc actcccaggg cagagggtgg   7620
gccgagctga cctctgtcca tgtggccctc gcaccccgtg ggtcccacct ttggctttgg   7680
agatggtttt ctcgatggag gacgggaggc ctttgttgga gaccttgcac ttgtactcct   7740
tgccgttcag ccagtcctgg tgcaggacgg tgaggacgct gaccacacgg tacgtgctgt   7800
tgaactgctc ctcccgcggc tttgtcttgg cattatgcac ctccacgcca tccacgtacc   7860
agttgaactg gacctcgggg tcttcctggc tcacgtccac caccacgcac gtgacctcag   7920
gggtccggga gatcatgaga gtgtccttgg gttttggggg gaacaggaag actgatggtc   7980
cccccaggaa ctcaggtgct gaggaagaga tggaggtgga tgcgtcagca cccggctggg   8040
gcctgtccct ggatgcaggc tactctaggg cacctgtccc gccttgagct ggagggcgag   8100
gcctgggttg gcttacctgg gcatgatggg catgggggac catatttgga ctctgcagag   8160
agaagattgg gagttactca gatctgggag gagagaaggt gtctgagctg agggagtgga   8220
gagtttggcc tttggggtgg gcttaggtca ggggcagggt cctcccggat atggctcttg   8280
gcaggtctga gcgcagcacc tgcccctgta tgcgcagggc ctggggtagg ggcatccagc   8340
ctgtggctgc ccggagcctg gtggaaaaat ccagaagacc ctctccctga gcatgagtgg   8400
ggtggtcaga ggcctccggg tgaggagaca gatggggcat gccttgctgc cctgggctgg   8460
ggctgcacag ccggggtgcg tccaggcagg agggctgagc ctggcttcca gcagacaccc   8520
tccctccctg tgctggcctc tcaccaactc tcttgtccac cttggtgttg ctgggcttgt   8580
gatctacgtt gcaggtgtag gtcttcgtgc ccaagctgct ggagggcacg gtcaccacgc   8640
tgctgaggga gtagagtcct gaggactgta ggacagccgg gaaggtgtgc acgccgctgg   8700
tcagggcgcc tgagttccac gacaccgtca ccggttcggg gaagtagtcc ttgaccaggc   8760
agcccagggc ggctgtgctc tcggaggtgc tcctggagca gggcgccagg gggaagacgg   8820
atgggccctt ggtggaagct gaggagacgg tgaccgtggt cccttggccc cagacgtcca   8880
taccgtagta gaagttcccc agtcttgcac agtaatacac agccatgtcc tcggctctca   8940
ggctgttcat ttgaagatac aaggagttct tggcattgtc tctggagatg gtgaatcggc   9000
ccttcacgga gtctgcatag tatgtggcac cacgagtatc aataactgat atccactcca   9060
gaccttttcc tggagcctgg cgaacccagt gcatagcaaa gctactgaag gtgaatccag   9120
aggctgcaca ggagagtctc agggaccccc caggatgtac caagcctccc ccagactgca   9180
ccagctgaac ctcacactgg acacctttta atatagcaac aaggaaaacc cagctcagcc   9240
caaactccat aagggcgaat tccaccacac tggactagtg gatccgagct cggtaccaag   9300
cttaagttta aacgctagcc agcttgggtc tccctatagt gagtcgtatt aatttcgata   9360
agccagtaag cagtgggttc tctagttagc cagagagctc tgcttatata gacctcccac   9420
cgtacacgcc taccgcccat ttgcgtcaat ggggcggagt tgttacgaca ttttggaaag   9480
tcccgttgat tttggtgcca aaacaaactc ccattgacgt caatggggtg gagacttgga   9540
aatccccgtg agtcaaaccg ctatccacgc ccattgatgt actgccaaaa ccgcatcacc   9600
atggtaatag cgatgactaa tacgtagatg tactgccaag taggaaagtc ccataaggtc   9660
atgtactggg cataatgcca ggcgggccat ttaccgtcat tgacgtcaat agggggcgta   9720
cttggcatat gatacacttg atgtactgcc aagtgggcag tttaccgtaa atagtccacc   9780
```

-continued

```
cattgacgtc aatggaaagt ccctattggc gttactatgg gaacatacgt cattattgac   9840
gtcaatgggc gggggtcgtt gggcggtcag ccaggcgggc catttaccgt aagttatgta   9900
acgcggaact ccatatatgg gctatgaact aatgaccccg taattgatta ctattaataa   9960
ctagtcaata atcaatgtca acgcgtatat ctggcccgta catcggtagc tgagggttta  10020
aacggcgcgc ggccggccgg taccacgcgt tggccacata tggcggccgc tcgcgattaa  10080
ttaatcgcga tggccacata tggagctctc tagagcttgt cgacagatcc ccctcttcat  10140
ttctttatgt tttaaatgca ctgacctccc acattccctt tttagtaaaa tattcagaaa  10200
taatttaaat acatcattgc aatgaaaata aatgtttttt attaggcaga atccagatgc  10260
tcaaggccct tcataatatc cccagttta gtagttggac ttagggaaca aaggaacctt  10320
taatagaaat tggacagcaa gaaagcgagg gggatctgga tcctccggag ggccccttct  10380
ccctctaaca ctctcccctg ttgaagctct ttgtgacggg cgagctcagg ccctgatggg  10440
tgacttcgca ggcgtagact ttgtgtttct cgtagtctgc tttgctcagc gtcagggtgc  10500
tgctgaggct gtaggtgctg tccttgctgt cctgctctgt gacactctcc tgggagttac  10560
ccgattggag ggcgttatcc accttccact gtactttggc ctctctggga tagaagttat  10620
tcagcaggca cacaacagag gcagttccag atttcaactg ctcatcagat ggcgggaaga  10680
tgaagacaga tggtgcagcc acagttcgtt tgatctccac cttggtccct ccgccgaaag  10740
tgtgaggtaa acgactactc tgatgacagt aatacgctgc agcatcttca gcttccaggc  10800
tattgatggt gagggtgaaa tctgtcccag atccactgcc actgaacctc gaggggaccc  10860
ctgagaggga ctgggaagca tacttgatga ggagctttgg agactgatct ggtttctgct  10920
ggtaccagtg taagctacta ccaatgctct gactggcccg gcaggtgatg gtgactttct  10980
cctttggagt cacagactga aagtctggaa cctgagtcag cacaatttca cccctggagg  11040
ctggaaccca gagcagcaga aacccaatga gttgtgatgg cgacatcttc ctgccttgac  11100
ttgtcagttt tgctcatgcc cccgcgtact ctgcgttgtt accactgctt gccctatagt  11160
gagtcgtatt agaagggcga attccaccac actggactag tggatccgag ctcggtacca  11220
agcttaagtt taaacgctag ccagcttggg tctccctata gtgagtcgta ttaatttcga  11280
taagccagta agcagtgggt tctctagtta gccagagagc tctgcttata tagacctccc  11340
accgtacacg cctaccgccc atttgcgtca atggggcgga gttgttacga cattttggaa  11400
agtcccgttg attttggtgc caaaacaaac tcccattgac gtcaatgggg tggagacttg  11460
gaaatccccg tgagtcaaac cgctatccac gcccattgat gtactgccaa aaccgcatca  11520
ccatggtaat agcgatgact aatacgtaga tgtactgcca agtaggaaag tcccataagg  11580
tcatgtactg ggcataatgc caggcgggcc atttaccgtc attgacgtca atagggggcg  11640
tacttggcat atgatacact tgatgtactg ccaagtgggc agtttaccgt aaatagtcca  11700
cccattgacg tcaatggaaa gtccctattg gcgttactat gggaacatac gtcattattg  11760
acgtcaatgg gcgggggtcg ttgggcggtc agccaggcgg gccatttacc gtaagttatg  11820
taacgcggaa ctccatatat gggctatgaa ctaatgaccc cgtaattgat tactattaat  11880
aactagtcaa taatcaatgt caacgcgtat atctggcccg tacatcggta actagtcgga  11940
ccggcccggg ccaccggtgc tcgaagcttg gatcgatcca gacatgataa gatacattga  12000
tgagtttgga caaaccacaa ctagaatgca gtgaaaaaaa tgctttattt gtgaaatttg  12060
tgatgctatt gctttatttg taaccattat aagctgcaat aaacaagtta acaacaacaa  12120
ttgcattcat tttatgtttc aggttcaggg ggaggtgtgg gaggtttttt aaagcaagta  12180
```

aaacctctac aaatgtggta tggctgatta tgatctctag tcaag 12225

<210> SEQ ID NO 8
<211> LENGTH: 13079
<212> TYPE: DNA
<213> ORGANISM: Artificial sequence
<220> FEATURE:
<223> OTHER INFORMATION: pAIG1FR(-)IL2LS plasmid

<400> SEQUENCE: 8
gcactataca tcaaatattc cttattaacc cctttacaaa ttaaaaagct aaaggtacac 60
aatttttgag catagttatt aatagcagac actctatgcc tgtgtggagt aagaaaaaac 120
agtatgttat gattataact gttatgccta cttataaagg ttacagaata tttttccata 180
attttcttgt atagcagtgc agctttttcc tttgtggtgt aaatagcaaa gcaagcaaga 240
gttctattac taaacacagc atgactcaaa aaacttagca attctgaagg aaagtccttg 300
gggtcttcta cctttctctt cttttttgga ggagtagaat gttgagagtc agcagtagcc 360
tcatcatcac tagatggcat ttcttctgag caaaacaggt tttcctcatt aaaggcattc 420
caccactgct cccattcatc agttccatag gttggaatct aaaatacaca aacaattaga 480
atcagtagtt taacacatta tacacttaaa aattttatat ttaccttaga gctttaaatc 540
tctgtaggta gtttgtccaa ttatgtcaca ccacagaagt aaggttcctt cacaaagatc 600
gatctaaagc cagcaaaagt cccatggtct tataaaaatg catagcttta ggaggggagc 660
agagaacttg aaagcatctt cctgttagtc tttcttctcg tagacttcaa acttatactt 720
gatgcctttt tcctcctgga cctcagagag gacgcctggg tattctggga gaagtttata 780
tttccccaaa tcaatttctg ggaaaaacgt gtcactttca aattcctgca tgatccttgt 840
cacaaagagt ctgaggtggc ctggttgatt catggcttcc tggtaaacag aactgcctcc 900
gactatccaa accatgtcta ctttacttgc caattccggt tgttcaataa gtcttaaggc 960
atcatccaaa cttttggcaa gaaaatgagc tcctcgtggt ggttctttga gttctctact 1020
gagaactata ttaattctgt cctttaaagg tcgattcttc tcaggaatgg agaaccaggt 1080
tttcctaccc ataatcacca gattctgttt accttccact gaagaggttg tggtcattct 1140
ttggaagtac ttgaactcgt tcctgagcgg aggccagggt aggtctccgt tcttgccaat 1200
ccccatattt tgggacacgg cgacgatgca gttcaatggt cgaaccatga tggcagcggg 1260
gataaaatcc taccagcctt cacgctagga ttgccgtcaa gtttggcgcg aaatcgcagc 1320
cctgagctgt cccccccccc aagctcagat ctgagcttgg tccctatggt gagtccgttc 1380
cgctcttgtg atgatagcca gacaagaaag agacaataca agacaaacac caaatagtag 1440
aaatagagac aagggtcact tatccgaggg tccctgttcg ggcgccagct gccgcagtcg 1500
gccgacctga gggtcgccgg ggtctgcggg gggaccctct ggaaagtgaa ggataagtga 1560
cgagcggaga cgggatggcg aacagacaca aacacacaag aggtgaatgt taggactgtt 1620
gcaagtttac tcaaaaaatc agcactcttt tatatcttgg tttacataag catttacata 1680
agatttggat aaattccaaa agaacatagg aaaatagaac actcagagct cagatcagaa 1740
cctttgatac caaaccaagt caggaaacca cttgtctcac atcctcgttt taagaacagt 1800
ttgtaaccaa aaacttactt aagccctggg aaccgcaagg ttgggccaat aaaggctatt 1860
cataataact catgccatga gtttttgcag aataatgttc tattagtcca gccactgtcc 1920
cctccttggt atggaaaatc tttccccaaa agtgcattcc tgttcctaga taaatataat 1980
catgtacctg ttgtttcatg tcgtcttttt cttcttgaga caacatacac caaggaggtc 2040

-continued

```
tagctctggc gagtctttca cgaaaaggga gggatctata taacacttta tagccattga   2100
ctgtaaccca cctatcccaa tttaagtcat atcttcctgt atatggtaag gggcatctg    2160
ttggtctgta gatgtaaggt cccctataag tccctggttg ccaccacctg tctcctattt   2220
tgacaaaaac actctttttt cccttttttta cttctaggcc tgtggtcaat agtccttgca  2280
cctgttcttc aattgaggtt gagcgtctct ttctattttc tattcccatt tctaacttct   2340
gaatttgagt aaaaatagta ctaaaagata atgattcatt tcttaacata gtaactaata   2400
atctacctat tggattggtc ttattggtaa aaatataatt tttagcaagc attcttattt   2460
ctatttctga aggacaaaat cgatgcggct tgtaagagga agttggctgt ggtccttgcc   2520
tcaggaggaa ggtcgagttc tccgaattgt ttagattgta atcttgcaca gaagagctat   2580
taaaagagtc aagggtgaga gccctgcgag cacgaaccgc aacttccccc aatagcccca   2640
ggcaaagcag agctatgcca agtttgcagc agagaatgaa tatgtctttg tctgatgggc   2700
tcatccgttt gtgcgcagac gggtcgtcct tggtgggaaa caaccccttg gctgcttctc   2760
ccctaggtgt aggacactct cgggagttca accatttctg cccaagctca gatctgagct   2820
ttaatgcggt agtttatcac agttaaattg ctaacgcagt caggcaccgt gtatgaaatc   2880
taacaatgcg ctcatcgtca tcctcggcac cgtcaccctg gatgctgtag gcataggctt   2940
ggttatgccg gtactgccgg gcctcttgcg ggatatcgtc cattccgaca gcatcgccag   3000
tcactatggc gtgctgctag cgctcttccg cttcctcgct cactgactcg ctgcgctcgg   3060
tcgttcggct gcggcgagcg gtatcagctc actcaaaggc ggtaatacgg ttatccacag   3120
aatcagggga taacgcagga aagaacatgt gagcaaaagg ccagcaaaag gccaggaacc   3180
gtaaaaaggc cgcgttgctg gcgtttttcc ataggctccg cccccctgac gagcatcaca   3240
aaaatcgacg ctcaagtcag aggtggcgaa acccgacagg actataaaga taccaggcgt   3300
ttccccctgg aagctccctc gtgcgctctc ctgttccgac cctgccgctt accggatacc   3360
tgtccgcctt tctcccttcg ggaagcgtgg cgctttctca tagctcacgc tgtaggtatc   3420
tcagttcggt gtaggtcgtt cgctccaagc tgggctgtgt gcacgaaccc cccgttcagc   3480
ccgaccgctg cgccttatcc ggtaactatc gtcttgagtc caacccggta agacacgact   3540
tatcgccact ggcagcagcc actggtaaca ggattagcag agcgaggtat gtaggcggtg   3600
ctacagagtt cttgaagtgg tggcctaact acggctacac tagaaggaca gtatttggta   3660
tctgcgctct gctgaagcca gttaccttcg gaaaaagagt tggtagctct tgatccggca   3720
aacaaaccac cgctggtagc ggtggttttt ttgtttgcaa gcagcagatt acgcgcagaa   3780
aaaaaggatc tcaagaagat cctttgatct tttctacggg gtctgacgct cagtggaacg   3840
aaaactcacg ttaagggatt ttggtcatga gattatcaaa aaggatcttc acctagatcc   3900
ttttaaatta aaaatgaagt tttaaatcaa tctaaagtat atatgagtaa acttggtctg   3960
acagttacca atgcttaatc agtgaggcac ctatctcagc gatctgtcta tttcgttcat   4020
ccatagttgc ctgactcccc gtcgtgtaga taactacgat acgggagggc ttaccatctg   4080
gccccagtgc tgcaatgata ccgcgagacc cacgctcacc ggctccagat ttatcagcaa   4140
taaaccagcc agccggaagg gccgagcgca gaagtggtcc tgcaacttta tccgcctcca   4200
tccagtctat taattgttgc cgggaagcta gagtaagtag ttcgccagtt aatagtttgc   4260
gcaacgttgt tgccattgct acaggcatcg tggtgtcacg ctcgtcgttt ggtatggctt   4320
cattcagctc cggttcccaa cgatcaaggc gagttacatg atcccccatg ttgtgcaaaa   4380
aagcggttag ctccttcggt cctccgatcg ttgtcagaag taagttggcc gcagtgttat   4440
```

-continued

```
cactcatggt tatggcagca ctgcataatt ctcttactgt catgccatcc gtaagatgct   4500
tttctgtgac tggtgagtac tcaaccaagt cattctgaga atagtgtatg cggcgaccga   4560
gttgctcttg cccggcgtca acacgggata ataccgcgcc acatagcaga actttaaaag   4620
tgctcatcat tggaaaacgt tcttcggggc gaaaactctc aaggatctta ccgctgttga   4680
gatccagttc gatgtaaccc actcgtgcac ccaactgatc ttcagcatct tttactttca   4740
ccagcgtttc tgggtgagca aaaacaggaa ggcaaaatgc cgcaaaaaag ggaataaggg   4800
cgacacggaa atgttgaata ctcatactct tcctttttca atattattga agcatttatc   4860
agggttattg tctcatgagc ggatacatat ttgaatgtat ttagaaaaat aaacaaatag   4920
gggttccgcg cacatttccc cgaaaagtgc cacctgacgt ctaagagacc attattatca   4980
tgacattaac ctataaaaat aggcgtatca cgaggccctt tcgtcttcaa gaattgtcta   5040
gaggcgcgct ggccggcctg tgcgaacgcc agcaagacgt agcccagcgc gtcggccgcc   5100
atgccctgct tcatccccgt ggcccgttgc tcgcgtttgc tggcggtgtc cccggaagaa   5160
atatatttgc atgtctttag ttctatgatg acacaaaccc cgcccagcgt cttgtcattg   5220
gcgaattcga acacgcagat gcagtcgggg cggcgcggtc ccaggtccac ttcgcatatt   5280
aaggtgacgc gtgtggcctc gaacaccgag cgaccctgca gcgacccgct taacagcgtc   5340
aacagcgtgc cgcagatccc gggcaatgag atatgaaaaa gcctgaactc accgcgacgt   5400
ctgtcgagaa gtttctgatc gaaaagttcg acagcgtctc cgacctgatg cagctctcgg   5460
agggcgaaga atctcgtgct ttcagcttcg atgtaggagg gcgtggatat gtcctgcggg   5520
taaatagctg cgccgatggt ttctacaaag atcgttatgt ttatcggcac tttgcatcgg   5580
ccgcgctccc gattccggaa gtgcttgaca ttggggaatt cagcgagagc ctgacctatt   5640
gcatctcccg ccgtgcacag ggtgtcacgt tgcaagacct gcctgaaacc gaactgcccg   5700
ctgttctgca gccggtcgcg gaggccatgg atgcgatcgc tgcggccgat cttagccaga   5760
cgagcgggtt cggcccattc ggaccgcaag gaatcggtca atacactaca tggcgtgatt   5820
tcatatgcgc gattgctgat ccccatgtgt atcactggca aactgtgatg gacgacaccg   5880
tcagtgcgtc cgtcgcgcag gctctcgatg agctgatgct ttgggccgag gactgccccg   5940
aagtccggca cctcgtgcac gcggatttcg gctccaacaa tgtcctgacg gacaatggcc   6000
gcataacagc ggtcattgac tggagcgagg cgatgttcgg ggattcccaa tacgaggtcg   6060
ccaacatctt cttctggagg ccgtggttgg cttgtatgga gcagcagacg cgctacttcg   6120
agcggaggca tccggagctt gcaggatcgc cgcggctccg ggcgtatatg ctccgcattg   6180
gtcttgacca actctatcag agcttggttg acggcaattt cgatgatgca gcttgggcgc   6240
agggtcgatg cgacgcaatc gtccgatccg gagccgggac tgtcgggcgt acacaaatcg   6300
cccgcagaag cgcggccgtc tggaccgatg gctgtgtaga agtactcgcc gatagtggaa   6360
accgacgccc cagcactcgt ccgagggcaa aggaataggg gagatggggg aggctaactg   6420
aaacacggaa ggagacaata ccggaaggaa cccgcgctat gacggcaata aaaagacaga   6480
ataaaacgca cgggtgttgg gtcgtttgtt cataaacgcg gggttcggtc ccagggctgg   6540
cactctgtcg ataccccacc gagaccccat tggggccaat acgcccgcgt ttcttccttt   6600
tccccacccc accccccaag ttcgggtgaa ggcccagggc tcgcagccaa cgtcggggcg   6660
gcaggccctg ccatagccac tggccccgtg ggttagggac ggggtccccc atggggaatg   6720
gtttatggtt cgtgggggtt attattttgg gcgttgcgtg gggtctggtc cacgactgga   6780
ctgagcagac agacccatgg tttttggatg gcctgggcat ggaccgcatg tactggcgcg   6840
```

acacgaacac cgggcgtctg tggctgccaa acaccccga cccccaaaaa ccaccgcgcg 6900
gatttctggc gcccagtggc acaggccggc ctgtacatga tcaacgcgtg agctctctag 6960
agcttgtcga cagatccccc tcttcatttc tttatgtttt aaatgcactg acctcccaca 7020
ttcccttttt agtaaaatat tcagaaataa tttaaataca tcattgcaat gaaaataaat 7080
gttttttatt aggcagaatc cagatgctca aggcccttca taatatcccc cagtttagta 7140
gttggactta gggaacaaag gaacctttaa tagaaattgg acagcaagaa agcgaggggg 7200
atctggatcc tccggacccg tatctagaat catcgattca tttacccgga gacagggaga 7260
ggctcttctg cgtgtagtgg ttgtgcagag cctcatgcat cacggagcat gagaagacgt 7320
tcccctgctg ccacctgctc ttgtccacgg tgagcttgct gtagaggaag aaggagccgt 7380
cggagtccag cacgggaggc gtggtcttgt agttgttctc cggctgccca ttgctctccc 7440
actccacggc gatgtcgctg ggatagaagc ctttgaccag gcaggtcagg ctgacctggt 7500
tcttggtcag ctcatcccgg gatgggggca gggtgtacac ctgtggttct cggggctgcc 7560
ctttggcttt ggagatggtt ttctcgatgg gggctgggag ggctttgttg gagaccttgc 7620
acttgtactc cttgccattc agccagtcct ggtgcaggac ggtgaggacg ctgaccacac 7680
ggtacgtgct gttgtactgc tcctcccgcg gctttgtctt ggcattatgc acctccacgc 7740
cgtccacgta ccagttgaac ttgacctcag ggtcttcgtg gctcacgtcc accaccacgc 7800
atgtgacctc aggggtccgg gagatcatga gggtgtcctt gggttttggg gggaagagga 7860
agactgacgg tccccccagg agttcaggtg ctgggcacgg tgggcatgtg tgagttttgt 7920
cacaagattt gggctcaact ttcttgtcca ccttggtgtt gctgggcttg tgattcacgt 7980
tgcagatgta ggtctgggtg cccaagctgc tggagggcac ggtcaccacg ctgctgaggg 8040
agtagagtcc tgaggactgt aggacagccg ggaaggtgtg cacgccgctg gtcagggcgc 8100
ctgagttcca cgacaccgtc accggttcgg ggaagtagtc cttgaccagg cagcccaggg 8160
ccgctgtgcc cccagaggtg ctcttggagg agggtgccag ggggaagacc gatgggccct 8220
tggtggaagc tgaggagacg gtgaccgtgg tcccttggcc ccagacgtcc ataccgtagt 8280
agaagttccc cagtcttgca cagtaataca cagcagtgtc ctcggctctc aggctgttca 8340
tttgaagata caaggagttc ttggcattgt ctctggagat ggtgaatcgg cccttcacgg 8400
agtctgcata gtatgtggca ccacgagtat caataactga tatccactcc agaccttttc 8460
ctggagcctg gcgaacccag tgcatagcaa agctactgaa ggtgaatcca gaggctgcac 8520
aggagagtct cagggacccc ccaggcttta ccaagcctcc cccagactgc accagctgaa 8580
cctcacactg gacacctttt aatatagcaa caaggaaaac ccagctcagc ccaaactcca 8640
taagggcgaa ttccaccaca ctggactagt ggatccgagc tcggtaccaa gcttaagttt 8700
aaacgctagc cagcttgggt ctccctatag tgagtcgtat taatttcgat aagccagtaa 8760
gcagtgggtt ctctagttag ccagagagct ctgcttatat agacctccca ccgtacacgc 8820
ctaccgccca tttgcgtcaa tggggcggag ttgttacgac attttggaaa gtcccgttga 8880
ttttggtgcc aaaacaaact cccattgacg tcaatggggt ggagacttgg aaatccccgt 8940
gagtcaaacc gctatccacg cccattgatg tactgccaaa accgcatcac catggtaata 9000
gcgatgacta atacgtagat gtactgccaa gtaggaaagt cccataaggt catgtactgg 9060
gcataatgcc aggcgggcca tttaccgtca ttgacgtcaa tagggggcgt acttggcata 9120
tgatacactt gatgtactgc caagtgggca gtttaccgta aatagtccac ccattgacgt 9180
caatggaaag tccctattgg cgttactatg ggaacatacg tcattattga cgtcaatggg 9240

-continued

```
cgggggtcgt tgggcggtca gccaggcggg ccatttaccg taagttatgt aacgcggaac   9300
tccatatatg ggctatgaac taatgacccc gtaattgatt actattaata actagtcaat   9360
aatcaatgtc aacgcgtata tctggcccgt acatcggtag ctgagggttt aaacggcgcg   9420
cggccggccg gtaccacgcg ttggccacat atggcggccg ctcgcgatta attaatcgcg   9480
atggccacat atggagctct ctagagcttg tcgacagatc cccctcttca tttctttatg   9540
ttttaaatgc actgacctcc cacattccct ttttagtaaa atattcagaa ataatttaaa   9600
tacatcattg caatgaaaat aaatgttttt tattaggcag aatccagatg ctcaaggccc   9660
ttcataatat cccccagttt agtagttgga cttagggaac aaaggaacct ttaatagaaa   9720
ttggacagca agaaagcgag gggatctgg atcctccgga gggcccctgc aggaattcga   9780
tggccgctag attgttcttc tactcttcct ctgtctccgc tgccaggtga gcccactcag   9840
gaggaggacg ctgatcagca ggaaaacaca gccggccact gctacctggt actctgttgt   9900
aaatatggac gtctccatgg ttgcagccat ttctgtctgt atttgaaaat ctgttgttgt   9960
gacgaggcag gaagtctcac tctcaggacg gccttcgggg cttgcctgag gcttctcttc  10020
acctggaaac tgactggtct ccatttcacc tgtgcatatg agctggggct gggtccacct  10080
tgtcttcccg tgggtcattt tgcagacgct ctcagcagga cctctgtgta gagccctgta  10140
tccctggacg cactgataat aaaccatctg ccccaccacg aaatgataaa ttctctctgt  10200
ggcttcattt tcccatggtg gaggttccct gcagtgacct ggaaggctcg cttggtccac  10260
tggctgcatt ggactttgca tttctgtggt tttcctttct ttctgttctt caggttgagg  10320
tgtcacttgt ttcgttgtgt tccgagtggc agagcttgtg cattgacatt ggttgtccca  10380
ggacgagtgg ctagagtttc ctgtacagag catatagagt gacccgcttt ttattctgcg  10440
gaaacctctc ttgcattcac agttcaacat ggttccttcc ttgtaggcca tggctttgaa  10500
tgtggcgtgt gggatctctg gcgggtcatc gtcacagagc tctgcctggc agccaggcac  10560
catgatgaac gtgagcagtc cccacatcag caggtatgaa tccatggtgg cggcaaccgg  10620
ttatcatcgt gtttttcaaa ggaaaaccac gtccccgtgg ttcgggggc ctagacgttt  10680
tttaacctcg actaaacaca tgtaaagcat gtgcaccgag gccccagatc agatcccata  10740
caatggggta ccttctgggc atccttcagc cccttgttga atacgcttga ggagagccat  10800
ttgactcttt ccacaactat ccaactcaca acgtggcact ggggttgtgc cgcctttgca  10860
ggtgtatctt atacacgtgg cttttggccg cagaggcacc tgtcgccagg tggggggttc  10920
cgctgcctgc aaagggtcgc tacagacgtt gtttgtcttc aagaagcttc cagaggaact  10980
gcttccttca cgacattcaa cagaccttgc attcctttgg cgagaggggga aagaccccta  11040
ggaatgctcg tcaagaagac agggccaggt ttccgggccc tcacattgcc aaaagacggc  11100
aatatggtgg aaaataacat atagacaaac gcacaccggc cttattccaa gcggcttcgg  11160
ccagtaacgt taggggggggg ggagggagag gggcgctcga gactagccgg agggcccctt  11220
ctccctctaa cactctcccc tgttgaagct ctttgtgacg ggcgagctca ggccctgatg  11280
ggtgacttcg caggcgtaga ctttgtgttt ctcgtagtct gctttgctca gcgtcagggt  11340
gctgctgagg ctgtaggtgc tgtccttgct gtcctgctct gtgacactct cctgggagtt  11400
acccgattgg agggcgttat ccaccttcca ctgtactttg gcctctctgg gatagaagtt  11460
attcagcagg cacacaacag aggcagttcc agatttcaac tgctcatcag atggcgggaa  11520
gatgaagaca gatggtgcag ccacagttcg tttgatctcc accttggtcc ctccgccgaa  11580
agtgtgaggt aaacgactac tctgatgaca gtaatacgct gcagcatctt cagcttccag  11640
```

```
gctattgatg gtgagggtga aatctgtccc agatccactg ccactgaacc tcgaggggac  11700
ccctgagagg gactgggaag catacttgat gaggagcttt ggagactgat ctggtttctg  11760
ctggtaccag tgtaagctac taccaatgct ctgactggcc cggcaggtga tggtgacttt  11820
ctcctttgga gtcacagact gaaagtctgg aacctgagtc agcacaattt cacccctgga  11880
ggctggaacc cagagcagca gaaacccaat gagttgtgat ggcgacatct tcctgccttg  11940
acttgtcagt tttgctcatg cccccgcgta ctctgcgttg ttaccactgc ttgccctata  12000
gtgagtcgta ttagaagggc gaattccacc acactggact agtggatccg agctcggtac  12060
caagcttaag tttaaacgct agccagcttg ggtctcccta tagtgagtcg tattaatttc  12120
gataagccag taagcagtgg gttctctagt tagccagaga gctctgctta tatagacctc  12180
ccaccgtaca cgcctaccgc ccatttgcgt caatggggcg gagttgttac gacattttgg  12240
aaagtcccgt tgattttggt gccaaaacaa actcccattg acgtcaatgg ggtggagact  12300
tggaaatccc cgtgagtcaa accgctatcc acgcccattg atgtactgcc aaaaccgcat  12360
caccatggta atagcgatga ctaatacgta gatgtactgc caagtaggaa agtcccataa  12420
ggtcatgtac tgggcataat gccaggcggg ccatttaccg tcattgacgt caataggggg  12480
cgtacttggc atatgataca cttgatgtac tgccaagtgg gcagtttacc gtaaatagtc  12540
cacccattga cgtcaatgga aagtccctat tggcgttact atgggaacat acgtcattat  12600
tgacgtcaat gggcgggggt cgttgggcgg tcagccaggc gggccattta ccgtaagtta  12660
tgtaacgcgg aactccatat atgggctatg aactaatgac cccgtaattg attactatta  12720
ataactagtc aataatcaat gtcaacgcgt atatctggcc cgtacatcgg taactagtcg  12780
gaccgccgcg gactagtgcc cgggccaccg gtgctcgaag cttggatcga tccagacatg  12840
ataagataca ttgatgagtt tggacaaacc acaactagaa tgcagtgaaa aaaatgcttt  12900
atttgtgaaa tttgtgatgc tattgcttta tttgtaacca ttataagctg caataaacaa  12960
gttaacaaca acaattgcat tcattttatg tttcaggttc agggggaggt gtgggaggtt  13020
ttttaaagca agtaaaacct ctacaaatgt ggtatggctg attatgatct ctagtcaag   13079
```

<210> SEQ ID NO 9
<211> LENGTH: 11520
<212> TYPE: DNA
<213> ORGANISM: Artificial sequence
<220> FEATURE:
<223> OTHER INFORMATION: pAIL10V3 plasmid

<400> SEQUENCE: 9

```
gcactataca tcaaatattc cttattaacc cctttacaaa ttaaaaagct aaaggtacac     60
aatttttgag catagttatt aatagcagac actctatgcc tgtgtggagt aagaaaaaac    120
agtatgttat gattataact gttatgccta cttataaagg ttacagaata tttttccata    180
atttcttgt atagcagtgc agctttttcc tttgtggtgt aaatagcaaa gcaagcaaga    240
gttctattac taaacacagc atgactcaaa aaacttagca attctgaagg aaagtccttg    300
gggtcttcta cctttctctt cttttttgga ggagtagaat gttgagagtc agcagtagcc    360
tcatcatcac tagatggcat ttcttctgag caaaacaggt tttcctcatt aaaggcattc    420
caccactgct cccattcatc agttccatag gttggaatct aaaatacaca aacaattaga    480
atcagtagtt taacacatta tacacttaaa aattttatat ttaccttaga gctttaaatc    540
tctgtaggta gtttgtccaa ttatgtcaca ccacagaagt aaggttcctt cacaaagatc    600
gatctaaagc cagcaaaagt cccatggtct tataaaaatg catagcttta ggaggggagc    660
```

```
agagaacttg aaagcatctt cctgttagtc tttcttctcg tagacttcaa acttatactt    720
gatgcctttt tcctcctgga cctcagagag gacgcctggg tattctggga gaagtttata    780
tttccccaaa tcaatttctg ggaaaaacgt gtcactttca aattcctgca tgatccttgt    840
cacaaagagt ctgaggtggc ctggttgatt catggcttcc tggtaaacag aactgcctcc    900
gactatccaa accatgtcta ctttacttgc caattccggt tgttcaataa gtcttaaggc    960
atcatccaaa cttttggcaa gaaaatgagc tcctcgtggt ggttctttga gttctctact   1020
gagaactata ttaattctgt cctttaaagg tcgattcttc tcaggaatgg agaaccaggt   1080
tttcctaccc ataatcacca gattctgttt accttccact gaagaggttg tggtcattct   1140
ttggaagtac ttgaactcgt tcctgagcgg aggccagggt aggtctccgt tcttgccaat   1200
ccccatattt tgggacacgg cgacgatgca gttcaatggt cgaaccatga tggcagcggg   1260
gataaaatcc taccagcctt cacgctagga ttgccgtcaa gtttggcgcg aaatcgcagc   1320
cctgagctgt cccccccccc aagctcagat ctgagcttgg tccctatggt gagtccgttc   1380
cgctcttgtg atgatagcca gacaagaaag agacaataca agacaaacac caaatagtag   1440
aaatagagac aagggtcact tatccgaggg tccctgttcg ggcgccagct gccgcagtcg   1500
gccgacctga gggtcgccgg ggtctgcggg gggaccctct ggaaagtgaa ggataagtga   1560
cgagcggaga cgggatggcg aacagacaca aacacacaag aggtgaatgt taggactgtt   1620
gcaagtttac tcaaaaaatc agcactcttt tatatcttgg tttacataag catttacata   1680
agatttggat aaattccaaa agaacatagg aaaatagaac actcagagct cagatcagaa   1740
cctttgatac caaaccaagt caggaaacca cttgtctcac atcctcgttt taagaacagt   1800
ttgtaaccaa aaacttactt aagccctggg aaccgcaagg ttgggccaat aaaggctatt   1860
cataataact catgccatga gtttttgcag aataatgttc tattagtcca gccactgtcc   1920
cctccttggt atggaaaatc tttccccaaa agtgcattcc tgttcctaga taaatataat   1980
catgtacctg ttgtttcatg tcgtcttttt cttcttgaga caacatacac caaggaggtc   2040
tagctctggc gagtctttca cgaaaaggga gggatctata taacacttta tagccattga   2100
ctgtaaccca cctatcccaa tttaagtcat atcttcctgt atatggtaag gggcatctg    2160
ttggtctgta gatgtaaggt cccctataag tccctggttg ccaccacctg tctcctattt   2220
tgacaaaaac actctttttt ccctttttta cttctaggcc tgtggtcaat agtccttgca   2280
cctgttcttc aattgaggtt gagcgtctct ttctattttc tattcccatt tctaacttct   2340
gaatttgagt aaaaatagta ctaaaagata atgattcatt tcttaacata gtaactaata   2400
atctacctat tggattggtc ttattggtaa aaatataatt tttagcaagc attcttattt   2460
ctatttctga aggacaaaat cgatgcggct tgtaagagga agttggctgt ggtccttgcc   2520
tcaggaggaa ggtcgagttc tccgaattgt ttagattgta atcttgcaca gaagagctat   2580
taaaagagtc aagggtgaga gccctgcgag cacgaaccgc aacttccccc aatagcccca   2640
ggcaaagcag agctatgcca agtttgcagc agagaatgaa tatgtctttg tctgatgggc   2700
tcatccgttt gtgcgcagac gggtcgtcct tggtgggaaa caaccccttg gctgcttctc   2760
ccctaggtgt aggacactct cgggagttca accatttctg cccaagctca gatctgagct   2820
ttaatgcggt agtttatcac agttaaattg ctaacgcagt caggcaccgt gtatgaaatc   2880
taacaatgcg ctcatcgtca tcctcggcac cgtcaccctg gatgctgtag gcataggctt   2940
ggttatgccg gtactgccgg gcctcttgcg ggatatcgtc cattccgaca gcatcgccag   3000
tcactatggc gtgctgctag cgctcttccg cttcctcgct cactgactcg ctgcgctcgg   3060
```

-continued

```
tcgttcggct gcggcgagcg gtatcagctc actcaaaggc ggtaatacgg ttatccacag   3120
aatcagggga taacgcagga aagaacatgt gagcaaaagg ccagcaaaag gccaggaacc   3180
gtaaaaaggc cgcgttgctg gcgtttttcc ataggctccg cccccctgac gagcatcaca   3240
aaaatcgacg ctcaagtcag aggtggcgaa acccgacagg actataaaga taccaggcgt   3300
ttccccctgg aagctccctc gtgcgctctc ctgttccgac cctgccgctt accggatacc   3360
tgtccgcctt tctcccttcg ggaagcgtgg cgctttctca tagctcacgc tgtaggtatc   3420
tcagttcggt gtaggtcgtt cgctccaagc tgggctgtgt gcacgaaccc cccgttcagc   3480
ccgaccgctg cgccttatcc ggtaactatc gtcttgagtc caacccggta agacacgact   3540
tatcgccact ggcagcagcc actggtaaca ggattagcag agcgaggtat gtaggcggtg   3600
ctacagagtt cttgaagtgg tggcctaact acggctacac tagaaggaca gtatttggta   3660
tctgcgctct gctgaagcca gttaccttcg gaaaaagagt tggtagctct tgatccggca   3720
aacaaaccac cgctggtagc ggtggttttt ttgtttgcaa gcagcagatt acgcgcagaa   3780
aaaaaggatc tcaagaagat cctttgatct tttctacggg gtctgacgct cagtggaacg   3840
aaaactcacg ttaagggatt ttggtcatga gattatcaaa aaggatcttc acctagatcc   3900
ttttaaatta aaaatgaagt tttaaatcaa tctaaagtat atatgagtaa acttggtctg   3960
acagttacca atgcttaatc agtgaggcac ctatctcagc gatctgtcta tttcgttcat   4020
ccatagttgc ctgactcccc gtcgtgtaga taactacgat acgggagggc ttaccatctg   4080
gccccagtgc tgcaatgata ccgcgagacc cacgctcacc ggctccagat ttatcagcaa   4140
taaaccagcc agccggaagg gccgagcgca gaagtggtcc tgcaacttta tccgcctcca   4200
tccagtctat taattgttgc cgggaagcta gagtaagtag ttcgccagtt aatagtttgc   4260
gcaacgttgt tgccattgct acaggcatcg tggtgtcacg ctcgtcgttt ggtatggctt   4320
cattcagctc cggttcccaa cgatcaaggc gagttacatg atcccccatg ttgtgcaaaa   4380
aagcggttag ctccttcggt cctccgatcg ttgtcagaag taagttggcc gcagtgttat   4440
cactcatggt tatggcagca ctgcataatt ctcttactgt catgccatcc gtaagatgct   4500
tttctgtgac tggtgagtac tcaaccaagt cattctgaga atagtgtatg cggcgaccga   4560
gttgctcttg cccggcgtca acacgggata ataccgcgcc acatagcaga actttaaaag   4620
tgctcatcat tggaaaacgt tcttcggggc gaaaactctc aaggatctta ccgctgttga   4680
gatccagttc gatgtaaccc actcgtgcac ccaactgatc ttcagcatct tttactttca   4740
ccagcgtttc tgggtgagca aaaacaggaa ggcaaaatgc cgcaaaaaag ggaataaggg   4800
cgacacggaa atgttgaata ctcatactct tcctttttca atattattga agcatttatc   4860
agggttattg tctcatgagc ggatacatat ttgaatgtat ttagaaaaat aaacaaatag   4920
gggttccgcg cacatttccc cgaaaagtgc cacctgacgt ctaagagacc attattatca   4980
tgacattaac ctataaaaat aggcgtatca cgaggccctt tcgtcttcaa gaattgtcta   5040
gaggcgcgct ggccggcctg tgcgaacgcc agcaagacgt agcccagcgc gtcggccgcc   5100
atgccctgct tcatccccgt ggcccgttgc tcgcgtttgc tggcggtgtc cccggaagaa   5160
atatatttgc atgtctttag ttctatgatg acacaaaccc cgcccagcgt cttgtcattg   5220
gcgaattcga acacgcagat gcagtcgggg cggcgcggtc ccaggtccac ttcgcatatt   5280
aaggtgacgc gtgtggcctc gaacaccgag cgaccctgca gcgacccgct taacagcgtc   5340
aacagcgtgc cgcagatccc gggcaatgag atatgaaaaa gcctgaactc accgcgacgt   5400
ctgtcgagaa gtttctgatc gaaaagttcg acagcgtctc cgacctgatg cagctctcgg   5460
```

-continued

```
agggcgaaga atctcgtgct ttcagcttcg atgtaggagg gcgtggatat gtcctgcggg   5520
taaatagctg cgccgatggt ttctacaaag atcgttatgt ttatcggcac tttgcatcgg   5580
ccgcgctccc gattccggaa gtgcttgaca ttggggaatt cagcgagagc ctgacctatt   5640
gcatctcccg ccgtgcacag ggtgtcacgt tgcaagacct gcctgaaacc gaactgcccg   5700
ctgttctgca gccggtcgcg gaggccatgg atgcgatcgc tgcggccgat cttagccaga   5760
cgagcgggtt cggcccattc ggaccgcaag gaatcggtca atacactaca tggcgtgatt   5820
tcatatgcgc gattgctgat ccccatgtgt atcactggca aactgtgatg gacgacaccg   5880
tcagtgcgtc cgtcgcgcag gctctcgatg agctgatgct ttgggccgag gactgccccg   5940
aagtccggca cctcgtgcac gcggatttcg gctccaacaa tgtcctgacg gacaatggcc   6000
gcataacagc ggtcattgac tggagcgagg cgatgttcgg ggattcccaa tacgaggtcg   6060
ccaacatctt cttctggagg ccgtggttgg cttgtatgga gcagcagacg cgctacttcg   6120
agcggaggca tccggagctt gcaggatcgc cgcggctccg ggcgtatatg ctccgcattg   6180
gtcttgacca actctatcag agcttggttg acggcaattt cgatgatgca gcttgggcgc   6240
agggtcgatg cgacgcaatc gtccgatccg gagccgggac tgtcgggcgt acacaaatcg   6300
cccgcagaag cgcggccgtc tggaccgatg gctgtgtaga agtactcgcc gatagtggaa   6360
accgacgccc cagcactcgt ccgagggcaa aggaataggg gagatggggg aggctaactg   6420
aaacacggaa ggagacaata ccggaaggaa cccgcgctat gacggcaata aaaagacaga   6480
ataaaacgca cgggtgttgg gtcgtttgtt cataaacgcg gggttcggtc ccagggctgg   6540
cactctgtcg ataccccacc gagaccccat tggggccaat acgcccgcgt ttcttccttt   6600
tccccacccc accccccaag ttcgggtgaa ggcccagggc tcgcagccaa cgtcggggcg   6660
gcaggccctg ccatagccac tggccccgtg ggttagggac ggggtccccc atggggaatg   6720
gtttatggtt cgtgggggtt attattttgg gcgttgcgtg gggtctggtc cacgactgga   6780
ctgagcagac agacccatgg tttttggatg gcctgggcat ggaccgcatg tactggcgcg   6840
acacgaacac cgggcgtctg tggctgccaa acacccccga cccccaaaaa ccaccgcgcg   6900
gatttctggc gcccagtggc acaggccggc ctgtacatga tcaacgcgtg agctctctag   6960
agcttgtcga cagatccccc tcttcatttc tttatgtttt aaatgcactg acctcccaca   7020
ttcccttttt agtaaaatat tcagaaataa tttaaataca tcattgcaat gaaaataaat   7080
gtttttttatt aggcagaatc cagatgctca aggcccttca taatatcccc cagtttagta   7140
gttggactta gggaacaaag gaacctttaa tagaaattgg acagcaagaa agcgaggggg   7200
atctggatcc tccggacccg tatctagaat catcgattca tttacccgga gacagggaga   7260
ggctcttctg cgtgtagtgg ttgtgcagag cctcatgcat cacggagcat gagaagacgt   7320
tcccctgctg ccacctgctc ttgtccacgg tgagcttgct gtagaggaag aaggagccgt   7380
cggagtccag cacgggaggc gtggtcttgt agttgttctc cggctgccca ttgctctccc   7440
actccacggc gatgtcgctg ggatagaagc ctttgaccag gcaggtcagg ctgacctggt   7500
tcttggtcag ctcatcccgg gatgggggca gggtgtacac ctgtggttct cggggctgcc   7560
ctttggcttt ggagatggtt ttctcgatgg gggctgggag ggctttgttg gagaccttgc   7620
acttgtactc cttgccattc agccagtcct ggtgcaggac ggtgaggacg ctgaccacac   7680
ggtacgtgct gttgtactgc tcctcccgcg gctttgtctt ggcattatgc acctccacgc   7740
cgtccacgta ccagttgaac ttgacctcag ggtcttcgtg gctcacgtcc accaccacgc   7800
atgtgacctc aggggtccgg gagatcatga gggtgtcctt gggttttggg gggaagagga   7860
```

```
agactgacgg tccccccagg agttcaggtg ctgggcacgg tgggcatgtg tgagttttgt   7920
cacaagattt gggctcaact ttcttgtcca ccttggtgtt gctgggcttg tgattcacgt   7980
tgcagatgta ggtctgggtg cccaagctgc tggagggcac ggtcaccacg ctgctgaggg   8040
agtagagtcc tgaggactgt aggacagccg ggaaggtgtg cacgccgctg gtcagggcgc   8100
ctgagttcca cgacaccgtc accggttcgg ggaagtagtc cttgaccagg cagcccaggg   8160
ccgctgtgcc cccagaggtg ctcttggagg agggtgccag ggggaagacc gatgggccct   8220
tggtgctagc cgacgagacg gtgaccaggg tgccttggcc ccagtaatca agccagacgc   8280
taaagcctcg atgtctcgca cagtaataca cagccgtgtc ctcagctctc aggctgttca   8340
tttgcagata cagcgtgttc ttggaattgt ctctggagat ggtgaagcgg ccgcgcacgg   8400
agtcgcgata gtaagtgtag gtagcatcaa gagtaatgct tgccacccac tccagcccct   8460
tgcctggagc ctggcggacc caggccatat gatagtcact gaaagtgaat ccagaggctg   8520
cacaggagag tctcagggac ctcccaggct ggaccacgcc tcccccagac tccaccagct   8580
gcacctggga taggacacag cttgggaatg tcaccaggca gaagagcagc cccaagacag   8640
ccatgttaac tttctggtac caagcttaag tttaaacgct agccagcttg ggtctcccta   8700
tagtgagtcg tattaatttc gataagccag taagcagtgg gttctctagt tagccagaga   8760
gctctgctta tatagacctc ccaccgtaca cgcctaccgc ccatttgcgt caatggggcg   8820
gagttgttac gacattttgg aaagtcccgt tgattttggt gccaaaacaa actcccattg   8880
acgtcaatgg ggtggagact tggaaatccc cgtgagtcaa accgctatcc acgcccattg   8940
atgtactgcc aaaaccgcat caccatggta atagcgatga ctaatacgta gatgtactgc   9000
caagtaggaa agtcccataa ggtcatgtac tgggcataat gccaggcggg ccatttaccg   9060
tcattgacgt caataggggg cgtacttggc atatgataca cttgatgtac tgccaagtgg   9120
gcagtttacc gtaaatagtc cacccattga cgtcaatgga aagtccctat tggcgttact   9180
atgggaacat acgtcattat tgacgtcaat gggcgggggt cgttgggcgg tcagccaggc   9240
gggccattta ccgtaagtta tgtaacgcgg aactccatat atgggctatg aactaatgac   9300
cccgtaattg attactatta ataactagtc aataatcaat gtcaacgcgt atatctggcc   9360
cgtacatcgg tagctgaggg tttaaacggc gcgcggccgg ccggtaccac gcgttggcca   9420
catatggcgg ccgctcgcga ttaattaatc gcgatggcca catatggagc tctctagagc   9480
ttgtcgacag atcccccctct tcatttcttt atgttttaaa tgcactgacc tcccacattc   9540
cctttttagt aaaatattca gaaataattt aaatacatca ttgcaatgaa aataaatgtt   9600
ttttattagg cagaatccag atgctcaagg cccttcataa tatcccccag tttagtagtt   9660
ggacttaggg aacaaaggaa cctttaatag aaattggaca gcaagaaagc gagggggatc   9720
tggatcctcc ggagggccct ggatcctcct acgtatctag aatcatcgat taacactctc   9780
ccctgttgaa gctctttgtg acgggcgagc tcaggccctg atgggtgact tcgcaggcgt   9840
agactttgtg tttctcgtag tctgctttgc tcagcgtcag ggtgctgctg aggctgtagg   9900
tgctgtcctt gctgtcctgc tctgtgacac tctcctggga gttacccgat tggagggcgt   9960
tatccacctt ccactgtact ttggcctctc tgggatagaa gttattcagc aggcacacaa  10020
cagaggcagt tccagatttc aactgctcat cagatggcgg gaagatgaag acagatggtg  10080
cagccaccgt acgtttcagt tccagcttgg tcccaggtcc aaacgtgtac ccgctataat  10140
actggtgaca gtagtaagtt gcaaaatctt caggttgcag actgctgatg gtgagagtga  10200
aatctgtccc agatccactg ccactgaacc ttgatgggac cccgcttgc aaagggcttg  10260
```

```
cattatagat caggagctta ggggctttcc ctggtttctg ctgataccag gccaagttct  10320
caaaaatgtt ctgacttgtc ttgcaagtga tggtgactct gtctcctaca gatgcagaca  10380
gggaggatgg agactgggtc atctggatgt cacatctcat ggctgggagg aagagcacca  10440
aaagccctaa aagttgaact ggagccatct cgagaattcc accacactgg actagtggat  10500
ccgagctcgg taccaagctt aagtttaaac gctagccagc ttgggtctcc ctatagtgag  10560
tcgtattaat ttcgataagc cagtaagcag tgggttctct agttagccag agagctctgc  10620
ttatatagac ctcccaccgt acacgcctac cgcccatttg cgtcaatggg gcggagttgt  10680
tacgacattt tggaaagtcc cgttgatttt ggtgccaaaa caaactccca ttgacgtcaa  10740
tggggtggag acttggaaat ccccgtgagt caaaccgcta tccacgccca ttgatgtact  10800
gccaaaaccg catcaccatg gtaatagcga tgactaatac gtagatgtac tgccaagtag  10860
gaaagtccca taaggtcatg tactgggcat aatgccaggc gggccattta ccgtcattga  10920
cgtcaatagg gggcgtactt ggcatatgat acacttgatg tactgccaag tgggcagttt  10980
accgtaaata gtccacccat tgacgtcaat ggaaagtccc tattggcgtt actatgggaa  11040
catacgtcat tattgacgtc aatgggcggg ggtcgttggg cggtcagcca ggcgggccat  11100
ttaccgtaag ttatgtaacg cggaactcca tatatgggct atgaactaat gaccccgtaa  11160
ttgattacta ttaataacta gtcaataatc aatgtcaacg cgtatatctg gcccgtacat  11220
cggtaactag tcggaccggc ccgggccacc ggtgctcgaa gcttggatcg atccagacat  11280
gataagatac attgatgagt ttggacaaac cacaactaga atgcagtgaa aaaaatgctt  11340
tatttgtgaa atttgtgatg ctattgcttt atttgtaacc attataagct gcaataaaca  11400
agttaacaac aacaattgca ttcattttat gtttcaggtt cagggggagg tgtgggaggt  11460
tttttaaagc aagtaaaacc tctacaaatg tggtatggct gattatgatc tctagtcaag  11520
```

<210> SEQ ID NO 10
<211> LENGTH: 155
<212> TYPE: DNA
<213> ORGANISM: Artificial sequence
<220> FEATURE:
<223> OTHER INFORMATION: multiple cloning site

<400> SEQUENCE: 10

```
aaatctagag gcgcgccgtt taaaccctca gctgatcatc cggatgtaca gcgcgcggcc     60
ggccggtacc acgcgttggc cacatatggc ggccgctcgc gattaattaa cggaccgccg    120
cggactagtg cccgggccac cggtgctcga gaaaa                               155
```

<210> SEQ ID NO 11
<211> LENGTH: 160
<212> TYPE: DNA
<213> ORGANISM: Artificial sequence
<220> FEATURE:
<223> OTHER INFORMATION: multiple cloning site

<400> SEQUENCE: 11

```
gggggcgcgc cgtttaaacc ctcagctacg taaagcttgg taccctcgag gtcgacatcg     60
atgatatcga attcctgcag ggcccccccg ggtccggagg atccgcggcc gctctagaga    120
gctcacgcgt tgatcatgta caggccggcc agcgcgcccc                          160
```

<210> SEQ ID NO 12
<211> LENGTH: 166
<212> TYPE: DNA
<213> ORGANISM: Artificial sequence
<220> FEATURE:
<223> OTHER INFORMATION: multiple cloning site

<400> SEQUENCE: 12
gggggcgcgc caccggtggc ccgggccggt ccgactagtt acgtaaagct tggtaccctc 60
gaggtcgaca tcgatgatat cgaattcctg caggggccct ccggaggatc cgcggccgct 120
ctagagagct ccatatgtgg ccatcgcgat taattaagcg cgcccc 166

<210> SEQ ID NO 13
<211> LENGTH: 6078
<212> TYPE: DNA
<213> ORGANISM: Artificial sequence
<220> FEATURE:
<223> OTHER INFORMATION: pSRXBLS plasmid

<400> SEQUENCE: 13
gcactataca tcaaatattc cttattaacc cctttacaaa ttaaaaagct aaaggtacac 60
aatttttgag catagttatt aatagcagac actctatgcc tgtgtggagt aagaaaaaac 120
agtatgttat gattataact gttatgccta cttataaagg ttacagaata tttttccata 180
attttcttgt atagcagtgc agctttttcc tttgtggtgt aaatagcaaa gcaagcaaga 240
gttctattac taaacacagc atgactcaaa aaacttagca attctgaagg aaagtccttg 300
gggtcttcta cctttctctt cttttttgga ggagtagaat gttgagagtc agcagtagcc 360
tcatcatcac tagatggcat ttcttctgag caaaacaggt tttcctcatt aaaggcattc 420
caccactgct cccattcatc agttccatag gttggaatct aaaatacaca aacaattaga 480
atcagtagtt taacacatta tacacttaaa aattttatat ttaccttaga gctttaaatc 540
tctgtaggta gtttgtccaa ttatgtcaca ccacagaagt aaggttcctt cacaaagatc 600
gatctaaagc cagcaaaagt cccatggtct tataaaaatg catagcttta ggaggggagc 660
agagaacttg aaagcatctt cctgttagtc tttcttctcg tagacttcaa acttatactt 720
gatgcctttt tcctcctgga cctcagagag gacgcctggg tattctggga gaagtttata 780
tttccccaaa tcaatttctg ggaaaaacgt gtcactttca aattcctgca tgatccttgt 840
cacaaagagt ctgaggtggc ctggttgatt catggcttcc tggtaaacag aactgcctcc 900
gactatccaa accatgtcta ctttacttgc caattccggt tgttcaataa gtcttaaggc 960
atcatccaaa cttttggcaa gaaaatgagc tcctcgtggt ggttctttga gttctctact 1020
gagaactata ttaattctgt cctttaaagg tcgattcttc tcaggaatgg agaaccaggt 1080
tttcctaccc ataatcacca gattctgttt accttccact gaagaggttg tggtcattct 1140
ttggaagtac ttgaactcgt tcctgagcgg aggccagggt aggtctccgt tcttgccaat 1200
ccccatattt tgggacacgg cgacgatgca gttcaatggt cgaaccatga tggcagcggg 1260
gataaaatcc taccagcctt cacgctagga ttgccgtcaa gtttggcgcg aaatcgcagc 1320
cctgagctgt cccccccccc aagctcagat ctgagcttgg tccctatggt gagtccgttc 1380
cgctcttgtg atgatagcca gacaagaaag agacaataca agacaaacac caaatagtag 1440
aaatagagac aagggtcact tatccgaggg tccctgttcg ggcgccagct gccgcagtcg 1500
gccgacctga gggtcgccgg ggtctgcggg gggaccctct ggaaagtgaa ggataagtga 1560
cgagcggaga cgggatggcg aacagacaca aacacacaag aggtgaatgt taggactgtt 1620
gcaagtttac tcaaaaaatc agcactcttt tatatcttgg tttacataag catttacata 1680
agatttggat aaattccaaa agaacatagg aaaatagaac actcagagct cagatcagaa 1740
cctttgatac caaaccaagt caggaaacca cttgtctcac atcctcgttt taagaacagt 1800

-continued

```
ttgtaaccaa aaacttactt aagccctggg aaccgcaagg ttgggccaat aaaggctatt   1860
cataataact catgccatga gtttttgcag aataatgttc tattagtcca gccactgtcc   1920
cctccttggt atggaaaatc tttccccaaa agtgcattcc tgttcctaga taaatataat   1980
catgtacctg ttgtttcatg tcgtcttttt cttcttgaga caacatacac caaggaggtc   2040
tagctctggc gagtctttca cgaaaaggga gggatctata taacacttta tagccattga   2100
ctgtaaccca cctatcccaa tttaagtcat atcttcctgt atatggtaag gggcatctg    2160
ttggtctgta gatgtaaggt cccctataag tccctggttg ccaccacctg tctcctattt   2220
tgacaaaaac actctttttt cccttttta cttctaggcc tgtggtcaat agtccttgca    2280
cctgttcttc aattgaggtt gagcgtctct ttctattttc tattcccatt tctaacttct   2340
gaatttgagt aaaaatagta ctaaaagata atgattcatt tcttaacata gtaactaata   2400
atctacctat tggattggtc ttattggtaa aaatataatt tttagcaagc attcttattt   2460
ctatttctga aggacaaaat cgatgcggct tgtaagagga agttggctgt ggtccttgcc   2520
tcaggaggaa ggtcgagttc tccgaattgt ttagattgta atcttgcaca gaagagctat   2580
taaaagagtc aagggtgaga gccctgcgag cacgaaccgc aacttccccc aatagcccca   2640
ggcaaagcag agctatgcca agtttgcagc agagaatgaa tatgtctttg tctgatgggc   2700
tcatccgttt gtgcgcagac gggtcgtcct tggtgggaaa caaccccttg gctgcttctc   2760
ccctaggtgt aggacactct cgggagttca accatttctg cccaagctca gatctgagct   2820
ttaatgcggt agtttatcac agttaaattg ctaacgcagt caggcaccgt gtatgaaatc   2880
taacaatgcg ctcatcgtca tcctcggcac cgtcaccctg gatgctgtag gcataggctt   2940
ggttatgccg gtactgccgg gcctcttgcg ggatatcgtc cattccgaca gcatcgccag   3000
tcactatggc gtgctgctag cgctcttccg cttcctcgct cactgactcg ctgcgctcgg   3060
tcgttcggct gcggcgagcg gtatcagctc actcaaaggc ggtaatacgg ttatccacag   3120
aatcagggga taacgcagga aagaacatgt gagcaaaagg ccagcaaaag gccaggaacc   3180
gtaaaaaggc cgcgttgctg gcgtttttcc ataggctccg cccccctgac gagcatcaca   3240
aaaatcgacg ctcaagtcag aggtggcgaa acccgacagg actataaaga taccaggcgt   3300
ttccccctgg aagctccctc gtgcgctctc ctgttccgac cctgccgctt accggatacc   3360
tgtccgcctt tctcccttcg ggaagcgtgg cgctttctca tagctcacgc tgtaggtatc   3420
tcagttcggt gtaggtcgtt cgctccaagc tgggctgtgt gcacgaaccc cccgttcagc   3480
ccgaccgctg cgccttatcc ggtaactatc gtcttgagtc caacccggta agacacgact   3540
tatcgccact ggcagcagcc actggtaaca ggattagcag agcgaggtat gtaggcggtg   3600
ctacagagtt cttgaagtgg tggcctaact acggctacac tagaaggaca gtatttggta   3660
tctgcgctct gctgaagcca gttaccttcg gaaaaagagt tggtagctct tgatccggca   3720
aacaaaccac cgctggtagc ggtggttttt ttgtttgcaa gcagcagatt acgcgcagaa   3780
aaaaaggatc tcaagaagat cctttgatct tttctacggg gtctgacgct cagtggaacg   3840
aaaactcacg ttaagggatt ttggtcatga gattatcaaa aaggatcttc acctagatcc   3900
ttttaaatta aaaatgaagt tttaaatcaa tctaaagtat atatgagtaa acttggtctg   3960
acagttacca atgcttaatc agtgaggcac ctatctcagc gatctgtcta tttcgttcat   31020
ccatagttgc ctgactcccc gtcgtgtaga taactacgat acgggagggc ttaccatctg   4080
gccccagtgc tgcaatgata ccgcgagacc cacgctcacc ggctccagat ttatcagcaa   4140
taaaccagcc agccggaagg gccgagcgca gaagtggtcc tgcaacttta tccgcctcca   4200
```

```
tccagtctat taattgttgc cgggaagcta gagtaagtag ttcgccagtt aatagtttgc   4260

gcaacgttgt tgccattgct acaggcatcg tggtgtcacg ctcgtcgttt ggtatggctt   4320

cattcagctc cggttcccaa cgatcaaggc gagttacatg atcccccatg ttgtgcaaaa   4380

aagcggttag ctccttcggt cctccgatcg ttgtcagaag taagttggcc gcagtgttat   4440

cactcatggt tatggcagca ctgcataatt ctcttactgt catgccatcc gtaagatgct   4500

tttctgtgac tggtgagtac tcaaccaagt cattctgaga atagtgtatg cggcgaccga   4560

gttgctcttg cccggcgtca acacgggata ataccgcgcc acatagcaga actttaaaag   4620

tgctcatcat tggaaaacgt tcttcggggc gaaaactctc aaggatctta ccgctgttga   4680

gatccagttc gatgtaaccc actcgtgcac ccaactgatc ttcagcatct tttactttca   4740

ccagcgtttc tgggtgagca aaaacaggaa ggcaaaatgc cgcaaaaaag ggaataaggg   4800

cgacacggaa atgttgaata ctcatactct tcctttttca atattattga agcatttatc   4860

agggttattg tctcatgagc ggatacatat ttgaatgtat ttagaaaaat aaacaaatag   4920

gggttccgcg cacatttccc cgaaaagtgc cacctgacgt ctaagagacc attattatca   4980

tgacattaac ctataaaaat aggcgtatca cgaggccctt tcgtcttcaa gaattgtcta   5040

gaggcgcgcc gtttaaaccc tcagctgatc atccggatgt acagcgcgcg gccggccggt   5100

accacgcgtt ggccacatat ggcggccgct cgcgattaat taacggaccg ccgcggacta   5160

gtgcccgggc caccggtgct cgaggagctt ggatctgtaa cggcgcagaa cagaaaacga   5220

aacaaagacg tagagttgag caagcagggt caggcaaagc gtggagagcc ggctgagtct   5280

aggtaggctc caagggagcg ccggacaaag gcccggtctc gacctgagct ttaaacttac   5340

ctagacggcg gacgcagttc aggaggcacc acaggcggga ggcggcagaa cgcgactcaa   5400

ccggcgtgga tggcggcctc aggtagggcg gcgggcgcgt gaaggagaga tgcgagcccc   5460

tcgatcgagg agctttttgc aaaagcctag gcctccaaaa aagcctcctc actacttctg   5520

gaatagctca gaggccgagg cggcctcggc ctctgcataa ataaaaaaaa ttagtcagcc   5580

atggggcgga gaatgggcgg aactgggcgg agttaggggc gggatgggcg gagttagggg   5640

cgggactatg gttgctgact aattgagatg catgctttgc atacttctgc ctgctgggga   5700

gcctggggac tttccacacc tggttgctga ctaattgaga tgcatgcttt gcatacttct   5760

gcctgctggg gagcctgggg actttccaca ccctaactga cacacattcc acagccaagc   5820

ttggatcgat ccagacatga taagatacat tgatgagttt ggacaaacca caactagaat   5880

gcagtgaaaa aaatgcttta tttgtgaaat ttgtgatgct attgctttat ttgtaaccat   5940

tataagctgc aataaacaag ttaacaacaa caattgcatt cattttatgt ttcaggttca   6000

gggggaggtg tgggaggttt tttaaagcaa gtaaaacctc tacaaatgtg gtatggctga   6060

ttatgatctc tagtcaag                                                 6078
```

```
<210> SEQ ID NO 14
<211> LENGTH: 6384
<212> TYPE: DNA
<213> ORGANISM: Artificial sequence
<220> FEATURE:
<223> OTHER INFORMATION: pDSRG plasmid

<400> SEQUENCE: 14

gcactataca tcaaatattc cttattaacc cctttacaaa ttaaaaagct aaaggtacac     60

aatttttgag catagttatt aatagcagac actctatgcc tgtgtggagt aagaaaaaac    120

agtatgttat gattataact gttatgccta cttataaagg ttacagaata tttttccata    180
```

```
attttcttgt atagcagtgc agctttttcc tttgtggtgt aaatagcaaa gcaagcaaga    240
gttctattac taaacacagc atgactcaaa aaacttagca attctgaagg aaagtccttg    300
gggtcttcta cctttctctt ctttttgga ggagtagaat gttgagagtc agcagtagcc    360
tcatcatcac tagatggcat ttcttctgag caaaacaggt tttcctcatt aaaggcattc    420
caccactgct cccattcatc agttccatag gttggaatct aaaatacaca aacaattaga    480
atcagtagtt taacacatta tacacttaaa aattttatat ttaccttaga gctttaaatc    540
tctgtaggta gtttgtccaa ttatgtcaca ccacagaagt aaggttcctt cacaaagatc    600
gatctaaagc cagcaaaagt cccatggtct tataaaaatg catagcttta ggaggggagc    660
agagaacttg aaagcatctt cctgttagtc tttcttctcg tagacttcaa acttatactt    720
gatgcctttt tcctcctgga cctcagagag gacgcctggg tattctggga gaagtttata    780
tttccccaaa tcaatttctg ggaaaaacgt gtcactttca aattcctgca tgatccttgt    840
cacaaagagt ctgaggtggc ctggttgatt catggcttcc tggtaaacag aactgcctcc    900
gactatccaa accatgtcta ctttacttgc caattccggt tgttcaataa gtcttaaggc    960
atcatccaaa cttttggcaa gaaaatgagc tcctcgtggt ggttctttga gttctctact   1020
gagaactata ttaattctgt cctttaaagg tcgattcttc tcaggaatgg agaaccaggt   1080
tttcctaccc ataatcacca gattctgttt accttccact gaagaggttg tggtcattct   1140
ttggaagtac ttgaactcgt tcctgagcgg aggccagggt aggtctccgt tcttgccaat   1200
ccccatattt tgggacacgg cgacgatgca gttcaatggt cgaaccatga tggcagcggg   1260
gataaaatcc taccagcctt cacgctagga ttgccgtcaa gtttggcgcg aaatcgcagc   1320
cctgagctgt cccccccccc aagctcagat ctgagcttgg tccctatggt gagtccgttc   1380
cgctcttgtg atgatagcca gacaagaaag agacaataca agacaaacac caaatagtag   1440
aaatagagac aagggtcact tatccgaggg tccctgttcg ggcgccagct gccgcagtcg   1500
gccgacctga gggtcgccgg ggtctgcggg gggaccctct ggaaagtgaa ggataagtga   1560
cgagcggaga cgggatggcg aacagacaca aacacacaag aggtgaatgt taggactgtt   1620
gcaagtttac tcaaaaaatc agcactcttt tatatcttgg tttacataag catttacata   1680
agatttggat aaattccaaa agaacatagg aaaatagaac actcagagct cagatcagaa   1740
cctttgatac caaaccaagt caggaaacca cttgtctcac atcctcgttt taagaacagt   1800
ttgtaaccaa aaacttactt aagccctggg aaccgcaagg ttgggccaat aaaggctatt   1860
cataataact catgccatga gtttttgcag aataatgttc tattagtcca gccactgtcc   1920
cctccttggt atggaaaatc tttccccaaa agtgcattcc tgttcctaga taaatataat   1980
catgtacctg ttgtttcatg tcgtcttttt cttcttgaga caacatacac caaggaggtc   2040
tagctctggc gagtctttca cgaaaaggga gggatctata taacacttta tagccattga   2100
ctgtaaccca cctatcccaa tttaagtcat atcttcctgt atatggtaag ggggcatctg   2160
ttggtctgta gatgtaaggt cccctataag tccctggttg ccaccacctg tctcctattt   2220
tgacaaaaac actctttttt ccctttttta cttctaggcc tgtggtcaat agtccttgca   2280
cctgttcttc aattgaggtt gagcgtctct ttctattttc tattcccatt tctaacttct   2340
gaatttgagt aaaaatagta ctaaaagata atgattcatt tcttaacata gtaactaata   2400
atctacctat tggattggtc ttattggtaa aaatataatt tttagcaagc attcttattt   2460
ctatttctga aggacaaaat cgatgcggct tgtaagagga agttggctgt ggtccttgcc   2520
tcaggaggaa ggtcgagttc tccgaattgt ttagattgta atcttgcaca gaagagctat   2580
```

-continued taaaagagtc aagggtgaga gccctgcgag cacgaaccgc aacttccccc aatagcccca 2640
ggcaaagcag agctatgcca agtttgcagc agagaatgaa tatgtctttg tctgatgggc 2700
tcatccgttt gtgcgcagac gggtcgtcct tggtgggaaa caaccccttg gctgcttctc 2760
ccctaggtgt aggacactct cgggagttca accatttctg cccaagctca gatctgagct 2820
ttaatgcggt agtttatcac agttaaattg ctaacgcagt caggcaccgt gtatgaaatc 2880
taacaatgcg ctcatcgtca tcctcggcac cgtcaccctg gatgctgtag gcataggctt 2940
ggttatgccg gtactgccgg gcctcttgcg ggatatcgtc cattccgaca gcatcgccag 3000
tcactatggc gtgctgctag cgctcttccg cttcctcgct cactgactcg ctgcgctcgg 3060
tcgttcggct gcggcgagcg gtatcagctc actcaaaggc ggtaatacgg ttatccacag 3120
aatcagggga taacgcagga aagaacatgt gagcaaaagg ccagcaaaag gccaggaacc 3180
gtaaaaaggc cgcgttgctg gcgtttttcc ataggctccg cccccctgac gagcatcaca 3240
aaaatcgacg ctcaagtcag aggtggcgaa acccgacagg actataaaga taccaggcgt 3300
ttccccctgg aagctccctc gtgcgctctc ctgttccgac cctgccgctt accggatacc 3360
tgtccgcctt tctcccttcg ggaagcgtgg cgctttctca tagctcacgc tgtaggtatc 3420
tcagttcggt gtaggtcgtt cgctccaagc tgggctgtgt gcacgaaccc cccgttcagc 3480
ccgaccgctg cgccttatcc ggtaactatc gtcttgagtc caacccggta agacacgact 3540
tatcgccact ggcagcagcc actggtaaca ggattagcag agcgaggtat gtaggcggtg 3600
ctacagagtt cttgaagtgg tggcctaact acggctacac tagaaggaca gtatttggta 3660
tctgcgctct gctgaagcca gttaccttcg gaaaaagagt tggtagctct tgatccggca 3720
aacaaaccac cgctggtagc ggtggttttt ttgtttgcaa gcagcagatt acgcgcagaa 3780
aaaaaggatc tcaagaagat cctttgatct tttctacggg gtctgacgct cagtggaacg 3840
aaaactcacg ttaagggatt ttggtcatga gattatcaaa aaggatcttc acctagatcc 3900
ttttaaatta aaaatgaagt tttaaatcaa tctaaagtat atatgagtaa acttggtctg 3960
acagttacca atgcttaatc agtgaggcac ctatctcagc gatctgtcta tttcgttcat 4020
ccatagttgc ctgactcccc gtcgtgtaga taactacgat acgggagggc ttaccatctg 4080
gccccagtgc tgcaatgata ccgcgagacc cacgctcacc ggctccagat ttatcagcaa 4140
taaaccagcc agccggaagg gccgagcgca gaagtggtcc tgcaacttta tccgcctcca 4200
tccagtctat taattgttgc cgggaagcta gagtaagtag ttcgccagtt aatagtttgc 4260
gcaacgttgt tgccattgct acaggcatcg tggtgtcacg ctcgtcgttt ggtatggctt 4320
cattcagctc cggttcccaa cgatcaaggc gagttacatg atcccccatg ttgtgcaaaa 4380
aagcggttag ctccttcggt cctccgatcg ttgtcagaag taagttggcc gcagtgttat 4440
cactcatggt tatggcagca ctgcataatt ctcttactgt catgccatcc gtaagatgct 4500
tttctgtgac tggtgagtac tcaaccaagt cattctgaga atagtgtatg cggcgaccga 4560
gttgctcttg cccggcgtca acacgggata ataccgcgcc acatagcaga actttaaaag 4620
tgctcatcat tggaaaacgt tcttcggggc gaaaactctc aaggatctta ccgctgttga 4680
gatccagttc gatgtaaccc actcgtgcac ccaactgatc ttcagcatct tttactttca 4740
ccagcgtttc tgggtgagca aaaacaggaa ggcaaaatgc cgcaaaaaag ggaataaggg 4800
cgacacggaa atgttgaata ctcatactct tcctttttca atattattga agcatttatc 4860
agggttattg tctcatgagc ggatacatat ttgaatgtat ttagaaaaat aaacaaatag 4920
gggttccgcg cacatttccc cgaaaagtgc cacctgacgt ctaagagacc attattatca 4980

```
tgacattaac ctataaaaat aggcgtatca cgaggccctt tcgtcttcaa gaattgtcta   5040

gagcttgtcg acagatcccc ctcttcattt ctttatgttt taaatgcact gacctcccac   5100

attccctttt tagtaaaata ttcagaaata atttaaatac atcattgcaa tgaaaataaa   5160

tgtttttat taggcagaat ccagatgctc aaggcccttc ataatatccc ccagtttagt   5220

agttggactt agggaacaaa ggaaccttta atagaaattg gacagcaaga aagcgagggg   5280

gatctggatc cctcgaggaa ttcccgggga tccgtcgacc tgcagcagct tttagagcag   5340

aagtaacact tccgtacagg cctagaagta aaggcaacat ccactgagga gcagttcttt   5400

gatttgcacc accaccggat ccgggacctg aaataaaaga caaaaagact aaacttacca   5460

gttaactttc tggtttttca gttcctcgag gagcttggat ctgtaacggc gcagaacaga   5520

aaacgaaaca aagacgtaga gttgagcaag cagggtcagg caaagcgtgg agagccggct   5580

gagtctaggt aggctccaag ggagcgccgg acaaaggccc ggtctcgacc tgagctttaa   5640

acttacctag acggcggacg cagttcagga ggcaccacag gcgggaggcg gcagaacgcg   5700

actcaaccgg cgtggatggc ggcctcaggt agggcggcgg gcgcgtgaag gagagatgcg   5760

agcccctcga tcgaggagct tttgcaaaa gcctaggcct ccaaaaaagc ctcctcacta   5820

cttctggaat agctcagagg ccgaggcggc ctcggcctct gcataaataa aaaaaattag   5880

tcagccatgg ggcggagaat gggcggaact gggcggagtt aggggcggga tgggcggagt   5940

taggggcggg actatggttg ctgactaatt gagatgcatg ctttgcatac ttctgcctgc   6000

tggggagcct ggggactttc cacacctggt tgctgactaa ttgagatgca tgctttgcat   6060

acttctgcct gctggggagc ctggggactt tccacaccct aactgacaca cattccacag   6120

ccaagcttgg atcgatccag acatgataag atacattgat gagtttggac aaaccacaac   6180

tagaatgcag tgaaaaaaat gctttatttg tgaaatttgt gatgctattg ctttatttgt   6240

aaccattata agctgcaata aacaagttaa caacaacaat tgcattcatt ttatgtttca   6300

ggttcagggg gaggtgtggg aggtttttta aagcaagtaa aacctctaca aatgtggtat   6360

ggctgattat gatctctagt caag                                          6384
```

```
<210> SEQ ID NO 15
<211> LENGTH: 384
<212> TYPE: DNA
<213> ORGANISM: Homo sapiens
<220> FEATURE:
<221> NAME/KEY: CDS
<222> LOCATION: 1..384
<220> FEATURE:
<221> NAME/KEY: sig_peptide
<222> LOCATION: 1..57

<400> SEQUENCE: 15

atg tcg cca tca caa ctc att ggg ttt ctg ctg ctc tgg gtt cca gcc       48
Met Ser Pro Ser Gln Leu Ile Gly Phe Leu Leu Leu Trp Val Pro Ala
1               5                   10                  15

tcc agg ggt gaa att gtg ctg act cag gtt cca gac ttt cag tct gtg       96
Ser Arg Gly Glu Ile Val Leu Thr Gln Val Pro Asp Phe Gln Ser Val
            20                  25                  30

act cca aag gag aaa gtc acc atc acc tgc cgg gcc agt cag agc att      144
Thr Pro Lys Glu Lys Val Thr Ile Thr Cys Arg Ala Ser Gln Ser Ile
        35                  40                  45

ggt agt agc tta cac tgg tac cag cag aaa cca gat cag tct cca aag      192
Gly Ser Ser Leu His Trp Tyr Gln Gln Lys Pro Asp Gln Ser Pro Lys
    50                  55                  60

ctc ctc atc aag tat gct tcc cag tcc ctc tca ggg gtc ccc tcg agg      240
```

```
Leu Leu Ile Lys Tyr Ala Ser Gln Ser Leu Ser Gly Val Pro Ser Arg
65                  70                  75                  80

ttc agt ggc agt gga tct ggg aca gat ttc acc ctc acc atc aat agc      288
Phe Ser Gly Ser Gly Ser Gly Thr Asp Phe Thr Leu Thr Ile Asn Ser
                85                  90                  95

ctg gaa gct gaa gat gct gca gcg tat tac tgt cat cag agt agt cgt      336
Leu Glu Ala Glu Asp Ala Ala Ala Tyr Tyr Cys His Gln Ser Ser Arg
            100                 105                 110

tta cct cac act ttc ggc gga ggg acc aag gtg gag atc aaa cga act      384
Leu Pro His Thr Phe Gly Gly Gly Thr Lys Val Glu Ile Lys Arg Thr
        115                 120                 125


<210> SEQ ID NO 16
<211> LENGTH: 128
<212> TYPE: PRT
<213> ORGANISM: Homo sapiens

<400> SEQUENCE: 16

Met Ser Pro Ser Gln Leu Ile Gly Phe Leu Leu Leu Trp Val Pro Ala
1               5                   10                  15

Ser Arg Gly Glu Ile Val Leu Thr Gln Val Pro Asp Phe Gln Ser Val
            20                  25                  30

Thr Pro Lys Glu Lys Val Thr Ile Thr Cys Arg Ala Ser Gln Ser Ile
        35                  40                  45

Gly Ser Ser Leu His Trp Tyr Gln Gln Lys Pro Asp Gln Ser Pro Lys
    50                  55                  60

Leu Leu Ile Lys Tyr Ala Ser Gln Ser Leu Ser Gly Val Pro Ser Arg
65                  70                  75                  80

Phe Ser Gly Ser Gly Ser Gly Thr Asp Phe Thr Leu Thr Ile Asn Ser
                85                  90                  95

Leu Glu Ala Glu Asp Ala Ala Ala Tyr Tyr Cys His Gln Ser Ser Arg
            100                 105                 110

Leu Pro His Thr Phe Gly Gly Gly Thr Lys Val Glu Ile Lys Arg Thr
        115                 120                 125


<210> SEQ ID NO 17
<211> LENGTH: 411
<212> TYPE: DNA
<213> ORGANISM: Homo sapiens
<220> FEATURE:
<221> NAME/KEY: CDS
<222> LOCATION: 1..411
<220> FEATURE:
<221> NAME/KEY: sig_peptide
<222> LOCATION: 1..57

<400> SEQUENCE: 17

atg gag ttt ggg ctg agc tgg gtt ttc ctt gtt gct ata tta aaa ggt       48
Met Glu Phe Gly Leu Ser Trp Val Phe Leu Val Ala Ile Leu Lys Gly
1               5                   10                  15

gtc cag tgt gag gtt cag ctg gtg cag tct ggg gga ggc ttg gta cat       96
Val Gln Cys Glu Val Gln Leu Val Gln Ser Gly Gly Gly Leu Val His
            20                  25                  30

cct ggg ggg tcc ctg aga ctc tcc tgt gca gcc tct gga ttc acc ttc      144
Pro Gly Gly Ser Leu Arg Leu Ser Cys Ala Ala Ser Gly Phe Thr Phe
        35                  40                  45

agt agc ttt gct atg cac tgg gtt cgc cag gct cca gga aaa ggt ctg      192
Ser Ser Phe Ala Met His Trp Val Arg Gln Ala Pro Gly Lys Gly Leu
    50                  55                  60

gag tgg ata tca gtt att gat act cgt ggt gcc aca tac tat gca gac      240
Glu Trp Ile Ser Val Ile Asp Thr Arg Gly Ala Thr Tyr Tyr Ala Asp
65                  70                  75                  80
```

-continued

```
tcc gtg aag ggc cga ttc acc atc tcc aga gac aat gcc aag aac tcc      288
Ser Val Lys Gly Arg Phe Thr Ile Ser Arg Asp Asn Ala Lys Asn Ser
                85                  90                  95

ttg tat ctt caa atg aac agc ctg aga gcc gag gac atg gct gtg tat      336
Leu Tyr Leu Gln Met Asn Ser Leu Arg Ala Glu Asp Met Ala Val Tyr
            100                 105                 110

tac tgt gca aga ctg ggg aac ttc tac tac ggt atg gac gtc tgg ggc      384
Tyr Cys Ala Arg Leu Gly Asn Phe Tyr Tyr Gly Met Asp Val Trp Gly
        115                 120                 125

caa ggg acc acg gtc acc gtc tcc tca                                  411
Gln Gly Thr Thr Val Thr Val Ser Ser
    130                 135


<210> SEQ ID NO 18
<211> LENGTH: 137
<212> TYPE: PRT
<213> ORGANISM: Homo sapiens

<400> SEQUENCE: 18

Met Glu Phe Gly Leu Ser Trp Val Phe Leu Val Ala Ile Leu Lys Gly
1               5                   10                  15

Val Gln Cys Glu Val Gln Leu Val Gln Ser Gly Gly Gly Leu Val His
            20                  25                  30

Pro Gly Gly Ser Leu Arg Leu Ser Cys Ala Ala Ser Gly Phe Thr Phe
        35                  40                  45

Ser Ser Phe Ala Met His Trp Val Arg Gln Ala Pro Gly Lys Gly Leu
    50                  55                  60

Glu Trp Ile Ser Val Ile Asp Thr Arg Gly Ala Thr Tyr Tyr Ala Asp
65                  70                  75                  80

Ser Val Lys Gly Arg Phe Thr Ile Ser Arg Asp Asn Ala Lys Asn Ser
                85                  90                  95

Leu Tyr Leu Gln Met Asn Ser Leu Arg Ala Glu Asp Met Ala Val Tyr
            100                 105                 110

Tyr Cys Ala Arg Leu Gly Asn Phe Tyr Tyr Gly Met Asp Val Trp Gly
        115                 120                 125

Gln Gly Thr Thr Val Thr Val Ser Ser
    130                 135


<210> SEQ ID NO 19
<211> LENGTH: 384
<212> TYPE: DNA
<213> ORGANISM: Homo sapiens
<220> FEATURE:
<221> NAME/KEY: CDS
<222> LOCATION: (1)..(384)

<400> SEQUENCE: 19

atg tcg cca tca caa ctc att ggg ttt ctg ctg ctc tgg gtt cca gcc       48
Met Ser Pro Ser Gln Leu Ile Gly Phe Leu Leu Leu Trp Val Pro Ala
1               5                   10                  15

tcc agg ggt gaa att gtg ctg act cag agc cca ggt acc ctg tct gtg       96
Ser Arg Gly Glu Ile Val Leu Thr Gln Ser Pro Gly Thr Leu Ser Val
            20                  25                  30

tct cca ggc gag aga gcc acc ctc tcc tgc cgg gcc agt cag agc att      144
Ser Pro Gly Glu Arg Ala Thr Leu Ser Cys Arg Ala Ser Gln Ser Ile
        35                  40                  45

ggt agt agc tta cac tgg tac cag cag aaa cca ggt cag gct cca agg      192
Gly Ser Ser Leu His Trp Tyr Gln Gln Lys Pro Gly Gln Ala Pro Arg
    50                  55                  60

ctt ctc atc aag tat gca tcc cag tcc ctc tca ggg atc ccc gat agg      240
```

```
Leu Leu Ile Lys Tyr Ala Ser Gln Ser Leu Ser Gly Ile Pro Asp Arg
65                  70                  75                  80

ttc agt ggc agt gga tct ggg aca gat ttc acc ctc acc atc agt aga      288
Phe Ser Gly Ser Gly Ser Gly Thr Asp Phe Thr Leu Thr Ile Ser Arg
                85                  90                  95

ctg gag cct gaa gat ttc gca gtg tat tac tgt cat cag agt agt cgt      336
Leu Glu Pro Glu Asp Phe Ala Val Tyr Tyr Cys His Gln Ser Ser Arg
            100                 105                 110

tta cct cac act ttc ggc caa ggg acc aag gtg gag atc aaa cgt aca      384
Leu Pro His Thr Phe Gly Gln Gly Thr Lys Val Glu Ile Lys Arg Thr
        115                 120                 125


<210> SEQ ID NO 20
<211> LENGTH: 128
<212> TYPE: PRT
<213> ORGANISM: Homo sapiens

<400> SEQUENCE: 20

Met Ser Pro Ser Gln Leu Ile Gly Phe Leu Leu Leu Trp Val Pro Ala
1               5                   10                  15

Ser Arg Gly Glu Ile Val Leu Thr Gln Ser Pro Gly Thr Leu Ser Val
            20                  25                  30

Ser Pro Gly Glu Arg Ala Thr Leu Ser Cys Arg Ala Ser Gln Ser Ile
        35                  40                  45

Gly Ser Ser Leu His Trp Tyr Gln Gln Lys Pro Gly Gln Ala Pro Arg
    50                  55                  60

Leu Leu Ile Lys Tyr Ala Ser Gln Ser Leu Ser Gly Ile Pro Asp Arg
65                  70                  75                  80

Phe Ser Gly Ser Gly Ser Gly Thr Asp Phe Thr Leu Thr Ile Ser Arg
                85                  90                  95

Leu Glu Pro Glu Asp Phe Ala Val Tyr Tyr Cys His Gln Ser Ser Arg
            100                 105                 110

Leu Pro His Thr Phe Gly Gln Gly Thr Lys Val Glu Ile Lys Arg Thr
        115                 120                 125


<210> SEQ ID NO 21
<211> LENGTH: 411
<212> TYPE: DNA
<213> ORGANISM: Homo sapiens
<220> FEATURE:
<221> NAME/KEY: CDS
<222> LOCATION: (1)..(411)

<400> SEQUENCE: 21

atg gag ttt ggg ctg agc tgg gtt ttc ctt gtt gct ata tta aaa ggt       48
Met Glu Phe Gly Leu Ser Trp Val Phe Leu Val Ala Ile Leu Lys Gly
1               5                   10                  15

gtc cag tgt gag gtt cag ctg gtg cag tct ggg gga ggc ttg gta aag       96
Val Gln Cys Glu Val Gln Leu Val Gln Ser Gly Gly Gly Leu Val Lys
            20                  25                  30

cct ggg ggg tcc ctg aga ctc tcc tgt gca gcc tct gga ttc acc ttc      144
Pro Gly Gly Ser Leu Arg Leu Ser Cys Ala Ala Ser Gly Phe Thr Phe
        35                  40                  45

agt agc ttt gct atg cac tgg gtt cgc cag gct cca gga aaa ggt ctg      192
Ser Ser Phe Ala Met His Trp Val Arg Gln Ala Pro Gly Lys Gly Leu
    50                  55                  60

gag tgg ata tca gtt att gat act cgt ggt gcc aca tac tat gca gac      240
Glu Trp Ile Ser Val Ile Asp Thr Arg Gly Ala Thr Tyr Tyr Ala Asp
65                  70                  75                  80

tcc gtg aag ggc cga ttc acc atc tcc aga gac aat gcc aag aac tcc      288
Ser Val Lys Gly Arg Phe Thr Ile Ser Arg Asp Asn Ala Lys Asn Ser
```

```
                85                  90                  95

ttg tat ctt caa atg aac agc ctg aga gcc gag gac act gct gtg tat      336
Leu Tyr Leu Gln Met Asn Ser Leu Arg Ala Glu Asp Thr Ala Val Tyr
            100                 105                 110

tac tgt gca aga ctg ggg aac ttc tac tac ggt atg gac gtc tgg ggc      384
Tyr Cys Ala Arg Leu Gly Asn Phe Tyr Tyr Gly Met Asp Val Trp Gly
        115                 120                 125

caa ggg acc acg gtc acc gtc tcc tca                                  411
Gln Gly Thr Thr Val Thr Val Ser Ser
    130                 135


<210> SEQ ID NO 22
<211> LENGTH: 137
<212> TYPE: PRT
<213> ORGANISM: Homo sapiens

<400> SEQUENCE: 22

Met Glu Phe Gly Leu Ser Trp Val Phe Leu Val Ala Ile Leu Lys Gly
1               5                   10                  15

Val Gln Cys Glu Val Gln Leu Val Gln Ser Gly Gly Gly Leu Val Lys
            20                  25                  30

Pro Gly Gly Ser Leu Arg Leu Ser Cys Ala Ala Ser Gly Phe Thr Phe
        35                  40                  45

Ser Ser Phe Ala Met His Trp Val Arg Gln Ala Pro Gly Lys Gly Leu
    50                  55                  60

Glu Trp Ile Ser Val Ile Asp Thr Arg Gly Ala Thr Tyr Tyr Ala Asp
65                  70                  75                  80

Ser Val Lys Gly Arg Phe Thr Ile Ser Arg Asp Asn Ala Lys Asn Ser
                85                  90                  95

Leu Tyr Leu Gln Met Asn Ser Leu Arg Ala Glu Asp Thr Ala Val Tyr
            100                 105                 110

Tyr Cys Ala Arg Leu Gly Asn Phe Tyr Tyr Gly Met Asp Val Trp Gly
        115                 120                 125

Gln Gly Thr Thr Val Thr Val Ser Ser
    130                 135


<210> SEQ ID NO 23
<211> LENGTH: 2960
<212> TYPE: DNA
<213> ORGANISM: Artificial Sequence
<220> FEATURE:
<223> OTHER INFORMATION: Nucleotide sequence of chicken lysozyme MAR
      element

<400> SEQUENCE: 23

gatccgtaat acaattgtac caggttttgg tttattacat gtgactgacg gcttcctgtg     60

cgtgctcagg aaacggcagt tgggcactgc actgcccggt gatggtgcca cggtggctcc    120

tgccgccttc tttgatattc actctgttgt atttcatctc ttcttgccga tgaaaggata    180

taacagtctg tgaggaaata cttggtattt cttctgatca gcgtttttat aagtaatgtt    240

gaatattgga taaggctgtg tgtcctttgt cttgggagac aaagcccaca gcaggtggtg    300

gttggggtgg tggcagctca gtgacaggag aggttttttt gcctgttttt tttgttgttt    360

ttttttttta agtaaggtgt tctttttct tagtaaaatt tctactggac tgtatgtttt    420

gacaggtcag aaacatttct tcaaaagaag aacctttgg aaactgtaca gcccttttct    480

ttcattccct ttttgctttc tgtgccaatg cctttggttc tgatttgcat tatggaaaac    540

gttgatcgga acttgaggtt tttatttata gtgtggcttg aaagcttgga tagctgttgt    600
```

-continued

```
tacatgagat accttattaa gtttaggcca gcttgatgct ttattttttt ccctttgaag    660
tagtgagcgt tctctggttt ttttcctttg aaactggcga ggcttagatt tttctaatgg    720
gattttttac ctgatgatct agttgcatac ccaaatgctt gtaaatgttt tcctagttaa    780
catgttgata acttcggatt tacatgttgt atatacttgt catctgtgtt tctagtaaaa    840
atatatggca tttatagaaa tacgtaattc ctgatttcct ttttttttta tctctatgct    900
ctgtgtgtac aggtcaaaca gacttcactc ctatttttat ttatagaatt ttatatgcag    960
tctgtcgttg gttcttgtgt tgtaaggata cagccttaaa tttcctagag cgatgctcag   1020
taaggcgggt tgtcacatgg gttcaaatgt aaaacgggca cgtttggctg ctgccttccc   1080
gagatccagg acactaaact gcttctgcac tgaggtataa atcgcttcag atcccaggga   1140
agtgtagatc cacgtgcata ttcttaaaga agaatgaata ctttctaaaa tattttggca   1200
taggaagcaa gctgcatgga tttgtttggg acttaaatta ttttggtaac ggagtgcata   1260
ggttttaaac acagttgcag catgctaacg agtcacagca tttatgcaga agtgatgcct   1320
gttgcagctg tttacggcac tgccttgcag tgagcgattt gcagataggg gtggggtgct   1380
ttgtgtcgtg ttcccacacg ctgccacaca gccacctccc ggaacacatc tcacctgctg   1440
ggtacttttc aaaccatctt agcagtagta gatgagttac tatgaaacag agaagttcct   1500
cagttggata ttctcatggg atgtcttttt tcccatgttg ggcaaagtat gataaagcat   1560
ctctatttgt aaattatgca cttgttagtt cctgaatcct ttctatagca ccacttattg   1620
cagcaggtgt aggctctggt gtggcctgtg tctgtgcttc aatcttttaa gcttctttgg   1680
aaatacactg acttgattga agtctcttga agatagtaaa cagtacttac ctttgatccc   1740
aatgaaatcg agcatttcag ttgtaaaaga attccgccta ttcataccat gtaatgtaat   1800
tttacacccc cagtgctgac actttggaat atattcaagt aatagacttt ggcctcaccc   1860
tcttgtgtac tgtattttgt aatagaaaat attttaaact gtgcatatga ttattacatt   1920
atgaaagaga cattctgctg atcttcaaat gtaagaaaat gaggagtgcg tgtgctttta   1980
taaatacaag tgattgcaaa ttagtgcagg tgtccttaaa aaaaaaaaaa agtaatataa   2040
aaaggaccag gtgttttaca agtgaaatac attcctattt ggtaaacagt tacattttta   2100
tgaagattac cagcgctgct gactttctaa acataaggct gtattgtctt cctgtaccat   2160
tgcatttcct cattcccaat ttgcacaagg atgtctgggt aaactattca agaaatggct   2220
ttgaaataca gcatgggagc ttgtctgagt tggaatgcag agttgcactg caaaatgtca   2280
ggaaatggat gtctctcaga atgcccaact ccaaaggatt ttatatgtgt atatagtaag   2340
cagtttcctg attccagcag gccaaagagt ctgctgaatg ttgcgttgcc ggagacctgt   2400
atttctcaac aaggtaagat ggtatcctag caactgcgga ttttaataca ttttcagcag   2460
aagtacttag ttaatctcta cctttaggga tcgtttcatc atttttagat gttatacttg   2520
aaatactgca taacttttag ctttcatggg ttccttttt tcagccttta ggagactgtt   2580
aagcaatttg ctgtccaact tttgtgttgg tcttaaactg caatagtagt ttaccttgta   2640
ttgaagaaat aaagaccatt tttatattaa aaaatacttt tgtctgtctt cattttgact   2700
tgtctgatat ccttgcagtg ctcattatgt cagttctgtc agatattcag acatcaaaac   2760
ttaacgtgag ctcagtggag ttacagctgc ggttttgatg ctgttattat ttctgaaact   2820
agaaatgatg ttgtcttcat ctgctcatca aacacttcat gcagagttta aggctagtga   2880
gaaatgcata catttattga tactttttta aagtcaactt tttatcagat ttttttttca   2940
tttggaaata tattgttttc                                               2960
```

<210> SEQ ID NO 24
<211> LENGTH: 14910
<212> TYPE: DNA
<213> ORGANISM: Artificial Sequence
<220> FEATURE:
<223> OTHER INFORMATION: Nucleotide sequence of pinAIL10/MAR(-)

<400> SEQUENCE: 24
gcactataca tcaaatattc cttattaacc cctttacaaa ttaaaaagct aaaggtacac 60
aatttttgag catagttatt aatagcagac actctatgcc tgtgtggagt aagaaaaaac 120
agtatgttat gattataact gttatgccta cttataaagg ttacagaata tttttccata 180
attttcttgt atagcagtgc agctttttcc tttgtggtgt aaatagcaaa gcaagcaaga 240
gttctattac taaacacagc atgactcaaa aaacttagca attctgaagg aaagtccttg 300
gggtcttcta cctttctctt cttttttgga ggagtagaat gttgagagtc agcagtagcc 360
tcatcatcac tagatggcat ttcttctgag caaaacaggt tttcctcatt aaaggcattc 420
caccactgct cccattcatc agttccatag gttggaatct aaaatacaca aacaattaga 480
atcagtagtt taacacatta tacacttaaa aattttatat ttaccttaga gctttaaatc 540
tctgtaggta gtttgtccaa ttatgtcaca ccacagaagt aaggttcctt cacaaagatc 600
gatctaaagc cagcaaaagt cccatggtct tataaaaatg catagcttta ggaggggagc 660
agagaacttg aaagcatctt cctgttagtc tttcttctcg tagacttcaa acttatactt 720
gatgcctttt tcctcctgga cctcagagag gacgcctggg tattctggga gaagtttata 780
tttccccaaa tcaatttctg ggaaaaacgt gtcactttca aattcctgca tgatccttgt 840
cacaaagagt ctgaggtggc ctggttgatt catggcttcc tggtaaacag aactgcctcc 900
gactatccaa accatgtcta ctttacttgc caattccggt tgttcaataa gtcttaaggc 960
atcatccaaa cttttggcaa gaaaatgagc tcctcgtggt ggttctttga gttctctact 1020
gagaactata ttaattctgt cctttaaagg tcgattcttc tcaggaatgg agaaccaggt 1080
tttcctaccc ataatcacca gattctgttt accttccact gaagaggttg tggtcattct 1140
ttggaagtac ttgaactcgt tcctgagcgg aggccagggt aggtctccgt tcttgccaat 1200
ccccatattt tgggacacgg cgacgatgca gttcaatggt cgaaccatga tggcagcggg 1260
gataaaatcc taccagcctt cacgctagga ttgccgtcaa gtttggcgcg aaatcgcagc 1320
cctgagctgt cccccccccc aagctcagat ctgagcttgg tccctatggt gagtccgttc 1380
cgctcttgtg atgatagcca gacaagaaag agacaataca agacaaacac caaatagtag 1440
aaatagagac aagggtcact tatccgaggg tccctgttcg ggcgccagct gccgcagtcg 1500
gccgacctga gggtcgccgg ggtctgcggg gggaccctct ggaaagtgaa ggataagtga 1560
cgagcggaga cgggatggcg aacagacaca aacacacaag aggtgaatgt taggactgtt 1620
gcaagtttac tcaaaaaatc agcactcttt tatatcttgg tttacataag catttacata 1680
agatttggat aaattccaaa agaacatagg aaaatagaac actcagagct cagatcagaa 1740
cctttgatac caaaccaagt caggaaacca cttgtctcac atcctcgttt taagaacagt 1800
ttgtaaccaa aaacttactt aagccctggg aaccgcaagg ttgggccaat aaaggctatt 1860
cataataact catgccatga gtttttgcag aataatgttc tattagtcca gccactgtcc 1920
cctccttggt atggaaaatc tttccccaaa agtgcattcc tgttcctaga taaatataat 1980
catgtacctg ttgtttcatg tcgtcttttt cttcttgaga caacatacac caaggaggtc 2040
tagctctggc gagtctttca cgaaaaggga gggatctata taacacttta tagccattga 2100

-continued

```
ctgtaaccca cctatcccaa tttaagtcat atcttcctgt atatggtaag ggggcatctg   2160
ttggtctgta gatgtaaggt cccctataag tccctggttg ccaccacctg tctcctattt   2220
tgacaaaaac actctttttt ccctttttta cttctaggcc tgtggtcaat agtccttgca   2280
cctgttcttc aattgaggtt gagcgtctct ttctattttc tattcccatt tctaacttct   2340
gaatttgagt aaaaatagta ctaaaagata atgattcatt tcttaacata gtaactaata   2400
atctacctat tggattggtc ttattggtaa aaatataatt tttagcaagc attcttattt   2460
ctatttctga aggacaaaat cgatgcggct tgtaagagga agttggctgt ggtccttgcc   2520
tcaggaggaa ggtcgagttc tccgaattgt ttagattgta atcttgcaca gaagagctat   2580
taaaagagtc aagggtgaga gccctgcgag cacgaaccgc aacttccccc aatagcccca   2640
ggcaaagcag agctatgcca agtttgcagc agagaatgaa tatgtctttg tctgatgggc   2700
tcatccgttt gtgcgcagac gggtcgtcct tggtgggaaa caaccccttg gctgcttctc   2760
ccctaggtgt aggacactct cgggagttca accatttctg cccaagctca gatctgagct   2820
ttaatgcggt agtttatcac agttaaattg ctaacgcagt caggcaccgt gtatgaaatc   2880
taacaatgcg ctcatcgtca tcctcggcac cgtcaccctg gatgctgtag gcataggctt   2940
ggttatgccg gtactgccgg gcctcttgcg ggatatcgtc cattccgaca gcatcgccag   3000
tcactatggc gtgctgctag cgctcttccg cttcctcgct cactgactcg ctgcgctcgg   3060
tcgttcggct gcggcgagcg gtatcagctc actcaaaggc ggtaatacgg ttatccacag   3120
aatcagggga taacgcagga aagaacatgt gagcaaaagg ccagcaaaag gccaggaacc   3180
gtaaaaaggc cgcgttgctg gcgtttttcc ataggctccg cccccctgac gagcatcaca   3240
aaaatcgacg ctcaagtcag aggtggcgaa acccgacagg actataaaga taccaggcgt   3300
ttccccctgg aagctccctc gtgcgctctc ctgttccgac cctgccgctt accggatacc   3360
tgtccgcctt tctcccttcg ggaagcgtgg cgctttctca tagctcacgc tgtaggtatc   3420
tcagttcggt gtaggtcgtt cgctccaagc tgggctgtgt gcacgaaccc cccgttcagc   3480
ccgaccgctg cgccttatcc ggtaactatc gtcttgagtc caacccggta agacacgact   3540
tatcgccact ggcagcagcc actggtaaca ggattagcag agcgaggtat gtaggcggtg   3600
ctacagagtt cttgaagtgg tggcctaact acggctacac tagaaggaca gtatttggta   3660
tctgcgctct gctgaagcca gttaccttcg gaaaaagagt tggtagctct tgatccggca   3720
aacaaaccac cgctggtagc ggtggttttt ttgtttgcaa gcagcagatt acgcgcagaa   3780
aaaaaggatc tcaagaagat cctttgatct tttctacggg gtctgacgct cagtggaacg   3840
aaaactcacg ttaagggatt ttggtcatga gattatcaaa aaggatcttc acctagatcc   3900
ttttaaatta aaaatgaagt tttaaatcaa tctaaagtat atatgagtaa acttggtctg   3960
acagttacca atgcttaatc agtgaggcac ctatctcagc gatctgtcta tttcgttcat   4020
ccatagttgc ctgactcccc gtcgtgtaga taactacgat acgggagggc ttaccatctg   4080
gccccagtgc tgcaatgata ccgcgagacc cacgctcacc ggctccagat ttatcagcaa   4140
taaaccagcc agccggaagg gccgagcgca gaagtggtcc tgcaacttta tccgcctcca   4200
tccagtctat taattgttgc cgggaagcta gagtaagtag ttcgccagtt aatagtttgc   4260
gcaacgttgt tgccattgct acaggcatcg tggtgtcacg ctcgtcgttt ggtatggctt   4320
cattcagctc cggttcccaa cgatcaaggc gagttacatg atcccccatg ttgtgcaaaa   4380
aagcggttag ctccttcggt cctccgatcg ttgtcagaag taagttggcc gcagtgttat   4440
cactcatggt tatggcagca ctgcataatt ctcttactgt catgccatcc gtaagatgct   4500
```

-continued

```
tttctgtgac tggtgagtac tcaaccaagt cattctgaga atagtgtatg cggcgaccga   4560
gttgctcttg cccggcgtca acacgggata ataccgcgcc acatagcaga actttaaaag   4620
tgctcatcat tggaaaacgt tcttcggggc gaaaactctc aaggatctta ccgctgttga   4680
gatccagttc gatgtaaccc actcgtgcac ccaactgatc ttcagcatct tttactttca   4740
ccagcgtttc tgggtgagca aaaacaggaa ggcaaaatgc cgcaaaaaag ggaataaggg   4800
cgacacggaa atgttgaata ctcatactct tcctttttca atattattga agcatttatc   4860
agggttattg tctcatgagc ggatacatat ttgaatgtat ttagaaaaat aaacaaatag   4920
gggttccgcg cacatttccc cgaaaagtgc cacctgacgt ctaagagacc attattatca   4980
tgacattaac ctataaaaat aggcgtatca cgaggccctt tcgtcttcaa gaattgtcta   5040
gaggcgcgct taattaatcg cgatggccac atatggagct ctctagaaaa caatatattt   5100
ccaaatgaaa aaaaaatctg ataaaaagtt gactttaaaa aagtatcaat aaatgtatgc   5160
atttctcact agccttaaac tctgcatgaa gtgtttgatg agcagatgaa gacaacatca   5220
tttctagttt cagaaataat aacagcatca aaaccgcagc tgtaactcca ctgagctcac   5280
gttaagtttt gatgtctgaa tatctgacag aactgacata atgagcactg caaggatatc   5340
agacaagtca aaatgaagac agacaaaagt atttttttaat ataaaaatgg tctttatttc   5400
ttcaatacaa ggtaaactac tattgcagtt taagaccaac acaaaagttg gacagcaaat   5460
tgcttaacag tctcctaaag gctgaaaaaa aggaacccat gaaagctaaa agttatgcag   5520
tatttcaagt ataacatcta aaaatgatga aacgatccct aaaggtagag attaactaag   5580
tacttctgct gaaaatgtat taaaatccgc agttgctagg ataccatctt accttgttga   5640
gaaatacagg tctccggcaa cgcaacattc agcagactct ttggcctgct ggaatcagga   5700
aactgcttac tatatacaca tataaaatcc tttggagttg ggcattctga gagacatcca   5760
tttcctgaca ttttgcagtg caactctgca ttccaactca gacaagctcc catgctgtat   5820
ttcaaagcca tttcttgaat agtttaccca gacatccttg tgcaaattgg gaatgaggaa   5880
atgcaatggt acaggaagac aatacagcct tatgtttaga aagtcagcag cgctggtaat   5940
cttcataaaa atgtaactgt ttaccaaata ggaatgtatt tcacttgtaa aacacctggt   6000
cctttttata ttactttttt tttttttaa ggacacctgc actaatttgc aatcacttgt   6060
atttataaaa gcacacgcac tcctcatttt cttacatttg aagatcagca gaatgtctct   6120
ttcataatgt aataatcata tgcacagttt aaaatatttt ctattacaaa atacagtaca   6180
caagagggtg aggccaaagt ctattacttg aatatattcc aaagtgtcag cactgggggt   6240
gtaaaattac attacatggt atgaataggc ggaattcttt tacaactgaa atgctcgatt   6300
tcattgggat caaaggtaag tactgtttac tatcttcaag agacttcaat caagtcagtg   6360
tatttccaaa gaagcttaaa agattgaagc acagacacag gccacaccag agcctacacc   6420
tgctgcaata agtggtgcta tagaaaggat tcaggaacta acaagtgcat aatttacaaa   6480
tagagatgct ttatcatact ttgcccaaca tgggaaaaaa gacatcccat gagaatatcc   6540
aactgaggaa cttctctgtt tcatagtaac tcatctacta ctgctaagat ggtttgaaaa   6600
gtacccagca ggtgagatgt gttccgggag gtggctgtgt ggcagcgtgt gggaacacga   6660
cacaaagcac cccaccccta tctgcaaatc gctcactgca aggcagtgcc gtaaacagct   6720
gcaacaggca tcacttctgc ataaatgctg tgactcgtta gcatgctgca actgtgttta   6780
aaacctatgc actccgttac caaaataatt taagtcccaa acaaatccat gcagcttgct   6840
tcctatgcca aatatttta gaaagtattc attcttcttt aagaatatgc acgtggatct   6900
```

-continued

```
acacttccct gggatctgaa gcgatttata cctcagtgca gaagcagttt agtgtcctgg   6960
atctcgggaa ggcagcagcc aaacgtgccc gttttacatt tgaacccatg tgacaacccg   7020
ccttactgag catcgctcta ggaaatttaa ggctgtatcc ttacaacaca agaaccaacg   7080
acagactgca tataaaattc tataaataaa aataggagtg aagtctgttt gacctgtaca   7140
cacagagcat agagataaaa aaaaaaggaa atcaggaatt acgtatttct ataaatgcca   7200
tatattttta ctagaaacac agatgacaag tatatacaac atgtaaatcc gaagttatca   7260
acatgttaac taggaaaaca tttacaagca tttgggtatg caactagatc atcaggtaaa   7320
aaatcccatt agaaaaatct aagcctcgcc agtttcaaag gaaaaaaacc agagaacgct   7380
cactacttca aagggaaaaa aataaagcat caagctggcc taaacttaat aaggtatctc   7440
atgtaacaac agctatccaa gctttcaagc cacactataa ataaaaacct caagttccga   7500
tcaacgtttt ccataatgca aatcagaacc aaaggcattg gcacagaaag caaaaaggga   7560
atgaaagaaa agggctgtac agtttccaaa aggttcttct tttgaagaaa tgtttctgac   7620
ctgtcaaaac atacagtcca gtagaaattt tactaagaaa aaagaacacc ttacttaaaa   7680
aaaaaaaaca acaaaaaaaa caggcaaaaa aacctctcct gtcactgagc tgccaccacc   7740
ccaaccacca cctgctgtgg gctttgtctc ccaagacaaa ggacacacag ccttatccaa   7800
tattcaacat tacttataaa aacgctgatc agaagaaata ccaagtattt cctcacagac   7860
tgttatatcc tttcatcggc aagaagagat gaaatacaac agagtgaata tcaaagaagg   7920
cggcaggagc caccgtggca ccatcaccgg gcagtgcagt gcccaactgc cgtttcctga   7980
gcacgcacag gaagccgtca gtcacatgta ataaaccaaa acctggtaca attgtattac   8040
ggatcccggt ggcgcgccgt ttaaaccctc agctaccgat gtacgggcca gatatacgcg   8100
ttgacattga ttattgacta gttattaata gtaatcaatt acggggtcat tagttcatag   8160
cccatatatg gagttccgcg ttacataact tacggtaaat ggcccgcctg gctgaccgcc   8220
caacgacccc cgcccattga cgtcaataat gacgtatgtt cccatagtaa cgccaatagg   8280
gactttccat tgacgtcaat gggtggacta tttacggtaa actgcccact tggcagtaca   8340
tcaagtgtat catatgccaa gtacgccccc tattgacgtc aatgacggta aatggcccgc   8400
ctggcattat gcccagtaca tgaccttatg ggactttcct acttggcagt acatctacgt   8460
attagtcatc gctattacca tggtgatgcg gttttggcag tacatcaatg ggcgtggata   8520
gcggtttgac tcacggggat ttccaagtct ccaccccatt gacgtcaatg ggagtttgtt   8580
ttggcaccaa aatcaacggg actttccaaa atgtcgtaac aactccgccc cattgacgca   8640
aatgggcggt aggcgtgtac ggtgggaggt ctatataagc agagctctct ggctaactag   8700
agaacccact gcttactggc ttatcgaaat taatacgact cactatagca attgcacgtg   8760
tggccacagg taagtttaaa gctcaggtcg agaccgggcc tttgtccggc gctcccttgg   8820
agcctaccta gactcagccg gctctccacg ctttgcctga ccctgcttgc tcaactctac   8880
gtctttgttt cgttttctgt tcctttctct ccacaggctt aagcttggta ccagaaagtt   8940
aacatggctg tcttggggct gctcttctgc ctggtgacat tcccaagctg tgtcctatcc   9000
caggtgcagc tggtggagtc tgggggaggc gtggtccagc ctgggaggtc cctgagactc   9060
tcctgtgcag cctctggatt cactttcagt gactatcata tggcctgggt ccgccaggct   9120
ccaggcaagg ggctggagtg ggtggcaagc attactcttg atgctaccta cacttactat   9180
cgcgactccg tgcgcggccg cttcaccatc tccagagaca attccaagaa cacgctgtat   9240
ctgcaaatga acagcctgag agctgaggac acggctgtgt attactgtgc gagacatcga   9300
```

-continued

```
ggctttagcg tctggcttga ttactggggc caaggcaccc tggtcaccgt ctcgtcggct   9360
agcaccaagg gcccatcggt cttcccccctg gcaccctcct ccaagagcac ctctgggggc   9420
acagcggccc tgggctgcct ggtcaaggac tacttccccg aaccggtgac ggtgtcgtgg   9480
aactcaggcg ccctgaccag cggcgtgcac accttcccgg ctgtcctaca gtcctcagga   9540
ctctactccc tcagcagcgt ggtgaccgtg ccctccagca gcttgggcac ccagacctac   9600
atctgcaacg tgaatcacaa gcccagcaac accaaggtgg acaagaaagt tgagcccaaa   9660
tcttgtgaca aaactcacac atgcccaccg tgcccagcac ctgaactcct ggggggaccg   9720
tcagtcttcc tcttcccccc aaaacccaag gacaccctca tgatctcccg gacccctgag   9780
gtcacatgcg tggtggtgga cgtgagccac gaagaccctg aggtcaagtt caactggtac   9840
gtggacggcg tggaggtgca taatgccaag acaaagccgc gggaggagca gtacaacagc   9900
acgtaccgtg tggtcagcgt cctcaccgtc ctgcaccagg actggctgaa tggcaaggag   9960
tacaagtgca aggtctccaa caaagccctc ccagccccca tcgagaaaac catctccaaa  10020
gccaaagggc agccccgaga accacaggtg tacaccctgc ccccatcccg ggatgagctg  10080
accaagaacc aggtcagcct gacctgcctg gtcaaaggct tctatcccag cgacatcgcc  10140
gtggagtggg agagcaatgg gcagccggag aacaactaca agaccacgcc tcccgtgctg  10200
gactccgacg gctccttctt cctctacagc aagctcaccg tggacaagag caggtggcag  10260
caggggaacg tcttctcatg ctccgtgatg catgaggctc tgcacaacca ctacacgcag  10320
aagagcctct ccctgtctcc gggtaaatga atcgatgatt ctagatacgg gtccggagga  10380
tccagatccc cctcgctttc ttgctgtcca atttctatta aaggttcctt tgttccctaa  10440
gtccaactac taaactgggg gatattatga agggccttga gcatctggat tctgcctaat  10500
aaaaaacatt tattttcatt gcaatgatgt atttaaatta tttctgaata ttttactaaa  10560
aagggaatgt gggaggtcag tgcatttaaa acataaagaa atgaagaggg ggatctgtcg  10620
acaagctcta gagagctcac gcgttgatca tgtacaggcc ggccaagctt tcgactagct  10680
tggcacgcca gaaatccgcg cggtggtttt tgggggtcgg gggtgtttgg cagccacaga  10740
cgcccggtgt tcgtgtcgcg ccagtacatg cggtccatgc ccaggccatc caaaaaccat  10800
gggtctgtct gctcagtcca gtcgtggacc tgaccccacg caacgcccaa aataataacc  10860
cccacgaacc ataaaccatt ccccatgggg gaccccgtcc ctaacccacg gggccagtgg  10920
ctatggcagg gcctgccgcc ccgacgttgg ctgcgagccc tgggccttca cccgaacttg  10980
gggggtgggg tggggaaaag gaagaaacgc gggcgtattg gccccaatgg ggtctcggtg  11040
gggtatcgac agagtgccag ccctgggacc gaaccccgcg tttatgaaca aacgacccaa  11100
cacccgtgcg ttttattctg tctttttatt gccgtcatag cgcgggttcc ttccggtatt  11160
gtctccttcc gtgtttcagt tagcctcccc catctcccga tccggacgag tgctggggcg  11220
tcggtttcca ctatcggcga gtacttctac acagccatcg gtccagacgg ccgcgcttct  11280
gcgggcgatt tgtgtacgcc cgacagtccc ggctccggat cggacgattg cgtcgcatcg  11340
accctgcgcc caagctgcat catcgaaatt gccgtcaacc aagctctgat agagttggtc  11400
aagaccaatg cggagcatat acgcccggag ccgcggcgat cctgcaagct ccggatgcct  11460
ccgctcgaag tagcgcgtct gctgctccat acaagccaac cacggcctcc agaagaagat  11520
gttggcgacc tcgtattggg aatccccgaa catcgcctcg ctccagtcaa tgaccgctgt  11580
tatgcggcca ttgtccgtca ggacattgtt ggagccgaaa tccgcgtgca cgaggtgccg  11640
gacttcgggg cagtcctcgg cccaaagcat cagctcatcg agagcctgcg cgacggacgc  11700
```

-continued

```
actgacggtg tcgtccatca cagtttgcca gtgatacaca tggggatcag caatcgcgca  11760
tatgaaatca cgccatgtag tgtattgacc gattccttgc ggtccgaatg ggccgaaccc  11820
gctcgtctgg ctaagatcgg ccgcagcgat cgcatccatg gcctccgcga ccggctgcag  11880
aacagcgggc agttcggttt caggcaggtc ttgcaacgtg acaccctgtg cacggcggga  11940
gatgcaatag gtcaggctct cgctgaattc cccaatgtca agcacttccg gaatcgggag  12000
cgcggccgat gcaaagtgcc gataaacata acgatctttg tagaaaccat cggcgcagct  12060
atttacccgc aggacatatc cacgccctcc tacatcgaag ctgaaagcac gagattcttc  12120
gccctccgag agctgcatca ggtcggagac gctgtcgaac ttttcgatca gaaacttctc  12180
gacagacgtc gcggtgagtt caggcttttt catatctcat tgcccccccgg gatctgcggc  12240
acgctgttga cgctgttaag cgggtcgctg cagggtcgct cggtgttcga ggccacacgc  12300
gtcaccttaa tatgcgaagt ggacctcgga ccgcgccgcc ccgactgcat ctgcgtgttc  12360
gaattcgcca atgacaagac gctgggcggg gtttgtgtca tcatagaact aaagacatgc  12420
aaatatattt cttccgggga caccgccagc aaacgcgagc aacgggccac ggggatgaag  12480
cagggcggca cctcgctaac ggattcacca ctccaagaat tggagccaat caattcttgc  12540
ggagaactgt gaatgcgcaa accaaccctt ggcagaacat atccatcgcg tccgccatct  12600
ccagcagccg cacgcggcgc atctcggggc cgacgcgctg ggctacgtct tgctggcgtt  12660
cgcacaggcc ggccagcgcg cggccggccg gtaccacgcg ttggccacat atggcggccg  12720
ctcgcgatta attaatcgcg atggccacat atggagctct ctagagcttg tcgacagatc  12780
cccctcttca tttctttatg ttttaaatgc actgacctcc cacattccct tttagtaaa  12840
atattcagaa ataatttaaa tacatcattg caatgaaaat aaatgttttt tattaggcag  12900
aatccagatg ctcaaggccc ttcataatat cccccagttt agtagttgga cttagggaac  12960
aaaggaacct ttaatagaaa ttggacagca agaaagcgag gggatctgg atcctccgga  13020
gggccctgga tcctcctacg tatctagaat catcgattaa cactctcccc tgttgaagct  13080
ctttgtgacg ggcgagctca ggccctgatg ggtgacttcg caggcgtaga ctttgtgttt  13140
ctcgtagtct gctttgctca gcgtcagggt gctgctgagg ctgtaggtgc tgtccttgct  13200
gtcctgctct gtgacactct cctgggagtt acccgattgg agggcgttat ccaccttcca  13260
ctgtactttg gcctctctgg gatagaagtt attcagcagg cacacaacag aggcagttcc  13320
agatttcaac tgctcatcag atggcgggaa gatgaagaca gatggtgcag ccaccgtacg  13380
tttcagttcc agcttggtcc caggtccaaa cgtgtacccg ctataatact ggtgacagta  13440
gtaagttgca aaatcttcag gttgcagact gctgatggtg agagtgaaat ctgtcccaga  13500
tccactgcca ctgaaccttg atgggacccc cgcttgcaaa gggcttgcat tatagatcag  13560
gagcttaggg gctttccctg gtttctgctg ataccaggcc aagttctcaa aaatgttctg  13620
acttgtcttg caagtgatgg tgactctgtc tcctacagat gcagacaggg aggatggaga  13680
ctgggtcatc tggatgtcac atctcatggc tgggaggaag agcaccaaaa gccctaaaag  13740
ttgaactgga gccatctcga gaattcttaa gcctgtggag agaaaggaac agaaaacgaa  13800
acaaagacgt agagttgagc aagcagggtc aggcaaagcg tggagagccg gctgagtcta  13860
ggtaggctcc aagggagcgc cggacaaagg cccggtctcg acctgagctt taaacttacc  13920
tgtggccaca cgtgcaattg ctatagtgag tcgtattaat ttcgataagc cagtaagcag  13980
tgggttctct agttagccag agagctctgc ttatatagac ctcccaccgt acacgcctac  14040
cgcccatttg cgtcaatggg gcggagttgt tacgacattt tggaaagtcc cgttgatttt  14100
```

-continued

```
ggtgccaaaa caaactccca ttgacgtcaa tggggtggag acttggaaat ccccgtgagt  14160
caaaccgcta tccacgccca ttgatgtact gccaaaaccg catcaccatg gtaatagcga  14220
tgactaatac gtagatgtac tgccaagtag gaaagtccca taaggtcatg tactgggcat  14280
aatgccaggc gggccattta ccgtcattga cgtcaatagg gggcgtactt ggcatatgat  14340
acacttgatg tactgccaag tgggcagttt accgtaaata gtccacccat tgacgtcaat  14400
ggaaagtccc tattggcgtt actatgggaa catacgtcat tattgacgtc aatgggcggg  14460
ggtcgttggg cggtcagcca ggcgggccat ttaccgtaag ttatgtaacg cggaactcca  14520
tatatgggct atgaactaat gaccccgtaa ttgattacta ttaataacta gtcaataatc  14580
aatgtcaacg cgtatatctg gcccgtacat cggtaactag tcggaccggc ccgggccacc  14640
ggtgctcgaa gcttggatcg atccagacat gataagatac attgatgagt ttggacaaac  14700
cacaactaga atgcagtgaa aaaaatgctt tatttgtgaa atttgtgatg ctattgcttt  14760
atttgtaacc attataagct gcaataaaca agttaacaac aacaattgca ttcattttat  14820
gtttcaggtt caggggaggg tgtgggaggt tttttaaagc aagtaaaacc tctacaaatg  14880
tggtatggct gattatgatc tctagtcaag                                   14910
```

<210> SEQ ID NO 25
<211> LENGTH: 15083
<212> TYPE: DNA
<213> ORGANISM: Artificial Sequence
<220> FEATURE:
<223> OTHER INFORMATION: Nucleotide sequence of pAIL10V1/puro/MAR(-)

<400> SEQUENCE: 25

```
gcactataca tcaaatattc cttattaacc cctttacaaa ttaaaaagct aaaggtacac     60
aatttttgag catagttatt aatagcagac actctatgcc tgtgtggagt aagaaaaaac    120
agtatgttat gattataact gttatgccta cttataaagg ttacagaata tttttccata    180
atttcttgt atagcagtgc agcttttttcc tttgtggtgt aaatagcaaa gcaagcaaga    240
gttctattac taaacacagc atgactcaaa aaacttagca attctgaagg aaagtccttg    300
gggtcttcta cctttctctt cttttttgga ggagtagaat gttgagagtc agcagtagcc    360
tcatcatcac tagatggcat ttcttctgag caaaacaggt tttcctcatt aaaggcattc    420
caccactgct cccattcatc agttccatag gttggaatct aaaatacaca aacaattaga    480
atcagtagtt taacacatta tacacttaaa aattttatat ttaccttaga gctttaaatc    540
tctgtaggta gtttgtccaa ttatgtcaca ccacagaagt aaggttcctt cacaaagatc    600
gatctaaagc cagcaaaagt cccatggtct tataaaaatg catagcttta ggaggggagc    660
agagaacttg aaagcatctt cctgttagtc tttcttctcg tagacttcaa acttatactt    720
gatgcctttt tcctcctgga cctcagagag gacgcctggg tattctggga gaagtttata    780
tttccccaaa tcaatttctg ggaaaaacgt gtcactttca aattcctgca tgatccttgt    840
cacaaagagt ctgaggtggc ctggttgatt catggcttcc tggtaaacag aactgcctcc    900
gactatccaa accatgtcta ctttacttgc caattccggt tgttcaataa gtcttaaggc    960
atcatccaaa cttttggcaa gaaaatgagc tcctcgtggt ggttctttga gttctctact   1020
gagaactata ttaattctgt cctttaaagg tcgattcttc tcaggaatgg agaaccaggt   1080
tttcctaccc ataatcacca gattctgttt accttccact gaagaggttg tggtcattct   1140
ttggaagtac ttgaactcgt tcctgagcgg aggccagggt aggtctccgt tcttgccaat   1200
ccccatattt tgggacacgg cgacgatgca gttcaatggt cgaaccatga tggcagcggg   1260
```

-continued

```
gataaaatcc taccagcctt cacgctagga ttgccgtcaa gtttggcgcg aaatcgcagc   1320
cctgagctgt cccccccccc aagctcagat ctgagcttgg tccctatggt gagtccgttc   1380
cgctcttgtg atgatagcca gacaagaaag agacaataca agacaaacac caaatagtag   1440
aaatagagac aagggtcact tatccgaggg tccctgttcg ggcgccagct gccgcagtcg   1500
gccgacctga gggtcgccgg ggtctgcggg gggaccctct ggaaagtgaa ggataagtga   1560
cgagcggaga cgggatggcg aacagacaca aacacacaag aggtgaatgt taggactgtt   1620
gcaagtttac tcaaaaaatc agcactcttt tatatcttgg tttacataag catttacata   1680
agatttggat aaattccaaa agaacatagg aaaatagaac actcagagct cagatcagaa   1740
cctttgatac caaaccaagt caggaaacca cttgtctcac atcctcgttt taagaacagt   1800
ttgtaaccaa aaacttactt aagccctggg aaccgcaagg ttgggccaat aaaggctatt   1860
cataataact catgccatga gtttttgcag aataatgttc tattagtcca gccactgtcc   1920
cctccttggt atggaaaatc tttccccaaa agtgcattcc tgttcctaga taaatataat   1980
catgtacctg ttgtttcatg tcgtcttttt cttcttgaga caacatacac caaggaggtc   2040
tagctctggc gagtctttca cgaaaaggga gggatctata taacacttta tagccattga   2100
ctgtaaccca cctatcccaa tttaagtcat atcttcctgt atatggtaag gggcatctg    2160
ttggtctgta gatgtaaggt cccctataag tccctggttg ccaccacctg tctcctattt   2220
tgacaaaaac actctttttt cccttttta cttctaggcc tgtggtcaat agtccttgca    2280
cctgttcttc aattgaggtt gagcgtctct ttctattttc tattcccatt tctaacttct   2340
gaatttgagt aaaaatagta ctaaaagata atgattcatt tcttaacata gtaactaata   2400
atctacctat tggattggtc ttattggtaa aaatataatt tttagcaagc attcttattt   2460
ctatttctga aggacaaaat cgatgcggct tgtaagagga agttggctgt ggtccttgcc   2520
tcaggaggaa ggtcgagttc tccgaattgt ttagattgta atcttgcaca gaagagctat   2580
taaaagagtc aagggtgaga gccctgcgag cacgaaccgc aacttccccc aatagcccca   2640
ggcaaagcag agctatgcca agtttgcagc agagaatgaa tatgtctttg tctgatgggc   2700
tcatccgttt gtgcgcagac gggtcgtcct tggtgggaaa caaccccttg gctgcttctc   2760
ccctaggtgt aggacactct cgggagttca accatttctg cccaagctca gatctgagct   2820
ttaatgcggt agtttatcac agttaaattg ctaacgcagt caggcaccgt gtatgaaatc   2880
taacaatgcg ctcatcgtca tcctcggcac cgtcaccctg gatgctgtag gcataggctt   2940
ggttatgccg gtactgccgg gcctcttgcg ggatatcgtc cattccgaca gcatcgccag   3000
tcactatggc gtgctgctag cgctcttccg cttcctcgct cactgactcg ctgcgctcgg   3060
tcgttcggct gcggcgagcg gtatcagctc actcaaaggc ggtaatacgg ttatccacag   3120
aatcagggga taacgcagga aagaacatgt gagcaaaagg ccagcaaaag gccaggaacc   3180
gtaaaaaggc cgcgttgctg gcgtttttcc ataggctccg cccccctgac gagcatcaca   3240
aaaatcgacg ctcaagtcag aggtggcgaa acccgacagg actataaaga taccaggcgt   3300
ttccccctgg aagctccctc gtgcgctctc ctgttccgac cctgccgctt accggatacc   3360
tgtccgcctt tctcccttcg ggaagcgtgg cgctttctca tagctcacgc tgtaggtatc   3420
tcagttcggt gtaggtcgtt cgctccaagc tgggctgtgt gcacgaaccc cccgttcagc   3480
ccgaccgctg cgccttatcc ggtaactatc gtcttgagtc caacccggta agacacgact   3540
tatcgccact ggcagcagcc actggtaaca ggattagcag agcgaggtat gtaggcggtg   3600
ctacagagtt cttgaagtgg tggcctaact acggctacac tagaaggaca gtatttggta   3660
```

-continued

```
tctgcgctct gctgaagcca gttaccttcg gaaaaagagt tggtagctct tgatccggca   3720
aacaaaccac cgctggtagc ggtggttttt ttgtttgcaa gcagcagatt acgcgcagaa   3780
aaaaaggatc tcaagaagat cctttgatct tttctacggg gtctgacgct cagtggaacg   3840
aaaactcacg ttaagggatt ttggtcatga gattatcaaa aaggatcttc acctagatcc   3900
ttttaaatta aaaatgaagt tttaaatcaa tctaaagtat atatgagtaa acttggtctg   3960
acagttacca atgcttaatc agtgaggcac ctatctcagc gatctgtcta tttcgttcat   4020
ccatagttgc ctgactcccc gtcgtgtaga taactacgat acgggagggc ttaccatctg   4080
gccccagtgc tgcaatgata ccgcgagacc cacgctcacc ggctccagat ttatcagcaa   4140
taaaccagcc agccggaagg gccgagcgca gaagtggtcc tgcaacttta tccgcctcca   4200
tccagtctat taattgttgc cgggaagcta gagtaagtag ttcgccagtt aatagtttgc   4260
gcaacgttgt tgccattgct acaggcatcg tggtgtcacg ctcgtcgttt ggtatggctt   4320
cattcagctc cggttcccaa cgatcaaggc gagttacatg atcccccatg ttgtgcaaaa   4380
aagcggttag ctccttcggt cctccgatcg ttgtcagaag taagttggcc gcagtgttat   4440
cactcatggt tatggcagca ctgcataatt ctcttactgt catgccatcc gtaagatgct   4500
tttctgtgac tggtgagtac tcaaccaagt cattctgaga atagtgtatg cggcgaccga   4560
gttgctcttg cccggcgtca acacgggata ataccgcgcc acatagcaga actttaaaag   4620
tgctcatcat tggaaaacgt tcttcggggc gaaaactctc aaggatctta ccgctgttga   4680
gatccagttc gatgtaaccc actcgtgcac ccaactgatc ttcagcatct tttactttca   4740
ccagcgtttc tgggtgagca aaaacaggaa ggcaaaatgc cgcaaaaaag ggaataaggg   4800
cgacacggaa atgttgaata ctcatactct tcctttttca atattattga agcatttatc   4860
agggttattg tctcatgagc ggatacatat ttgaatgtat ttagaaaaat aaacaaatag   4920
gggttccgcg cacatttccc cgaaaagtgc cacctgacgt ctaagagacc attattatca   4980
tgacattaac ctataaaaat aggcgtatca cgaggccctt tcgtcttcaa gaattgtcta   5040
gaggcgcgct taattaatcg cgatggccac atatggagct ctctagaaaa caatatattt   5100
ccaaatgaaa aaaaaatctg ataaaaagtt gactttaaaa aagtatcaat aaatgtatgc   5160
atttctcact agccttaaac tctgcatgaa gtgtttgatg agcagatgaa gacaacatca   5220
tttctagttt cagaaataat aacagcatca aaaccgcagc tgtaactcca ctgagctcac   5280
gttaagtttt gatgtctgaa tatctgacag aactgacata atgagcactg caaggatatc   5340
agacaagtca aaatgaagac agacaaaagt atttttttaat ataaaaatgg tctttatttc   5400
ttcaatacaa ggtaaactac tattgcagtt taagaccaac acaaaagttg gacagcaaat   5460
tgcttaacag tctcctaaag gctgaaaaaa aggaacccat gaaagctaaa agttatgcag   5520
tatttcaagt ataacatcta aaaatgatga aacgatccct aaaggtagag attaactaag   5580
tacttctgct gaaaatgtat taaaatccgc agttgctagg ataccatctt accttgttga   5640
gaaatacagg tctccggcaa cgcaacattc agcagactct ttggcctgct ggaatcagga   5700
aactgcttac tatatacaca tataaaatcc tttggagttg ggcattctga gagacatcca   5760
tttcctgaca ttttgcagtg caactctgca ttccaactca gacaagctcc catgctgtat   5820
ttcaaagcca tttcttgaat agtttaccca gacatccttg tgcaaattgg gaatgaggaa   5880
atgcaatggt acaggaagac aatacagcct tatgtttaga aagtcagcag cgctggtaat   5940
cttcataaaa atgtaactgt ttaccaaata ggaatgtatt tcacttgtaa aacacctggt   6000
ccttttttata ttactttttt ttttttttaa ggacacctgc actaatttgc aatcacttgt   6060
```

-continued

```
atttataaaa gcacacgcac tcctcatttt cttacatttg aagatcagca gaatgtctct   6120
ttcataatgt aataatcata tgcacagttt aaaatatttt ctattacaaa atacagtaca   6180
caagagggtg aggccaaagt ctattacttg aatatattcc aaagtgtcag cactgggggt   6240
gtaaaattac attacatggt atgaataggc ggaattcttt tacaactgaa atgctcgatt   6300
tcattgggat caaaggtaag tactgtttac tatcttcaag agacttcaat caagtcagtg   6360
tatttccaaa gaagcttaaa agattgaagc acagacacag gccacaccag agcctacacc   6420
tgctgcaata agtggtgcta tagaaaggat tcaggaacta acaagtgcat aatttacaaa   6480
tagagatgct ttatcatact ttgcccaaca tgggaaaaaa gacatcccat gagaatatcc   6540
aactgaggaa cttctctgtt tcatagtaac tcatctacta ctgctaagat ggtttgaaaa   6600
gtacccagca ggtgagatgt gttccgggag gtggctgtgt ggcagcgtgt gggaacacga   6660
cacaaagcac cccaccccta tctgcaaatc gctcactgca aggcagtgcc gtaaacagct   6720
gcaacaggca tcacttctgc ataaatgctg tgactcgtta gcatgctgca actgtgttta   6780
aaacctatgc actccgttac caaaataatt taagtcccaa acaaatccat gcagcttgct   6840
tcctatgcca aaatatttta gaaagtattc attcttcttt aagaatatgc acgtggatct   6900
acacttccct gggatctgaa gcgatttata cctcagtgca gaagcagttt agtgtcctgg   6960
atctcgggaa ggcagcagcc aaacgtgccc gttttacatt tgaacccatg tgacaacccg   7020
ccttactgag catcgctcta ggaaatttaa ggctgtatcc ttacaacaca agaaccaacg   7080
acagactgca tataaaattc tataaataaa aataggagtg aagtctgttt gacctgtaca   7140
cacagagcat agagataaaa aaaaaaggaa atcaggaatt acgtatttct ataaatgcca   7200
tatattttta ctagaaacac agatgacaag tatatacaac atgtaaatcc gaagttatca   7260
acatgttaac taggaaaaca tttacaagca tttgggtatg caactagatc atcaggtaaa   7320
aaatcccatt agaaaaatct aagcctcgcc agtttcaaag gaaaaaaacc agagaacgct   7380
cactacttca aagggaaaaa aataaagcat caagctggcc taaacttaat aaggtatctc   7440
atgtaacaac agctatccaa gctttcaagc cacactataa ataaaaacct caagttccga   7500
tcaacgtttt ccataatgca aatcagaacc aaaggcattg gcacagaaag caaaaaggga   7560
atgaaagaaa agggctgtac agtttccaaa aggttcttct tttgaagaaa tgtttctgac   7620
ctgtcaaaac atacagtcca gtagaaattt tactaagaaa aaagaacacc ttacttaaaa   7680
aaaaaaaaca acaaaaaaaa caggcaaaaa aacctctcct gtcactgagc tgccaccacc   7740
ccaaccacca cctgctgtgg gctttgtctc ccaagacaaa ggacacacag ccttatccaa   7800
tattcaacat tacttataaa aacgctgatc agaagaaata ccaagtattt cctcacagac   7860
tgttatatcc tttcatcggc aagaagagat gaaatacaac agagtgaata tcaaagaagg   7920
cggcaggagc caccgtggca ccatcaccgg gcagtgcagt gcccaactgc cgtttcctga   7980
gcacgcacag gaagccgtca gtcacatgta ataaaccaaa acctggtaca attgtattac   8040
ggatcccggt ggcgcgccgt ttaaaccctc agctaccgat gtacgggcca gatatacgcg   8100
ttgacattga ttattgacta gttattaata gtaatcaatt acggggtcat tagttcatag   8160
cccatatatg gagttccgcg ttacataact tacggtaaat ggcccgcctg gctgaccgcc   8220
caacgacccc cgcccattga cgtcaataat gacgtatgtt cccatagtaa cgccaatagg   8280
gactttccat tgacgtcaat gggtggacta tttacggtaa actgcccact tggcagtaca   8340
tcaagtgtat catatgccaa gtacgccccc tattgacgtc aatgacggta aatggcccgc   8400
ctggcattat gcccagtaca tgaccttatg ggactttcct acttggcagt acatctacgt   8460
```

-continued

```
attagtcatc gctattacca tggtgatgcg gttttggcag tacatcaatg ggcgtggata   8520
gcggtttgac tcacggggat ttccaagtct ccaccccatt gacgtcaatg ggagtttgtt   8580
ttggcaccaa aatcaacggg actttccaaa atgtcgtaac aactccgccc cattgacgca   8640
aatgggcggt aggcgtgtac ggtgggaggt ctatataagc agagctctct ggctaactag   8700
agaacccact gcttactggc ttatcgaaat taatacgact cactatagca attgcacgtg   8760
tggccacagg taagtttaaa gctcaggtcg agaccgggcc tttgtccggc gctcccttgg   8820
agcctaccta gactcagccg gctctccacg ctttgcctga ccctgcttgc tcaactctac   8880
gtctttgttt cgttttctgt tcctttctct ccacaggctt aagcttggta ccagaaagtt   8940
aacatggctg tcttggggct gctcttctgc ctggtgacat tcccaagctg tgtcctatcc   9000
caggtgcagc tggtggagtc tgggggaggc gtggtccagc ctgggaggtc cctgagactc   9060
tcctgtgcag cctctggatt cactttcagt gactatcata tggcctgggt ccgccaggct   9120
ccaggcaagg ggctggagtg ggtggcaagc attactcttg atgctaccta cacttactat   9180
cgcgactccg tgcgcggccg cttcaccatc tccagagaca attccaagaa cacgctgtat   9240
ctgcaaatga acagcctgag agctgaggac acggctgtgt attactgtgc gagacatcga   9300
ggctttagcg tctggcttga ttactggggc caaggcaccc tggtcaccgt ctcgtcggct   9360
agcaccaagg gcccatcggt cttccccctg gcaccctcct ccaagagcac ctctgggggc   9420
acagcggccc tgggctgcct ggtcaaggac tacttccccg aaccggtgac ggtgtcgtgg   9480
aactcaggcg ccctgaccag cggcgtgcac accttcccgg ctgtcctaca gtcctcagga   9540
ctctactccc tcagcagcgt ggtgaccgtg ccctccagca gcttgggcac ccagacctac   9600
atctgcaacg tgaatcacaa gcccagcaac accaaggtgg acaagaaagt tgagcccaaa   9660
tcttgtgaca aaactcacac atgcccaccg tgcccagcac ctgaactcct ggggggaccg   9720
tcagtcttcc tcttcccccc aaaacccaag gacaccctca tgatctcccg gacccctgag   9780
gtcacatgcg tggtggtgga cgtgagccac gaagaccctg aggtcaagtt caactggtac   9840
gtggacggcg tggaggtgca taatgccaag acaaagccgc gggaggagca gtacaacagc   9900
acgtaccgtg tggtcagcgt cctcaccgtc ctgcaccagg actggctgaa tggcaaggag   9960
tacaagtgca aggtctccaa caaagccctc ccagccccca tcgagaaaac catctccaaa  10020
gccaaagggc agccccgaga accacaggtg tacaccctgc ccccatcccg ggatgagctg  10080
accaagaacc aggtcagcct gacctgcctg gtcaaaggct tctatcccag cgacatcgcc  10140
gtggagtggg agagcaatgg gcagccggag aacaactaca agaccacgcc tcccgtgctg  10200
gactccgacg gctccttctt cctctacagc aagctcaccg tggacaagag caggtggcag  10260
caggggaacg tcttctcatg ctccgtgatg catgaggctc tgcacaacca ctacacgcag  10320
aagagcctct ccctgtctcc gggtaaatga atcgatgatt ctagatacgg gtccggagga  10380
tccagatccc cctcgctttc ttgctgtcca atttctatta aaggttcctt tgttccctaa  10440
gtccaactac taaactgggg gatattatga agggccttga gcatctggat tctgcctaat  10500
aaaaaacatt tattttcatt gcaatgatgt atttaaatta tttctgaata ttttactaaa  10560
aagggaatgt gggaggtcag tgcatttaaa acataaagaa atgaagaggg ggatctgtcg  10620
acaagctcta gagagctcac gcgttgatca ttaatcagcc ataccacatt tgtagaggtt  10680
ttacttgctt taaaaaacct cccacacctc cccctgaacc tgaaacataa aatgaatgca  10740
attgttgttg ttaacttgtt tattgcagct tataatggtt acaaataaag caatagcatc  10800
acaaatttca caaataaagc atttttttca ctgcattcta gttgtggttt gtccaaactc  10860
```

-continued

```
atcaatgtat cttatcatgt ctggatcgcg gccgctctag aactagttat taatagtaat  10920
caattacggg gtcattagtt catagcccat atatggagtt ccgcgttaca taacttacgg  10980
taaatggccc gcctggctga ccgcccaacg acccccgccc attgacgtca ataatgacgt  11040
atgttcccat agtaacgcca atagggactt tccattgacg tcaatgggtg gagtatttac  11100
ggtaaactgc ccacttggca gtacatcaag tgtatcatat gccaagtacg ccccctattg  11160
acgtcaatga cggtaaatgg cccgcctggc attatgccca gtacatgacc ttatgggact  11220
ttcctacttg gcagtacatc tacgtattag tcatcgctat taccatggtg atgcggtttt  11280
ggcagtacat caatgggcgt ggatagcggt ttgactcacg gggatttcca agtctccacc  11340
ccattgacgt caatgggagt ttgttttggc accaaaatca acgggacttt ccaaaatgtc  11400
gtaacaactc cgccccattg acgcaaatgg gcggtaggcg tgtacggtgg gaggtctata  11460
taagcagagc tcgtttagtg aaccgtctag acgatggaga cgccatccac gctgttttga  11520
cctccataga agacaccggg accgatccag cctccgcggc cgggaacggt gcattggaac  11580
gcggattccc cgtgccaaga gtgacgtaag taccgcctat agagtctata ggcccacccc  11640
cttggcttct tatgcatgct cccctgctcc gacccgggct cctcgcccgc ccggacccac  11700
aggccaccct caaccgtcct ggccccggac ccaaacccca cccctcactc tgcttctccc  11760
cgcaggagaa ttcgagatcc cggtgccgcc accatcccct gacccacgcc cctgacccct  11820
cacaaggaga cgaccttcca tgaccgagta caagcccacg gtgcgcctcg ccacccgcga  11880
cgacgtcccc cgggccgtac gcaccctcgc cgccgcgttc gccgactacc ccgccacgcg  11940
ccacaccgtc gacccggacc gccacatcga gcgggtcacc gagctgcaag aactcttcct  12000
cacgcgcgtc gggctcgaca tcggcaaggt gtgggtcgcg gacgacggcg ccgcggtggc  12060
ggtctggacc acgccggaga gcgtcgaagc gggggcggtg ttcgccgaga tcggcccgcg  12120
catggccgag ttgagcggtt cccggctggc cgcgcagcaa cagatggaag gcctcctggc  12180
gccgcaccgg cccaaggagc ccgcgtggtt cctggccacc gtcggcgtct cgcccgacca  12240
ccagggcaag ggtctgggca gcgccgtcgt gctccccgga gtggaggcgg ccgagcgcgc  12300
cggggtgccc gccttcctgg agacctccgc gccccgcaac ctccccttct acgagcggct  12360
cggcttcacc gtcaccgccg acgtcgagtg cccgaaggac cgcgcgacct ggtgcatgac  12420
ccgcaagccc ggtgcctgac gcccgcccca cgacccgcag cgcccgaccg aaaggagcgc  12480
acgaccccat ggctccgacc gaagccgacc cgggcggccc cgccgacccc gcacccgccc  12540
ccgaggccca ccgactctag aggatcataa tcagccatac cacatttgta gaggttttac  12600
ttgctttaaa aaacctccca cacctccccc tgaacctgaa acataaaatg aatgcaattg  12660
ttgttgttaa cttgtttatt gcagcttata atggttacaa ataaagcaat agcatcacaa  12720
atttcacaaa taaagcattt ttttcactgc attctagttg tggtttgtcc aaactcatca  12780
atgtatctta tcatgtctgg ctctagctat cccgccccta actccgccca gttccgccca  12840
ttctccgccc catggctgac taattttttt tatttatgca gaggccgagg ccgcctggag  12900
ttaattaatc gcgatggcca catatggagc tctctagagc ttgtcgacag atccccctct  12960
tcatttcttt atgttttaaa tgcactgacc tcccacattc cctttttagt aaaatattca  13020
gaaataattt aaatacatca ttgcaatgaa aataaatgtt ttttattagg cagaatccag  13080
atgctcaagg cccttcataa tatcccccag tttagtagtt ggacttaggg aacaaaggaa  13140
cctttaatag aaattggaca gcaagaaagc gagggggatc tggatcctcc ggagggccct  13200
ggatcctcct acgtatctag aatcatcgat taacactctc ccctgttgaa gctctttgtg  13260
```

```
acgggcgagc tcaggccctg atgggtgact tcgcaggcgt agactttgtg tttctcgtag  13320

tctgctttgc tcagcgtcag ggtgctgctg aggctgtagg tgctgtcctt gctgtcctgc  13380

tctgtgacac tctcctggga gttacccgat tggagggcgt tatccacctt ccactgtact  13440

ttggcctctc tgggatagaa gttattcagc aggcacacaa cagaggcagt tccagatttc  13500

aactgctcat cagatggcgg gaagatgaag acagatggtg cagccaccgt acgtttcagt  13560

tccagcttgg tcccaggtcc aaacgtgtac ccgctataat actggtgaca gtagtaagtt  13620

gcaaaatctt caggttgcag actgctgatg gtgagagtga aatctgtccc agatccactg  13680

ccactgaacc ttgatgggac ccccgcttgc aaagggcttg cattatagat caggagctta  13740

ggggctttcc ctggtttctg ctgataccag gccaagttct caaaaatgtt ctgacttgtc  13800

ttgcaagtga tggtgactct gtctcctaca gatgcagaca gggaggatgg agactgggtc  13860

atctggatgt cacatctcat ggctgggagg aagagcacca aaagccctaa aagttgaact  13920

ggagccatct cgagaattct taagcctgtg gagagaaagg aacagaaaac gaaacaaaga  13980

cgtagagttg agcaagcagg gtcaggcaaa gcgtggagag ccggctgagt ctaggtaggc  14040

tccaagggag cgccggacaa aggcccggtc tcgacctgag ctttaaactt acctgtggcc  14100

acacgtgcaa ttgctatagt gagtcgtatt aatttcgata agccagtaag cagtgggttc  14160

tctagttagc cagagagctc tgcttatata gacctcccac cgtacacgcc taccgcccat  14220

ttgcgtcaat ggggcggagt tgttacgaca ttttggaaag tcccgttgat tttggtgcca  14280

aaacaaactc ccattgacgt caatggggtg gagacttgga aatccccgtg agtcaaaccg  14340

ctatccacgc ccattgatgt actgccaaaa ccgcatcacc atggtaatag cgatgactaa  14400

tacgtagatg tactgccaag taggaaagtc ccataaggtc atgtactggg cataatgcca  14460

ggcgggccat ttaccgtcat tgacgtcaat agggggcgta cttggcatat gatacacttg  14520

atgtactgcc aagtgggcag tttaccgtaa atagtccacc cattgacgtc aatggaaagt  14580

ccctattggc gttactatgg gaacatacgt cattattgac gtcaatgggc gggggtcgtt  14640

gggcggtcag ccaggcgggc catttaccgt aagttatgta acgcggaact ccatatatgg  14700

gctatgaact aatgaccccg taattgatta ctattaataa ctagtcaata atcaatgtca  14760

acgcgtatat ctggcccgta catcggtaac tagtcggacc ggcccgggcc accggtgctc  14820

gaagcttgga tcgatccaga catgataaga tacattgatg agtttggaca aaccacaact  14880

agaatgcagt gaaaaaaatg ctttatttgt gaaatttgtg atgctattgc tttatttgta  14940

accattataa gctgcaataa acaagttaac aacaacaatt gcattcattt tatgtttcag  15000

gttcaggggg aggtgtggga ggttttttaa agcaagtaaa acctctacaa atgtggtatg  15060

gctgattatg atctctagtc aag                                          15083
```

<210> SEQ ID NO 26
<211> LENGTH: 14937
<212> TYPE: DNA
<213> ORGANISM: Artificial Sequence
<220> FEATURE:
<223> OTHER INFORMATION: Nucleotide sequence of pAIGFRLCb2/MAR(-)

<400> SEQUENCE: 26

```
gcactataca tcaaatattc cttattaacc cctttacaaa ttaaaaagct aaaggtacac     60

aatttttgag catagttatt aatagcagac actctatgcc tgtgtggagt aagaaaaaac    120

agtatgttat gattataact gttatgccta cttataaagg ttacagaata tttttccata    180

attttcttgt atagcagtgc agctttttcc tttgtggtgt aaatagcaaa gcaagcaaga    240
```

```
gttctattac taaacacagc atgactcaaa aaacttagca attctgaagg aaagtccttg    300

gggtcttcta cctttctctt ctttttttgga ggagtagaat gttgagagtc agcagtagcc    360

tcatcatcac tagatggcat ttcttctgag caaaacaggt tttcctcatt aaaggcattc    420

caccactgct cccattcatc agttccatag gttggaatct aaaatacaca aacaattaga    480

atcagtagtt taacacatta tacacttaaa aattttatat ttaccttaga gctttaaatc    540

tctgtaggta gtttgtccaa ttatgtcaca ccacagaagt aaggttcctt cacaaagatc    600

gatctaaagc cagcaaaagt cccatggtct tataaaaatg catagcttta ggaggggagc    660

agagaacttg aaagcatctt cctgttagtc tttcttctcg tagacttcaa acttatactt    720

gatgcctttt tcctcctgga cctcagagag gacgcctggg tattctggga gaagtttata    780

tttccccaaa tcaatttctg ggaaaaacgt gtcactttca aattcctgca tgatccttgt    840

cacaaagagt ctgaggtggc ctggttgatt catggcttcc tggtaaacag aactgcctcc    900

gactatccaa accatgtcta ctttacttgc caattccggt tgttcaataa gtcttaaggc    960

atcatccaaa cttttggcaa gaaaatgagc tcctcgtggt ggttctttga gttctctact   1020

gagaactata ttaattctgt cctttaaagg tcgattcttc tcaggaatgg agaaccaggt   1080

tttcctaccc ataatcacca gattctgttt accttccact gaagaggttg tggtcattct   1140

ttggaagtac ttgaactcgt tcctgagcgg aggccagggt aggtctccgt tcttgccaat   1200

ccccatattt tgggacacgg cgacgatgca gttcaatggt cgaaccatga tggcagcggg   1260

gataaaatcc taccagcctt cacgctagga ttgccgtcaa gtttggcgcg aaatcgcagc   1320

cctgagctgt cccccccccc aagctcagat ctgagcttgg tccctatggt gagtccgttc   1380

cgctcttgtg atgatagcca gacaagaaag agacaataca agacaaacac caaatagtag   1440

aaatagagac aagggtcact tatccgaggg tccctgttcg ggcgccagct gccgcagtcg   1500

gccgacctga gggtcgccgg ggtctgcggg gggaccctct ggaaagtgaa ggataagtga   1560

cgagcggaga cgggatggcg aacagacaca aacacacaag aggtgaatgt taggactgtt   1620

gcaagtttac tcaaaaaatc agcactcttt tatatcttgg tttacataag catttacata   1680

agatttggat aaattccaaa agaacatagg aaaatagaac actcagagct cagatcagaa   1740

cctttgatac caaaccaagt caggaaacca cttgtctcac atcctcgttt taagaacagt   1800

ttgtaaccaa aaacttactt aagccctggg aaccgcaagg ttgggccaat aaaggctatt   1860

cataataact catgccatga gttttttgcag aataatgttc tattagtcca gccactgtcc   1920

cctccttggt atggaaaatc tttccccaaa agtgcattcc tgttcctaga taaatataat   1980

catgtacctg ttgtttcatg tcgtcttttt cttcttgaga caacatacac caaggaggtc   2040

tagctctggc gagtctttca cgaaaaggga gggatctata taacacttta tagccattga   2100

ctgtaaccca cctatcccaa tttaagtcat atcttcctgt atatggtaag ggggcatctg   2160

ttggtctgta gatgtaaggt cccctataag tccctggttg ccaccacctg tctcctattt   2220

tgacaaaaac actctttttt ccctttttta cttctaggcc tgtggtcaat agtccttgca   2280

cctgttcttc aattgaggtt gagcgtctct ttctattttc tattcccatt tctaacttct   2340

gaatttgagt aaaaatagta ctaaaagata atgattcatt tcttaacata gtaactaata   2400

atctacctat tggattggtc ttattggtaa aaatataatt tttagcaagc attcttattt   2460

ctatttctga aggacaaaat cgatgcggct tgtaagagga agttggctgt ggtccttgcc   2520

tcaggaggaa ggtcgagttc tccgaattgt ttagattgta atcttgcaca gaagagctat   2580

taaaagagtc aagggtgaga gccctgcgag cacgaaccgc aacttccccc aatagcccca   2640
```

-continued

```
ggcaaagcag agctatgcca agtttgcagc agagaatgaa tatgtctttg tctgatgggc   2700
tcatccgttt gtgcgcagac gggtcgtcct tggtgggaaa caaccccttg gctgcttctc   2760
ccctaggtgt aggacactct cgggagttca accatttctg cccaagctca gatctgagct   2820
ttaatgcggt agtttatcac agttaaattg ctaacgcagt caggcaccgt gtatgaaatc   2880
taacaatgcg ctcatcgtca tcctcggcac cgtcaccctg gatgctgtag gcataggctt   2940
ggttatgccg gtactgccgg gcctcttgcg ggatatcgtc cattccgaca gcatcgccag   3000
tcactatggc gtgctgctag cgctcttccg cttcctcgct cactgactcg ctgcgctcgg   3060
tcgttcggct gcggcgagcg gtatcagctc actcaaaggc ggtaatacgg ttatccacag   3120
aatcagggga taacgcagga aagaacatgt gagcaaaagg ccagcaaaag gccaggaacc   3180
gtaaaaaggc cgcgttgctg gcgtttttcc ataggctccg cccccctgac gagcatcaca   3240
aaaatcgacg ctcaagtcag aggtggcgaa acccgacagg actataaaga taccaggcgt   3300
ttccccctgg aagctccctc gtgcgctctc ctgttccgac cctgccgctt accggatacc   3360
tgtccgcctt tctcccttcg ggaagcgtgg cgctttctca tagctcacgc tgtaggtatc   3420
tcagttcggt gtaggtcgtt cgctccaagc tgggctgtgt gcacgaaccc cccgttcagc   3480
ccgaccgctg cgccttatcc ggtaactatc gtcttgagtc caacccggta agacacgact   3540
tatcgccact ggcagcagcc actggtaaca ggattagcag agcgaggtat gtaggcggtg   3600
ctacagagtt cttgaagtgg tggcctaact acggctacac tagaaggaca gtatttggta   3660
tctgcgctct gctgaagcca gttaccttcg gaaaaagagt tggtagctct tgatccggca   3720
aacaaaccac cgctggtagc ggtggttttt ttgtttgcaa gcagcagatt acgcgcagaa   3780
aaaaaggatc tcaagaagat cctttgatct tttctacggg gtctgacgct cagtggaacg   3840
aaaactcacg ttaagggatt ttggtcatga gattatcaaa aaggatcttc acctagatcc   3900
ttttaaatta aaaatgaagt tttaaatcaa tctaaagtat atatgagtaa acttggtctg   3960
acagttacca atgcttaatc agtgaggcac ctatctcagc gatctgtcta tttcgttcat   4020
ccatagttgc ctgactcccc gtcgtgtaga taactacgat acgggagggc ttaccatctg   4080
gccccagtgc tgcaatgata ccgcgagacc cacgctcacc ggctccagat ttatcagcaa   4140
taaaccagcc agccggaagg gccgagcgca gaagtggtcc tgcaacttta tccgcctcca   4200
tccagtctat taattgttgc cgggaagcta gagtaagtag ttcgccagtt aatagtttgc   4260
gcaacgttgt tgccattgct acaggcatcg tggtgtcacg ctcgtcgttt ggtatggctt   4320
cattcagctc cggttcccaa cgatcaaggc gagttacatg atcccccatg ttgtgcaaaa   4380
aagcggttag ctccttcggt cctccgatcg ttgtcagaag taagttggcc gcagtgttat   4440
cactcatggt tatggcagca ctgcataatt ctcttactgt catgccatcc gtaagatgct   4500
tttctgtgac tggtgagtac tcaaccaagt cattctgaga atagtgtatg cggcgaccga   4560
gttgctcttg cccggcgtca acacgggata ataccgcgcc acatagcaga actttaaaag   4620
tgctcatcat tggaaaacgt tcttcggggc gaaaactctc aaggatctta ccgctgttga   4680
gatccagttc gatgtaaccc actcgtgcac ccaactgatc ttcagcatct tttactttca   4740
ccagcgtttc tgggtgagca aaaacaggaa ggcaaaatgc cgcaaaaaag ggaataaggg   4800
cgacacggaa atgttgaata ctcatactct tcctttttca atattattga agcatttatc   4860
agggttattg tctcatgagc ggatacatat ttgaatgtat ttagaaaaat aaacaaatag   4920
gggttccgcg cacatttccc cgaaaagtgc cacctgacgt ctaagagacc attattatca   4980
tgacattaac ctataaaaat aggcgtatca cgaggccctt tcgtcttcaa gaattgtcta   5040
```

-continued

```
gaggcgcgct taattaatcg cgatggccac atatggagct ctctagaaaa caatatattt   5100
ccaaatgaaa aaaaaatctg ataaaaagtt gactttaaaa aagtatcaat aaatgtatgc   5160
atttctcact agccttaaac tctgcatgaa gtgtttgatg agcagatgaa gacaacatca   5220
tttctagttt cagaaataat aacagcatca aaaccgcagc tgtaactcca ctgagctcac   5280
gttaagtttt gatgtctgaa tatctgacag aactgacata atgagcactg caaggatatc   5340
agacaagtca aaatgaagac agacaaaagt attttttaat ataaaaatgg tctttatttc   5400
ttcaatacaa ggtaaactac tattgcagtt taagaccaac acaaaagttg gacagcaaat   5460
tgcttaacag tctcctaaag gctgaaaaaa aggaacccat gaaagctaaa agttatgcag   5520
tatttcaagt ataacatcta aaaatgatga aacgatccct aaaggtagag attaactaag   5580
tacttctgct gaaaatgtat taaaatccgc agttgctagg ataccatctt accttgttga   5640
gaaatacagg tctccggcaa cgcaacattc agcagactct ttggcctgct ggaatcagga   5700
aactgcttac tatatacaca tataaaatcc tttggagttg ggcattctga gagacatcca   5760
tttcctgaca ttttgcagtg caactctgca ttccaactca gacaagctcc catgctgtat   5820
ttcaaagcca tttcttgaat agtttaccca gacatccttg tgcaaattgg gaatgaggaa   5880
atgcaatggt acaggaagac aatacagcct tatgtttaga aagtcagcag cgctggtaat   5940
cttcataaaa atgtaactgt ttaccaaata ggaatgtatt tcacttgtaa aacacctggt   6000
ccttttttata ttactttttt ttttttttaa ggacacctgc actaatttgc aatcacttgt   6060
atttataaaa gcacacgcac tcctcatttt cttacatttg aagatcagca gaatgtctct   6120
ttcataatgt aataatcata tgcacagttt aaaatatttt ctattacaaa atacagtaca   6180
caagagggtg aggccaaagt ctattacttg aatatattcc aaagtgtcag cactgggggt   6240
gtaaaattac attacatggt atgaataggc ggaattcttt tacaactgaa atgctcgatt   6300
tcattgggat caaaggtaag tactgtttac tatcttcaag agacttcaat caagtcagtg   6360
tatttccaaa gaagcttaaa agattgaagc acagacacag gccacaccag agcctacacc   6420
tgctgcaata agtggtgcta tagaaaggat tcaggaacta acaagtgcat aatttacaaa   6480
tagagatgct ttatcatact ttgcccaaca tgggaaaaaa gacatcccat gagaatatcc   6540
aactgaggaa cttctctgtt tcatagtaac tcatctacta ctgctaagat ggtttgaaaa   6600
gtacccagca ggtgagatgt gttccgggag gtggctgtgt ggcagcgtgt gggaacacga   6660
cacaaagcac cccaccccta tctgcaaatc gctcactgca aggcagtgcc gtaaacagct   6720
gcaacaggca tcacttctgc ataaatgctg tgactcgtta gcatgctgca actgtgttta   6780
aaacctatgc actccgttac caaaataatt taagtcccaa acaaatccat gcagcttgct   6840
tcctatgcca aaatatttta gaaagtattc attcttcttt aagaatatgc acgtggatct   6900
acacttccct gggatctgaa gcgatttata cctcagtgca gaagcagttt agtgtcctgg   6960
atctcgggaa ggcagcagcc aaacgtgccc gttttacatt tgaacccatg tgacaacccg   7020
ccttactgag catcgctcta ggaaatttaa ggctgtatcc ttacaacaca agaaccaacg   7080
acagactgca tataaaattc tataaataaa aataggagtg aagtctgttt gacctgtaca   7140
cacagagcat agagataaaa aaaaaaggaa atcaggaatt acgtatttct ataaatgcca   7200
tatattttta ctagaaacac agatgacaag tatatacaac atgtaaatcc gaagttatca   7260
acatgttaac taggaaaaca tttacaagca tttgggtatg caactagatc atcaggtaaa   7320
aaatcccatt agaaaaatct aagcctcgcc agtttcaaag gaaaaaaacc agagaacgct   7380
cactacttca aagggaaaaa aataaagcat caagctggcc taaacttaat aaggtatctc   7440
```

-continued

```
atgtaacaac agctatccaa gctttcaagc cacactataa ataaaaacct caagttccga   7500
tcaacgtttt ccataatgca aatcagaacc aaaggcattg gcacagaaag caaaaaggga   7560
atgaaagaaa agggctgtac agtttccaaa aggttcttct tttgaagaaa tgtttctgac   7620
ctgtcaaaac atacagtcca gtagaaattt tactaagaaa aaagaacacc ttacttaaaa   7680
aaaaaaaaca acaaaaaaaa caggcaaaaa aacctctcct gtcactgagc tgccaccacc   7740
ccaaccacca cctgctgtgg gctttgtctc ccaagacaaa ggacacacag ccttatccaa   7800
tattcaacat tacttataaa aacgctgatc agaagaaata ccaagtattt cctcacagac   7860
tgttatatcc tttcatcggc aagaagagat gaaatacaac agagtgaata tcaaagaagg   7920
cggcaggagc caccgtggca ccatcaccgg gcagtgcagt gcccaactgc cgtttcctga   7980
gcacgcacag gaagccgtca gtcacatgta ataaaccaaa acctggtaca attgtattac   8040
ggatcccggt ggcgcgccgt ttaaaccctc agctaccgat gtacgggcca gatatacgcg   8100
ttgacattga ttattgacta gttattaata gtaatcaatt acggggtcat tagttcatag   8160
cccatatatg gagttccgcg ttacataact tacggtaaat ggcccgcctg gctgaccgcc   8220
caacgacccc cgcccattga cgtcaataat gacgtatgtt cccatagtaa cgccaatagg   8280
gactttccat tgacgtcaat gggtggacta tttacggtaa actgcccact tggcagtaca   8340
tcaagtgtat catatgccaa gtacgccccc tattgacgtc aatgacggta aatggcccgc   8400
ctggcattat gcccagtaca tgaccttatg ggactttcct acttggcagt acatctacgt   8460
attagtcatc gctattacca tggtgatgcg gttttggcag tacatcaatg ggcgtggata   8520
gcggtttgac tcacggggat ttccaagtct ccaccccatt gacgtcaatg ggagtttgtt   8580
ttggcaccaa aatcaacggg actttccaaa atgtcgtaac aactccgccc cattgacgca   8640
aatgggcggt aggcgtgtac ggtgggaggt ctatataagc agagctctct ggctaactag   8700
agaacccact gcttactggc ttatcgaaat taatacgact cactatagca attgcacgtg   8760
tggccacagg taagtttaaa gctcaggtcg agaccgggcc tttgtccggc gctcccttgg   8820
agcctaccta gactcagccg gctctccacg ctttgcctga ccctgcttgc tcaactctac   8880
gtctttgttt cgttttctgt tcctttctct ccacaggctt aagcttggta ccgagctcgg   8940
atccactagt ccagtgtggt ggaattcgcc cttatggagt ttgggctgag ctgggttttc   9000
cttgttgcta tattaaaagg tgtccagtgt gaggttcagc tggtgcagtc tgggggaggc   9060
ttggtaaagc ctgggggtc cctgagactc tcctgtgcag cctctggatt caccttcagt   9120
agctttgcta tgcactgggt tcgccaggct ccaggaaaag gtctggagtg gatatcagtt   9180
attgatactc gtggtgccac atactatgca gactccgtga agggccgatt caccatctcc   9240
agagacaatg ccaagaactc cttgtatctt caaatgaaca gcctgagagc cgaggacact   9300
gctgtgtatt actgtgcaag actggggaac ttctactacg gtatggacgt ctggggccaa   9360
gggaccacgg tcaccgtctc ctcagcttcc accaagggcc catcggtctt ccccctggca   9420
ccctcctcca agagcacctc tgggggcaca gcggccctgg gctgcctggt caaggactac   9480
ttccccgaac cggtgacggt gtcgtggaac tcaggcgccc tgaccagcgg cgtgcacacc   9540
ttcccggctg tcctacagtc ctcaggactc tactccctca gcagcgtggt gaccgtgccc   9600
tccagcagct tgggcaccca gacctacatc tgcaacgtga atcacaagcc cagcaacacc   9660
aaggtggaca agaaagttga gcccaaatct tgtgacaaaa ctcacacatg cccaccgtgc   9720
ccagcacctg aactcctggg gggaccgtca gtcttcctct tcccccaaa acccaaggac   9780
accctcatga tctcccggac ccctgaggtc acatgcgtgg tggtggacgt gagccacgaa   9840
```

-continued

```
gaccctgagg tcaagttcaa ctggtacgtg gacggcgtgg aggtgcataa tgccaagaca   9900
aagccgcggg aggagcagta caacagcacg taccgtgtgg tcagcgtcct caccgtcctg   9960
caccaggact ggctgaatgg caaggagtac aagtgcaagg tctccaacaa agccctccca  10020
gcccccatcg agaaaaccat ctccaaagcc aaagggcagc cccgagaacc acaggtgtac  10080
accctgcccc catcccggga tgagctgacc aagaaccagg tcagcctgac ctgcctggtc  10140
aaaggcttct atcccagcga catcgccgtg gagtgggaga gcaatgggca gccggagaac  10200
aactacaaga ccacgcctcc cgtgctggac tccgacggct ccttcttcct ctacagcaag  10260
ctcaccgtgg acaagagcag gtggcagcag gggaacgtct tctcatgctc cgtgatgcat  10320
gaggctctgc acaaccacta cacgcagaag agcctctccc tgtctccggg taaatgaatc  10380
gatgattcta gatacgggtc cggaggatcc agatccccct cgctttcttg ctgtccaatt  10440
tctattaaag gttcctttgt tccctaagtc caactactaa actgggggat attatgaagg  10500
gccttgagca tctggattct gcctaataaa aaacatttat tttcattgca atgatgtatt  10560
taaattattt ctgaatattt tactaaaaag ggaatgtggg aggtcagtgc atttaaaaca  10620
taaagaaatg aagaggggga tctgtcgaca agctctagag agctcacgcg ttgatcatgt  10680
acaggccggc caagctttcg actagcttgg cacgccagaa atccgcgcgg tggtttttgg  10740
gggtcggggg tgtttggcag ccacagacgc ccggtgttcg tgtcgcgcca gtacatgcgg  10800
tccatgccca ggccatccaa aaaccatggg tctgtctgct cagtccagtc gtggacctga  10860
ccccacgcaa cgcccaaaat aataaccccc acgaaccata aaccattccc catgggggac  10920
cccgtcccta acccacgggg ccagtggcta tggcagggcc tgccgccccg acgttggctg  10980
cgagccctgg gccttcaccc gaacttgggg ggtggggtgg ggaaaaggaa gaaacgcggg  11040
cgtattggcc ccaatggggt ctcggtgggg tatcgacaga gtgccagccc tgggaccgaa  11100
ccccgcgttt atgaacaaac gacccaacac ccgtgcgttt tattctgtct ttttattgcc  11160
gtcatagcgc gggttccttc cggtattgtc tccttccgtg tttcagttag cctcccccat  11220
ctcccgatcc ggacgagtgc tggggcgtcg gtttccacta tcggcgagta cttctacaca  11280
gccatcggtc cagacggccg cgcttctgcg ggcgatttgt gtacgcccga cagtcccggc  11340
tccggatcgg acgattgcgt cgcatcgacc ctgcgcccaa gctgcatcat cgaaattgcc  11400
gtcaaccaag ctctgataga gttggtcaag accaatgcgg agcatatacg cccggagccg  11460
cggcgatcct gcaagctccg gatgcctccg ctcgaagtag cgcgtctgct gctccataca  11520
agccaaccac ggcctccaga agaagatgtt ggcgacctcg tattgggaat ccccgaacat  11580
cgcctcgctc cagtcaatga ccgctgttat gcggccattg tccgtcagga cattgttgga  11640
gccgaaatcc gcgtgcacga ggtgccggac ttcggggcag tcctcggccc aaagcatcag  11700
ctcatcgaga gcctgcgcga cggacgcact gacggtgtcg tccatcacag tttgccagtg  11760
atacacatgg ggatcagcaa tcgcgcatat gaaatcacgc catgtagtgt attgaccgat  11820
tccttgcggt ccgaatgggc cgaacccgct cgtctggcta agatcggccg cagcgatcgc  11880
atccatggcc tccgcgaccg gctgcagaac agcgggcagt tcggtttcag gcaggtcttg  11940
caacgtgaca ccctgtgcac ggcgggagat gcaataggtc aggctctcgc tgaattcccc  12000
aatgtcaagc acttccggaa tcgggagcgc ggccgatgca aagtgccgat aaacataacg  12060
atctttgtag aaaccatcgg cgcagctatt tacccgcagg acatatccac gccctcctac  12120
atcgaagctg aaagcacgag attcttcgcc ctccgagagc tgcatcaggt cggagacgct  12180
gtcgaacttt tcgatcagaa acttctcgac agacgtcgcg gtgagttcag gcttttttcat 12240
```

-continued

```
atctcattgc cccccgggat ctgcggcacg ctgttgacgc tgttaagcgg gtcgctgcag  12300
ggtcgctcgg tgttcgaggc cacacgcgtc accttaatat gcgaagtgga cctcggaccg  12360
cgccgccccg actgcatctg cgtgttcgaa ttcgccaatg acaagacgct gggcggggtt  12420
tgtgtcatca tagaactaaa gacatgcaaa tatatttctt ccggggacac cgccagcaaa  12480
cgcgagcaac gggccacggg gatgaagcag ggcggcacct cgctaacgga ttcaccactc  12540
caagaattgg agccaatcaa ttcttgcgga gaactgtgaa tgcgcaaacc aacccttggc  12600
agaacatatc catcgcgtcc gccatctcca gcagccgcac gcggcgcatc tcggggccga  12660
cgcgctgggc tacgtcttgc tggcgttcgc acaggccggc cagcgcgcgg ccggccggta  12720
ccacgcgttg gccacatatg gcggccgctc gcgattaatt aatcgcgatg gccacatatg  12780
gagctctcta gagcttgtcg acagatcccc ctcttcattt ctttatgttt taaatgcact  12840
gacctcccac attccctttt tagtaaaata ttcagaaata atttaaatac atcattgcaa  12900
tgaaaataaa tgttttttat taggcagaat ccagatgctc aaggcccttc ataatatccc  12960
ccagtttagt agttggactt agggaacaaa ggaaccttta atagaaattg gacagcaaga  13020
aagcgagggg gatctggatc ctccggaggg ccccttctcc ctctaacact ctcccctgtt  13080
gaagctcttt gtgacgggcg agctcaggcc ctgatgggtg acttcgcagg cgtagacttt  13140
gtgtttctcg tagtctgctt tgctcagcgt cagggtgctg ctgaggctgt aggtgctgtc  13200
cttgctgtcc tgctctgtga cactctcctg ggagttaccc gattggaggg cgttatccac  13260
cttccactgt actttggcct ctctgggata gaagttattc agcaggcaca caacagaggc  13320
agttccagat ttcaactgct catcagatgg cgggaagatg aagacagatg gtgcagccac  13380
tgtacgtttg atctccacct tggtcccttg gccgaaagtg tgaggtaaac gactactctg  13440
atgacagtaa tacactgcga aatcttcagg ctccagtcta ctgatggtga gggtgaaatc  13500
tgtcccagat ccactgccac tgaacctatc ggggatccct gagagggact gggatgcata  13560
cttgatgaga agccttggag cctgacctgg tttctgctgg taccagtgta agctactacc  13620
aatgctctga ctggcccggc aggagagggt ggctctctcg cctggagaca cagacagggt  13680
acctgggctc tgagtcagca caatttcacc cctggaggct ggaacccaga gcagcagaaa  13740
cccaatgagt tgtgatggcg acatgttaaa cgctagaatt cttaagcctg tggagagaaa  13800
ggaacagaaa acgaaacaaa gacgtagagt tgagcaagca gggtcaggca aagcgtggag  13860
agccggctga gtctaggtag gctccaaggg agcgccggac aaaggcccgg tctcgacctg  13920
agctttaaac ttacctgtgg ccacacgtgc aattgctata gtgagtcgta ttaatttcga  13980
taagccagta agcagtgggt tctctagtta gccagagagc tctgcttata tagacctccc  14040
accgtacacg cctaccgccc atttgcgtca atggggcgga gttgttacga cattttggaa  14100
agtcccgttg attttggtgc caaaacaaac tcccattgac gtcaatgggg tggagacttg  14160
gaaatccccg tgagtcaaac cgctatccac gcccattgat gtactgccaa aaccgcatca  14220
ccatggtaat agcgatgact aatacgtaga tgtactgcca agtaggaaag tcccataagg  14280
tcatgtactg ggcataatgc caggcgggcc atttaccgtc attgacgtca atagggggcg  14340
tacttggcat atgatacact tgatgtactg ccaagtgggc agtttaccgt aaatagtcca  14400
cccattgacg tcaatggaaa gtccctattg gcgttactat gggaacatac gtcattattg  14460
acgtcaatgg gcgggggtcg ttgggcggtc agccaggcgg gccatttacc gtaagttatg  14520
taacgcggaa ctccatatat gggctatgaa ctaatgaccc cgtaattgat tactattaat  14580
aactagtcaa taatcaatgt caacgcgtat atctggcccg tacatcggta actagtcgga  14640
```

-continued

```
ccgccgcgga ctagtgcccg ggccaccggt gctcgaagct tggatcgatc cagacatgat  14700

aagatacatt gatgagtttg gacaaaccac aactagaatg cagtgaaaaa aatgctttat  14760

ttgtgaaatt tgtgatgcta ttgctttatt tgtaaccatt ataagctgca ataaacaagt  14820

taacaacaac aattgcattc attttatgtt tcaggttcag ggggaggtgt gggaggtttt  14880

ttaaagcaag taaaacctct acaaatgtgg tatggctgat tatgatctct agtcaag     14937
```

<210> SEQ ID NO 27
<211> LENGTH: 15110
<212> TYPE: DNA
<213> ORGANISM: Artificial Sequence
<220> FEATURE:
<223> OTHER INFORMATION: Nucleotide sequence of pAIGFRLCb2/puro/MAR(-)

<400> SEQUENCE: 27

```
gcactataca tcaaatattc cttattaacc cctttacaaa ttaaaaagct aaaggtacac     60

aatttttgag catagttatt aatagcagac actctatgcc tgtgtggagt aagaaaaaac    120

agtatgttat gattataact gttatgccta cttataaagg ttacagaata tttttccata    180

attttcttgt atagcagtgc agctttttcc tttgtggtgt aaatagcaaa gcaagcaaga    240

gttctattac taaacacagc atgactcaaa aaacttagca attctgaagg aaagtccttg    300

gggtcttcta cctttctctt cttttttgga ggagtagaat gttgagagtc agcagtagcc    360

tcatcatcac tagatggcat ttcttctgag caaaacaggt tttcctcatt aaaggcattc    420

caccactgct cccattcatc agttccatag gttggaatct aaaatacaca aacaattaga    480

atcagtagtt taacacatta tacacttaaa aattttatat ttaccttaga gctttaaatc    540

tctgtaggta gtttgtccaa ttatgtcaca ccacagaagt aaggttcctt cacaaagatc    600

gatctaaagc cagcaaaagt cccatggtct tataaaaatg catagcttta ggaggggagc    660

agagaacttg aaagcatctt cctgttagtc tttcttctcg tagacttcaa acttatactt    720

gatgcctttt tcctcctgga cctcagagag gacgcctggg tattctggga gaagtttata    780

tttccccaaa tcaatttctg ggaaaaacgt gtcactttca aattcctgca tgatccttgt    840

cacaaagagt ctgaggtggc ctggttgatt catggcttcc tggtaaacag aactgcctcc    900

gactatccaa accatgtcta ctttacttgc caattccggt tgttcaataa gtcttaaggc    960

atcatccaaa cttttggcaa gaaaatgagc tcctcgtggt ggttctttga gttctctact   1020

gagaactata ttaattctgt cctttaaagg tcgattcttc tcaggaatgg agaaccaggt   1080

tttcctaccc ataatcacca gattctgttt accttccact gaagaggttg tggtcattct   1140

ttggaagtac ttgaactcgt tcctgagcgg aggccagggt aggtctccgt tcttgccaat   1200

ccccatattt tgggacacgg cgacgatgca gttcaatggt cgaaccatga tggcagcggg   1260

gataaaatcc taccagcctt cacgctagga ttgccgtcaa gtttggcgcg aaatcgcagc   1320

cctgagctgt cccccccccc aagctcagat ctgagcttgg tccctatggt gagtccgttc   1380

cgctcttgtg atgatagcca gacaagaaag agacaataca agacaaacac caaatagtag   1440

aaatagagac aagggtcact tatccgaggg tccctgttcg ggcgccagct gccgcagtcg   1500

gccgacctga gggtcgccgg ggtctgcggg gggaccctct ggaaagtgaa ggataagtga   1560

cgagcggaga cgggatggcg aacagacaca aacacacaag aggtgaatgt taggactgtt   1620

gcaagtttac tcaaaaaatc agcactcttt tatatcttgg tttacataag catttacata   1680

agatttggat aaattccaaa agaacatagg aaaatagaac actcagagct cagatcagaa   1740

cctttgatac caaaccaagt caggaaacca cttgtctcac atcctcgttt taagaacagt   1800
```

-continued

```
ttgtaaccaa aaacttactt aagccctggg aaccgcaagg ttgggccaat aaaggctatt   1860
cataataact catgccatga gtttttgcag aataatgttc tattagtcca gccactgtcc   1920
cctccttggt atggaaaatc tttccccaaa agtgcattcc tgttcctaga taaatataat   1980
catgtacctg ttgtttcatg tcgtcttttt cttcttgaga caacatacac caaggaggtc   2040
tagctctggc gagtctttca cgaaaaggga gggatctata taacacttta tagccattga   2100
ctgtaaccca cctatcccaa tttaagtcat atcttcctgt atatggtaag gggcatctg   2160
ttggtctgta gatgtaaggt cccctataag tccctggttg ccaccacctg tctcctattt   2220
tgacaaaaac actctttttt cccttttta cttctaggcc tgtggtcaat agtccttgca   2280
cctgttcttc aattgaggtt gagcgtctct ttctattttc tattcccatt tctaacttct   2340
gaatttgagt aaaaatagta ctaaaagata atgattcatt tcttaacata gtaactaata   2400
atctacctat tggattggtc ttattggtaa aaatataatt tttagcaagc attcttattt   2460
ctatttctga aggacaaaat cgatgcggct tgtaagagga agttggctgt ggtccttgcc   2520
tcaggaggaa ggtcgagttc tccgaattgt ttagattgta atcttgcaca gaagagctat   2580
taaaagagtc aagggtgaga gccctgcgag cacgaaccgc aacttccccc aatagcccca   2640
ggcaaagcag agctatgcca agtttgcagc agagaatgaa tatgtctttg tctgatgggc   2700
tcatccgttt gtgcgcagac gggtcgtcct tggtgggaaa caacccttg gctgcttctc   2760
ccctaggtgt aggacactct cgggagttca accatttctg cccaagctca gatctgagct   2820
ttaatgcggt agtttatcac agttaaattg ctaacgcagt caggcaccgt gtatgaaatc   2880
taacaatgcg ctcatcgtca tcctcggcac cgtcaccctg gatgctgtag gcataggctt   2940
ggttatgccg gtactgccgg gcctcttgcg ggatatcgtc cattccgaca gcatcgccag   3000
tcactatggc gtgctgctag cgctcttccg cttcctcgct cactgactcg ctgcgctcgg   3060
tcgttcggct gcggcgagcg gtatcagctc actcaaaggc ggtaatacgg ttatccacag   3120
aatcagggga taacgcagga aagaacatgt gagcaaaagg ccagcaaaag gccaggaacc   3180
gtaaaaaggc cgcgttgctg gcgtttttcc ataggctccg cccccctgac gagcatcaca   3240
aaaatcgacg ctcaagtcag aggtggcgaa acccgacagg actataaaga taccaggcgt   3300
ttccccctgg aagctccctc gtgcgctctc ctgttccgac cctgccgctt accggatacc   3360
tgtccgcctt tctcccttcg ggaagcgtgg cgctttctca tagctcacgc tgtaggtatc   3420
tcagttcggt gtaggtcgtt cgctccaagc tgggctgtgt gcacgaaccc cccgttcagc   3480
ccgaccgctg cgccttatcc ggtaactatc gtcttgagtc caacccggta agacacgact   3540
tatcgccact ggcagcagcc actggtaaca ggattagcag agcgaggtat gtaggcggtg   3600
ctacagagtt cttgaagtgg tggcctaact acggctacac tagaaggaca gtatttggta   3660
tctgcgctct gctgaagcca gttaccttcg gaaaaagagt tggtagctct tgatccggca   3720
aacaaaccac cgctggtagc ggtggttttt ttgtttgcaa gcagcagatt acgcgcagaa   3780
aaaaaggatc tcaagaagat cctttgatct tttctacggg gtctgacgct cagtggaacg   3840
aaaactcacg ttaagggatt ttggtcatga gattatcaaa aaggatcttc acctagatcc   3900
ttttaaatta aaaatgaagt tttaaatcaa tctaaagtat atatgagtaa acttggtctg   3960
acagttacca atgcttaatc agtgaggcac ctatctcagc gatctgtcta tttcgttcat   4020
ccatagttgc ctgactcccc gtcgtgtaga taactacgat acgggagggc ttaccatctg   4080
gccccagtgc tgcaatgata ccgcgagacc cacgctcacc ggctccagat ttatcagcaa   4140
taaaccagcc agccggaagg gccgagcgca gaagtggtcc tgcaacttta tccgcctcca   4200
```

-continued

```
tccagtctat taattgttgc cgggaagcta gagtaagtag ttcgccagtt aatagtttgc   4260
gcaacgttgt tgccattgct acaggcatcg tggtgtcacg ctcgtcgttt ggtatggctt   4320
cattcagctc cggttcccaa cgatcaaggc gagttacatg atcccccatg ttgtgcaaaa   4380
aagcggttag ctccttcggt cctccgatcg ttgtcagaag taagttggcc gcagtgttat   4440
cactcatggt tatggcagca ctgcataatt ctcttactgt catgccatcc gtaagatgct   4500
tttctgtgac tggtgagtac tcaaccaagt cattctgaga atagtgtatg cggcgaccga   4560
gttgctcttg cccggcgtca acacgggata ataccgcgcc acatagcaga actttaaaag   4620
tgctcatcat tggaaaacgt tcttcggggc gaaaactctc aaggatctta ccgctgttga   4680
gatccagttc gatgtaaccc actcgtgcac ccaactgatc ttcagcatct tttactttca   4740
ccagcgtttc tgggtgagca aaaacaggaa ggcaaaatgc cgcaaaaaag ggaataaggg   4800
cgacacggaa atgttgaata ctcatactct tcctttttca atattattga agcatttatc   4860
agggttattg tctcatgagc ggatacatat ttgaatgtat ttagaaaaat aaacaaatag   4920
gggttccgcg cacatttccc cgaaaagtgc cacctgacgt ctaagagacc attattatca   4980
tgacattaac ctataaaaat aggcgtatca cgaggccctt tcgtcttcaa gaattgtcta   5040
gaggcgcgct taattaatcg cgatggccac atatggagct ctctagaaaa caatatattt   5100
ccaaatgaaa aaaaaatctg ataaaaagtt gactttaaaa aagtatcaat aaatgtatgc   5160
atttctcact agccttaaac tctgcatgaa gtgtttgatg agcagatgaa gacaacatca   5220
tttctagttt cagaaataat aacagcatca aaaccgcagc tgtaactcca ctgagctcac   5280
gttaagtttt gatgtctgaa tatctgacag aactgacata atgagcactg caaggatatc   5340
agacaagtca aaatgaagac agacaaaagt atttttaat ataaaaatgg tctttatttc   5400
ttcaatacaa ggtaaactac tattgcagtt taagaccaac acaaaagttg gacagcaaat   5460
tgcttaacag tctcctaaag gctgaaaaaa aggaacccat gaaagctaaa agttatgcag   5520
tatttcaagt ataacatcta aaaatgatga aacgatccct aaaggtagag attaactaag   5580
tacttctgct gaaaatgtat taaaatccgc agttgctagg ataccatctt accttgttga   5640
gaaatacagg tctccggcaa cgcaacattc agcagactct ttggcctgct ggaatcagga   5700
aactgcttac tatatacaca tataaaatcc tttggagttg ggcattctga gagacatcca   5760
tttcctgaca ttttgcagtg caactctgca ttccaactca gacaagctcc catgctgtat   5820
ttcaaagcca tttcttgaat agtttaccca gacatccttg tgcaaattgg gaatgaggaa   5880
atgcaatggt acaggaagac aatacagcct tatgtttaga aagtcagcag cgctggtaat   5940
cttcataaaa atgtaactgt ttaccaaata ggaatgtatt tcacttgtaa aacacctggt   6000
cctttttata ttactttttt ttttttttaa ggacacctgc actaatttgc aatcacttgt   6060
atttataaaa gcacacgcac tcctcatttt cttacatttg aagatcagca gaatgtctct   6120
ttcataatgt aataatcata tgcacagttt aaaatatttt ctattacaaa atacagtaca   6180
caagagggtg aggccaaagt ctattacttg aatatattcc aaagtgtcag cactgggggt   6240
gtaaaattac attacatggt atgaataggc ggaattcttt tacaactgaa atgctcgatt   6300
tcattgggat caaaggtaag tactgtttac tatcttcaag agacttcaat caagtcagtg   6360
tatttccaaa gaagcttaaa agattgaagc acagacacag gccacaccag agcctacacc   6420
tgctgcaata agtggtgcta tagaaaggat tcaggaacta acaagtgcat aatttacaaa   6480
tagagatgct ttatcatact ttgcccaaca tgggaaaaaa gacatcccat gagaatatcc   6540
aactgaggaa cttctctgtt tcatagtaac tcatctacta ctgctaagat ggtttgaaaa   6600
```

-continued

```
gtacccagca ggtgagatgt gttccgggag gtggctgtgt ggcagcgtgt gggaacacga   6660
cacaaagcac cccacccta tctgcaaatc gctcactgca aggcagtgcc gtaaacagct   6720
gcaacaggca tcacttctgc ataaatgctg tgactcgtta gcatgctgca actgtgttta   6780
aaacctatgc actccgttac caaaataatt taagtcccaa acaaatccat gcagcttgct   6840
tcctatgcca aaatatttta gaaagtattc attcttcttt aagaatatgc acgtggatct   6900
acacttccct gggatctgaa gcgatttata cctcagtgca gaagcagttt agtgtcctgg   6960
atctcgggaa ggcagcagcc aaacgtgccc gttttacatt tgaacccatg tgacaacccg   7020
ccttactgag catcgctcta ggaaatttaa ggctgtatcc ttacaacaca agaaccaacg   7080
acagactgca tataaaattc tataaataaa aataggagtg aagtctgttt gacctgtaca   7140
cacagagcat agagataaaa aaaaaaggaa atcaggaatt acgtatttct ataaatgcca   7200
tatattttta ctagaaacac agatgacaag tatatacaac atgtaaatcc gaagttatca   7260
acatgttaac taggaaaaca tttacaagca tttgggtatg caactagatc atcaggtaaa   7320
aaatcccatt agaaaaatct aagcctcgcc agtttcaaag gaaaaaaacc agagaacgct   7380
cactacttca aagggaaaaa aataaagcat caagctggcc taaacttaat aaggtatctc   7440
atgtaacaac agctatccaa gctttcaagc cacactataa ataaaaacct caagttccga   7500
tcaacgtttt ccataatgca aatcagaacc aaaggcattg gcacagaaag caaaaaggga   7560
atgaaagaaa agggctgtac agtttccaaa aggttcttct tttgaagaaa tgtttctgac   7620
ctgtcaaaac atacagtcca gtagaaattt tactaagaaa aaagaacacc ttacttaaaa   7680
aaaaaaaaca acaaaaaaaa caggcaaaaa aacctctcct gtcactgagc tgccaccacc   7740
ccaaccacca cctgctgtgg gctttgtctc ccaagacaaa ggacacacag ccttatccaa   7800
tattcaacat tacttataaa aacgctgatc agaagaaata ccaagtattt cctcacagac   7860
tgttatatcc tttcatcggc aagaagagat gaaatacaac agagtgaata tcaaagaagg   7920
cggcaggagc caccgtggca ccatcaccgg gcagtgcagt gcccaactgc cgtttcctga   7980
gcacgcacag gaagccgtca gtcacatgta ataaaccaaa acctggtaca attgtattac   8040
ggatcccggt ggcgcgccgt ttaaaccctc agctaccgat gtacgggcca gatatacgcg   8100
ttgacattga ttattgacta gttattaata gtaatcaatt acggggtcat tagttcatag   8160
cccatatatg gagttccgcg ttacataact tacggtaaat ggcccgcctg gctgaccgcc   8220
caacgacccc cgcccattga cgtcaataat gacgtatgtt cccatagtaa cgccaatagg   8280
gactttccat tgacgtcaat gggtggacta tttacggtaa actgcccact tggcagtaca   8340
tcaagtgtat catatgccaa gtacgccccc tattgacgtc aatgacggta aatggcccgc   8400
ctggcattat gcccagtaca tgaccttatg ggactttcct acttggcagt acatctacgt   8460
attagtcatc gctattacca tggtgatgcg gttttggcag tacatcaatg ggcgtggata   8520
gcggtttgac tcacggggat ttccaagtct ccaccccatt gacgtcaatg ggagtttgtt   8580
ttggcaccaa aatcaacggg actttccaaa atgtcgtaac aactccgccc cattgacgca   8640
aatgggcggt aggcgtgtac ggtgggaggt ctatataagc agagctctct ggctaactag   8700
agaacccact gcttactggc ttatcgaaat taatacgact cactatagca attgcacgtg   8760
tggccacagg taagtttaaa gctcaggtcg agaccgggcc tttgtccggc gctcccttgg   8820
agcctaccta gactcagccg gctctccacg ctttgcctga ccctgcttgc tcaactctac   8880
gtctttgttt cgttttctgt tcctttctct ccacaggctt aagcttggta ccgagctcgg   8940
atccactagt ccagtgtggt ggaattcgcc cttatggagt ttgggctgag ctgggttttc   9000
```

-continued

```
cttgttgcta tattaaaagg tgtccagtgt gaggttcagc tggtgcagtc tgggggaggc    9060
ttggtaaagc ctggggggtc cctgagactc tcctgtgcag cctctggatt caccttcagt    9120
agctttgcta tgcactgggt tcgccaggct ccaggaaaag gtctggagtg gatatcagtt    9180
attgatactc gtggtgccac atactatgca gactccgtga agggccgatt caccatctcc    9240
agagacaatg ccaagaactc cttgtatctt caaatgaaca gcctgagagc cgaggacact    9300
gctgtgtatt actgtgcaag actggggaac ttctactacg gtatggacgt ctggggccaa    9360
gggaccacgg tcaccgtctc ctcagcttcc accaagggcc catcggtctt ccccctggca    9420
ccctcctcca agagcacctc tgggggcaca gcggccctgg gctgcctggt caaggactac    9480
ttccccgaac cggtgacggt gtcgtggaac tcaggcgccc tgaccagcgg cgtgcacacc    9540
ttcccggctg tcctacagtc ctcaggactc tactccctca gcagcgtggt gaccgtgccc    9600
tccagcagct tgggcaccca gacctacatc tgcaacgtga atcacaagcc cagcaacacc    9660
aaggtggaca agaaagttga gcccaaatct tgtgacaaaa ctcacacatg cccaccgtgc    9720
ccagcacctg aactcctggg gggaccgtca gtcttcctct tccccccaaa acccaaggac    9780
accctcatga tctcccggac ccctgaggtc acatgcgtgg tggtggacgt gagccacgaa    9840
gaccctgagg tcaagttcaa ctggtacgtg gacggcgtgg aggtgcataa tgccaagaca    9900
aagccgcggg aggagcagta caacagcacg taccgtgtgg tcagcgtcct caccgtcctg    9960
caccaggact ggctgaatgg caaggagtac aagtgcaagg tctccaacaa agccctccca   10020
gcccccatcg agaaaaccat ctccaaagcc aaagggcagc cccgagaacc acaggtgtac   10080
accctgcccc catcccggga tgagctgacc aagaaccagg tcagcctgac ctgcctggtc   10140
aaaggcttct atcccagcga catcgccgtg gagtgggaga gcaatgggca gccggagaac   10200
aactacaaga ccacgcctcc cgtgctggac tccgacggct ccttcttcct ctacagcaag   10260
ctcaccgtgg acaagagcag gtggcagcag gggaacgtct tctcatgctc cgtgatgcat   10320
gaggctctgc acaaccacta cacgcagaag agcctctccc tgtctccggg taaatgaatc   10380
gatgattcta gatacgggtc cggaggatcc agatccccct cgctttcttg ctgtccaatt   10440
tctattaaag gttcctttgt tccctaagtc caactactaa actgggggat attatgaagg   10500
gccttgagca tctggattct gcctaataaa aaacatttat tttcattgca atgatgtatt   10560
taaattattt ctgaatattt tactaaaaag ggaatgtggg aggtcagtgc atttaaaaca   10620
taaagaaatg aagaggggga tctgtcgaca agctctagag agctcacgcg ttgatcatta   10680
atcagccata ccacatttgt agaggtttta cttgctttaa aaaacctccc acacctcccc   10740
ctgaacctga aacataaaat gaatgcaatt gttgttgtta acttgtttat tgcagcttat   10800
aatggttaca aataaagcaa tagcatcaca aatttcacaa ataaagcatt tttttcactg   10860
cattctagtt gtggtttgtc caaactcatc aatgtatctt atcatgtctg gatcgcggcc   10920
gctctagaac tagttattaa tagtaatcaa ttacggggtc attagttcat agcccatata   10980
tggagttccg cgttacataa cttacggtaa atggcccgcc tggctgaccg cccaacgacc   11040
cccgcccatt gacgtcaata atgacgtatg ttcccatagt aacgccaata gggactttcc   11100
attgacgtca atgggtggag tatttacggt aaactgccca cttggcagta catcaagtgt   11160
atcatatgcc aagtacgccc cctattgacg tcaatgacgg taaatggccc gcctggcatt   11220
atgcccagta catgacctta tgggactttc ctacttggca gtacatctac gtattagtca   11280
tcgctattac catggtgatg cggttttggc agtacatcaa tgggcgtgga tagcggtttg   11340
actcacgggg atttccaagt ctccacccca ttgacgtcaa tgggagtttg ttttggcacc   11400
```

-continued

```
aaaatcaacg ggactttcca aaatgtcgta acaactccgc cccattgacg caaatgggcg  11460
gtaggcgtgt acggtgggag gtctatataa gcagagctcg tttagtgaac cgtctagacg  11520
atggagacgc catccacgct gttttgacct ccatagaaga caccgggacc gatccagcct  11580
ccgcggccgg gaacggtgca ttggaacgcg gattccccgt gccaagagtg acgtaagtac  11640
cgcctataga gtctataggc ccaccccctt ggcttcttat gcatgctccc ctgctccgac  11700
ccgggctcct cgcccgcccg gacccacagg ccaccctcaa ccgtcctggc cccggaccca  11760
aaccccaccc ctcactctgc ttctccccgc aggagaattc gagatcccgg tgccgccacc  11820
atcccctgac ccacgcccct gacccctcac aaggagacga ccttccatga ccgagtacaa  11880
gcccacggtg cgcctcgcca cccgcgacga cgtcccccgg gccgtacgca ccctcgccgc  11940
cgcgttcgcc gactaccccg ccacgcgcca caccgtcgac ccggaccgcc acatcgagcg  12000
ggtcaccgag ctgcaagaac tcttcctcac gcgcgtcggg ctcgacatcg gcaaggtgtg  12060
ggtcgcggac gacggcgccg cggtggcggt ctggaccacg ccggagagcg tcgaagcggg  12120
ggcggtgttc gccgagatcg gcccgcgcat ggccgagttg agcggttccc ggctggccgc  12180
gcagcaacag atggaaggcc tcctggcgcc gcaccggccc aaggagcccg cgtggttcct  12240
ggccaccgtc ggcgtctcgc ccgaccacca gggcaagggt ctgggcagcg ccgtcgtgct  12300
ccccggagtg gaggcggccg agcgcgccgg ggtgcccgcc ttcctggaga cctccgcgcc  12360
ccgcaacctc cccttctacg agcggctcgg cttcaccgtc accgccgacg tcgagtgccc  12420
gaaggaccgc gcgacctggt gcatgacccg caagcccggt gcctgacgcc cgccccacga  12480
cccgcagcgc ccgaccgaaa ggagcgcacg accccatggc tccgaccgaa gccgacccgg  12540
gcggccccgc cgaccccgca cccgcccccg aggcccaccg actctagagg atcataatca  12600
gccataccac atttgtagag gttttacttg ctttaaaaaa cctcccacac ctccccctga  12660
acctgaaaca taaaatgaat gcaattgttg ttgttaactt gtttattgca gcttataatg  12720
gttacaaata aagcaatagc atcacaaatt tcacaaataa agcatttttt tcactgcatt  12780
ctagttgtgg tttgtccaaa ctcatcaatg tatcttatca tgtctggctc tagctatccc  12840
gcccctaact ccgcccagtt ccgcccattc tccgccccat ggctgactaa ttttttttat  12900
ttatgcagag gccgaggccg cctggagtta attaatcgcg atggccacat atggagctct  12960
ctagagcttg tcgacagatc cccctcttca tttctttatg ttttaaatgc actgacctcc  13020
cacattccct tttagtaaa atattcagaa ataatttaaa tacatcattg caatgaaaat  13080
aaatgttttt tattaggcag aatccagatg ctcaaggccc ttcataatat cccccagttt  13140
agtagttgga cttagggaac aaaggaacct ttaatagaaa ttggacagca agaaagcgag  13200
ggggatctgg atcctccgga gggcccctc tccctctaac actctcccct gttgaagctc  13260
tttgtgacgg gcgagctcag gccctgatgg gtgacttcgc aggcgtagac tttgtgtttc  13320
tcgtagtctg ctttgctcag cgtcagggtg ctgctgaggc tgtaggtgct gtccttgctg  13380
tcctgctctg tgacactctc ctgggagtta cccgattgga gggcgttatc caccttccac  13440
tgtactttgg cctctctggg atagaagtta ttcagcaggc acacaacaga ggcagttcca  13500
gatttcaact gctcatcaga tggcgggaag atgaagacag atggtgcagc cactgtacgt  13560
ttgatctcca ccttggtccc ttggccgaaa gtgtgaggta aacgactact ctgatgacag  13620
taatacactg cgaaatcttc aggctccagt ctactgatgg tgagggtgaa atctgtccca  13680
gatccactgc cactgaacct atcggggatc cctgagaggg actgggatgc atacttgatg  13740
agaagccttg gagcctgacc tggtttctgc tggtaccagt gtaagctact accaatgctc  13800
```

-continued

```
tgactggccc ggcaggagag ggtggctctc tcgcctggag acacagacag ggtacctggg  13860

ctctgagtca gcacaatttc acccctggag gctggaaccc agagcagcag aaacccaatg  13920

agttgtgatg gcgacatgtt aaacgctaga attcttaagc ctgtggagag aaaggaacag  13980

aaaacgaaac aaagacgtag agttgagcaa gcagggtcag gcaaagcgtg gagagccggc  14040

tgagtctagg taggctccaa gggagcgccg gacaaaggcc cggtctcgac ctgagcttta  14100

aacttacctg tggccacacg tgcaattgct atagtgagtc gtattaattt cgataagcca  14160

gtaagcagtg ggttctctag ttagccagag agctctgctt atatagacct cccaccgtac  14220

acgcctaccg cccatttgcg tcaatggggc ggagttgtta cgacattttg gaaagtcccg  14280

ttgattttgg tgccaaaaca aactcccatt gacgtcaatg gggtggagac ttggaaatcc  14340

ccgtgagtca aaccgctatc cacgcccatt gatgtactgc caaaaccgca tcaccatggt  14400

aatagcgatg actaatacgt agatgtactg ccaagtagga aagtcccata aggtcatgta  14460

ctgggcataa tgccaggcgg gccatttacc gtcattgacg tcaatagggg gcgtacttgg  14520

catatgatac acttgatgta ctgccaagtg ggcagtttac cgtaaatagt ccacccattg  14580

acgtcaatgg aaagtcccta ttggcgttac tatgggaaca tacgtcatta ttgacgtcaa  14640

tgggcggggg tcgttgggcg gtcagccagg cgggccattt accgtaagtt atgtaacgcg  14700

gaactccata tatgggctat gaactaatga ccccgtaatt gattactatt aataactagt  14760

caataatcaa tgtcaacgcg tatatctggc ccgtacatcg gtaactagtc ggaccgccgc  14820

ggactagtgc ccgggccacc ggtgctcgaa gcttggatcg atccagacat gataagatac  14880

attgatgagt ttggacaaac cacaactaga atgcagtgaa aaaaatgctt tatttgtgaa  14940

atttgtgatg ctattgcttt atttgtaacc attataagct gcaataaaca agttaacaac  15000

aacaattgca ttcattttat gtttcaggtt cagggggagg tgtgggaggt tttttaaagc  15060

aagtaaaacc tctacaaatg tggtatggct gattatgatc tctagtcaag             15110
```

Figure 2:
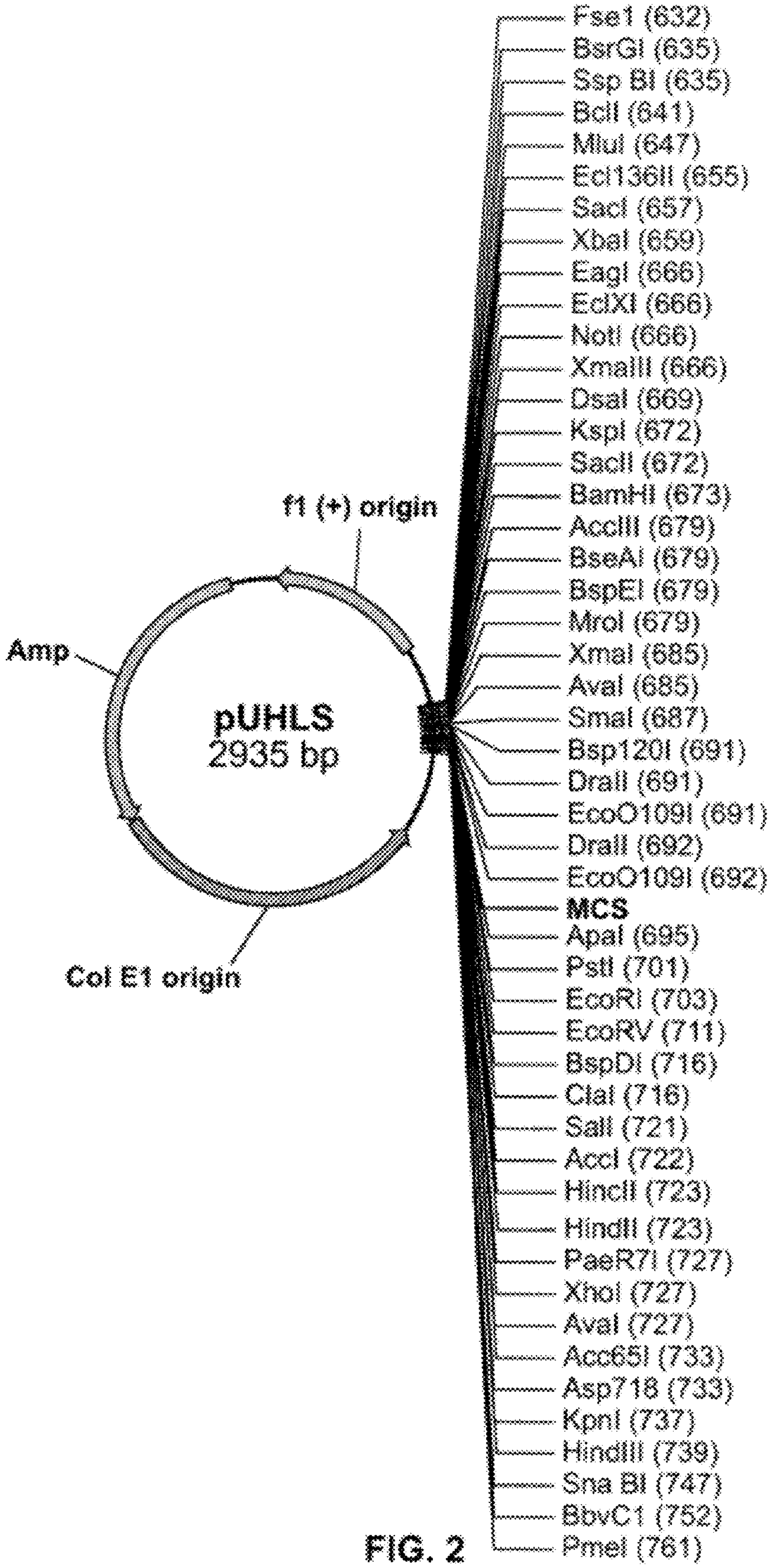
FIG. 2. Plasmid map of universal transfer vector pUHLS.
Amp: Start: 1949 End: 2806
MCS: Start: 620 End: 766
f1 (+) origin: Start: 3 End: 459
Col EI origin: Start: 1006 End: 1946
Figure 3:
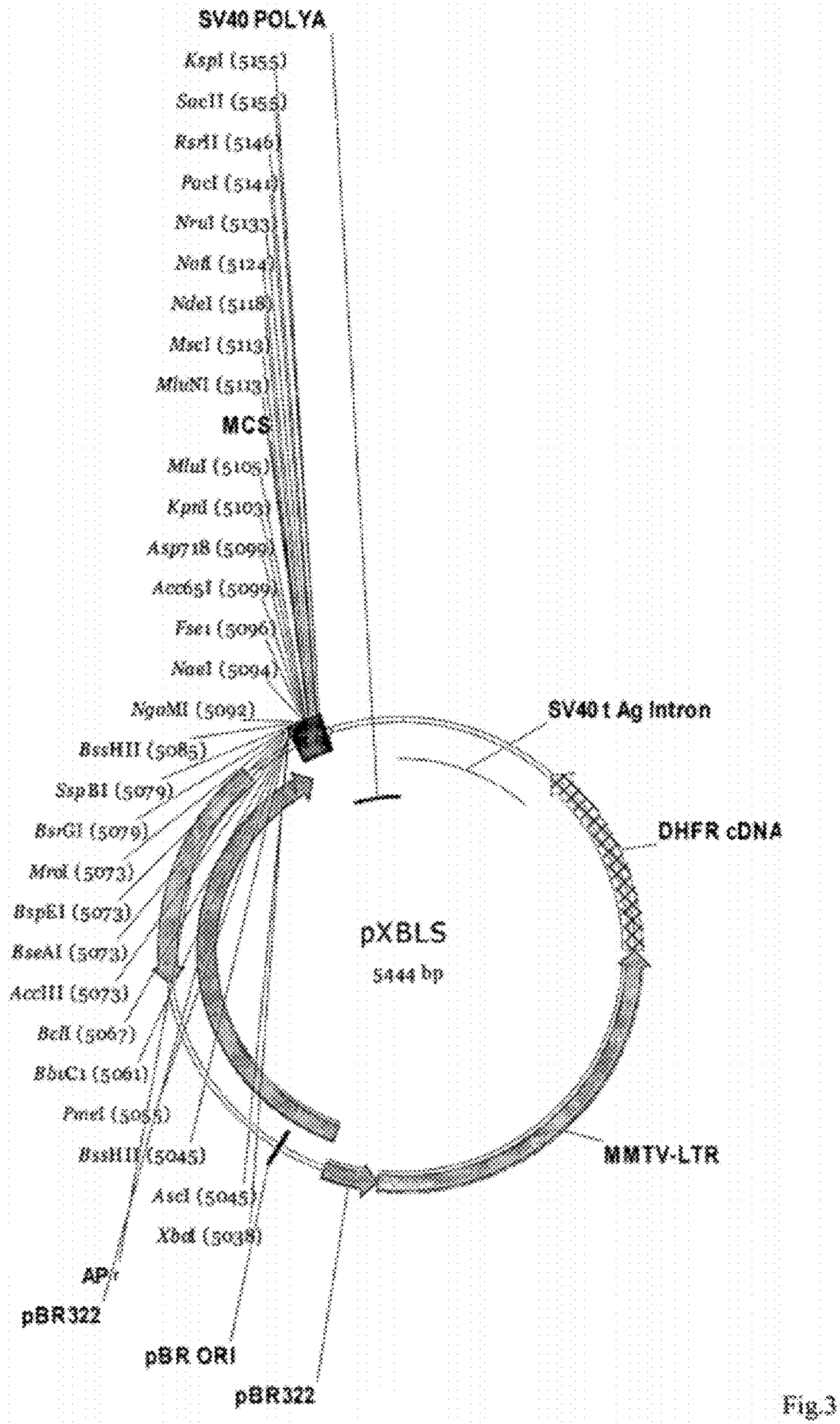
FIG. 3. Plasmid map of amplifiable vector pXBLS.
SV40 T-antigen (t Ag) Intron: Start: 5431 End: 600
SV40 POLY A signal: Start: 5184 End: 5432
MCS: Start: 5037 End: 5183
Ampicillin resistance (Amp): Start: 3965 End: 4828
pBR ORI: Start: 3207 End: 3207
pBR322 sequences: Start: 3020 End: 5033
pBR322 sequences: Start: 2811 End: 3019
MMTV-LTR promoter: Start: 1348 End: 2810
DHFR cDNA: Start: 601 End: 1347.

I claim:

1. An isolated host cell comprising a recombined amplifiable vector which is the product of a method comprising:

(a) introducing one or more expression cassettes into a first multiple cloning site of a first universal transfer vector wherein said first universal transfer vector comprises the plasmid map set forth in FIG. 2; wherein the first multiple cloning site comprises nucleotides 620-766 of the nucleotide sequence set forth in SEQ ID NO: 2; and wherein said first multiple cloning site is in said orientation or in a reverse orientation;

(b) introducing one or more expression cassettes, different from the cassettes introduced into said first universal transfer vector, into a second multiple cloning site of a second universal transfer vector which second multiple cloning site comprises nucleotides 620-772 of the nucleotide sequence set forth in SEQ ID NO: 1; wherein said second multiple cloning site is in said orientation or in a reverse orientation; and (c) introducing said cassettes from steps (a) and (b) into a third multiple cloning site of an amplifiable vector; wherein said amplifiable vector comprises the plasmid map set forth in FIG. 3; wherein said third multiple cloning site comprises nucleotides 5037-5183 of the nucleotide sequence set forth in SEQ ID NO: 3; wherein said third multiple cloning site is in said orientation or in a reverse orientation; and (d) introducing said amplifiable vector comprising said cassettes from steps (a) and (b) into a host cell.

2. An isolated host cell comprising a recombined amplifiable vector which comprises the nucleotide sequence set forth in SEQ ID NO: 26 which is the product of a method comprising:

(a) introducing one or more expression cassettes into a first multiple cloning site of a first universal transfer vector which first multiple cloning site comprises nucleotides 620-766 of the nucleotide sequence set forth in SEQ ID NO: 2; wherein said first multiple cloning site is in said orientation or in a reverse orientation;

(b) introducing one or more expression cassettes, different from the cassettes introduced into said first universal transfer vector, into a second multiple cloning site of a second universal transfer vector which second multiple cloning site comprises nucleotides 620-772 of the nucleotide sequence set forth in SEQ ID NO: 1; wherein said second multiple cloning site is in said orientation or in a reverse orientation; and (c) introducing said cassettes from steps (a) and (b) into a third multiple cloning site of an amplifiable vector wherein said third multiple cloning site comprises nucleotides 5037-5183 of the nucleotide sequence set forth in SEQ ID NO: 3; wherein said third multiple cloning site is in said orientation or in a reverse orientation; and (d) introducing said amplifiable vector comprising said cassettes from steps (a) and (b) into a host cell.

* * * * *